(12) United States Patent
Sabbadini et al.

(10) Patent No.: US 7,956,173 B2
(45) Date of Patent: Jun. 7, 2011

(54) NUCLEIC ACIDS CODING FOR HUMANIZED ANTIBODIES FOR BINDING SPHINGOSINE-1-PHOSPHATE

(75) Inventors: Roger A. Sabbadini, Lakeside, CA (US); William A. Garland, San Clemente, CA (US); Genevieve Hansen, San Diego, CA (US); Steven Tarran Jones, Radlett (GB); David Gareth Williams, Epsom (GB)

(73) Assignee: Lpath, Inc., San Diego, CA (US)

( * ) Notice: Subject to any disclaimer, the term of this patent is extended or adjusted under 35 U.S.C. 154(b) by 46 days.

(21) Appl. No.: 12/258,353

(22) Filed: Oct. 24, 2008

(65) Prior Publication Data

US 2009/0137037 A1 May 28, 2009

Related U.S. Application Data

(63) Continuation of application No. 11/924,890, filed on Oct. 26, 2007, now Pat. No. 7,829,674.

(60) Provisional application No. 60/854,971, filed on Oct. 27, 2006.

(51) Int. Cl.
- C07H 21/04 (2006.01)
- C07K 16/00 (2006.01)
- C12P 21/08 (2006.01)
- A61K 39/395 (2006.01)
- A61K 39/00 (2006.01)

(52) U.S. Cl. ............ 536/23.53; 530/387.1; 530/387.3; 530/388.1; 424/130.1; 424/133.1; 424/134.1

(58) Field of Classification Search .................. None
See application file for complete search history.

(56) References Cited

U.S. PATENT DOCUMENTS

| | | |
|---|---|---|
| 4,150,949 A | 4/1979 | Smith |
| 4,816,450 A | 3/1989 | Bell et al. |
| 4,937,232 A | 6/1990 | Bell et al. |
| 5,079,263 A | 1/1992 | Zeeck et al. |
| 5,137,919 A | 8/1992 | Igarashi et al. |
| 5,151,360 A | 9/1992 | Handa et al. |
| 5,248,824 A | 9/1993 | Igarashi et al. |
| 5,260,288 A | 11/1993 | Igarashi et al. |
| 5,331,014 A | 7/1994 | Kimura et al. |
| 5,369,030 A | 11/1994 | Hannun et al. |
| 5,391,800 A | 2/1995 | Igarashi et al. |
| 5,430,160 A | 7/1995 | Holton |
| 5,444,087 A | 8/1995 | Patel et al. |
| 5,585,476 A | 12/1996 | MacLennan et al. |
| 5,627,171 A | 5/1997 | Park et al. |
| 5,663,404 A | 9/1997 | Igarashi et al. |
| 5,667,337 A | 9/1997 | Wei et al. |
| 5,677,288 A | 10/1997 | Marangos |
| 5,851,782 A | 12/1998 | Hannun et al. |
| 5,877,167 A | 3/1999 | Igarashi et al. |
| 5,919,687 A | 7/1999 | Chatterjee |
| 5,929,039 A | 7/1999 | Woodcock et al. |
| 5,989,803 A | 11/1999 | Tabas et al. |
| 6,051,598 A | 4/2000 | Shayman et al. |
| 6,057,126 A | 5/2000 | Munroe et al. |
| 6,130,067 A | 10/2000 | Tsui |
| 6,140,060 A | 10/2000 | Chun et al. |
| 6,187,562 B1 | 2/2001 | Duckworth et al. |
| 6,210,976 B1 | 4/2001 | Sabbadini |
| 6,284,798 B1 | 9/2001 | Amtmann et al. |
| 6,306,911 B1 | 10/2001 | Wachter et al. |
| 6,323,201 B1 | 11/2001 | Carson et al. |
| 6,352,844 B1 | 3/2002 | Maurer et al. |
| 6,423,527 B1 | 7/2002 | Saba et al. |
| 6,534,322 B1 | 3/2003 | Sabbadini |
| 6,534,323 B1 | 3/2003 | Sabbadini |
| 6,610,835 B1 | 8/2003 | Liotta et al. |
| 6,613,322 B2 | 9/2003 | Tabas et al. |
| 6,649,362 B2 | 11/2003 | Gamble et al. |
| 6,858,383 B2 | 2/2005 | Sabbadini |
| 6,881,546 B2 | 4/2005 | Sabbadini |
| 7,169,390 B2 | 1/2007 | Sabbadini |
| 2001/0041688 A1 | 11/2001 | Waeber et al. |
| 2002/0150582 A1 | 10/2002 | Friedrichs et al. |
| 2003/0125533 A1 | 7/2003 | Kossida et al. |
| 2003/0219782 A1 | 11/2003 | Saba et al. |
| 2008/0213274 A1* | 9/2008 | Sabbadini et al. .......... 424/141.1 |
| 2009/0176263 A1* | 7/2009 | Mandala et al. ............... 435/15 |

FOREIGN PATENT DOCUMENTS

| | | |
|---|---|---|
| EP | 0173648 | 3/1986 |
| EP | 0173663 | 3/1986 |
| JP | 09-110722 | 4/1987 |
| JP | 2000-293181 | 10/2000 |
| WO | WO 97/44019 | 11/1997 |
| WO | WO 98/03529 | 1/1998 |
| WO | WO 98/28445 | 7/1998 |
| WO | WO 98/40349 | 9/1998 |
| WO | WO 98/57179 | 12/1998 |
| WO | WO 99/07855 | 2/1999 |

(Continued)

OTHER PUBLICATIONS

Lewin, Genes IV, 1990. Oxford University Press, p. 810.*
Abe et al., "Structural and stereochemical studies of potent inhibitors and glucosylceramide synthase and tumor cell growth," *J. Lipid Res.* 36(3):611-621 (1995).
Abe et al., "Glycosphingolipid depletion in Fabry disease lymphoblasts with potent inhibitors of glucosylceramide synthase," *Kidney Int.* 57(2):446-454 (2000).
Abe et al., "Use of Sulfobutyl Ether-Cyclodextrin as a Vehicle for D-threo-1-Phenyl-2-decanoylamino-3-morpholinopropanol-Related Glucosylceramide Synthase Inhibitors," *Anal. Biochem.* 287(2):344-347 (2000).
Ambati, "Age-related macular degeneration: etiology, pathogenesis, and therapeutic strategies," *Surv. Ophthalmol.* 48(3):257-293 (2003) (Abstract Only).

(Continued)

Primary Examiner — Anne M. Gussow
(74) Attorney, Agent, or Firm — Daniel M. Chambers; BioTechnology Law Group

(57) ABSTRACT

The present invention relates to anti-S1P agents, particularly humanized monoclonal antibodies (and antigen binding fragments thereof) specifically reactive with S1P, compositions containing such antibodies (or fragments), and the use of such antibodies (or fragments), for example, to treat diseases and conditions associated with aberrant levels of S1P.

17 Claims, 18 Drawing Sheets

FOREIGN PATENT DOCUMENTS

| | | |
|---|---|---|
| WO | WO 99/12890 | 3/1999 |
| WO | WO 99/16888 | 4/1999 |
| WO | WO 99/33972 | 7/1999 |
| WO | WO 99/38983 | 8/1999 |
| WO | WO 99/41265 | 8/1999 |
| WO | WO 99/41266 | 8/1999 |
| WO | WO 99/46277 | 9/1999 |
| WO | WO 99/61581 | 12/1999 |
| WO | WO 00/00593 | 1/2000 |
| WO | WO 00/21919 | 4/2000 |
| WO | WO 00/040262 | 7/2000 |
| WO | WO 00/52173 | 9/2000 |
| WO | WO 00/56135 | 9/2000 |
| WO | WO 00/58448 | 10/2000 |
| WO | WO 00/58491 | 10/2000 |
| WO | WO 00/59517 | 10/2000 |
| WO | WO 00/70028 | 11/2000 |
| WO | WO 00/72833 | 12/2000 |
| WO | WO 01/04108 | 1/2001 |
| WO | WO 01/04139 | 1/2001 |
| WO | WO 01/07418 | 2/2001 |
| WO | WO 01/31029 | 5/2001 |
| WO | WO 01/38295 | 5/2001 |
| WO | WO 01/55410 | 8/2001 |
| WO | WO 01/57057 | 8/2001 |
| WO | WO 01/60990 | 8/2001 |
| WO | WO 01/71045 | 9/2001 |
| WO | WO 01/72701 | 10/2001 |
| WO | WO 01/80903 | 11/2001 |
| WO | WO 01/85953 | 11/2001 |
| WO | WO 2007053447 A2 * | 5/2007 |

OTHER PUBLICATIONS

An et al., "Identification of cDNAs encoding two G protein-coupled receptors for lysosphingolipids," *FEBS Letts.* 417(3):279-282 (1997).

An et al., "Characterization of a Novel Subtype of Human G Protein-coupled Receptor for Lysophosphotatidic Acid," *J. Biol. Chem.* 273(14):7906-7910 (1998).

An et al., "Sphingosine 1-phosphate-induced cell proliferation, survival, and related signaling events mediated by G protein-coupled receptors Edg3 and Edg5," *J. Biol. Chem.* 275(1):288-296 (2000).

Ancellin et al., "Extracelluar export of sphingosine kinase-1 enzyme: Sphingosine 1 phosphate generation and the induction of angiogenic vascular maturation," *J. Biol. Chem.* 277(8):6667-6675 (2001).

Andrieu-Abadie et al., "L-camitine prevents doxorubicin-induced apoptosis of cardiac myocytes: role of inhibition of ceramide generation," *FASEB J.* 13(12):1501-1510 (1999).

Arenz et al., "Synthese des ersten selektiven irreverilben Inhibitors der neutralen Sphingomyelinase," *Angew Chem.* 112:1498-1500 (2000) (German); "Synthesis of the First Selective Irreversible Inhibitor of Neutral Sphingomyelinase," *Angew. Chem. Int. Ed.* 39(8):1440-1442 (2000) (English Equivalent).

Arenz et al., "Manumycin A and its Analogues Are Irreversible Inhibitors of Neutral Sphingomyelinase," *Chem. Biochem.* 2(2):141-143 (2001).

Arenz et al., "Synthesis and Biochemical Investigation of Scyphostatin Analogues as Inhibitors of Neutral Sphingomyelinase," *Bioorg. Medicinal Chem.* 9(11):2901-2904 (2001).

Arenz et al., "Synthesis of the First Selective Irreversible Inhibitor of Neutral Sphingomyelinase," *Eur. J. Org. Chem.* 2001(1):137-140 (2001).

Ariga et al., "Role of Sphingolipid-mediated cell death in neurodegenerative diseases," *J. Lip. Res.* 39(1):1-16 (1998).

Bajjalieh et al., "Ceramide Kinase," *Methods Enzymol.* 311:207-215 (1999).

Barbone et al., "Robotic Assay of Sphingomyelinase Activity for High Throughput Screening," *Meth. Enzymol.* 311:168-176 (1999).

Bawab et al., "Molecular Clonging and Characterization of a Human Mitochondrial Ceramidase," *J. Biol. Chem.* 275(28):21508-21513 (2000).

Bernardo et al., "Purification and Characterization of Magnesium-dependent Neutral Sphingomyelinase from Bovine Brain," *J. Biol. Chem.* 275(11):7641-7647 (2000).

Betto et al., "Sphingosylphosphocholine modulates the ryanodine receptor/calcium-release channel of cardiac sarcoplasmic reticulum memberances," *Biochem. J.* 322(1):327-333 (1997).

Bielawska et al., "(1S,2R)-D-erhthro-2-(N-My-ristoylamino)-1-phenyl-1-propanol as an Inhibitor of Ceramidase," *J. Biol. Chem.* 271(21):12646-12654 (1996).

Bielawska et al., "Ceramide Is Involved in Triggering of Cardiomyocyte Apoptosis Induced by Ischemia and Reperfusion," *Am. J. Pathol.* 151(5):1257-1263 (1997).

Boudker et al., "Detection and Characterization of Ceramide-1-phosphate Phosphatase Activity in Rat Liver Plasma Membrane," *J. Biot. Chem.* 268(29):22150-22155 (1993).

Brady et al., "The metabolism of sphingomyelin. II. Evidence of an enzymatic deficiency in Niemann-Pick disease," *Proc. Natl. Acad. Sci. USA* 55(2):366-369 (1966).

Brindley et al., "Analysis of Ceramide 1-phosphate and Sphingosine-1-phosphate Phosphatase Activities," *Methods Enzymol.* 311:233-244 (1999).

Brownlee, "Intracellular signalling: sphingosine-1-phosphate branches out," *Current Biol.* 11(13):R535-R538 (2001).

Burton et al., "Human antibodies from combinatorial libraries," *Adv. Immunol.* 57:191-280 (1994).

Byers, "What can randomized control trials tell us about nutrition and cancer prevention?," CA Canc. J. 49(6):353-361 (1999).

Cain et al., "Therapeutic Strategies to Reduce TNF-a Mediated Cardiac Contractile Depression Following Ischemia and Reperfusion," *J. Mol. Cell. Cardiol.* 31(5):931-947 (1999).

Caligan et al., "A High-Performance Liquid Chromatographic Method to Measure Sphingosine 1-Phosphate and Related Compounds from Sphingosine Kinase Assays and Other Biological Samples," *Anal. Biochem.* 281(1):36-44 (2000).

Chan et al., "Ceramide Path in Human Lung Cell Death," *Am. J. Respir. Cell Mol. Biol.* 22(4):460-468 (2000).

Chan et al., "Purification and Characterization of Neutral Sphingomyelinase from Helicobacter pylori," *Biochemistry* 39(16):4838-4845 (2000).

Chatterjee, "Sphingolipids in Atherosclerosis and Vascular Biology," *Arterioscler. Throm. Vasc. Biol.* 18(10):1523-1533 (1998).

Chatterjee, "Neutral Sphingomyelinase," *Adv. Lip. Res.* 26:25-48 (1993).

Chatterjee, "Neutral Sphingomyelinase: past, present, and future," *Chem. Phys. Lipids* 102(1):79-96 (1999).

Chatterjee et al., "Molecular Cloning, Characterization, and Expression of a Novel Human Neutral Sphingomyelinase," *J. Biol. Chem.* 274(52):37407-37412 (1999).

Chau et al., "Synthesis of Simple Aryl Neutral Sphingomyelinase Inhibitors," *Am. Chem. Soc.* (2001) (Abstract Only).

Chun, "Lysophospholipid receptors: implications for neural signaling," *Crit. Rev. Neuro.* 13(2):151-168 (1999).

Chun et al., "A Growing Family of Receptor Genes for Lysophosphatidic Acid (LPA) and other Lysophospholipids (LPs)," *Cell Biochem. Biophys.* 30(2):213-242 (1999).

Cordis et al., "HPTLC analysis of sphingomylein, ceramide and sphingosine in ischemic/reperfused rat heart," *J. Pharm. Biomed. Anal.* 16(7):1189-1193 (1998).

Cuvlilier et al., "Suppression of ceramide-mediated programmed cell death by sphingosine-1-phosphate," *Nature* 381(6585):800-803 (1996).

Dickson et al., "Serine Palmitoyltransferase," *Methods Enzymol.* 311:3-9 (1999).

Edsall et al., "N, N-Dimethylsphingosine is a potent competitive, inhibitor of sphingosine kinase but not of protein kinase C: modulation of cellular levels of sphingosine 1-phosphate and ceramide," *Biochem.* 37(37):12892-12898 (1998).

Edson et al.,."The Aminoglycosides," *Mayo Clin. Proc.* 74(5):519-528 (1999).

Eichler et al., "Peptide, peptidomimetic, and organic synthetic combinatorial libraries," *Med. Res. Rev.* 15(6):481-496 (1995).

Fensome et al., "A Neutral Magnesium-dependent Sphingomyelinase Isoform Associated with Intracellular Membranes and Reversibly Inhibited by Reactive Oxygen Species," *J. Biol. Chem.* 275(2):1128-1136 (2000).

Fujii et al., "Mg2+ binding and catalytic function of sphingomyelinase from Bacillus cereus," *J. Biochem* (Tokyo) 124(6):1178-1187 (1998).

Fukushima et al., "A single receptor encoded by vzg-1/lp$_{A1}$/edg-2 couples to G proteins and mediates multiple cellular responses to lysophosphatidic acid," Proc. Nett. Acad. Sci. USA 95(11):6151-6156 (1998).

Furneisen et al., "Enzymological properties of the LPP1-encoded lipid phosphatase from Saccharomyces cerevisiae" *Biochim. Biophys.* Acta 1484(1):71-82 (2000).

Garcia-Ruiz, "Human placenta sphingomyelinase, an exogenous acidic pH-optimum sphingomyelinase, induces oxidative stress, glutathione depletion, and apoptosis in rat hepatocytes," *Hepatology* 32(1):56-65 (2000).

Gates et al., "Serum amyloid p component: its role in platelet activation stimulated by sphingomyelinase d purified from the venom of the brown recluse spider (Loxosceles reclusa)," *Toxicon.* 28(11):1303-1315 (1990).

Gatt et al., "Niemann Pick disease: presence of the magnesium-dependent sphingomyelinase in brain of the infantile form of the disease," *J. Neurochem.* 31(2):547-550 (1978).

Gavrilenko et al., "Nucleotide sequence of phospholipase C and sphingomyelinase genes from Bacillus cereus BKM-B164," *Bioorg. Khim.* 19(1):133-138 (1993).

Geeraert et al., "Conversion of dihydroceramide into ceramide: involvement of a desaturase," *Biochem. J.* 327(125):125-132 (1997).

Ghosh et al., "Effects of gentamicin on sphingomyelinase activity in cultured human renal proximal tubular cells," *J. Biol. Chem.* 262(26):12550-12556 (1987).

Ghosh et al., "Identification, partial purification, and localization of a neutral sphingomyelinase in rabbit skeletal muscle: Neutral sphingomyelinase in skeletal muscle," *Mol. Cell. Biochem.* 189(1-2):161-168 (1998).

Gilmore et al., "A Bacillus cereus cytolytic determinant, cereolysin AB, which comprises the phospholipase C and sphingomyelinase genes: a nucleotide sequence and genetic linkage," *J. Bacteriol.* 171(2):744-753 (1989).

Glickman et al., "Molecular Cloning, Tissue-Specific Expression, and Chromosomal Localization of a Novel Nerve Growth Factor-Regulated G-ProteinCoupled Receptor, nrg-1," *Mol. Cel. Neurosci.* 14(2):141-152 (1999).

Goetzl et al., "Diversity of cellular receptors and functions for the lysophospholipid growth factors lysophosphatidic acid and sphingosine 1-phosphate," *Faseb J.* 12(15):1589-1598 (1998).

Goetzl et al., "Eicosanoids and Other Bioactive Lipids in Cancer, Inflammation, and Radiation Injury, 4. 38: A Subfamily of G Protein-Coupled Cellular Receptors for Lysophospholipids and Lysosphingolipids, Introduction: The Biochemistry and Biology of Lipid Phosphoric Acids," *Adv. Exp. Med. Biol.* 469:259-264 (1999).

Gonda, et al., "The novel sphingosine 1-phosphate receptor AGR16 is coupled via pertussis toxin-sensitive and -insensitive G-proteins to multiple signalling pathways," *Biochem. J.* 337(Part 1):67-75 (1999).

Gonzalez-Zorn et al., "The smcL gene of Listeria ivanovii encodes a sphingomyelinase C that mediates bacterial escape from the phagocytic vacuole," *Mol. Microbial.* 33(3):510-523 (1999).

Graler et al., "Edge, a Novel G-Protein-Coupled Receptor Related to Receptors for Bioactive Lysophospholipids, Is Specifically Expressed in Lymphoid Tissue, " *Genomics* 53(2):164-169 (1998).

Granziero et al., "Adoptive immunotherapy prevents prostate cancer in a transgenic animal model," *Eur. J. Immunol.* 29(4):1127-1138 (1999).

Gunther, "Myocardial contractility after infarction and carnitine palmitoyltransferase I inhibition in rats," *Eur. J. Pharma.* 406(1):123-126 (2000).

Hakogi et al., "Stereocontrolled synthesis of a sphingomyelin methylene analogue as a sphingomyelinase inhibitor," *Org. Lett.* 2(17):2627-2629 (2000).

Hanada et al., "Specificity of Inhibitors of Seine Palmitoyltransferase (SPT), a Key Enzyme in Sphingolipid Biosynthesis in Intact Cells: A novel evaluation system using an SPT-defective mammalian cell mutant," *Biochem. Pharmacol.* 59(10):1211-1216 (2000).

Hannun et al., "Functions of Sphingolipids and Sphingolipid Breakdown Products in Cellular Regulation," *Science* 243(4890):500-507 (1989).

Hannun et al., "The Sphingomyelin Cycle: A Prototypic Sphingolipid Signaling Pathway," *Adv. Lipid Res.* 25:27-41 (1993).

Hannun, "Functions of Ceramide in Coordinating Cellular Responses to Stress," *Science* 274(5294):1855-1859 (1996).

Hannun at al, "Ceramide in the eukaryotic stress response," *Trends Cell Biol.* 10(2):73-80 (2000).

He et al., "A Fluorescence-Based High-Performance Liquid Chromatography Assay to Determine Acid Ceramidase Activity," *Anal. Biochem.* 274(2):264-269 (1999).

Heringdorf et al., "Stimulation of intracellular sphingosine-1-phosphate production by G-protein-coupled sphingosine-1-phosphate receptors," *Eur. J. Pharmacol.* 414(2-3):145-154 (2001).

Hernandez et al., "Rapid Activation of Neutral Sphingomyelinase by Hypoxia-Reoxygenation of Cardiac Myocytes," *Circ. Res.* 86(2):198-204 (2000).

Hetland et al., "Phospholipase C from *Bacillus cereus* has sphingomyelinase activity," *Scand. J. Clin. Lab. Invest.* 42(1):57-61 (1982).

Higuchi et al., "Acidic sphingomyelinase-generated ceramide is needed but not sufficient for TNF-induced apoptosis and nuclear factor-kappa B activation," *J. Immunol.* 157M:297-304 (1996).

Hinkovska-Glacheva et al., "Activation of a Plasma Membrane-Associated Neutral Sphingomyelinase and Concomitant Ceramide Accumulation During IgG-Dependent Phagocytosis in Human Polymorphonuclear Leukocytes," *Blood* 91(12):4761-4769 (1998).

Hise et al., "Fatty Acyl Chain Composition in the Determination of Renal Membrane Order," *J. Clin. Invest.* 77(3):768-773 (1986).

HLA et al., "An Abundant Transcript Induced in Differentiating Human Endothelial Cells Encodes a Polypeptide with Structural Similarities to G-Protein-coupled Receptors," *J. Biol. Chem.* 265(16):9308-9313 (1990).

Hofmann et al., "Cloning and characterization of the mammalian brain-specific, $Mg^{2+}$-dependent neutral sphingomyelinase," *Proc. Natl. Acad. Sci.* USA 97(11):5895-5900 (2000).

Hofstadler et al., "Multiplexed Screening of Neutral Mass-Tagged RNA Targets against Ligand Libraries with Electrospray Ionization FTICR MS: a Paradigm for High-Throughput Affinity Screening," *Anal. Chem.* 71(16):3436-3440 (1999).

Holopainen et al., "Sphingomyelinase Activity. Associated with Human Plasma Low Density Lipoprotein," *J Biol. Chem.* 275(22):16484-16489 (2000).

Horn et al., "Sphingofungins E and F: Novel Serinepalmitoyl Trans-Ferase Inhibitors From Paecilomyces variotii," *J. Antibiot* (Tokyo) 45(10):1692-1696 (1992).

Hoye et al., "Synthesis (and Alternative Proof of Configuration) of the Scyphostatin C(1')-C(20') Trienoyl Fragment," *Organic Letts.* 2(10):1481-1483 (2000).

Hudson, "Recombinant antibody fragments," *Curr. Op. Biotechnol.* 9(4):395-402 (1999).

Humpf et al., "Acylation of naturally occurring and synthetic 1-deoxysphinganines by ceramide synthase. Formation of N-palmitoyl-aminopentol produces a toxic metabolite of hydrolyzed fumonisin, AP1, and a new category of ceramide synthase inhibitor," *J. Biot. Chem.* 273(30):19060-19064 (1998).

Huwiler et al., "Physiology and pathophysiology of sphingolipid metabolism and signling," *Biochim. Biophys. Acta* 1485(2-3):63-99 (2000).

Igarashi, "Functional Roles of Sphingosine, Sphingosine 1-Phosphate, and Methylsphingosines: In Regard to Membrane Sphingolipid Signaling Pathways," *J. Biochem.* 122(6):1080-1087 (1997).

Ikezawa et al., "Studies on Sphingomyelinase of *Bacillus Cereus*. 1. Purification and Properties," *Biochim. Biophys.* Acta 528(2):247-256 (1978).

Im et al., "Characterization of a novel sphingosine 1-phosphate receptor, Edg-8," *J. Biol. Chem.* 275(19):14281-14286 (2000).

Im et al., "Molecular Cloning and Characterization of a Lysophosphatidic Acid Receptor, Edg-7, Expressed in Prostate," *Mol. Pharmacol.* 57(4):753-759 (2000).

Izuhara et al., "Studies toward the Total Synthesis of Scyphostatin: First Entry to the Highly Functionalized Cyclohexenone Segment," *Organic Lett.* 3(11):1653-1656 (2001).

Jimbo et al., "Development of a New Inhibitor of Glucosylceramide Synthase," *J. Biochem.* 127(3):485-491 (2000).

Johansen et al., "*Bacillus cereus* strain SE-1: nucleotide sequence of the sphingomyelinase C gene," *Nucl. Acids Res.* 16(21):10370 (1998).

Jonghe et al., "Structure-Activity Relationship of Short-Chain Sphingoid Bases As Inhibitors of Sphingosine Kinase", *Bioorg. Medicinal Chem. Lett.* 9(21):3175-3180 (1999).

Kajstura et al., "Apoptotic and Necrotic Myocyte Cell Deaths Are Independent Contributing Variables of Infarct Size in Rats," *Lab. Invest.* 74(1):86-107 (1996).

Kanfer et al., "The Metabolism of Sphingomyelin. I. Purification and properties of a sphingomyelin-cleaving enzyme from rat liver tissue," *J. Biol. Chem.* 241(5):1081-1084 (1966).

Katircioglu et al., "Myocardial preservation in acute coronary artery occlusion with coronary sinus retroperfusion and carnitine," *J. Cardiovasc. Surg.* (Torino) 41(1):45-50 (1999).

Kay et al., "Identification of enzyme inhibitors from phage-displayed combinatorial peptide libraries," *Comb. Chem. High Throughput Screen* 4(7):535-543 (2001).

Kester, "Sphingolipid Metabolites and the Cellular Phenotype," *Trends Glycosci. Glycotechnol.* 9(50):447-460 (1997).

Kihara et al., "Direct Measurement of Changes in Intercellular Calcium Transients During Hypoxia, Ischemia, and Reperfusion of the Intact Mammalian Heart," *Circ. Res.* 65(4):1029-1044 (1989).

Kimura et al., "Two Novel Xenopus Homologs of Mammalian $LP_{A1}$/EDG-2 Function as Lysophosphatidic Acid Receptors in Xenopus Oocytes and Mammalian Cells," *J. Biol. Chem.* 276(18):15208-15215 (2001).

Kita et al., "Reverse hydrolysis reaction of a recombinant alkaline ceramidase of Pseudomonas aeruginosa," *Biochim. Biophys. Acta* 1485(2-3):111-120 (2000).

Kohama et al., "Molecular cloning and functional characterization of murine sphingosine kinase," *J. Biol. Chem.* 273(37):23722-23728 (1998).

Kolesnick et al., "Characterization of a Ceramide Kinase Activity from Human Leukemia (HL-60) Cells: Separation From Diacylglycerol Kinase Activity," *J. Biol. Chem.* 265(31):18803-18808 (1990).

Kolesnick, "The thereapeutic potential of modulating the ceramide/sphingomyelin pathway," *J. Clin. Inv.* 110(1):3-8 (2002).

Krown et al., "Tumor necrosis factor alpha-induced apoptosis in cardiac myocytes. Involvement of the sphingolipid signaling cascade in cardiac cell death," *J. Clin. Invest.* 98(12):2854-2865 (1996).

Kubota et al., "Accumulation of ceramide in ischemic human brain of an acute case of cerebral occlusion," *Japan J. Exp. Med.* 59(2):59-64 (1989).

Kubota et al., "Sphingomyelin changes in rat cerebral cortex during focal ischemia," *Neurol. Res.* 18(4):337-341 (1996).

Lanterman et al., "Characterization of sphingosine kinase (SK) activity in Saccharomyces cerevisiae and isolation of SK-deficient mutants," *Biochem. J.* 332(Part 2):525-531 (1998).

Lee et al., "Effect of Ischemia on Calcium-Dependent Fluorescence Transients in Rabbit Hearts Containing Indo 1. Correlation with Monophasic Action Potentials and Contraction," *Circ.* 78(4)1047-1059 (1988).

Lee et al., "Cell-cycle-dependent changes in ceramide levels preceding retinoblastoma protein dephosphorylation in G2/M," *Biochem. J.* 334(Part 2):457-461 (1998).

Lee et al., "Improved Inhibitors of Glucosylceramide Synthase," *J. Bio. Chem.* 274(21):14662-14669 (1999).

Lee et al., "Sphingosine 1-Phosphate Induces Angiogenesis: Its Angiogenic Action and Signaling Mechanism in Human Umbilical Endothelial Cells," *Biochem. Biophys. Res. Commun.* 264(3):743-750 (1999).

Lee et al., "Lysophosphatidic acid and sphingosine 1-phosphate stimulate endothelial cell wound healing," *Am. J. Physiol. Cell Physiol.* 278(3):C612-C618 (2000).

Levade, et al., "Sphingomyelinases and Niemann-Pick disease," *J. Clin. Chem. Clin. Biochem.* 24(4):205-220 (1986).

Li et al., "The Human Acid Ceramidase Genes (ASAH): Structure, Chromosomal Location, Mutation Analysis, and Expression," *Genomics* 62(2):223-231 (1999).

Liliom at al, "Sphingosylphosphocholine is a naturally occurring lipid mediator in blood plasma: a possible role in regulating cardiac function via sphingolipid receptors," *Biochem. J.* 355(Part 1):189-197 (2001).

Lin et al., "Identification of neutral and acidic sphingomyelinases in Helicobacter pylori," *FEBS Lett.* 423(2):249-253 (1998).

Linn et al., "Regulation of de novo sphingolipid biosynthesis and the toxic consequences of its disruption," *Biochem. Soc.* 29(Part 6):831-835 (2001).

Lister et al., "Interaction of sphingomyelinase with sphingomyelin analogs modified at the G1 and C-3 positions of the sphingosine backbone," *Biochim. Biophys. Acta* 1256(1):25-30 (1995).

Little at al, "Surface display of antibodies," *Biotechn. Adv.* 12(3):539-555 (1994).

Liu et al., "Inhibition of the neutral magnesium-dependent sphingomyelinase by glutathione," *J. Biol. Chem.* 272(26):16281-16287 (1997).

Liu et al., "Purification and Characterization of a Membrane Bound Neutral pH Optimum Magnesium-dependent and Phosphatidylserine-stimulated Sphingomyelinase from Rat Brain," *J. Biol. Chem.* 273(51):34472-34479 (1998).

Liu et al., "Glutathione regulation of neutral sphingomyelinase in tumor necrosis factor-alpha-induced cell death," *J. Biol. Chem.* 273(18):11313-11320 (1998).

Liu at al, "Advances in the signal transduction of ceramide and related sphingolipids," *Crit. Rev. Clin. Lab. Sci.* 36(6):511-573 (1999).

Liu et al., "Molecular Cloning and Functional Characterization of a Novel Mammalian Sphingosine Kinase Type 2 Isoform," *J. Biol. Chem.* 275(26):19513-19520 (2000).

Liu et al., "Sphingomyelinase Assay Using Radiolabeled Substrate," *Meth. Enzymol.* 311:164-167 (2000).

Lochhead at al, "Fluorinated anesthetic exposure "activates" the renal cortical sphingomyelinase cascade," *Kidney Int.* 54(2):373-381 (1998).

Luberto et al., "Sphingomyelin synthase, a potential regulator of intracellular levels of ceramide and diacylglycerol during SV40 transformation. Does sphingomyelin synthase account for the putative phosphatidylcholine-specific phopholipase C?," J. Biot. Chem. 273(23):14550-14559 (1998).

Luberto et al., "Sphingolipid Metabolism in the Regulation of Bioactive Molecules," *Lipids* 34(Supp. 1):S5-S11 (1999).

Lynch at al, "Life on the edg," *Trends Pharmacol. Sci.* 20(12):473-475 (1999).

Magnelli et al., "BCL-2 Overexpression Abolishes Early Calcium Waving Preceding Apoptosis in NIH-3T3 Murine," *Biochem. Biophys. Res. Comm.* 204(1):84-90 (1994).

Mandala et al., "Inhibition of Serine Palmitoyl-Transferase Activity by Lipdxamycin," *J. Antibiot.* (Tokyo) 47(3):376-379 (1994).

Mandala et al., "The Discovery of Australifungin, a novel Inhibitor of Sphinganine N-Acyltransferase from Sporormiella australis. Producing Organism, Fermentation, Isolation, and Biological Activity," *J. Antibiot.* (Tokyo) 48(5):349-356 (1995).

Mandala et al., "Khafrefungin, a novel inhibitor of sphingolipid synthesis," *J. Biol. Chem.* 272(51):32709-32714 (1997).

Mandala et al., "Viridiofungins, Novel Inhibitors of Sphingolipid Synthesis," *J. Antibiot* (Tokyo) 50(4):339-343 (1997).

Mandala et al., "Sphingoid base 1-phosphate phosphatase: a key regulator of sphingolipid metabolism and stress response," *Proc. Natl. Acad. Sci. USA* 95(1):150-155 (1998).

Mandala et al., "Isolation and Characterization of Novel Inhibitors of Sphingolipid Synthesis: Australifungin, Viridiofungins, Rustmicin, and Khafrefungin," *Methods Enzymol.* 311:335-348 (1999).

Mandala et al., "Molecular cloning and characterization of a lipid phosphohydrolase that degrades sphingosine-1-phosphate and induces cell death," *Proc. Natl. Acad. Sci. USA* 97(14):7859-7864 (2000).

Mandala et al., "Sphingosine-1-Phosphate Phosphatases," *Prostaglandins & Other Lipid Mediators* 64(1-4):143-156 (2001).

Mao et al., "Molecular cloning and characterization of SCaMPER, a Sphingolipid Ca2+ release-mediating protein from endoplasmic reticulum," *Proc. Natl. Acad. Sci. USA* 93(5):1993-1996 (1996).

Mao et al., "Cloning of an Alkaline Ceramidase from Saccharomyces cerevisiae: An Enzyme with Reverse (CoA-Independent) Ceramide Synthase Activity," *J. Biol. Chem.* 275(10):6876-6884 (2000).

Mao et al., "Cloning and Characterization of a Saccharomyces cerevisiae Alkaliine Ceramidase with Specificity for Dihydroceramide," *J. Biol. Chem.* 275(40):31369-31378 (2000).

Mao et al., "Cloning and Characterization of a Novel Human Alkaline Ceramidase: A Mammalian Enzyme That Hydrolyzes Phytoceramide," *J. Biol. Chem.* 276(28):26577-26588 (2001).

Marks et al., "Methods for Studying Glucosylceramide Synthase," *Methods Enzymol.* 311:50-59 (1999).

Martin et al., "Neutral Magnesium-Dependent Sphingomyelinase from Liver Plasma Membrane: Purification and Inhibition by Ubiquinol," *J. Bioenerg. Biomember.* 33(2):143-153 (2001).

Meacci et al., "Receptor-mediated activation of phospholipase D by sphingosine 1-phosphate in skeletal muscle C2C12 cells: A role for protein kinase C," *FEBS Lett.* 457(2):184-188 (1999).

Meldrum, "Tumor necrosis factor in the heart," *Am. J. Physiol.* 274(3):R577-R595 (1998).

Melendez et al., "Human sphingosine kinase: molecular cloning, functional characterization and tissue distribution," *Gene* 251(1):19-26 (2000).

Meroni et al., "Effect of N-Acetylsphingosine (C2) and the Ceramidase Inhibitor (1S,2R)-D-erythro-2-(n-myristoylamino)-1 phenyl-1-propanol on the Regulation of Sertoli Cell Function," *J. Andral.* 20(5):619-625 (1999).

Merrill et al., "Activities of serine palmitoyltransferase (3-ketosphinganine synthase) in microsomes from different rat tissues," *J. Lipid Res.* 26(5):617-622 (1993).

Michel et al., "Characterization of Ceramide Synthesis. A Dihydroceramide Desaturase Introduces the 4,5-TRANS-Double Bond of Sphingosine At the Level of Dihydroceramide," *J. Biol. Chem.* 272(36):22432-22437 (1997).

Milstien et al., "Targeting sphingosine-1-phosphate: A novel avenue for cancer therapeutics," *Cancer Cell.* 9(3):148-150 (2006) (Abstract Only).

Mingeot-Leclercq et al., "Aminoglycosides: activity and resistance," *Antimicrob. Agents Chemother.* 43(4):727-737 (1999).

Mingeot-Leclercq et al., "Aminoglycosides: nephrotoxicity," *Antimicrob. Agents Chemother.* 43(5):1003-1012 (1999).

Mitsutake et al., "Purification, Characterization, Molecular Cloning, and Subcellular Distribution of Neutral Ceramidase of Rat Kidney," J. Biol. Chem. 276(28):26249-26259 (2001).

Miyake, "Serine palmitoyltransferase is the primary target of a sphingosine-like immunosuppressant, ISP-1/myriocin," *Biochem. Biophys. Res. Commun.* 211(2):396-403 (1995).

Mohan et al., "Evidence that Neutral Sphingomyelinase of Cultured Murine Neuroblastoma Cells is Oriented Externally on the Plasma Membrane," *Biochem. Biophys. Acta* 777(2):339-342 (1984).

Mohler et al., "Soluble Tumor Necrosis Factor (TNF) Receptors Are Effective Therapeutic Agents in Lethal Endotoxemia and Function Simultaneously as Both TNF Carries and TNF Antagonists," *J. Immunol.* 151(3):1548-1561 (1993).

Nakajima et al., "Expression and characterization of Edg-1 receptors in rat cardiomyocytes: Calcium deregulation in response to sphingosine 1-phosphate," *Eur. J. Biochem.* 267(18):5679-5686 (2000).

Nakajima et al., *Biophysical J.* 78:319 A (2000).

Napoli et al., "Ischaemic preconditioning of rat myocardium: effects on postischaemic coronary endothelium hypermaebility and microcirculatory damage," *J. Clin. Bas. Cardiol.* 1(1):37-42 (1998).

Nikolova-Karakashian et al., "Ceramidases," *Meth. Enzymol.* 311:194-201 (1999).

Ohta et al., "A possible role of sphingosine in induction of apoptosis by tumor necrosis factor-a in human neutrophils," *FEBS Lett.* 355(3):267-270 (1994).

Ohta et al., "Induction of apoptosis by sphingosine in human leukemic HL-60 cells: a possible endogenous modulator of apoptotic DNA fragmentation occurring during phorbol ester-induced differentiation," *Cancer Res.* 55(3):691-697 (1995).

Okamoto et al., "EDG1 Is a Functional Sphingosine-1-phosphate Receptor That Is Linked via a $G_{i/o}$ to Multiple Signaling Pathways, Including Phospholipase C Activation, $Ca^{2+}$ Mobilization, Ras-Mitogen-activated Protein Kinase Activation, and Adenylate Cyclase Inhibition," *J. Biol. Chem.* 273(42):27104-27110 (1998).

Okamoto et al., "EDG3 Is a Functional Receptor Specific for Sphingosine 1-Phosphate and Sphingosylphosphorylcholine with Signaling Characteristics Distinct from EDG1 and AGR16," *Biochem. Biophys. Res. Commun.* 260(1):203-208 (1999).

Okazaki et al., "Characteristics and partial purification of a novel cytosolic, magnesium-independent, neutral sphingomyelinase activated in the early signal transduction of 1 alpha,25-dihydroxyvitamin D3-induced HL-60 cell differentiation," *J. Biol. Chem.* 269(6):4070-4077 (1994).

Okino et al., "Molecular Cloning, Sequencing, and Expression of the Gene Encoding Alkaline Ceramidase from Pseudomonas aeruginosa: Cloning of A Ceramidase Homologue from mycobacterium Tuberculosis," *J. Biol. Chem.* 274(51):36616-36622 (1999).

Olivera et al., "Sphingosine-1-phosphate as second messenger in cell proliferation induced by PDGF and FCS mitogens," *Nature* 365(6446):557-560 (1993).

Olivera et al., "Assaying Sphingosine Kinase Activity," *Methods Enzymol.* 311:215-223 (1999).

Olshefski et al., "Glucosylceramide Synthase Inhibition Enhances Vincristine-Induced Cytotoxicity," *Int. J. Cancer* 93(1):131-138 (2001).

Oral et al., "Sphingosine mediates the immediate negative inotropic effects of tumor necrosis factor-alpha in the adult mammalian cardiac myocyte," *J. Biol. Chem.* 272(8):4836-4842 (1997).

Parrill et al., "Identification of Edg1 Receptor Residues That Recognize Sphingosine 1-Phosphate," *J. Biol. Chem.* 275(50):39379-39384 (2000).

Pitson et al., "Human sphingosine kinase: purification, molecular cloning and characterization of the native and recombinant enzymes," *Biochem J.* 350(Part 2):429-441 (2000).

Pitson et al., "Expression of a catalytically inactive sphingosine kinase mutant blocks agonist-induced sphingosine kinase activation. A dominant-negative sphingosine kinase," *J. Biol. Chem.* 275(43):33945-33950 (2000).

Presta et al., "Humanization of an Anti-Vascular Endothelial Growth Factor Monoclonal Antibody for the Therapy of Solid Tumors and Other Disorders," *Canc. Res.* 57(20):4593-4599 (1997).

Raag et al., "Single-chain Fvs," *FASEB J.* 9(1):73-80 (1995).

Rani et al., "Cell Cycle Arrest Induced by an Inhibitor of Glucosylceramide Synthase," *J: Biol. Chem.* 270(6):2859-2867 (1995).

Riley et al., "Alteration of tissue and serum sphinganine to sphingosine ratio: an early biomarker of exposure to fumonisin-containing feeds in pigs," *Toxicol. Appl. Pharmacol.* 118(1):105-112 (1993).

Riley et al., "Fermentation, partial purification, and use of serine palmitoyltransferase inhibitors from Isaria (= Cordyceps) sinclairii," *Meth. Enzymol.* 311:348-361 (1999).

Romiti et al., "Characterization of sphingomyelinase activity released by thrombin-stimulated platelets," *Mol. Cell. Biochem.* 205(1-2):75-81 (2000).

Runcie at al, "A Short and Efficient Route to Novel Scyphostatin Analogues," *Organic Lett.* 3(21):3237-3239 (2001).

Sabbadini et al., "Sphingosine is endogenous to cardiac and skeletal muscle," *Biochem. Biophys. Res. Comm.* 193(2):752-758 (1993).

Sabbadini et al., "The Mirf trial: predicting the incidence and severity of CAD using serum sphingolipids," *Circ.* 102(18)II699 (2000).

Saint-Joanis et al., "Gene cloning shows the alpha-toxin of Clostridium perfringens to contain both sphingomyelinase and lecithinase activities," *Mol. Gen. Genet.* 219(3):453-60 (1989).

Saito et al., "Absolute Configuration of Scyphostatin," *Organic Letts* 2(4):505-506 (2000).

Sakai et al., "A devise for recording left ventricular contraction and electrocardiogram in nonworking isolated perfused rat heart," *Jpn J. Pharmacol.* 28(2):223-229 (1978).

Sawada et al., "Ordering of ceramide formation, caspase activation, and Bax/BcI-2 expression during etoposide-induced apoptosis in C6 glioma cells," *Cell Death Differentiation* 7(9):761-7672 (2000).

Sato, "A new role of lipid receptors in vascular and cardiac morphogenesis," *J. Clin. Invest.* 106(8):939-940 (2000).

Sawai et al., "Function of the Cloned Putative Neutral Sphingomyelinase as Lyso-platelet Activating FactorPhospholipase C," *J. Biol. Chem.* 274(53):38131-38139 (1999).

Sawai et al., "Identification of ISC1 (YER019w) as Inositol Phosphosphingolipid Phospholipase C Saccharomyces cerevisiae," *J. Biol. Chem.* 275(50):39793-39798 (2000).

Schissel et al., "$Zn^{2+}$-stimulated Sphingomyelinase Is Secreted by Many Cell Types and Is a Product of the Acid Sphingomyelinase Gene," *J. Biol. Chem.* 271(31):18431-18436 (1996).

Sergeyev et al., "Lipid Spectrum of the Myocardium of White Rats Exposed to Hypoxic Hypoxia," *Kosm. Biot. Aviakosm. Med.* (Russian) 15(6):71-74 (1981).

Shayman et al., "Glucosylceramide Synthase: Assay and Properties," *Methods Enzymol.* 311:42-49 (1999).

Shayman et al., "Inhibitors of Glucosylceramide Synthase," *Methods Enzymol.* 311:373-387 (1999).

Shinghal et al., "Ceramide 1-Phosphate Phosphatase Activity in Brain," *J. Neurochem.* 61(6):2279-2285 (1993).

Siehler et al., "Sphingosine 1-Phosphate Activates Nuclear Factor-kappa B through Edg Receptors: Activation Through Edg-3 and Edg-5, but not Edg-1, in Human Embryonic Kidney 293 Cells," *J. Biol. Chem.* 276(52):48733-48739 (2001).

Siess et al., "Lysophosphatidic Acid and Sphingosine 1-Phosphate: Two Lipid Villains Provoking Cardiovascular Diseases?" *IUBMB Life* 49(3):161-171 (2000).

Smith et al., "Hypoxia, calcium fluxes, and inotropic state: Studies in cultured heart cells," *Am. Heart J.* 103(4 Part 2):716-723 (1982).

Smith et al., "Purified Fumonisin $B_1$ Decreases Cardiovascular Function but does not Alter Pulmonary Capillary Permeability in Swine," *Toxicol. Sci.* 56(1):240-249 (2000).

Spence, "Sphingomyelinases," *Adv. Lipid Res.* 26:3-23 (1993).

Spence et al., "A new Zn2+-stimulated sphingomyelinase in fetal bovine serum," *J. Biol. Chem.* 264(10):5358-5363 (1989).

Spiegel et al., "Sphingolipid metabolism and cell growth regulation," *FASEB J.* 10(12):1388-1397 (1996).

Spiegel et al., "Review: Roles of Sphingosine-1-phosphate in Cell Growth, Differentiation, and Death," *Biochemistry (Mosc).* 63(1):69-83 (1998).

Spiegel et al., "Functions of a new family of sphingosine-1-phosphate receptors," *Biochim. Biophys. Acta* 1484(2-3):107-116 (2000).

Sucheck et al., "Combinatorial synthesis of aminoglycoside libraries," *Curr. Opin. Drug Disc. Develop.* 4(4):462-470 (2001).

Sugita at al, "Ceramidase and ceramide synthesis in human kidney and cerebellum. Description of a new alkaline ceramidase," *Biochim. Biophys. Acta* 398(1):125-131 (1975).

Sugiyama et al., "Sphingosine 1-phosphate induces sinus tachycardia and coronary vasoconstriction in the canine heart," *Cardiovasc. Res.* 46(1):119-125 (2000).

Sumnicht et al., "Lipid Composition of Transverse Tubular Membranes from Normal and Dystrophic Skeletal Muscle," *Arch. Biochem. Biophys.* 215(2):628-637 (1982).

Szulc et al., "A facile regioselective synthesis of sphingosine 1-phosphate and ceramide 1-phosphate," *Tetrahedron Lett.* 41(41):7821-7824 (2000).

Tamura et al., "Mass Production of Sphingomyelinase of *Bacillus cereus* by a Protein-Hyperproducing Strain, Bacillus brevis 47, and Its Purification," *J. Biochem.* (Tokyo) 112(4):488-491 (1992).

Tanaka et al., "Structural Elucidation of Scyphostatin, an Inhibitor of Membrane-Bound Neutral Sphingomyelinase," *J. Am. Chem. Soc.* 199(33):7871-7872 (1997).

Tani et al., "Purification and Characterization of a Neutral Ceramidase from Mouse Liver: a single Protein Catalyzes the Reversible Reaction in Which Ceramide is Both Hydrolyzed and Synthesized," *J. Biot. Chem.* 275(5):3462-3468 (2000).

Tazabekova et al., "Synthesis of sphingomyelin phosphonate analogues and preparation of an affinity sorbent for the sphingomyelinase purification," *Bioorg. Khim.* 13(5):648-653 (1987).

Tomita et al.., "Secondary structure of sphingomyelinase from *Bacillus cereus*," *J. Biochem.* (Tokyo) 108(5):811-815 (1990).

Torley et al., "A turbidometric assay for phospholipase C and sphingomyelinase," *Anal. Biochem.* 222(2):461-464 (1994).

Tosaka et al., "Sphingosine 1-phosphate contracts canine basilar arteries in vitro and in vivo: possible role in pathogenesis of cerebral vasospasm," *Stroke* 32(12):2913-2919 (2001).

Triola et al., "Synthesis of a Cyclopropene Analogue of Ceramide, a Potent Inhibitor of Dihydroceramide Desaturase,"*Angew. Chem. Int. Ed.* 40(10):1960-1962 (2001).

Tsunoda et al., "Early Fumonisin B1 Toxicity in Relation to Disrupted Sphingolipid Metabolism in Male BALB/c Mice," *J. Biochem. Mol. Toxicol.* 12(5):281-289 (1998).

Uchida et al., "Alutenusin, a Specific Neutral Sphingomyelinase Inhibitor, Produced by Penicillium sp. FO-7436,"*J: Antibiot.* (Tokyo) 52(6):572-574 (1999).

Urdal, "The Biochemistry of Tumor Associated Gangliotriosylceramide and the Use of This Glycolipid as a Target for Antibody Dependent, Avidin Mediated Drug Killing of Tumor Cells," *Dissertation Abstracts Int.* 41(11B):4062-4063 (1980).

Usta et al., "Structural Requirements of Ceramide and Sphingosine Based Inhibitors of Mitochondrial Ceramidase," *Biochemistry* 40(32):9657-9668 (2000).

Van Brocklyn et al., "Sphingosine 1-phosphate-induced cell rounding and neurite retraction are mediated by the G protein-coupled receptor H218," *J. Biol. Chem.* 274(8):4626-4632 (1999).

Van Veldhoven et al., "Sphingosine-Phosphate Lyase," *Adv. Lipid Res.* 26:69-98 (1993).

Van Veldhoven, "Shingosine-1-phosphate Lyase," *Methods Enzymol.* 311:244-254 (1999).

Van Veldhoven et al., "Human sphingosine-1-phosphate lyase: cDNA cloning, functional expression studies and mapping to chromosome 10q22(1)," *Biochim. Biophys. Acta* 1487(2-3):128-134 (2000).

Visentin et al., "Validation of an anti-sphingosine-1-phosphate antibody as a potential therapeutic in reducing growth, invasion, and angiogenesis in multiple tumor lineages," *Cancer Cell.* 9(3):225-238 (2006).

Vivekananda et al., "Sphingomyelin metabolites inhibit sphingomyelin synthase and CTP:phosphocholine cytidylyltransferase," *Am. J. Physiol. Lung Cell. Mol. Physiol.* 228(1):L98-L107 (2001).

Walev et al., "Selective killing of human monocytes and cytokine release provoked by sphingomyelinase (beta-toxin) of Staphylococcus aureus," *Infect. Immun.* 64(8):2974-2979 (1996).

Wang et al., "A Single Amino Acid Determines Lysophospholipid Specificity of the S1 P1 (EDG1) and LPA1 (EDG2) Phospholipid Growth Factor Receptors," *J. Biol. Chem.* 276(52):49213-49220 (2001).

Wang et al., "Fumonisins and other inhibitors of de novo sphingolipid biosynthesis," *Adv. Lipid Res.* 26:215-234 (1993).

Webster's Dictionary, p. 1135 (1990).

Winter et al., "Making antibodies by phage display technology," *Annu. Rev. Immunol.* 12:433-455 (1994).

Wright et al., "Genetically engineered antibodies: progress and prospects," *Crit. Rev. Immunol.* 12(3-4):125-168 (1992).

Xia et al., "Tumor necrosis factor-alpha induces adhesion molecule expression through the sphingosine kinase pathway," *Proc. Natl. Acad. Sci.* (USA) 95(24):14196-14201 (1988).

Xia et al., "High density lipoproteins (HDL) interrupt the sphingosine kinase signaling pathway. A possible mechanism for protection against atherosclerosis by HDL," *J. Biot. Chem.* 274(46):33143-33147 (1999).

Xu et al., "Involvement of de novo ceramide biosynthesis in tumor necrosis factor-alpha/cycloheximide-induced cerebral endothelial cell death," *J. Biol. Chem.* 273(26):16521-16526 (1998).

Xu et al., "Sphingosylphosphorylcholine is a ligand for ovarian cancer G-protein-coupled receptor 1," *Nat. Cell Biol.* 2(5):261-267 (2000).

Yada et al., "Purification and biochemical characterization of membrane-bound epidermal ceramidases from guinea pig skin," *J. Biol. Chem.* 270(21):12677-12684 (1995).

Yamada et al., "Nucleotide sequence and expression in *Escherichia coli* of the gene coding for sphingomyelinase of *Bacillus cereus*," *Eur. J. Biochem.* 175(2):213-220 (1988).

Yamaji et al., "Lysenin, a novel sphingomyelin-specific binding protein," *J. Biol. Chem.* 273(9):5300-5306 (1998).

Yamanaka et al., "Acid Sphingomyelinase of Human Brain: Purification to Homogeneity," *J. Neurochem.* 38(6):1753-1764 (1982).

Yamazaki et al., "Edg-6 as a Putative Sphingosine 1-Phosphate Receptor Coupling to Ca2+ Signaling Pathway," *Biochem. Biophys. Res. Commun.* 268(2):583-589 (2000).

Yatomi et al., "Sphiongosine-1-Phosphate: A Platelet-Activating Sphingolipid Released from Agonist Stimulated Human Platelets," *Blood* 86(1):193-202 (1995).

Yatomi et al., "Sphingosine 1-phosphate, a bioactive sphingolipid abundantly stored in platelets, is a normal constituent of human plasma and serum," *J. Biochem.* 121(5):969-973 (1997).

Yatomi et al., "Sphingosine 1-phosphate induces platelet activation through an extracellular action and shares a platelet surface receptor with lysophosphatidic acid," *J. Biol. Chem.* 272(8):5291-5297 (1997).

Yellon et al., "Ischaemic preconditioning limits infarct size in the rat heart," *Cardiovasc. Res.* 26(10):983-987 (1992).

Yoshimura et al., "Inhibition of Neutral Sphingomyelinase Activation and Ceramide Formation by Glutathione in Hypoxic PC12 Cell Death," *J. Neurochem.* 73(2):675-683 (1999).

Yu et al., "Picotal role for acidic sphingomyelinase in cerebral ischemia-induced ceramide and cytokine production, and neuronal apoptosis," *J. Mol. Neurosci.* 15(2):85-97 (2000).

Zager et al., "Decreased expression of mitochondrial-derived $H_2O_2$ and hydroxyl radical in cytoresistant proximal tubules," *Kidney Int.* 52(4):942-952 (1997).

Zechner et al., "MKK6 inhibits myocardial cell apoptosis via a p38 MAP kinase-dependent pathway," *J. Biol. Chem.* 273(14):8232-8239 (1998).

Zelinski et al., "Phosphatidylcholine biosynthesis in isolated hamster heart," *J. Biol. Chem.* 255(23):11423-11428 (1980).

Zhang et al., "Comparative analysis of three murine G-protein coupled receptors activated by sphingosine-1-phosphate," *Gene* 227(1):89-99 (1999).

Zhang et al., "Human Acid Ceramidase Gene: Novel Mutations in Farber Disease," *Mol. Genet. Metab.* 70(4):301-309 (2000).

Zhou et al., "Identification of the First Mammalian Sphingosine Phosphate Lyase Gene and its Functional Expression in Yeast," *Biochem. Biophys. Res. Comm.* 242(3):502-507 (1998).

Zweerink et al., "Characterization of a Novel, Potent, and Specific Inhibitor of Serine Palmitoyltransferase," *J. Biol. Chem.* 267(35):25032-25038 (1992).

\* cited by examiner

SEQUENCE LISTING

<160> NUMBER OF SEQ ID NOS: 53

<210> SEQ ID NO 1
<211> LENGTH: 26

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atggratgga gckggrtctt tmtctt                                          26

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagtggatag acagatgggg g                                               21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagtggatag accgatgggg c                                               21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagtggatag actgatgggg g                                               21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caagggatag acagatgggg c                                               21

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtctctgatt ctagggca                                                   18

<210> SEQ ID NO 7
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 7
actggatggt gggaagatgg                                                    20

<210> SEQ ID NO 8
<211> LENGTH: 120
<212> TYPE: PRT
<213> ORGANISM: Mus sp.

<400> SEQUENCE: 8
```

Gln Ala His Leu Gln Gln Ser Asp Ala Glu Leu Val Lys Pro Gly Ala
1               5                   10                  15

Ser Val Lys Ile Ser Cys Lys Val Ser Gly Phe Ile Phe Ile Asp His
                20                  25                  30

Thr Ile His Trp Met Lys Gln Arg Pro Glu Gln Gly Leu Glu Trp Ile
            35                  40                  45

Gly Cys Ile Ser Pro Arg His Asp Ile Thr Lys Tyr Asn Glu Met Phe
        50                  55                  60

Arg Gly Lys Ala Thr Leu Thr Ala Asp Lys Ser Ser Thr Thr Ala Tyr
65                  70                  75                  80

Ile Gln Val Asn Ser Leu Thr Phe Glu Asp Ser Ala Val Tyr Phe Cys
                85                  90                  95

Ala Arg Gly Gly Phe Tyr Gly Ser Thr Ile Trp Phe Asp Phe Trp Gly
            100                 105                 110

Gln Gly Thr Thr Leu Thr Val Ser
            115                 120

```
<210> SEQ ID NO 9
<211> LENGTH: 107
<212> TYPE: PRT
<213> ORGANISM: Mus sp.

<400> SEQUENCE: 9
```

Glu Thr Thr Val Thr Gln Ser Pro Ala Ser Leu Ser Met Ala Ile Gly
1               5                   10                  15

Glu Lys Val Thr Ile Arg Cys Ile Thr Thr Thr Asp Ile Asp Asp Asp
                20                  25                  30

Met Asn Trp Phe Gln Gln Lys Pro Gly Glu Pro Pro Asn Leu Leu Ile
            35                  40                  45

Ser Glu Gly Asn Ile Leu Arg Pro Gly Val Pro Ser Arg Phe Ser Ser
        50                  55                  60

Ser Gly Tyr Gly Thr Asp Phe Leu Phe Thr Ile Glu Asn Met Leu Ser
65                  70                  75                  80

Glu Asp Val Ala Asp Tyr Tyr Cys Leu Gln Ser Asp Asn Leu Pro Phe
                85                  90                  95

Thr Phe Gly Ser Gly Thr Lys Leu Glu Ile Lys
            100                 105

```
<210> SEQ ID NO 10
<211> LENGTH: 11
<212> TYPE: PRT
<213> ORGANISM: Mus sp.

<400> SEQUENCE: 10
```

Ile Thr Thr Thr Asp Ile Asp Asp Asp Met Asn
1               5                   10

```
<210> SEQ ID NO 11
<211> LENGTH: 7
<212> TYPE: PRT
<213> ORGANISM: Mus sp.

<400> SEQUENCE: 11

Glu Gly Asn Ile Leu Arg Pro
1               5

<210> SEQ ID NO 12
<211> LENGTH: 9
<212> TYPE: PRT
<213> ORGANISM: Mus sp.

<400> SEQUENCE: 12

Leu Gln Ser Asp Asn Leu Pro Phe Thr
1               5

<210> SEQ ID NO 13
<211> LENGTH: 5
<212> TYPE: PRT
<213> ORGANISM: Mus sp.

<400> SEQUENCE: 13

Asp His Thr Ile His
1               5

<210> SEQ ID NO 14
<211> LENGTH: 17
<212> TYPE: PRT
<213> ORGANISM: Mus sp.

<400> SEQUENCE: 14

Cys Ile Ser Pro Arg His Asp Ile Thr Lys Tyr Asn Glu Met Phe Arg
1               5                   10                  15

Gly

<210> SEQ ID NO 15
<211> LENGTH: 12
<212> TYPE: PRT
<213> ORGANISM: Mus sp.

<400> SEQUENCE: 15

Gly Gly Phe Tyr Gly Ser Thr Ile Trp Phe Asp Phe
1               5                   10

<210> SEQ ID NO 16
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gly Ser Thr Ala Ile Leu Ala Leu Leu Ala Val Leu Gln Gly
1               5                   10                  15

Val Cys Ser Glu Val Gln Leu Val Gln Ser Gly Ala Glu Val Lys Lys
                20                  25                  30

Pro Gly Glu Ser Leu Lys Ile Ser Cys Gln Ser Phe Gly Tyr Ile Phe
            35                  40                  45

Ile Asp His Thr Ile His Trp Val Arg Gln Met Pro Gly Gln Gly Leu
        50                  55                  60
```

```
Glu Trp Met Gly Cys Ile Ser Pro Arg His Asp Ile Thr Lys Tyr Asn
 65                  70                  75                  80

Glu Met Phe Arg Gly Gln Val Thr Ile Ser Ala Asp Lys Ser Ser Ser
                 85                  90                  95

Thr Ala Tyr Leu Gln Trp Ser Ser Leu Lys Ala Ser Thr Ala Met
            100                 105                 110

Tyr Phe Cys Ala Arg Gly Gly Phe Tyr Gly Ser Thr Ile Trp Phe Asp
            115                 120                 125

Phe Trp Gly Gln Gly Thr Met Val Thr Val Ser Ser Ala Ser Thr Lys
        130                 135                 140

Gly Pro Ser
145

<210> SEQ ID NO 17
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Asp Met Arg Val Pro Ala Gln Leu Leu Gly Leu Leu Leu Leu Trp
 1               5                  10                  15

Leu Pro Gly Ala Arg Cys Glu Thr Thr Leu Thr Gln Ser Pro Ser Phe
                 20                  25                  30

Leu Ser Ala Ser Val Gly Asp Arg Val Thr Ile Thr Cys Ile Thr Thr
            35                  40                  45

Thr Asp Ile Asp Asp Asp Met Asn Trp Tyr Gln Gln Glu Pro Gly Lys
 50                  55                  60

Ala Pro Lys Leu Leu Ile Tyr Glu Gly Asn Ile Leu Arg Pro Gly Val
 65                  70                  75                  80

Pro Ser Arg Phe Ser Gly Ser Gly Ser Gly Thr Asp Phe Thr Leu Thr
                 85                  90                  95

Ile Ser Lys Leu Gln Pro Glu Asp Phe Ala Thr Tyr Tyr Cys Leu Gln
            100                 105                 110

Ser Asp Asn Leu Pro Phe Thr Phe Gly Gln Gly Thr Lys Leu Glu Ile
            115                 120                 125

Lys Arg Glu Trp Ile Pro
        130

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ataaccacca ctgatattga tgatgatatg aac                               33

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
```

-continued gaaggcaata ttcttcgtcc t                                              21

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttgcagagtg ataacttacc attcacg                                        27

<210> SEQ ID NO 21
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gaccatactt cac                                                       13

<210> SEQ ID NO 22
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tgtatttctc ccagacatga tattactaaa tacaatgaga tgttcagggg c              51

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23 gggggggttct acggtagtac tatctggttt gactttt                             36

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gctatttctc ccagacatga tattactaaa tacaatgaga tgttcagggg c              51

<210> SEQ ID NO 25
<211> LENGTH: 455
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
cgccaagctt gccgccacca tggggtcaac cgccatcctc gccctcctcc tggctgttct     60

```
ccaaggagtc tgttccgagg tgcagctggt gcagtctgga gcagaggtga aaaagcccgg    120
ggagtctctg aagatctcct gtcagagttt tggatacatc tttatcgacc atacttcact    180
gggtgcgcca gatgcccggg caaggcctgg agtggatgtg tatttctccc agacatgata    240
ttactaaata caatgagatg ttcaggggcc aggtcaccat ctcagccgac aagtccagca    300
gcaccgccta cttgcagtgg agcagcctga aggcctcgga caccgccatg tatttctgtg    360
cgagaggggg gttctacggt agtactatct ggtttgactt ttggggccaa gggacaatgg    420
tcaccgtctc ttcagcctcc accaagggcc catcg    455
```

<210> SEQ ID NO 26
<211> LENGTH: 452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
cgccaagctt gccgccacca tggggtcaac cgccatcctc gccctcctcc tggctgttct    60
ccaaggagtc tgttccgagg tgcagctggt gcagtctgga gcagaggtga aaaagcccgg    120
ggagtctctg aagatctcct gtcagagttt tggatacatc gaccatactt cactggatgc    180
gccagatgcc cgggcaaggc ctggagtgga tgggggctat ttctcccaga catgatatta    240
ctaaatacaa tgagatgttc aggggccagg tcaccatctc agccgacaag tccagcagca    300
ccgcctactt gcagtggagc agcctgaagg cctcggacac cgccatgtat ttctgtgcga    360 gagggggggtt ctacggtagt actatctggt ttgacttttg gggccaaggg acaatggtca    420
ccgtctcttc agcctccacc aagggcccat cg    452
```

<210> SEQ ID NO 27
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Met Gly Ser Thr Ala Ile Leu Ala Leu Leu Ala Val Leu Gln Gly
1               5                   10                  15

Val Cys Ser Glu Val Gln Leu Val Gln Ser Gly Ala Glu Val Lys Lys
            20                  25                  30

Pro Gly Glu Ser Leu Lys Ile Ser Cys Gln Ser Phe Gly Tyr Ile Phe
        35                  40                  45

Ile Asp His Thr Ile His Trp Met Arg Gln Met Pro Gly Gln Gly Leu
    50                  55                  60

Glu Trp Met Gly Ala Ile Ser Pro Arg His Asp Ile Thr Lys Tyr Asn
65                  70                  75                  80

Glu Met Phe Arg Gly Gln Val Thr Ile Ser Ala Asp Lys Ser Ser Ser
                85                  90                  95

Thr Ala Tyr Leu Gln Trp Ser Ser Leu Lys Ala Ser Asp Thr Ala Met
            100                 105                 110

Tyr Phe Cys Ala Arg Gly Gly Phe Tyr Gly Ser Thr Ile Trp Phe Asp
        115                 120                 125

Phe Trp Gly Gln Gly Thr Met Val Thr Val Ser Ser Ala Ser Thr Lys
    130                 135                 140

Gly Pro Ser
145
```

<210> SEQ ID NO 28
<211> LENGTH: 419
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
cgccaagctt gccgccacca tggacatgag ggtccccgct cagctcctgg ggctcctgct    60
gctctggctc ccaggtgcca gatgtgaaac gacactcacg cagtctccat ccttcctgtc   120
tgcatctgta ggagacagag tcaccatcac ataaccacca ctgatattga tgatgatatg   180
aactggtatc agcaggaacc agggaaagcc cctaagctcc tgatctatga aggcaatatt   240
cttcgtcctg ggtcccatc aaggttcagc ggcagtggat ctggcacaga tttcactctc   300
accatcagca aattgcagcc tgaagatttt gcaacttatt actgtttgca gagtgataac   360
ttaccattca cgttcggcca agggaccaag ctggagatca aacgtgagtg atcccgcg    419
```

<210> SEQ ID NO 29
<211> LENGTH: 407
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
cgccaagctt gccgccacca tggacatgag ggtccccgct cagctcctgg ggctcctgct    60
gctctggctc ccaggggcca gatgtgaaac gacagtgacg cagtctccat ccttcctgtc   120
tgcatctgta ggagacagag tcaccatcac ttgcataacc accactgata ttgatgatga   180
tatgaactgg ttccagcagg aaccagggaa agccccctaag ctcctgatct ccgaaggcaa   240
tattcttcgt cctggggtcc catcaagatt cagcagcagt ggatatggca cagatttcac   300
tctcaccatc agcaaattgc agcctgaaga ttttgcaact tattactgtt tgcagagtga   360
taacttacca ttcactttcg gccaagggac caagctggag atcaaac               407
```

<210> SEQ ID NO 30
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Met Arg Val Pro Ala Gln Leu Leu Gly Leu Leu Leu Trp Leu Pro
  1               5                  10                  15

Gly Ala Arg Cys Glu Thr Thr Val Thr Gln Ser Pro Ser Phe Leu Ser
                 20                  25                  30

Ala Ser Val Gly Asp Arg Val Thr Ile Thr Cys Ile Thr Thr Asp
             35                  40                  45

Ile Asp Asp Asp Met Asn Trp Phe Gln Glu Pro Gly Lys Ala Pro Lys
         50                  55                  60

Leu Leu Ile Ser Glu Gly Asn Ile Leu Arg Pro Gly Val Pro Ser Arg
 65                  70                  75                  80

Phe Ser Ser Ser Gly Tyr Gly Thr Asp Phe Thr Leu Thr Ile Ser Lys
                 85                  90                  95
```

```
Leu Gln Pro Glu Asp Phe Ala Thr Tyr Tyr Cys Leu Gln Ser Asp Asn
                100                 105                 110

Leu Pro Phe Thr Phe Gly Gln Gly Thr Lys Leu Glu Ile Lys
            115                 120                 125

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ile Ser Pro Arg His Asp Ile Thr Lys Tyr Asn Glu Met Phe Arg
1               5                   10                  15

Gly

<210> SEQ ID NO 32
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
            20                  25                  30

Pro Gly Glu Ser Leu Lys Ile Ser Cys Gln Ser Phe Gly Tyr Ile Phe
        35                  40                  45

Ile Asp His Thr Ile His Trp Met Arg Gln Met Pro Gly Gln Gly Leu
    50                  55                  60

Glu Trp Met Gly Ala Ile Ser Pro Arg His Asp Ile Thr Lys Tyr Asn
65                  70                  75                  80

Glu Met Phe Arg Gly Gln Val Thr Ile Ser Ala Asp Lys Ser Ser Ser
                85                  90                  95

Thr Ala Tyr Leu Gln Trp Ser Ser Leu Lys Ala Ser Asp Thr Ala Met
            100                 105                 110

Tyr Phe Cys Ala Arg Gly Gly Phe Tyr Gly Ser Thr Ile Trp Phe Asp
        115                 120                 125

Phe Trp Gly Gln Gly Thr Met Val Thr Val Ser Ser
    130                 135                 140

<210> SEQ ID NO 33
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Ser Val Pro Thr Gln Val Leu Gly Leu Leu Leu Leu Trp Leu Thr
1               5                   10                  15

Asp Ala Arg Cys Glu Thr Thr Val Thr Gln Ser Pro Ser Phe Leu Ser
            20                  25                  30

Ala Ser Val Gly Asp Arg Val Thr Ile Thr Cys Ile Thr Thr Thr Asp
        35                  40                  45
```

```
Ile Asp Asp Asp Met Asn Trp Phe Gln Gln Glu Pro Gly Lys Ala Pro
     50                  55                  60
Lys Leu Leu Ile Ser Glu Gly Asn Ile Leu Arg Pro Gly Val Pro Ser
 65                  70                  75                  80
Arg Phe Ser Ser Ser Gly Tyr Gly Thr Asp Phe Thr Leu Thr Ile Ser
                 85                  90                  95
Lys Leu Gln Pro Glu Asp Phe Ala Thr Tyr Tyr Cys Leu Gln Ser Asp
            100                 105                 110
Asn Leu Pro Phe Thr Phe Gly Gln Gly Thr Lys Leu Glu Ile Lys
            115                 120                 125

<210> SEQ ID NO 34
<211> LENGTH: 2034
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
```

| | | | | | |
|---|---|---|---|---|---|
| aagcttgccg | ccaccatgga | atggagctgg | gtgttcctgt | tctttctgtc | cgtgaccaca | 60 |
| ggcgtgcatt | ctgaggtgca | gctggtgcag | tctggagcag | aggtgaaaaa | gcccggggag | 120 |
| tctctgaaga | tctcctgtca | gagttttgga | tacatcttta | tcgaccatac | tattcactgg | 180 |
| atgcgccaga | tgcccgggca | aggcctggag | tggatggggg | ctatttctcc | agacatgat | 240 |
| attactaaat | acaatgagat | gttcagggc | caggtcacca | tctcagccga | caagtccagc | 300 |
| agcaccgcct | acttgcagtg | gagcagcctg | aaggcctcgg | acaccgccat | gtatttctgt | 360 |
| gcgagagggg | ggttctacgg | tagtactatc | tggtttgact | tttggggcca | agggacaatg | 420 |
| gtcaccgtct | cttcagcctc | caccaagggc | ccatcggtct | tccccctggc | accctcctcc | 480 |
| aagagcacct | ctgggggcac | agcggccctg | ggctgcctgg | tcaaggacta | cttccccgaa | 540 |
| ccggtgacgg | tgtcgtggaa | ctcaggcgcc | ctgaccagcg | gcgtgcacac | cttcccggct | 600 |
| gtcctacagt | cctcaggact | ctactccctc | agcagcgtgg | tgaccgtgcc | ctccagcagc | 660 |
| ttgggcaccc | agacctacat | ctgcaacgtg | aatcacaagc | ccagcaacac | caaggtggac | 720 |
| aagagagttg | gtgagaggcc | agcacaggga | gggagggtgt | ctgctggaag | ccaggctcag | 780 |
| cgctcctgcc | tggacgcatc | ccggctatgc | agtcccagtc | cagggcagca | aggcaggccc | 840 |
| cgtctgcctc | ttcacccgga | ggcctctgcc | cgccccactc | atgctcaggg | agagggtctt | 900 |
| ctggcttttt | ccccaggctc | tgggcaggca | caggctaggt | gcccctaacc | caggccctgc | 960 |
| acacaaaggg | gcaggtgctg | ggctcagacc | tgccaagagc | catatccggg | aggaccctgc | 1020 |
| ccctgaccta | agcccacccc | aaaggccaaa | ctctccactc | cctcagctcg | acaccttct | 1080 |
| ctcctcccag | attccagtaa | ctcccaatct | tctctctgca | gagcccaaat | cttgtgacaa | 1140 |
| aactcacaca | tgcccaccgt | gcccaggtaa | gccagcccag | gcctcgccct | ccagctcaag | 1200 |
| gcgggacagg | tgccctagag | tagcctgcat | ccagggacag | gccccagccg | ggtgctgaca | 1260 |
| cgtccacctc | catctcttcc | tcagcacctg | aactcctggg | gggaccgtca | gtcttcctct | 1320 |
| tccccccaaa | acccaaggac | accctcatga | tctcccggac | ccctgaggtc | acatgcgtgg | 1380 |
| tggtggacgt | gagccacgaa | gaccctgagg | tcaagttcaa | ctggtacgtg | gacggcgtgg | 1440 |
| aggtgcataa | tgccaagaca | aagccgcggg | aggagcagta | caacagcacg | taccgtgtgg | 1500 |
| tcagcgtcct | caccgtcctg | caccaggact | ggctgaatgg | caaggagtac | aagtgcaagg | 1560 |
| tctccaacaa | agccctccca | gcccccatcg | agaaaaccat | ctccaaagcc | aaaggtggga | 1620 |

```
cccgtggggt gcgagggcca catggacaga ggccggctcg gcccaccctc tgccctgaga    1680
gtgaccgctg taccaacctc tgtccctaca gggcagcccc gagaaccaca ggtgtacacc    1740
ctgcccccat cccggagga gatgaccaag aaccaggtca gcctgacctg cctggtcaaa     1800
ggcttctatc ccagcgacat cgccgtggag tgggagagca atgggcagcc ggagaacaac    1860
tacaagacca cgcctcccgt gctggactcc gacggctcct tcttcctcta tagcaagctc    1920
accgtggaca agagcaggtg gcagcagggg aacgtcttct catgctccgt gatgcatgag    1980
gctctgcaca accactacac gcagaagagc ctctccctgt ctccgggtaa atag          2034
```

<210> SEQ ID NO 35
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
            20                  25                  30

Pro Gly Glu Ser Leu Lys Ile Ser Cys Gln Ser Phe Gly Tyr Ile Phe
        35                  40                  45

Ile Asp His Thr Ile His Trp Met Arg Gln Met Pro Gly Gln Gly Leu
    50                  55                  60

Glu Trp Met Gly Ala Ile Ser Pro Arg His Asp Ile Thr Lys Tyr Asn
65                  70                  75                  80

Glu Met Phe Arg Gly Gln Val Thr Ile Ser Ala Asp Lys Ser Ser Ser
                85                  90                  95

Thr Ala Tyr Leu Gln Trp Ser Ser Leu Lys Ala Ser Asp Thr Ala Met
            100                 105                 110

Tyr Phe Cys Ala Arg Gly Gly Phe Tyr Gly Ser Thr Ile Trp Phe Asp
        115                 120                 125

Phe Trp Gly Gln Gly Thr Met Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285
```

```
Gly Val Glu Val His Asn Ala Lys Thr Lys Pro Arg Glu Glu Gln Tyr
        290                 295                 300

Asn Ser Thr Tyr Arg Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 36
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
aagcttgccg ccaccatgtc tgtgcctacc caggtgctgg gactgctgct gctgtggctg      60
acagacgccc gctgtgaaac gacagtgacg cagtctccat ccttcctgtc tgcatctgta     120
ggagacagag tcaccatcac ttgcataacc accactgata ttgatgatga tatgaactgg     180
ttccagcagg aaccagggaa agcccctaag ctcctgatct ccgaaggcaa tattcttcgt     240
cctggggtcc catcaagatt cagcagcagt ggatatggca cagatttcac tctcaccatc     300
agcaaattgc agcctgaaga ttttgcaact tattactgtt tgcagagtga taacttacca     360
ttcactttcg gccagggac caagctggag atcaaacgta cggtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct caacagggg agagtgttag     720

<210> SEQ ID NO 37
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Ser Val Pro Thr Gln Val Leu Gly Leu Leu Leu Leu Trp Leu Thr
```

```
                1               5                   10                  15
Asp Ala Arg Cys Glu Thr Thr Val Thr Gln Ser Pro Ser Phe Leu Ser
                20                  25                  30

Ala Ser Val Gly Asp Arg Val Thr Ile Thr Cys Ile Thr Thr Thr Asp
                35                  40                  45

Ile Asp Asp Asp Met Asn Trp Phe Gln Gln Glu Pro Gly Lys Ala Pro
 50                  55                  60

Lys Leu Leu Ile Ser Glu Gly Asn Ile Leu Arg Pro Gly Val Pro Ser
 65                  70                  75                  80

Arg Phe Ser Ser Gly Tyr Gly Thr Asp Phe Thr Leu Thr Ile Ser
                85                  90                  95

Lys Leu Gln Pro Glu Asp Phe Ala Thr Tyr Tyr Cys Leu Gln Ser Asp
                100                 105                 110

Asn Leu Pro Phe Thr Phe Gly Gln Gly Thr Lys Leu Glu Ile Lys Arg
                115                 120                 125

Thr Val Ala Ala Pro Ser Val Phe Ile Phe Pro Pro Ser Asp Glu Gln
                130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
                210                 215                 220

Val Thr Lys Ser Phe Asn Arg Gly Glu Cys
225                 230

<210> SEQ ID NO 38
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Gln Ser Gly Ala Glu Val Lys Lys Pro Gly Glu
1               5                   10                  15

Ser Leu Lys Ile Ser Cys Gln Ser Phe Gly Tyr Ile Phe Ile Asp His
                20                  25                  30

Thr Ile His Trp Met Arg Gln Met Pro Gly Gln Gly Leu Glu Trp Met
                35                  40                  45

Gly Ala Ile Ser Pro Arg His Asp Ile Thr Lys Tyr Asn Glu Met Phe
 50                  55                  60

Arg Gly Gln Val Thr Ile Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gly Gly Phe Tyr Gly Ser Thr Ile Trp Phe Asp Phe Trp Gly
                100                 105                 110

Gln Gly Thr Met Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
```

```
                130                 135                 140
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 39
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Gly Ser Thr Ala Ile Leu Ala Leu Leu Ala Val Leu Gln Gly
1               5                   10                  15

Val Cys Ser Glu Val Gln Leu Val Gln Ser Gly Ala Glu Val Lys Lys
                20                  25                  30

Pro Gly Glu Ser Leu Lys Ile Ser Cys Gln Ser Phe Gly Tyr Ile Phe
```

```
                35                  40                  45
Ile Asp His Thr Ile His Trp Met Arg Gln Met Pro Gly Gln Gly Leu
 50                  55                  60

Glu Trp Met Gly Cys Ile Ser Pro Arg His Asp Ile Thr Lys Tyr Asn
 65                  70                  75                  80

Glu Met Phe Arg Gly Gln Val Thr Ile Ser Ala Asp Lys Ser Ser Ser
                 85                  90                  95

Thr Ala Tyr Leu Gln Trp Ser Ser Leu Lys Ala Ser Asp Thr Ala Met
                100                 105                 110

Tyr Phe Cys Ala Arg Gly Gly Phe Tyr Gly Ser Thr Ile Trp Phe Asp
                115                 120                 125

Phe Trp Gly Gln Gly Thr Met Val Thr Val Ser Ser Ala Ser Thr Lys
130                 135                 140

Gly Pro Ser
145

<210> SEQ ID NO 40
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Gly Ser Thr Ala Ile Leu Ala Leu Leu Ala Val Leu Gln Gly
 1               5                  10                  15

Val Cys Ser Glu Val Gln Leu Val Gln Ser Gly Ala Glu Val Lys Lys
                 20                  25                  30

Pro Gly Glu Ser Leu Lys Ile Ser Cys Gln Ser Phe Gly Phe Ile Phe
                 35                  40                  45

Ile Asp His Thr Ile His Trp Met Arg Gln Met Pro Gly Gln Gly Leu
 50                  55                  60

Glu Trp Ile Gly Cys Ile Ser Pro Arg His Asp Ile Thr Lys Tyr Asn
 65                  70                  75                  80

Glu Met Phe Arg Gly Gln Val Thr Ile Ser Ala Asp Lys Ser Ser Ser
                 85                  90                  95

Thr Ala Tyr Leu Gln Trp Ser Ser Leu Lys Ala Ser Asp Thr Ala Met
                100                 105                 110

Tyr Phe Cys Ala Arg Gly Gly Phe Tyr Gly Ser Thr Ile Trp Phe Asp
                115                 120                 125

Phe Trp Gly Gln Gly Thr Met Val Thr Val Ser Ser Ala Ser Thr Lys
130                 135                 140

Gly Pro Ser
145

<210> SEQ ID NO 41
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Gly Ser Thr Ala Ile Leu Ala Leu Leu Ala Val Leu Gln Gly
 1               5                  10                  15

Val Cys Ser Glu Val Gln Leu Val Gln Ser Gly Ala Glu Val Lys Lys
                 20                  25                  30
```

```
Pro Gly Glu Ser Leu Lys Ile Ser Cys Gln Ser Phe Gly Tyr Ile Phe
            35                  40                  45

Ile Asp His Thr Ile His Trp Val Arg Gln Met Pro Gly Gln Gly Leu
    50                  55                  60

Glu Trp Ile Gly Cys Ile Ser Pro Arg His Asp Ile Thr Lys Tyr Asn
65                  70                  75                  80

Glu Met Phe Arg Gly Gln Val Thr Ile Ser Ala Asp Lys Ser Ser Ser
                85                  90                  95

Thr Ala Tyr Leu Gln Trp Ser Ser Leu Lys Ala Ser Asp Thr Ala Met
            100                 105                 110

Tyr Phe Cys Ala Arg Gly Gly Phe Tyr Gly Ser Thr Ile Trp Phe Asp
            115                 120                 125

Phe Trp Gly Gln Gly Thr Met Val Thr Val Ser Ser Ala Ser Thr Lys
        130                 135                 140

Gly Pro Ser
145

<210> SEQ ID NO 42
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Gly Ser Thr Ala Ile Leu Ala Leu Leu Leu Ala Val Leu Gln Gly
1               5                   10                  15

Val Cys Ser Glu Val Gln Leu Val Gln Ser Gly Ala Glu Val Lys Lys
            20                  25                  30

Pro Gly Glu Ser Leu Lys Ile Ser Cys Gln Ser Phe Gly Phe Ile Phe
            35                  40                  45

Ile Asp His Thr Ile His Trp Val Arg Gln Met Pro Gly Gln Gly Leu
    50                  55                  60

Glu Trp Met Gly Cys Ile Ser Pro Arg His Asp Ile Thr Lys Tyr Asn
65                  70                  75                  80

Glu Met Phe Arg Gly Gln Val Thr Ile Ser Ala Asp Lys Ser Ser Ser
                85                  90                  95

Thr Ala Tyr Leu Gln Trp Ser Ser Leu Lys Ala Ser Asp Thr Ala Met
            100                 105                 110

Tyr Phe Cys Ala Arg Gly Gly Phe Tyr Gly Ser Thr Ile Trp Phe Asp
            115                 120                 125

Phe Trp Gly Gln Gly Thr Met Val Thr Val Ser Ser Ala Ser Thr Lys
        130                 135                 140

Gly Pro Ser
145

<210> SEQ ID NO 43
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gly Ser Thr Ala Ile Leu Ala Leu Leu Leu Ala Val Leu Gln Gly
1               5                   10                  15
```

```
Val Cys Ser Glu Val Gln Leu Val Gln Ser Gly Ala Glu Val Lys Lys
            20                  25                  30

Pro Gly Glu Ser Leu Lys Ile Ser Cys Gln Ser Phe Gly Phe Ile Phe
            35                  40                  45

Ile Asp His Thr Ile His Trp Met Arg Gln Met Pro Gly Gln Gly Leu
 50                  55                  60

Glu Trp Ile Gly Cys Ile Ser Pro Arg His Asp Ile Thr Lys Tyr Asn
 65                  70                  75                  80

Glu Met Phe Arg Gly Gln Ala Thr Leu Ser Ala Asp Lys Ser Ser Ser
                85                  90                  95

Thr Ala Tyr Leu Gln Trp Ser Ser Leu Lys Ala Ser Asp Thr Ala Met
            100                 105                 110

Tyr Phe Cys Ala Arg Gly Gly Phe Tyr Gly Ser Thr Ile Trp Phe Asp
            115                 120                 125

Phe Trp Gly Gln Gly Thr Met Val Thr Val Ser Ser Ala Ser Thr Lys
130                 135                 140

Gly Pro Ser
145

<210> SEQ ID NO 44
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Gly Ser Thr Ala Ile Leu Ala Leu Leu Leu Ala Val Leu Gln Gly
1               5                   10                  15

Val Cys Ser Glu Ala Gln Leu Val Gln Ser Gly Ala Glu Val Lys Lys
            20                  25                  30

Pro Gly Glu Ser Leu Lys Ile Ser Cys Gln Ser Phe Gly Phe Ile Phe
            35                  40                  45

Ile Asp His Thr Ile His Trp Met Arg Gln Met Pro Gly Gln Gly Leu
 50                  55                  60

Glu Trp Ile Gly Cys Ile Ser Pro Arg His Asp Ile Thr Lys Tyr Asn
 65                  70                  75                  80

Glu Met Phe Arg Gly Gln Ala Thr Leu Ser Ala Asp Lys Ser Ser Ser
                85                  90                  95

Thr Ala Tyr Leu Gln Trp Ser Ser Leu Lys Ala Ser Asp Thr Ala Met
            100                 105                 110

Tyr Phe Cys Ala Arg Gly Gly Phe Tyr Gly Ser Thr Ile Trp Phe Asp
            115                 120                 125

Phe Trp Gly Gln Gly Thr Met Val Thr Val Ser Ser Ala Ser Thr Lys
130                 135                 140

Gly Pro Ser
145

<210> SEQ ID NO 45
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Gly Ser Thr Ala Ile Leu Ala Leu Leu Leu Ala Val Leu Gln Gly
```

```
                   1               5                  10                  15

Val Cys Ser Glu Val Gln Leu Val Gln Ser Gly Ala Glu Val Lys Lys
                20                  25                  30

Pro Gly Glu Ser Leu Lys Ile Ser Cys Gln Ser Phe Gly Tyr Ile Phe
                35                  40                  45

Ile Asp His Thr Ile His Trp Met Arg Gln Met Pro Gly Gln Gly Leu
    50                  55                  60

Glu Trp Met Gly Ala Ile Ser Pro Arg His Asp Ile Thr Lys Tyr Asn
65                  70                  75                  80

Glu Met Phe Arg Gly Gln Val Thr Ile Ser Ala Asp Lys Ser Ser
                85                  90                  95

Thr Ala Tyr Leu Gln Trp Ser Ser Leu Lys Ala Ser Asp Thr Ala Met
                100                 105                 110

Tyr Phe Cys Ala Arg Gly Gly Phe Tyr Gly Ser Thr Ile Trp Phe Asp
                115                 120                 125

Phe Trp Gly Gln Gly Thr Met Val Thr Val Ser Ser Ala Ser Thr Lys
    130                 135                 140

Gly Pro Ser
145

<210> SEQ ID NO 46
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Asp Met Arg Val Pro Ala Gln Leu Leu Gly Leu Leu Leu Leu Trp
1               5                   10                  15

Leu Pro Gly Ala Arg Cys Glu Thr Thr Leu Thr Gln Ser Pro Ser Phe
                20                  25                  30

Leu Ser Ala Ser Val Gly Asp Arg Val Thr Ile Thr Cys Ile Thr Thr
                35                  40                  45

Thr Asp Ile Asp Asp Asp Met Asn Trp Tyr Gln Gln Glu Pro Gly Lys
    50                  55                  60

Ala Pro Lys Leu Leu Ile Ser Glu Gly Asn Ile Leu Arg Pro Gly Val
65                  70                  75                  80

Pro Ser Arg Phe Ser Gly Ser Gly Ser Gly Thr Asp Phe Thr Leu Thr
                85                  90                  95

Ile Ser Lys Leu Gln Pro Glu Asp Phe Ala Thr Tyr Tyr Cys Leu Gln
                100                 105                 110

Ser Asp Asn Leu Pro Phe Thr Phe Gly Gln Gly Thr Lys Leu Glu Ile
                115                 120                 125

Lys Arg Glu Trp Ile Pro
    130

<210> SEQ ID NO 47
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Asp Met Arg Val Pro Ala Gln Leu Leu Gly Leu Leu Leu Leu Trp
1               5                   10                  15
```

Leu Pro Gly Ala Arg Cys Glu Thr Thr Leu Thr Gln Ser Pro Ser Phe
            20                  25                  30

Leu Ser Ala Ser Val Gly Asp Arg Val Thr Ile Thr Cys Ile Thr Thr
        35                  40                  45

Thr Asp Ile Asp Asp Asp Met Asn Trp Phe Gln Gln Glu Pro Gly Lys
    50                  55                  60

Ala Pro Lys Leu Leu Ile Tyr Glu Gly Asn Ile Leu Arg Pro Gly Val
65                  70                  75                  80

Pro Ser Arg Phe Ser Gly Ser Gly Ser Gly Thr Asp Phe Thr Leu Thr
                85                  90                  95

Ile Ser Lys Leu Gln Pro Glu Asp Phe Ala Thr Tyr Tyr Cys Leu Gln
            100                 105                 110

Ser Asp Asn Leu Pro Phe Thr Phe Gly Gln Gly Thr Lys Leu Glu Ile
        115                 120                 125

Lys Arg Glu Trp Ile Pro
    130

<210> SEQ ID NO 48
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Asp Met Arg Val Pro Ala Gln Leu Leu Gly Leu Leu Leu Leu Trp
1               5                   10                  15

Leu Pro Gly Ala Arg Cys Glu Thr Thr Val Thr Gln Ser Pro Ser Phe
            20                  25                  30

Leu Ser Ala Ser Val Gly Asp Arg Val Thr Ile Thr Cys Ile Thr Thr
        35                  40                  45

Thr Asp Ile Asp Asp Asp Met Asn Trp Tyr Gln Gln Glu Pro Gly Lys
    50                  55                  60

Ala Pro Lys Leu Leu Ile Ser Glu Gly Asn Ile Leu Arg Pro Gly Val
65                  70                  75                  80

Pro Ser Arg Phe Ser Gly Ser Gly Ser Gly Thr Asp Phe Thr Leu Thr
                85                  90                  95

Ile Ser Lys Leu Gln Pro Glu Asp Phe Ala Thr Tyr Tyr Cys Leu Gln
            100                 105                 110

Ser Asp Asn Leu Pro Phe Thr Phe Gly Gln Gly Thr Lys Leu Glu Ile
        115                 120                 125

Lys Arg Glu Trp Ile
    130

<210> SEQ ID NO 49
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Asp Met Arg Val Pro Ala Gln Leu Leu Gly Leu Leu Leu Leu Trp
1               5                   10                  15

Leu Pro Gly Ala Arg Cys Glu Thr Thr Leu Thr Gln Ser Pro Ser Phe
            20                  25                  30

-continued

Leu Ser Ala Ser Val Gly Asp Arg Val Thr Ile Thr Cys Ile Thr Thr
        35                  40                  45

Thr Asp Ile Asp Asp Asp Met Asn Trp Phe Gln Gln Glu Pro Gly Lys
    50                  55                  60

Ala Pro Lys Leu Leu Ile Ser Glu Gly Asn Ile Leu Arg Pro Gly Val
65                  70                  75                  80

Pro Ser Arg Phe Ser Gly Ser Gly Ser Gly Thr Asp Phe Thr Leu Thr
                85                  90                  95

Ile Ser Lys Leu Gln Pro Glu Asp Phe Ala Thr Tyr Tyr Cys Leu Gln
                100                 105                 110

Ser Asp Asn Leu Pro Phe Thr Phe Gly Gln Gly Thr Lys Leu Glu Ile
            115                 120                 125

Lys Arg Glu Trp Ile Pro
        130

<210> SEQ ID NO 50
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Asp Met Arg Val Pro Ala Gln Leu Leu Gly Leu Leu Leu Leu Trp
1               5                   10                  15

Leu Pro Gly Ala Arg Cys Glu Thr Thr Val Thr Gln Ser Pro Ser Phe
            20                  25                  30

Leu Ser Ala Ser Val Gly Asp Arg Val Thr Ile Thr Cys Ile Thr Thr
        35                  40                  45

Thr Asp Ile Asp Asp Asp Met Asn Trp Phe Gln Gln Glu Pro Gly Lys
    50                  55                  60

Ala Pro Lys Leu Leu Ile Ser Glu Gly Asn Ile Leu Arg Pro Gly Val
65                  70                  75                  80

Pro Ser Arg Phe Ser Gly Ser Gly Ser Gly Thr Asp Phe Thr Leu Thr
                85                  90                  95

Ile Ser Lys Leu Gln Pro Glu Asp Phe Ala Thr Tyr Tyr Cys Leu Gln
                100                 105                 110

Ser Asp Asn Leu Pro Phe Thr Phe Gly Gln Gly Thr Lys Leu Glu Ile
            115                 120                 125

Lys Arg Glu Trp
        130

<210> SEQ ID NO 51
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Asp Met Arg Val Pro Ala Gln Leu Leu Gly Leu Leu Leu Leu Trp
1               5                   10                  15

Leu Pro Gly Ala Arg Cys Glu Thr Thr Val Thr Gln Ser Pro Ser Phe
            20                  25                  30

Leu Ser Ala Ser Val Gly Asp Arg Val Thr Ile Thr Cys Ile Thr Thr
        35                  40                  45

Thr Asp Ile Asp Asp Asp Met Asn Trp Phe Gln Gln Glu Pro Gly Lys

```
                    50                  55                  60
Ala Pro Lys Leu Leu Ile Ser Glu Gly Asn Ile Leu Arg Pro Gly Val
 65                  70                  75                  80

Pro Ser Arg Phe Ser Ser Ser Gly Ser Gly Thr Asp Phe Thr Leu Thr
                 85                  90                  95

Ile Ser Lys Leu Gln Pro Glu Asp Phe Ala Thr Tyr Tyr Cys Leu Gln
                100                 105                 110

Ser Asp Asn Leu Pro Phe Thr Phe Gly Gln Gly Thr Lys Leu Glu Ile
            115                 120                 125

Lys Arg Glu Trp
        130

<210> SEQ ID NO 52
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Asp Met Arg Val Pro Ala Gln Leu Leu Gly Leu Leu Leu Leu Trp
 1               5                  10                  15

Leu Pro Gly Ala Arg Cys Glu Thr Thr Val Thr Gln Ser Pro Ser Phe
                 20                  25                  30

Leu Ser Ala Ser Val Gly Asp Arg Val Thr Ile Thr Cys Ile Thr Thr
             35                  40                  45

Thr Asp Ile Asp Asp Asp Met Asn Trp Phe Gln Gln Glu Pro Gly Lys
 50                  55                  60

Ala Pro Lys Leu Leu Ile Ser Glu Gly Asn Ile Leu Arg Pro Gly Val
 65                  70                  75                  80

Pro Ser Arg Phe Ser Ser Ser Gly Tyr Gly Thr Asp Phe Thr Leu Thr
                 85                  90                  95

Ile Ser Lys Leu Gln Pro Glu Asp Phe Ala Thr Tyr Tyr Cys Leu Gln
                100                 105                 110

Ser Asp Asn Leu Pro Phe Thr Phe Gly Gln Gly Thr Lys Leu Glu Ile
            115                 120                 125

Lys Arg Glu Trp Ile Pro
        130

<210> SEQ ID NO 53
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Asp Met Arg Val Pro Ala Gln Leu Leu Gly Leu Leu Leu Leu Trp
 1               5                  10                  15

Leu Pro Gly Ala Arg Cys Glu Thr Thr Leu Thr Gln Ser Pro Ser Phe
                 20                  25                  30

Leu Ser Ala Ser Val Gly Asp Arg Val Thr Ile Thr Cys Ile Thr Thr
             35                  40                  45

Thr Asp Ile Asp Asp Asp Met Asn Trp Tyr Gln Gln Glu Pro Gly Lys
 50                  55                  60

Ala Pro Lys Leu Leu Ile Ser Glu Gly Asn Ile Leu Arg Pro Gly Val
 65                  70                  75                  80
```

```
Pro Ser Arg Phe Ser Ser Gly Tyr Gly Thr Asp Phe Thr Leu Thr
            85              90              95

Ile Ser Lys Leu Gln Pro Glu Asp Phe Ala Thr Tyr Tyr Cys Leu Gln
            100             105                 110

Ser Asp Asn Leu Pro Phe Thr Phe Gly Gln Gly Thr Lys Leu Glu Ile
            115             120             125

Lys Arg Glu Trp Ile Pro
    130
```

NUCLEIC ACIDS CODING FOR HUMANIZED ANTIBODIES FOR BINDING SPHINGOSINE-1-PHOSPHATE

RELATED APPLICATION

This application claims the benefit of and priority to U.S. provisional application Ser. No. 60/854,971, filed on Oct. 27, 2006, and U.S. non-provisional patent application Ser. No. 11/924,890, filed 26 Oct. 2007, the contents of each of which are herein incorporated by reference in their entirety for any and all purposes.

SEQUENCE LISTING

This application has been filed with, and includes, the sequence listing concurrently submitted herewith, which sequence listing has been prepared and filed in accordance with applicable regulations and procedures. This sequence listing is hereby incorporated by reference for any and all purposes.

BACKGROUND OF THE INVENTION

1. Field of the Invention

The present invention relates to agents that bind sphingosine-1-phosphate (S1P), particularly to humanized monoclonal antibodies, antibody fragments, and antibody derivatives specifically reactive to S1P under physiological conditions. Such agents can be used in the treatment and/or prevention of various diseases or disorders through the delivery of pharmaceutical compositions that contain such agents.

The following description includes information that may be useful in understanding the present invention. It is not an admission that any of the information provided herein, or any publication specifically or implicitly referenced herein, is prior art, or even particularly relevant, to the presently claimed invention.

2. Background

Bioactive Signaling Lipids

Lipids and their derivatives are now recognized as important targets for medical research, not as just simple structural elements in cell membranes or as a source of energy for β-oxidation, glycolysis or other metabolic processes. In particular, certain bioactive lipids function as signaling mediators important in animal and human disease. Although most of the lipids of the plasma membrane play an exclusively structural role, a small proportion of them are involved in relaying extracellular stimuli into cells. "Lipid signaling" refers to any of a number of cellular signal transduction pathways that use cell membrane lipids as second messengers, as well as referring to direct interaction of a lipid signaling molecule with its own specific receptor. Lipid signaling pathways are activated by a variety of extracellular stimuli, ranging from growth factors to inflammatory cytokines, and regulate cell fate decisions such as apoptosis, differentiation and proliferation. Research into bioactive lipid signaling is an area of intense scientific investigation as more and more bioactive lipids are identified and their actions characterized.

Examples of bioactive lipids include the eicosanoids (including the cannabinoids, leukotrienes, prostaglandins, lipoxins, epoxyeicosatrienoic acids, and isoeicosanoids), non-eicosanoid cannabinoid mediators, phospholipids and their derivatives such as phosphatidic acid (PA) and phosphatidylglycerol (PG), platelet activating factor (PAF) and cardiolipins as well as lysophospholipids such as lysophosphatidyl choline (LPC) and various lysophosphatidic acids (LPA). Bioactive signaling lipid mediators also include the sphingolipids such as sphingomyelin, ceramide, ceramide-1-phosphate, sphingosine, sphingosylphosphoryl choline, sphinganine, sphinganine-1-phosphate (Dihydro-S1P) and sphingosine-1-phosphate. Sphingolipids and their derivatives represent a group of extracellular and intracellular signaling molecules with pleiotropic effects on important cellular processes. Other examples of bioactive signaling lipids include phosphatidylserine (PS), phosphatidylinositol (PI), phosphatidylethanolamine (PEA), diacylglyceride (DG), sulfatides, gangliosides, and cerebrosides.

Sphingolipids are a unique class of lipids that were named, due to their initially mysterious nature, after the Sphinx. Sphingolipids were initially characterized as primary structural components of cell membranes, but recent studies indicate that sphingolipids also serve as cellular signaling and regulatory molecules (Hannun, et al., Adv. Lipid Res. 25:27-41, 1993; Speigel, et al., FASEB J. 10:1388-1397, 1996; Igarashi, J. Biochem 122:1080-1087, 1997; Hla, T. (2004). *Semin Cell Dev Biol,* 15, 513-2; Gardell, S. E., Dubin, A. E. & Chun, J. (2006). *Trends Mol Med,* 12, 65-75). Sphingolipids are primary structural components of cell membranes that also serve as cellular signaling and regulatory molecules (Hannun and Bell, Adv. Lipid Res. 25: 27-41, 1993; Igarashi, J. Biochem 122: 1080-1087, 1997). The sphingolipid signaling mediators, ceramide (CER), sphingosine (SPH) and sphingosine-1-phosphate (S1P), have been most widely studied and have recently been appreciated for their roles in the cardiovascular system, angiogenesis and tumor biology (Claus, et al., Curr Drug Targets 1: 185-205, 2000; Levade, et al., Circ. Res. 89: 957-968, 2001; Wang, et al., J. Biol. Chem. 274: 35343-50, 1999; Wascholowski and Giannis, Drug News Perspect. 14: 581-90, 2001; Spiegel, S. & Milstien, S. (2003). Sphingosine-1-phosphate: an enigmatic signaling lipid. *Nat Rev Mol Cell Biol,* 4, 397-407).

For a review of sphingolipid metabolism, see Liu, et al., Crit Rev. Clin. Lab. Sci. 36:511-573, 1999. For reviews of the sphingomyelin signaling pathway, see Hannun, et al., Adv. Lipid Res. 25:27-41, 1993; Liu, et al., Crit. Rev. Clin. Lab. Sci. 36:511-573, 1999; Igarashi, J. Biochem. 122:1080-1087, 1997; Oral, et al., J. Biol. Chem. 272:4836-4842, 1997; and Spiegel et al., Biochemistry (Moscow) 63:69-83, 1998.

S1P is a mediator of cell proliferation and protects from apoptosis through the activation of survival pathways (Maceyka, et al. (2002), BBA, vol. 1585): 192-201, and Spiegel, et al. (2003), Nature Reviews Molecular Cell Biology, vol. 4: 397-407). It has been proposed that the balance between CER/SPH levels and S1P provides a rheostat mechanism that decides whether a cell is directed into the death pathway or is protected from apoptosis. The key regulatory enzyme of the rheostat mechanism is sphingosine kinase (SPHK) whose role is to convert the death-promoting bioactive signaling lipids (CER/SPH) into the growth-promoting S1P. S1P has two fates: S1P can be degraded by S1P lyase, an enzyme that cleaves S1P to phosphoethanolamine and hexadecanal, or, less common, hydrolyzed by S1P phosphatase to SPH.

The pleiotropic biological activities of S1P are mediated via a family of G protein-coupled receptors (GPCRs) originally known as Endothelial Differentiation Genes (EDG). Five GPCRs have been identified as high-affinity S1P receptors (S1PRs): $S1P_1$/EDG-1, $S1P_2$/EDG-5, $S1P_3$/EDG-3, $S1P_4$/EDG-6, and $S1P_5$/EDG-8 only identified as late as 1998 (Lee, et al., 1998). Many responses evoked by S1P are coupled to different heterotrimeric G proteins ($G_{q^-}$, $G_i$, $G_{12-13}$) and the small GTPases of the Rho family (Gardell, et al., 2006).

In the adult, S1P is released from platelets (Murata et al., 2000) and mast cells to create a local pulse of free S1P (sufficient enough to exceed the $K_d$ of the S1PRs) for promoting wound healing and participating in the inflammatory response. Under normal conditions, the total S1P in the plasma is quite high (300-500 nM); however, it has been hypothesized that most of the S1P may be 'buffered' by serum proteins, particularly lipoproteins (e.g., HDL>LDL>VLDL) and albumin, so that the bio-available S1P (or the free fraction of S1P) is not sufficient to appreciably activate S1PRs (Murata et al., 2000). If this were not the case, inappropriate angiogenesis and inflammation would result. Intracellular actions of S1P have also been suggested (see, e.g., Spiegel S, Kolesnick R (2002), Leukemia, vol. 16: 1596-602; Suomalainen, et al (2005), Am J Pathol, vol. 166: 773-81).

Widespread expression of the cell surface S1P receptors allows S1P to influence a diverse spectrum of cellular responses, including proliferation, adhesion, contraction, motility, morphogenesis, differentiation, and survival. This spectrum of response appears to depend upon the overlapping or distinct expression patterns of the S1P receptors within the cell and tissue systems. In addition, crosstalk between S1P and growth factor signaling pathways, including platelet-derived growth factor (PDGF), vascular endothelial growth factor (VEGF), and basic fibroblastic growth factor (bFGF), have recently been demonstrated (see, e.g., Baudhuin, et al. (2004), FASEB J, vol. 18: 341-3). The regulation of various cellular processes involving S1P has particular impact on neuronal signaling, vascular tone, wound healing, immune cell trafficking, reproduction, and cardiovascular function, among others. Alterations of endogenous levels of S1P within these systems can have detrimental effects, eliciting several pathophysiological conditions, including cancer, inflammation, angiogenesis, heart disease, asthma, and autoimmune diseases.

A recent novel approach to the treatment of various diseases and disorders, including cardiovascular diseases, cerebrovascular diseases, and various cancers, involves reducing levels of biologically available S1P, either alone or in combination with other treatments. While sphingolipid-based treatment strategies that target key enzymes of the sphingolipid metabolic pathway, such as SPHK, have been proposed, interference with the lipid mediator S1P itself has not until recently been emphasized, largely because of difficulties in directly mitigating this lipid target, in particular because of the difficulty first in raising and then in detecting antibodies against the S1P target.

Recently, the generation of antibodies specific for S1P has been described. See, e.g., commonly owned, U.S. patent application Serial No. 20070148168; WO2007/053447. Such antibodies, which can, for example, selectively adsorb S1P from serum, act as molecular sponges to neutralize extracellular S1P. See also commonly owned U.S. Pat. Nos. 6,881, 546 and 6,858,383 and U.S. patent application Ser. No. 10/029,372. SPHINGOMAB™, the murine monoclonal antibody (mAb) developed by Lpath, Inc. and described in certain patents or patent applications listed above, has been shown to be effective in models of human disease. In some situations, a humanized antibody may be preferable to a murine antibody, particularly for therapeutic uses in humans, where human-anti-mouse antibody (HAMA) response may occur. Such a response may reduce the effectiveness of the antibody by neutralizing the binding activity and/or by rapidly clearing the antibody from circulation in the body. The HAMA response can also cause toxicities with subsequent administrations of mouse antibodies.

A humanized anti-S1P antibody has now been developed and is described herein. This antibody is expected to have all the advantages of the murine mAb in terms of efficacy in binding S1P, neutralizing S1P and modulating disease states related to S1P, but with none of the potential disadvantages of the murine mAb when used in a human context. As described in the examples hereinbelow, this humanized antibody (referred to as LT1009 or sonepcizumab) has in fact shown activity greater than that of the parent (murine) antibody in animal models of disease.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings. In the event of conflict, the present specification, including definitions, will control.

An "immune-derived moiety" includes any antibody (Ab) or immunoglobulin (Ig), and refers to any form of a peptide, polypeptide derived from, modeled after or encoded by, an immunoglobulin gene, or a fragment of such peptide or polypeptide that is capable of binding an antigen or epitope (see, e.g., Immunobiology, 5th Edition, Janeway, Travers, Walport, Shlomchiked. (editors), Garland Publishing (2001)). In the present invention, the antigen is a bioactive lipid molecule.

An "anti-S1P antibody" or an "immune-derived moiety reactive against S1P" refers to any antibody or antibody-derived molecule that binds S1P. As will be understood from these definitions, antibodies or immune-derived moieties may be polyclonal or monoclonal and may be generated through a variety of means, and/or may be isolated from an animal, including a human subject.

A "bioactive lipid" refers to a lipid signaling molecule. In general, a bioactive lipid does not reside in a biological membrane when it exerts its signaling effects, which is to say that while such a lipid species may exist at some point in a biological membrane (for example, a cell membrane, a membrane of a cell organelle, etc.), when associated with a biological membrane it is not a "bioactive lipid" but is instead a "structural lipid" molecule. Bioactive lipids are distinguished from structural lipids (e.g., membrane-bound phospholipids) in that they mediate extracellular and/or intracellular signaling and thus are involved in controlling the function of many types of cells by modulating differentiation, migration, proliferation, secretion, survival, and other processes. In vivo, bioactive lipids can be found in extracellular fluids, where they can be complexed with other molecules, for example serum proteins such as albumin and lipoproteins, or in "free" form, i.e., not complexed with another molecule species. As extracellular mediators, some bioactive lipids alter cell signaling by activating membrane-bound ion channels or G-protein coupled receptors that, in turn, activate complex signaling systems that result in changes in cell function or survival. As intracellular mediators, bioactive lipids can exert their actions by directly interacting with intracellular components such as enzymes and ion channels. Representative examples of bioactive lipids include LPA and S1P.

The term "therapeutic agent" means an agent to mitigate angiogenesis and/or neovascularization, e.g., CNV and BV maturation, edema, vascular permeability and fibrosis, fibrogenesis and scarring associated with, or part of the underlying pathology of, ocular diseases and conditions.

The term "combination therapy" refers to a therapeutic regimen that involves the provision of at least two distinct therapies to achieve an indicated therapeutic effect. For example, a combination therapy may involve the administration of two or more chemically distinct active ingredients, for example, an anti-LPA antibody and an anti-S1P antibody. Alternatively, a combination therapy may involve the administration of an immune-derived moiety reactive against a bioactive lipid and the administration of one or more other chemotherapeutic agents. Combination therapy may, alternatively, involve administration of an anti-lipid antibody together with the delivery of another treatment, such as radiation therapy and/or surgery. Further, a combination therapy may involve administration of an anti-lipid antibody together with one or more other biological agents (e.g., anti-VEGF, TGFβ, PDGF, or bFGF agent), chemotherapeutic agents and another treatment such as radiation and/or surgery. In the context of combination therapy using two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending physician. Similarly, when one or more anti-lipid antibody species, for example, an anti-LPA antibody, alone or in conjunction with one or more chemotherapeutic agents are combined with, for example, radiation and/or surgery, the drug(s) may be delivered before or after surgery or radiation treatment.

An "anti-S1P agent" refers to any agent that is specifically reactive to S1P, and includes antibodies or antibody-derived molecules or non-antibody-derived moieties that bind S1P and its variants.

A "hapten" refers to a molecule adapted for conjugation to a hapten, thereby rendering the hapten immunogenic. A representative, non-limiting class of hapten molecules is proteins, examples of which include albumin, keyhole limpet hemocyanin, hemaglutanin, tetanus, and diphtheria toxoid. Other classes and examples of hapten molecules suitable for use in accordance with the invention are known in the art. These, as well as later discovered or invented naturally occurring or synthetic haptens, can be adapted for application in accordance with the invention.

The term "chemotherapeutic agent" means anti-cancer and other anti-hyperproliferative agents. Put simply, a "chemotherapeutic agent" refers to a chemical intended to destroy cells and tissues. Such agents include, but are not limited to: (1) DNA damaging agents and agents that inhibit DNA synthesis: anthracyclines (doxorubicin, donorubicin, epirubicin), alkylating agents (bendamustine, busulfan, carboplatin, carmustine, cisplatin, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine), platinum derivatives (cisplatin, carboplatin, cis diamminedichloroplatinum), telomerase and topoisomerase inhibitors (Camptosar), (2) tubulin-depolymerizing agents: taxoids (Paclitaxel, docetaxel, BAY 59-8862), (3) anti-metabolites such as capecitabine, chlorodeoxyadenosine, cytarabine (and its activated form, ara-CMP), cytosine arabinoside, dacabazine, floxuridine, fludarabine, 5-fluorouracil, 5-DFUR, gemcitibine, hydroxyurea, 6-mercaptopurine, methotrexate, pentostatin, trimetrexate, and 6-thioguanine (4) anti-angiogenics (Avastin, thalidomide, sunitinib, lenalidomide), vascular disrupting agents (flavonoids/flavones, DMXAA, combretastatin derivatives such as CA4DP, ZD6126, AVE8062A, etc.), (5) biologics such as antibodies or antibody fragments (Herceptin, Avastin, Panorex, Rituxan, Zevalin, Mylotarg, Campath, Bexar, Erbitux, Lucentis), and (6) endocrine therapy: aromatase inhibitors (4-hydroandrostendione, exemestane, aminoglutehimide, anastrozole, letozole), anti-estrogens (Tamoxifen, Toremifine, Raoxifene, Faslodex), steroids such as dexamethasone, (7) immunomodulators: cytokines such as IFN-beta and IL2), inhibitors to integrins, other adhesion proteins and matrix metalloproteinases), (8) histone deacetylase inhibitors, (9) inhibitors of signal transduction such as inhibitors of tyrosine kinases like imatinib (Gleevec), (10) inhibitors of heat shock proteins, (11) retinoids such as all trans retinoic acid, (12) inhibitors of growth factor receptors or the growth factors themselves, (13) anti-mitotic compounds such as navelbine, Paclitaxel, taxotere, vinblastine, vincristine, vindesine, and vinorelbine, (14) anti-inflammatories such as COX inhibitors and (15) cell cycle regulators, e.g., check point regulators and telomerase inhibitors.

The term "sphingolipid" as used herein refers to the class of compounds in the art known as sphingolipids, including, but not limited to the following compounds (see http//www.lipidmaps.org as the site containing the links indicated by the bracketed alphanumeric strings below, which links contain chemical formulas, structural information, etc. for the corresponding compounds):

Sphingoid bases [SP01]
Sphing-4-enines (Sphingosines) [SP0101]
Sphinganines [SP0102]
4-Hydroxysphinganines (Phytosphingosines) [SP0103]
Sphingoid base homologs and variants [SP0104]
Sphingoid base 1-phosphates [SP0105]
Lysosphingomyelins and lysoglycosphingolipids [SP0106]
N-methylated sphingoid bases [SP0107]
Sphingoid base analogs [SP0108]
Ceramides [SP02]
N-acylsphingosines (ceramides) [SP0201]
N-acylsphinganines (dihydroceramides) [SP0202]
N-acyl-4-hydroxysphinganines (phytoceramides) [SP0203]
Acylceramides [SP0204]
Ceramide 1-phosphates [SP0205]
Phosphosphingolipids [SP03]
Ceramide phosphocholines (sphingomyelins) [SP0301]
Ceramide phosphoethanolamines [SP0302]
Ceramide phosphoinositols [SP0303]
Phosphonosphingolipids [SP04]
Neutral glycosphingolipids [SP05]
Simple Glc series (GlcCer, LacCer, etc) [SP0501]
GalNAcb1-3Gala1-4Galb1-4Glc-(Globo series) [SP0502]
GalNAcb1-4Galb1-4Glc-(Ganglio series) [SP0503]
Galb1-3GlcNAcb1-3Galb1-4Glc-(Lacto series) [SP0504]
Galb1-4GlcNAcb1-3Galb1-4Glc-(Neolacto series) [SP0505]
GalNAcb1-3Gala1-3Galb1-4Glc-(Isoglobo series) [SP0506]
GlcNAcb1-2Mana1-3Manb1-4Glc-(Mollu series) [SP0507]
GalNAcb1-4GlcNAcb1-3Manb1-4Glc-(Arthro series) [SP0508]
Gal-(Gala series) [SP0509]
Other [SP0510]
Acidic glycosphingolipids [SP06]

Gangliosides [SP0601]
Sulfoglycosphingolipids (sulfatides) [SP0602]
Glucuronosphingolipids [SP0603]
Phosphoglycosphingolipids [SP0604]
Other [SP0600]
Basic glycosphingolipids [SP07]
Amphoteric glycosphingolipids [SP08]
Arsenosphingolipids [SP09]

The present invention provides anti-sphingolipid S1P agents that are useful for treating or preventing hyperproliferative disorders such as cancer and cardiovascular or cerebrovascular diseases and disorders and various ocular disorders, as described in greater detail below. In particular the invention is drawn to S1P and its variants including but are not limited to sphingosine-1-phosphate [sphingene-1-phosphate; D-erythro-sphingosine-1-phosphate; sphing-4-enine-1-phosphate; (E,2S,3R)-2-amino-3-hydroxy-octadec-4-enoxy] phosphonic acid (AS 26993-30-6), DHS1P is defined as dihydrosphingosine-1-phosphate [sphinganine-1-phosphate; [(2S,3R)-2-amino-3-hydroxy-octadecoxy]phosphonic acid; D-Erythro-dihydro-D-sphingosine-1-phosphate (CAS 19794-97-9]; SPC is sphingosylphosphoryl choline, lysosphingomyelin, sphingosylphosphocholine, sphingosine phosphorylcholine, ethanaminium; 2-((((2-amino-3-hydroxy-4-octadecenyl)oxy)hydroxyphosphinyl)oxy)-N,N,N-trimethyl-, chloride, (R—(R*,S*-(E))), 2-[[(E,2R,3 S)-2-amino-3-hydroxy-octadec-4-enoxy]-hydroxy-phosphoryl] oxyethyl-trimethyl-azanium chloride (CAS 10216-23-6).

The term "epitope" or "antigenic determinant" when used herein, unless indicated otherwise, refers to the region of S1P to which an anti-S1P agent is reactive to.

The term "hyperproliferative disorder" refers to diseases and disorders associated with, the uncontrolled proliferation cells, including but not limited to uncontrolled growth of organ and tissue cells resulting in cancers or neoplasia and benign tumors. Hyperproliferative disorders associated with endothelial cells can result in diseases of angiogenesis such as angiomas, endometriosis, obesity, age-related macular degeneration and various retinopathies, as well as the proliferation of endothelial cells and smooth muscle cells that cause restenosis as a consequence of stenting in the treatment of atherosclerosis. Hyperproliferative disorders involving fibroblasts (for example, fibrogenesis) include but are not limited to disorders of excessive scarring (for example, fibrosis) such as age-related macular degeneration, cardiac remodeling and failure associated with myocardial infarction, excessive wound healing such as commonly occurs as a consequence of surgery or injury, keloids, and fibroid tumors and stenting.

The compositions of the invention are used in methods of sphingolipid-based therapy. "Therapy" refers to the prevention and/or treatment of diseases, disorders or physical trauma.

"Cardiovascular therapy" encompasses cardiac therapy as well as the prevention and/or treatment of other diseases associated with the cardiovascular system, such as heart disease. The term "heart disease" encompasses any type of disease, disorder, trauma or surgical treatment that involves the heart or myocardial tissue. Of particular interest are heart diseases that relate to hypoxia and/or ischemia of myocardial tissue and/or heart failure. One type of heart disease that can result from ischemia is reperfusion injury, such as can occur when anti-coagulants, thrombolytic agents, or anti-anginal medications are used in therapy, or when the cardiac vasculature is surgically opened by angioplasty or by coronary artery grafting. Another type of heart disease to which the invention is directed is coronary artery disease (CAD), which can arise from arteriosclerosis, particularly atherosclerosis, a common cause of ischemia. CAD has symptoms such as stable or unstable angina pectoris, and can lead to myocardial infarctions (MI) and sudden cardiac death. Conditions of particular interest include, but are not limited to, myocardial ischemia; acute myocardial infarction (AMI); coronary artery disease (CAD); acute coronary syndrome (ACS); cardiac cell and tissue damage that may occur during or as a consequence of pericutaneous revascularization (coronary angioplasty) with or without stenting; coronary bypass grafting (CABG) or other surgical or medical procedures or therapies that may cause ischemic or ischemic/reperfusion damage in humans; and cardiovascular trauma. The term "heart failure" encompasses acute myocardial infarction, myocarditis, a cardiomyopathy, congestive heart failure, septic shock, cardiac trauma and idiopathic heart failure. The spectrum of ischemic conditions that result in heart failure is referred to as Acute Coronary Syndrome (ACS).

The term "cardiotherapeutic agent" refers to an agent that is therapeutic to diseases and diseases caused by or associated with cardiac and myocardial diseases and disorders.

"Cerebrovascular therapy" refers to therapy directed to the prevention and/or treatment of diseases and disorders associated with cerebral ischemia and/or hypoxia. Of particular interest is cerebral ischemia and/or hypoxia resulting from global ischemia resulting from a heart disease, including without limitation heart failure.

The term "sphingolipid metabolite" refers to a compound from which a sphingolipid is made, as well as a that results from the degradation of a particular sphingolipid. In other words, a "sphingolipid metabolite" is a compound that is involved in the sphingolipid metabolic pathways. Metabolites include metabolic precursors and metabolic products. The term "metabolic precursors" refers to compounds from which sphingolipids are made. Metabolic precursors of particular interest include but are not limited to SPC, sphingomyelin, dihydrosphingosine, dihydroceramide, and 3-ketosphinganine. The term "metabolic products" refers to compounds that result from the degradation of sphingolipids, such as phosphorylcholine (e.g., phosphocholine, choline phosphate), fatty acids, including free fatty acids, and hexadecanal (e.g., palmitaldehyde).

As used herein, the term "therapeutic" encompasses the fill spectrum of treatments for a disease or disorder. A "therapeutic" agent of the invention may act in a manner that is prophylactic or preventive, including those that incorporate procedures designed to target individuals that can be identified as being at risk (pharmacogenetics); or in a manner that is ameliorative or curative in nature; or may act to slow the rate or extent of the progression of at least one symptom of a disease or disorder being treated; or may act to minimize the time required, the occurrence or extent of any discomfort or pain, or physical limitations associated with recuperation from a disease, disorder or physical trauma; or may be used as an adjuvant to other therapies and treatments.

"Treatment" refers to both therapeutic treatment and prophylactic or preventative measures. Those in need of treatment include those already with the disorder as well as those in which the disorder is to be prevented.

The term "combination therapy" refers to a therapeutic regimen that involves the provision of at least two distinct therapies to achieve an indicated therapeutic effect. For example, a combination therapy may involve the administration of two or more chemically distinct active ingredients, for example, a fast-acting chemotherapeutic agent and an anti-lipid antibody. Alternatively, a combination therapy may involve the administration of an anti-lipid antibody and/or one or more chemotherapeutic agents, alone or together with the delivery of another treatment, such as radiation therapy and/or surgery. Further, a combination therapy may involve administration of an anti-lipid antibody together with one or more other biological agents (e.g., anti-VEGF, TGFβ, PDGF, or bFGF agent), chemotherapeutic agents and another treatment such as radiation and/or surgery. In the context of the administration of two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending physician. Similarly, when one or more anti-lipid antibody species, for example, an anti-LPA antibody, alone or in conjunction with one or more chemotherapeutic agents are combined with, for example, radiation and/or surgery, the drug(s) may be delivered before or after surgery or radiation treatment.

"Monotherapy" refers to a treatment regimen based on the delivery of one therapeutically effective compound, whether administered as a single dose or several doses over time.

"Neoplasia" or "cancer" refers to abnormal and uncontrolled cell growth. A "neoplasm", or tumor or cancer, is an abnormal, unregulated, and disorganized proliferation of cell growth, and is generally referred to as cancer. A neoplasm may be benign or malignant. A neoplasm is malignant, or cancerous, if it has properties of destructive growth, invasiveness, and metastasis. Invasiveness refers to the local spread of a neoplasm by infiltration or destruction of surrounding tissue, typically breaking through the basal laminas that define the boundaries of the tissues, thereby often entering the body's circulatory system. Metastasis typically refers to the dissemination of tumor cells by lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

"Mammal" for purposes of treatment refers to any animal classified as a mammal, including humans, domestic and farm animals, and zoo, sports, or pet animals, such as dogs, horses, cats, cows, etc. Preferably, the mammal is human.

"Native antibodies" and "native immunoglobulins" are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" region comprises framework and CDRs (otherwise known as hypervariables) and refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the α-sheet structure. The hypervariable regions in each chain are held together in close proximity by the FRs and, with the hypervariable regions from the other chain, contribute to the formation of the antigen-binding site of antibodies (see Kabat, et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen binding. The hypervariable region comprises amino acid residues from a "complementarity determining region" or "CDR" (for example, residues 24-34 (L1), 50-56 (L2), and 89-97 (L3) in the light chain variable domain and 31-35 (H1), 50-65 (H2), and 95-102 (H3) in the heavy chain variable domain; Kabat, et al. (1991), above) and/or those residues from a "hypervariable loop" (for example residues 26-32 (L1), 50-52 (L2), and 91-96 (L3) in the light chain variable domain and 26-32 (H1), 53-55 (H2), and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment that contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. Presently there are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The term "antibody" herein is used in the broadest sense and specifically covers monoclonal antibodies (including full length monoclonal antibodies), polyclonal antibodies, multi-specific antibodies (e.g., bispecific antibodies), antibody fragments, and binding agents that employ the CDRs (or variant thereof that retain antigen binding activity) of the parent antibody. Antibodies are defined herein as retaining at least one desired activity of the parent antibody. Desired activities can include the ability to bind the antigen specifically, the ability to inhibit proleration in vitro, the ability to inhibit angiogenesis in vivo, and the ability to alter cytokine profile in vitro. "Antibody fragments" comprise a portion of a full-length antibody, generally the antigen binding or variable domain thereof. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, for example, the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler, et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson, et al., Nature 352:624-628 (1991) and Marks et al., J. Mol. Biol. 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison, et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones, et al., Nature 321:522-525 (1986); Reichmann, et al., Nature 332:323-329 (1988); and Presta, Curr. Op. Struct. Biol. 2:593-596 (1992) and Hansen, WO2006105062.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger, et al., Proc. Natl. Acad. Sci. USA 90:6444-6448 (1993).

The expression "linear antibodies" when used throughout this application refers to the antibodies described in Zapata, et al. Protein Eng. 8(10): 1057-1062 (1995). Briefly, these antibodies comprise a pair of tandem Fd segments ($V_H$-$C_H$1-$V_H$-$C_H$1) that form a pair of antigen binding regions. Linear antibodies can be bispecific or monospecific.

A "variant" anti-sphingolipid antibody, refers herein to a molecule which differs in amino acid sequence from a "parent" anti-sphingolipid antibody amino acid sequence by virtue of addition, deletion, and/or substitution of one or more amino acid residue(s) in the parent antibody sequence and retains at least one desired activity of the parent anti-binding antibody. Desired activities can include the ability to bind the antigen specifically, the ability to inhibit proleration in vitro, the ability to inhibit angiogenesis in vivo, and the ability to alter cytokine profile in vitro. In one embodiment, the variant comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 50% amino acid sequence identity with the parent antibody heavy or light chain variable domain sequences, more preferably at least 65%, more preferably at least 75%, more preferably at least 80%, more preferably at least 85%, more preferably at least 90%, and most preferably at least 95% sequence identity. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind a sphingolipid and preferably has desired activities which are superior to those of the parent antibody. For example, the variant may have a stronger binding affinity, enhanced ability to reduce angiogenesis and/or halt tumor progression. To analyze such desired properties (for example less immunogenic, longer half-life, enhanced stability, enhanced potency), one should compare a Fab form of the variant to a Fab form of the parent antibody or a full length form of the variant to a full length form of the parent antibody, for example, since it has been found that the format of the anti-sphingolipid antibody impacts its activity in the biological activity assays disclosed herein. The variant antibody of particular interest herein can be one which displays at least about 5%, preferably at least about 10%, 25%, 59%, or more of at least one desired activity. The preferred variant is one that has superior biophysical properties as measured in vitro or superior activities biological as measured in vitro or in vivo when compared to the parent antibody.

The "parent" antibody herein is one that is encoded by an amino acid sequence used for the preparation of the variant. Preferably, the parent antibody has a human framework region and, if present, has human antibody constant region(s). For example, the parent antibody may be a humanized or human antibody.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition that is conjugated directly or indirectly to the antibody. The label may itself be detectable by itself (e.g., radioisotope labels or fluorescent labels) or, in the case of an enzymatic label, may catalyze chemical alteration of a substrate compound or composition that is detectable.

By "solid phase" is meant a non-aqueous matrix to which the antibody of the present invention can adhere or upon which the antibody or other anti-S1P binding reagent can otherwise become immobilized. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate, while in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant that is useful for delivery of a drug (such as the anti-sphingolipid antibodies disclosed herein and, optionally, a chemotherapeutic agent) to a mammal. The components of the liposome are commonly arranged in a bilayer formation, similar to the lipid arrangement of biological membranes. An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the nucleic acid molecules being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell", "cell line", and "cell culture" are used interchangeably and all such designations include progeny. Thus, the words "transformants" and "transformed cells" include the primary subject cell and cultures derived there from without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

A "patentable" composition, process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the unpatentable embodiment(s). Also, the claims appended hereto are to be interpreted both to provide the broadest reasonable scope, as well as to preserve their validity. Furthermore, the claims are to be interpreted in a way that (1) preserves their validity and (2) provides the broadest reasonable interpretation under the circumstances, if one or more of the statutory requirements for patentability are amended or if the standards change for assessing whether a particular statutory requirement for patentability is satisfied from the time this application is filed or issues as a patent to a time the validity of one or more of the appended claims is questioned.

The term "pharmaceutically acceptable salt" refers to salts which retain the biological effectiveness and properties of the agents and compounds of this invention and which are not biologically or otherwise undesirable. In many cases, the agents and compounds of this invention are capable of forming acid and/or base salts by virtue of the presence of charged groups, for example, charged amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts (see Berge, et al. (1977) J. Pharm. Sci., vol. 66, 1-19).

A "plurality" means more than one.

The terms "separated", "purified", "isolated", and the like mean that one or more components of a sample contained in a sample-holding vessel are or have been physically removed from, or diluted in the presence of, one or more other sample components present in the vessel. Sample components that may be removed or diluted during a separating or purifying step include, chemical reaction products, unreacted chemicals, proteins, carbohydrates, lipids, and unbound molecules.

The term "species" is used herein in various contexts, e.g., a particular species of chemotherapeutic agent. In each context, the term refers to a population of chemically indistinct molecules of the sort referred in the particular context.

"Specifically associate" and "specific association" and the like refer to a specific, non-random interaction between two molecules, which interaction depends on the presence of structural, hydrophobic/hydrophilic, and/or electrostatic features that allow appropriate chemical or molecular interactions between the molecules.

A "subject" or "patient" refers to an animal in need of treatment that can be effected by molecules of the invention. Animals that can be treated in accordance with the invention include vertebrates, with mammals such as bovine, canine, equine, feline, ovine, porcine, and primate (including humans and non-human primates) animals being particularly preferred examples.

A "therapeutically effective amount" (or "effective amount") refers to an amount of an active ingredient, e.g., an agent according to the invention, sufficient to effect treatment when administered to a subject or patient. Accordingly, what constitutes a therapeutically effective amount of a composition according to the invention may be readily determined by one of ordinary skill in the art. In the context of ocular therapy, a "therapeutically effective amount" is one that produces an objectively measured change in one or more parameters associated with treatment of the ocular disease or condition including an increase or decrease in the expression of one or more genes correlated with the ocular disease or condition, induction of apoptosis or other cell death pathways, clinical improvement in symptoms, a decrease in aberrant neovascularization or in inflammation, etc. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art. It will be appreciated that in the context of combination therapy, what constitutes a therapeutically effective amount of a particular active ingredient may differ from what constitutes a therapeutically effective amount of the active ingredient when administered as a monotherapy (ie., a therapeutic regimen that employs only one chemical entity as the active ingredient).

The term "treatment" or "treating" of a disease or disorder includes preventing or protecting against the disease or disorder (that is, causing the clinical symptoms not to develop); inhibiting the disease or disorder (i.e., arresting or suppressing the development of clinical symptoms; and/or relieving the disease or disorder (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing." The term "treatment" thus includes "prophylaxis".

The term "therapeutic regimen" means any treatment of a disease or disorder using chemotherapeutic drugs, radiation therapy, surgery, gene therapy, DNA vaccines and therapy, antisense-based therapies including siRNA therapy, anti-angiogenic therapy, immunotherapy, bone marrow transplants, aptamers and other biologics such as antibodies and antibody variants, receptor decoys and other protein-based therapeutics.

SUMMARY OF THE INVENTION

This invention concerns patentable humanized anti-sphingolipid agents, including antibodies and anti-sphingolipid antibody variants with desirable properties from a therapeutic and/or diagnostic perspective, including strong binding affinity for sphingolipids, the ability to bind and neutralize sphingosine-1-phosphate (S1P), particularly in physiological contexts (e.g., in living tissue, blood, etc.) and under physiological conditions, as well as isoforms, variants, isomers, and related compounds. In particular, the invention is drawn to antibodies, particularly monoclonal antibodies, more particularly humanized monoclonal antibodies and variants thereof, directed to S1P. Such antibodies and variants are preferably included in pharmaceutical compositions suitable for administration to subjects in known or suspected to need treatment with such compounds. In addition to compositions, the invention also provides kits including such compositions, methods of making such anti-S1P antibodies and variants, and methods of treatment using such agents.

In one embodiment, isolated anti-S1P antibody heavy chains and light chains comprising variable domains of newly identified preferred sequences, particularly SEQ ID NO: 27 and SEQ ID NO: 35 for heavy chains and SEQ ID NO: 30 and SEQ ID NO: 37 for light chains, are provided. In another embodiment, anti-S1P agents are provided that are reactive against sphingosine-1-phosphate (S1P) under physiological conditions and which comprises at least one CDR peptide having at least 50% amino acid sequence identity, and up to and including 100% identity, with the CDR sequences specified elsewhere herein.

In one embodiment, an anti-sphingolipid antibody according to the invention has a light chain variable domain comprises hypervariable complementarity determining regions (CDRs) with the following amino acid sequences: ITTTDID-DDMN (SEQ ID NO:10; CDRL1), EGNILRP (SEQ ID NO: 11; CDRL2) and LQSDNLPFT (SEQ ID NO: 12; CDRL3). Preferably the heavy chain variable domain comprises CDRs having the amino acid sequences DHTIH (SEQ ID NO:13; CDRH1), GGFYGSTIWFDF (SEQ ID NO:15; CDRH3) and CISPRHDITKYNEMFRG (SEQ ID NO: 14; CDRH2) or AISPRHDITKYNEMFRG (SEQ ID NO:31; CDRH2). In particularly preferred embodiments of the invention, one or more of the CDRs is(are) grafted into a framework in such a way that the CDRs retain their ability to bind and neutralize S1P. Without being limited to the following example, the framework could represent the human sequence of an antibody light and heavy chains immediately flanking the CDRs, but could also represent any structure that presents the CDRs in a way that optimizes the performance characteristics of the humanized antibody in its binding to the S1P or in other characteristics that enhance potency, stability, expression, biological half-life, solubility, immunogenicity, pharmacodistribution, and shelf-life of the antibody.

Preferably, the three heavy chain hypervariable CDR regions are provided in a human framework region, e.g., as a contiguous sequence represented by the following formula: FR1-CDRH1-FR2-CDRH2-FR3-CDRH3-FR4.

The invention further provides an anti-sphingolipid antibody heavy chain variable domain comprising the amino acid sequence represented herein by SEQ ID NO:27. One particularly useful heavy chain variable domain sequence is that of the humanized antibody described in Example 12, below, and comprises the heavy chain variable domain sequence of SEQ ID NO: 32. Such preferred heavy chain variable domain sequences may be combined with, for example, a polypeptide comprising the light chain variable domain sequence represented herein by SEQ ID NO: 33, or with other light chain variable domain sequences, provided that the resulting molecule binds a sphingolipid.

In another embodiment, the invention provides a humanized anti-sphingolipid antibody light chain variable domain comprising the amino acid sequence represented herein by SEQ ID NO: 17. In one embodiment, one useful light chain variable domain sequence is that of the humanized antibody of Example 12, below, and comprises the light chain variable domain sequence of SEQ ID NO:30 or SEQ ID NO:37.

In one preferred embodiment, the invention provides a humanized anti-sphingolipid antibody having a light chain comprising the amino acid sequence of SEQ ID NO:37 and a heavy chain comprising the amino acid sequence of SEQ ID NO:35.

The light chain variable domain may comprise hypervariable regions with the following amino acid sequences: CDRL1 (SEQ ID NO: 10), CDRL2 (SEQ ID NO:11), and CDRL3 (SEQ ID NO:12). Preferably, the three light chain hypervariable regions are provided in a human framework region, e.g., as a contiguous sequence represented by the following formula: FR1-CDRL1-FR2-CDRL2-FR3-CDRL3-FR4.

The invention also provides variants of parent anti-sphingolipid antibodies, preferably wherein the parent antibody is a humanized or human anti-sphingolipid antibody. Such variants bind a sphingolipid, particularly S1P, and comprise an amino acid substitution in a hypervariable region of the heavy or light chain variable domain of the parent anti-sphingolipid antibody. Such a variant preferably has one or more substitution(s) in one or more hypervariable region(s) of the anti-sphingolipid antibody. According to one embodiment, the substitution(s) are in the heavy chain variable domain of the parent antibody. For example, the amino acid substitution(s) can be in the CDRH1 and/or CDRH3 of the heavy chain variable domain. There can be substitutions in both these hypervariable regions. Such "affinity matured" variants are demonstrated herein to bind sphingolipid more strongly than the parent anti-sphingolipid antibody from which they were generated. For example, an antibody produced by affinity maturation can have a $K_d$ value that is significantly less than that of the parent anti-sphingolipid antibody.

A representative example of affinity maturation involves altering human IgG kappa1 light and heavy chain frameworks into which murine anti-S1P CDRs were grafted. This resulted in an increased affinity of the humanized antibody against its target ligand, i.e., S1P. In other embodiments, one or more of the CDRs could be supported by amino acid sequences other than human IgG frameworks. Affinity maturation by altering the amino acid sequence or sequences in the hypervariable CDR regions can be performed to improve antibody performance and/or characteristics described above. An example of this form of affinity maturation is shown in Example 12, below, where a cysteine residue in a heavy chain CDR was changed by site-directed mutagenesis to an alanine residue, resulting in a substantial increase in S1P-binding affinity and stability. In one such heavy chain variant, the variable region included the amino acid sequence of SEQ ID NO:27. Such heavy chain variable domain sequences in CDRH2 can optionally be combined with a light chain variable domain, for example, a light chain variable comprising the amino acid sequence of SEQ ID NO: 17, or preferably the light chain variable domain amino acid sequence of SEQ ID NO:30.

Various anti-S1P molecules are contemplated herein. For example, the anti-S1P agent may be an antibody, an antibody derivative, or a non-antibody-derived moiety. For example, the anti-S1P agent can be an antibody, including a full-length antibody (e.g., an antibody having an intact human Fc region) or an antibody fragment (e.g., an Fab, Fab', or F(ab')$_2$ molecule), a chimeric antibody, a humanized antibody, a human antibody, or an affinity matured antibody. Without limiting the invention, such anti-S1P agents can be produced to improve or otherwise alter antibody stability, half-life, potency, pharmacodistribution, and/or immunogenicity. For example, a humanized Fc domain could be altered in its amino acid composition to improve its immunogenicity or other performance characteristics.

In other embodiments, the anti-S1P agent can be conjugated to a moiety such as a polymer, a radionuclide, a chemotherapeutic agent, and a detection agent.

In certain preferred embodiments, the anti-S1P agent is formulated with a carrier such as a pharmaceutically acceptable carrier. In one embodiment, the anti-S1P agent is combined with a second agent such as an antibody, an antibody fragment, an antibody derivative, an antibody variant, a therapeutic agent other than an anti-S1P agent, or an agent that can bind a molecule other than S1P.

The instant invention also provides isolated nucleic acid molecules that encode the various components of antibodies, antibody variants, and fragments according to the invention, including various heavy and light chain sequences and CDRs. Vectors and host cells containing these nucleic acid molecules are also provided. Further provided are isolated polypeptides comprising one or more of the preferred amino acid sequences, such as CDR sequences or antibody light and/or heavy chain sequences.

In preferred embodiments of the invention, isolated antibody molecules are provided that contain precisely defined CDR sequences in each heavy chain and each light chain. In one such embodiment, the isolated antibody molecule is a humanized antibody molecule.

Multivalent binding molecules having a ligand binding element that is reactive with S1P and that contain one or more of the preferred CDR sequences are also provided. These multivalent molecules may contain at least one, and up to 10,000 or more, ligand binding elements that are reactive with S1P. Ligand binding elements reactive a different ligand can also be included, if desired, as can different ligand binding element species each reactive with S1P but differing from other S1P binding elements in one or more characteristics (e.g., molecular structure, binding affinity, etc).

Also provided are methods of treating or preventing diseases or disorders correlated with aberrant levels, particularly elevated levels, of S1P. In general, such methods comprise administering to a subject, such as a human, in need of such treatment one of the anti-S1P compositions of the invention. Diseases or disorders amenable to treatment by such methods include cancer, inflammatory disorders, cerebrovascular diseases, cardiovascular diseases, ocular disorders, diseases and disorders associated with excessive fibrogenesis, and diseases or disorders associated with pathologic angiogenesis. Anti-S1P compositions can also be administered in combination with another therapeutic agent or therapeutic regimen.

A related aspect concerns methods of reducing toxicity of a therapeutic regimen for treatment or prevention of a hyperproliferative disorder. Such methods comprise administering to a subject suffering from a hyperproliferative disorder an effective amount of an agent (or a plurality of different agent species) according to the invention before, during, or after administration of a therapeutic regimen intended to treat or prevent the hyperproliferative disorder. In a preferred embodiment, the antibody and the therapeutic regimen have additive effects, and addition of the antibody to the therapeutic regimen may allow reduction of the dosage of the therapeutic regimen, thus reducing treatment-associated toxicity.

Yet another aspect of the invention concerns diagnostic uses for the anti-S1P agents of the invention. In one diagnostic application, the invention provides methods for determining the presence in a sample of a target sphingolipid. In general, such methods are performed by exposing a sample (such as a bodily fluid or tissue biopsy sample) suspected of containing a particular sphingolipid (i.e., the "target" sphingolipid) to an anti-S1P agent such as anti-sphingolipid antibody of the invention and determining whether an aberrant level (i.e., a level associated or correlated with a disease, condition, or disorder) of the target sphingolipid (e.g., S1P) exists in the sample. For certain of these applications, kits containing the antibody and instructions for its use are provided.

Still another aspect of the invention concerns methods of making an anti-S1P agent. Preferred examples of such agents include antibodies, antibody variants, and antibody derivatives (e.g., antibody fragments). In preferred embodiments, particularly those that concern anti-S1P agents that comprise on or more polypetides, biological production systems such as cell lines are preferred. Of course, synthetic chemistry methods can also be employed.

These and other aspects and embodiments of the invention are discussed in greater detail in the sections that follow. The foregoing and other aspects of the invention will become more apparent from the following detailed description, accompanying drawings, and the claims. Although methods and materials similar or equivalent to those described herein can be used in the practice or testing of the present invention, suitable methods and materials are described below. In addition, the materials, methods, and examples below are illustrative only and not intended to be limiting.

BRIEF DESCRIPTION OF THE DRAWINGS

A brief summary of each of the figures is provided below.

FIG. 1 has two panels, A and B. shows Panel A graphically illustrates the results of a competitive ELISA for S1P, SPH, LPA, SPC, and other structurally similar biolipids competing for a biotin-conjugated anti-S1P monoclonal antibody. These results indicate that the antibody is specific and sensitive for S1P and does not recognize structurally similar bioactive lipids. As described in Example 1, below, bound antibody was detected by a second antibody, specific for the mouse or human IgG, conjugated with HRP. Chromogenic reactions were measured and reported as optical density (OD). The concentration of lipids used for the competition is indicated on the X-axis. No interaction of the secondary antibody with S1P coated matrix alone could be detected (data not shown). Panel B shows the structures of the bioactive lipids similar to S1P that are listed in Panel A.

FIG. 4. FIG. 4 has two parts, A and B. The experiments giving rise to the data represented in this Figure are detailed in Example 4, below. Briefly, these data show that SPHINGOMAB reduced CNV and scar formation in ocular lesions. Mice were treated with SPHINGOMAB or an isotype-matched non-specific monoclonal antibody. CNV lesions were induced by laser rupture of Bruchs membrane. Shown are graphs and representative images of lesions from each treatment group stained with rhodamine-conjugated *R. communis* agglutinin I for vascularization (A) or Masson's Trichrome for collagen scar formation (B).

FIG. 5 has two panels, A and B. In panel A, S1P is shown to promote neovascularization through induction of HUVECs tube formation and migration, which is reduced by SPHINGOMAB. Panel 5A shows four micrographs of HUVECs seeded on Matrigel and incubated for 6 hr. to evaluate tube formation. Panel 5B shows data for HUVECs that were treated with 1 μM S1P±SPHINGOMAB (1 μg/ml) for 6 hr. in a Matrigel invasion chamber. The number of cells that migrated to the Matrigel membrane were counted in five independent fields.

FIG. 6. FIG. 6 contains several photographs (A) and graphs (B and C) for experiments described in Example, 6, below, which were performed using SPHINGOMAB. SPHINGOMAB neutralizes S1P-, VEGF- and bFGF-induced neovascularization.

FIG. 7 shows 5 graphs, labeled A-E, and two pcolor photos. This data was generated using the anti-S1P monoclonal antibody SPHINGOMAB. See Example 7, below, for experimental details. Briefly, these data show that SPHINGOMAB neutralizes S1P-stimulated scar formation. In these experiments, fibroblasts were serum-starved and then treated with 0, 0.1, 0.5, or 1 μM S1P+/−1 μg/mL SPHINGOMAB for 12-24 hr. The data show S1P-stimulated Swiss 3T3 fibroblast proliferation, as measured by 3H-thymidine incorporation (A), murine cardiac fibroblast migration in a scratch assay (B), collagen gene expression (relative fluorescence) in isolated cardiac fibroblasts from transgenic mice expressing collagen-GFP (C), and WI-38 cell differentiation into myofibroblasts as measured by decreased cellular proliferation and increased α-SMA expression (D). SPHINGOMAB neutralized each of these S1P effects. SPHINGOMAB reduced perivascular fibrosis in vivo in a murine model of a permanent myocardial infarction (E).

FIG. 8 has three panel, 8A, 8B, and 8C. These data show that S1P promotes transformation of ocular epithelial cells and fibroblasts into contractile, scar tissue-producing myofibroblasts. As described in Example 8, below, the effects of S1P on myofibroblast transformation of several human ocular cell lines were examined. S1P was found to stimulate production of α-Smooth muscle actin (α-SMA; a myofibroblast marker) in human retinal pigmented epithelial cells (FIG. 8A) and human conjunctiva fibroblasts (FIG. 8B). These data demonstrate, for the first time, that S1P is among the factors that promote transformation of ocular epithelial cells and fibroblasts into contractile, scar tissue-producing myofibroblasts. The effects of S1P on expression of plasminogen activator inhibitor (PAI-1) in human conjunctiva fibroblasts were also examined. Increased PAI-1 expression correlates with a decrease in the proteolytic degradation of connective tissue and is upregulated in association with several fibrotic diseases that involve increased scarring.

FIG. 9 shows two bar graphs, A and B, showing experimetnak1 data generated using an anti-S1P monoclonal antibody called SPHINGOMAB. SPHINGOMAB reduced immune-cell wound infiltration in vivo. Mice were subjected to MI, treated with saline or 25 mg/kg SPHINGOMAB 48 hr. after surgery and then sacrificed on day 4. SPHINGOMAB reduced macrophage (A) and mast cell (B) infiltration into the wound. Data are represented as fold decrease of saline-treated values.

FIG. 10 has two panels, 10A and 10B. Each panel show a map of a cloning vector for expression of murine anti-S1P monoclonal antibody $V_L$ and $V_H$ domains. FIG. 10A is a map of a pG1D200 vector for the cloning of the $V_H$ domain.

FIG. 11 presents data showing the binding properties of several murine, chimeric, and recombinant humanized anti-S1P antibodies. The binding to S1P for the mouse (muMAbS1P; curve generated from square data points) and chimeric (chMAb S1P; curve generated from upright triangular data points) were compared in an ELISA binding assay to the first version of the humanized antibody (pATH200+ pATH300; curve generated from inverted triangular data points).

FIG. 12 has two panels, A and B, that show data from in vitro cell assays performed using several humanized monoclonal antibody variants. Panel A shows the humanized mAb is able to prevent S1P from protecting SKOV3 cells from Taxol-induced apoptosis. As described in Example 16, below, SKOV3 cells were treated for 48 hr. with 500 nM Taxol (Tax) in the presence or absence of 500 nM S1P with huMAbHCLC$_3$ (309), huMAbHCLC$_5$ (308), muMAb S1P (muMAb), or non-specific IgG1 (NS) at a concentration of 1 μg/mL. Values represent means±SEM (n=3) with triplicates run for each data point. "NT" means not treated, and "Veh" stans for vehicle only. Panel B shows IL-8 secretion in ovarian cancer (OVCAR3) cells treated with S1P and one of several different the anti-S1P monoclonal antibodies or a control monoclonal antibody. In the experiments described in detail in Example 16, below, 100,000 OVCAR3 cells/well were starved overnight and 1 uM S1P was added to the culture media alone or pre-incubated with 1 ug/ml of non-specific antibody (NS), pATH201+pATH309 (LC3), pATH201+ pATH308 (LC5), pATH207+pATH309 (cysLC3), pATH207+pATH308 (cysLC5), and 0.1 ug/ml (M0.1), 1 ug/ml (M1) or 10 ug/ml (M10) of anti-S1P murine antibody. After 22 hours of incubation, cell supernatants were collected and IL-8 secretion was measured by ELISA using an R&D system Quantikine human CXCL8/IL-8 kit. In the figure "NT" refers to non-treated cells.

FIG. 13 shows the in vivo efficacy of several human monoclonal antibody variants as compared to a mouse anti-S1P monoclonal antibody and controls in a CNV animal model. As described in Example 17, below, in these experiments mice were administered with 0.5 ug twice (day 0 and day 6) of a murine (Mu) anti-S1P monoclonal antibody, several humanized anti-S1P monoclonal antibody variants (i.e., variants LC3, LC5, HCcysLC3, and HCcysLC5), or a non-specific monoclonal antibody (NS) by intravitreal administration and then subjected to laser rupture of the Bruch's membrane. Mice were sacrificed 14 days post-laser surgery. Sclera-RPE-choroid complexes were dissected and stained with a Rhodamine-conjugated *R. communis* agglutinin I antibody. CNV lesion volumes are represented as the means±SEM.

DETAILED DESCRIPTION OF THE INVENTION

Figure 1A:
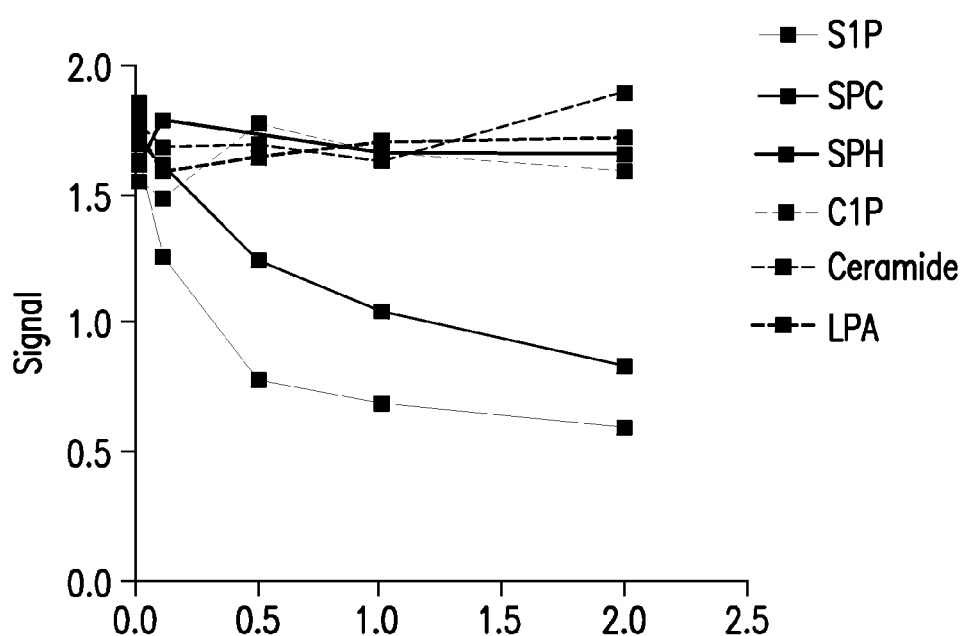
FIG. 1.

1. Compounds.

The present invention describes certain anti-S1P agents, particularly those that are immune-derived moieties, including antibodies, which are specifically reactive with the bioactive lipid S1P; in other words, the bioactive lipid to which the anti-S1P agent reacts is S1P.

Antibody molecules or immunoglobulins are large glycoprotein molecules with a molecular weight of approximately 150 kDa, usually composed of two different kinds of polypeptide chain. One polypeptide chain, termed the "heavy" chain (H) is approximately 50 kDa. The other polypeptide, termed the "light" chain (L), is approximately 25 kDa. Each immunoglobulin molecule usually consists of two heavy chains and two light chains. The two heavy chains are linked to each other by disulfide bonds, the number of which varies between the heavy chains of different immunoglobulin isotypes. Each light chain is linked to a heavy chain by one covalent disulfide bond. In any given naturally occurring antibody molecule, the two heavy chains and the two light chains are identical, harboring two identical antigen-binding sites, and are thus said to be divalent, i.e., having the capacity to bind simultaneously to two identical molecules.

The "light" chains of antibody molecules from any vertebrate species can be assigned to one of two clearly distinct types, kappa (k) and lambda (l), based on the amino acid sequences of their constant domains. The ratio of the two types of light chain varies from species to species. As a way of example, the average k to l ratio is 20:1 in mice, whereas in humans it is 2:1 and in cattle it is 1:20.

The "heavy" chains of antibody molecules from any vertebrate species can be assigned to one of five clearly distinct types, called isotypes, based on the amino acid sequences of their constant domains. Some isotypes have several subtypes. The five major classes of immunoglobulin are immunoglobulin M (IgM), immunoglobulin D (IgD), immunoglobulin G (IgG), immunoglobulin A (IgA), and immunoglobulin E (IgE). IgG is the most abundant isotype and has several subclasses (IgG1, 2, 3, and 4 in humans). The Fc fragment and hinge regions differ in antibodies of different isotypes, thus determining their functional properties. However, the overall organization of the domains is similar in all isotypes.

The term "variable region" refers to the N-terminal portion of the antibody molecule or a fragment thereof. In general, each of the four chains has a variable (V) region in its amino terminal portion, which contributes to the antigen-binding site, and a constant (C) region, which determines the isotype. The light chains are bound to the heavy chains by many noncovalent interactions and by disulfide bonds and the V regions of the heavy and light chains pair in each arm of antibody molecule to generate two identical antigen-binding sites. Some amino acid residues are believed to form an interface between the light- and heavy-chain variable domains [see Kabat, et al. (1991), Sequences of Proteins of Immunological Interest, Fifth Edition, National Institute of Health, Bethesda, Md. and Clothia et al. (1985), J. Mol. Biol, vol 186: 651].

Of note, variability is not uniformly distributed throughout the variable domains of antibodies, but is concentrated in three segments called "complementarity-determining regions" (CDRs) or "hypervariable regions" both in the light-chain and the heavy-chain variable domains. The more highly conserved portions of variable domains are called the "framework region" (FR). The variable domains of native heavy and light chains each comprise four FR regions connected by three CDRs. The CDRs in each chain are held together in close proximity by the FR regions and, with the CDRs from the other chains, form the antigen-binding site of antibodies [see Kabat, et al. (1991), Sequences of Proteins of Immunological Interest, Fifth Edition, National Institute of Health, Bethesda, Md.]. Collectively, the 6 CDRs contribute to the binding properties of the antibody molecule for the antigen. However, even a single variable domain (or half of an Fv, comprising only three CDRs specific for an antigen) has the ability to recognize and bind antigen [see Pluckthun (1994), in The Pharmacology of Monoclonal Antibodies, vol. 113, Rosenburg and Moore eds., Springer-Verlag, New York, pp. 269-315].

The term "constant domain" refers to the C-terminal region of an antibody heavy or light chain. Generally, the constant domains are not directly involved in the binding properties of an antibody molecule to an antigen, but exhibit various effector functions, such as participation of the antibody in antibody-dependent cellular toxicity. Here, "effector functions" refer to the different physiological effects of antibodies (e.g., opsonization, cell lysis, mast cell, basophil and eosinophil degranulation, and other processes) mediated by the recruitment of immune cells by the molecular interaction between the Fc domain and proteins of the immune system. The isotype of the heavy chain determines the functional properties of the antibody. Their distinctive functional properties are conferred by the carboxy-terminal portions of the heavy chains, where they are not associated with light chains.

As used herein, "antibody fragment" refers to a portion of an intact antibody that includes the antigen binding site or variable regions of an intact antibody, wherein the portion can be free of the constant heavy chain domains (e.g., CH2, CH3, and CH4) of the Fc region of the intact antibody. Alternatively, portions of the constant heavy chain domains (e.g., CH2, CH3, and CH4) can be included in the "antibody fragment". Examples of antibody fragments are those that retain antigen-binding and include Fab, Fab', F(ab')2, Fd, and Fv fragments; diabodies; triabodies; single-chain antibody molecules (sc-Fv); minibodies, nanobodies, and multispecific antibodies formed from antibody fragments. By way of example, a Fab fragment also contains the constant domain of a light chain and the first constant domain (CH1) of a heavy chain.

The term "variant" refers to an amino acid sequence which differs from the native amino acid sequence of an antibody by at least one amino acid residue or modification. A native or parent or wild-type amino acid sequence refers to the amino acid sequence of an antibody found in nature. "Variant" of the antibody molecule includes, but is not limited to, changes within a variable region or a constant region of a light chain and/or a heavy chain, including the hypervariable or CDR region, the Fc region, the Fab region, the CH1 domain, the CH2 domain, the CH3 domain, and the hinge region.

The term "specific" refers to the selective binding of an antibody to its target epitope. Antibody molecules can be tested for specificity of binding by comparing binding of the antibody to the desired antigen to binding of the antibody to unrelated antigen or analogue antigen or antigen mixture under a given set of conditions. Preferably, an antibody according to the invention will lack significant binding to unrelated antigens, or even analogs of the target antigen. Here, the term "antigen" refers to a molecule that is recognized and bound by an antibody molecule or immune-derived moiety that binds to the antigen. The specific portion of an antigen that is bound by an antibody is termed the "epitope." A "hapten" refers to a small molecule that can, under most circumstances, elicit an immune response (i.e., act as an antigen) only when attached to a carrier molecule, for example, a protein, polyethylene glycol (PEG), colloidal gold, silicone beads, and the like. The carrier may be one that also does not elicit an immune response by itself.

The term "antibody" is used in the broadest sense, and encompasses monoclonal, polyclonal, multispecific (e.g., bispecific, wherein each arm of the antibody is reactive with a different epitope or the same or different antigen), minibody, heteroconjugate, diabody, triabody, chimeric, and synthetic antibodies, as well as antibody fragments that specifically bind an antigen with a desired binding property and/or biological activity.

The term "monoclonal antibody" (mAb) refers to an antibody, or population of like antibodies, obtained from a population of substantially homogeneous antibodies, and is not to be construed as requiring production of the antibody by any particular method. For example, monoclonal antibodies can be made by the hybridoma method first described by Kohler and Milstein (1975), Nature, vol 256: 495-497, or by recombinant DNA methods.

The term "chimeric" antibody (or immunoglobulin) refers to a molecule comprising a heavy and/or light chain which is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity [Cabilly et al. (1984), infra; Morrison et al., Proc. Natl. Acad. Sci. U.S.A. 81:6851].

The term "humanized antibody" refers to forms of antibodies that contain sequences from non-human (eg, murine) antibodies as well as human antibodies. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins. For the most part, humanized antibodies are human immunoglobulins (recipient antibody) in which residues from a complementary-determining region (CDR) of the recipient are replaced by residues from a CDR of a non-human species (donor antibody) such as mouse, rat, camel, bovine, goat, or rabbit having the desired properties. Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1; Queen et al. (1989) Proc. Nat'l Acad. Sci. USA, vol 86:10029-10033).

The term "bispecific antibody" can refer to an antibody, or a monoclonal antibody, having binding properties for at least two different epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. Alternatively, bispecific antibodies can be prepared using chemical linkage. Bispecific antibodies include bispecific antibody fragments.

The term "heteroconjugate antibody" can refer to two covalently joined antibodies. Such antibodies can be prepared using known methods in synthetic protein chemistry, including using crosslinking agents. As used herein, the term "conjugate" refers to molecules formed by the covalent attachment of one or more antibody fragment(s) or binding moieties to one or more polymer molecule(s).

The term "biologically active" refers to an antibody or antibody fragment that is capable of binding the desired epitope and in some way exerting a biologic effect. Biological effects include, but are not limited to, the modulation of a growth signal, the modulation of an anti-apoptotic signal, the modulation of an apoptotic signal, the modulation of the effector function cascade, and modulation of other ligand interactions.

The term "recombinant DNA" refers to nucleic acids and gene products expressed therefrom that have been engineered, created, or modified by man. "Recombinant" polypeptides or proteins are polypeptides or proteins produced by recombinant DNA techniques, for example, from cells transformed by an exogenous DNA construct encoding the desired polypeptide or protein. "Synthetic" polypeptides or proteins are those prepared by chemical synthesis.

The term "expression cassette" refers to a nucleotide molecule capable of affecting expression of a structural gene (i.e., a protein coding sequence, such as an antibody of the invention) in a host compatible with such sequences. Expression cassettes include at least a promoter operably linked with the polypeptide-coding sequence, and, optionally, with other sequences, e.g., transcription termination signals. Additional regulatory elements necessary or helpful in effecting expression may also be used, e.g., enhancers. Thus, expression cassettes include plasmids, expression vectors, recombinant viruses, any form of recombinant "naked DNA" vector, and the like.

Sources of antibody are not limited to those exemplified herein (e.g., murine and humanized murine antibody). Antibodies may be raised in many species including mammalian species (for example, mouse, rat, camel, bovine, goat, horse, guinea pig, hamster, sheep and rabbit) and birds (duck, chicken). Antibodies raised may derive from a different species from the animal in which they are raised. For example, the XenoMouse™ (Abgenix, Inc., Fremont Calif.) produces fully human monoclonal antibodies. For certain purposes, native human antibodies, such as autoantibodies to S1P isolated from individuals who may show a titer of such S1P autoantibody may be used. Alternatively, a human antibody sequence library may be used to generate antibodies comprising a human sequence.

2. Applications.

The invention is drawn to compositions and methods for treating or preventing certain diseases and conditions, using one or more therapeutic agents that alter the activity or concentration of one or more undesired bioactive lipids, or precursors or metabolites thereof. The therapeutic methods and compositions of the invention act by changing the effective concentration, i.e., the absolute, relative, effective and/or available concentration and/or activities, of certain undesired bioactive lipids. Lowering the effective concentration of the bioactive lipid may be said to "neutralize" the target lipid or its undesired effects, including downstream effects. Here, "undesired" refers to a bioactive lipid that is unwanted due to its involvement in a disease process, for example, as a signaling molecule, or to an unwanted amount of a bioactive lipid which contributes to disease when present in excess.

Without wishing to be bound by any particular theory, it is believed that inappropriate concentrations of S1P and/or its metabolites or downstream effectors, may cause or contribute to the development of various diseases and disorders. As such, the compositions and methods can be used to treat these diseases and disorders, particularly by decreasing the effective in vivo concentration of a particular target lipid, for example, S1P or its variants. In particular, it is believed that the compositions and methods of the invention are useful in treating diseases characterized, at least in part, by aberrant neovascularization, angiogenesis, fibrogenesis, fibrosis, scarring, inflammation, and immune response.

Examples of several classes of diseases that may be treated in accordance with the invention are described below. It will be appreciated that many disease and conditions are characterized, at least in part, by multiple pathological processes (for example, both pathological neovascularization and scarring) and that the classifications provided herein are for descriptive convenience and do not limit the invention.

S1P and Hyperproliferative Disorders

One aspect of the invention concerns methods for treating a hyperproliferative disorder. These methods comprise administering to a mammal (e.g., a bovine, canine, equine, ovine, or porcine animal, particularly a human) known or suspected to suffer from an S1P-associated hyperproliferative disorder a therapeutically effective amount of a composition comprising an agent that interferes with S1P activity, preferably in a pharmaceutically or veterinarily acceptable carrier, as the intended application may require. S1P-associated hyperproliferative disorders include neoplasias, disorder associated with endothelial cell proliferation, and disorders associated with fibrogenesis. Most often, the neoplasia will be a cancer. Typical disorders associated with endothelial cell proliferation are angiogenesis-dependent disorders, for example, cancers caused by a solid tumors, hematological tumors, and age-related macular degeneration. Disorders associated with fibrogenesis include those than involve aberrant cardiac remodeling, such as cardiac failure.

There are many known hyperproliferative disorders, in which cells of various tissues and organs exhibit aberrant patterns of growth, proliferation, migration, signaling, senescence, and death. While a number of treatments have been developed to address some of these diseases, many still remain largely untreatable with existing technologies, while in other cases, while treatments are available, they are frequently less than optimal and are seldom curative.

Cancer represents perhaps the most widely recognized class of hyperproliferative disorders. Cancers are a devastating class of diseases, and together, they have a mortality rate second only to cardiovascular disease. Many cancers are not fully understood on a molecular level. As a result, cancer is a major focus of research and development programs for both the United States government and pharmaceutical companies. The result has been an unprecedented R&D effort and the production of many valuable therapeutic agents to help in the fight against cancer.

Unfortunately the enormous amount of cancer research has not been enough to overcome the significant damage caused by cancer. There are still over one million new cases of cancer diagnosed annually and over five hundred thousand deaths in the United States alone. This is a dramatic demonstration that even though an enormous effort has been put forth to discover new therapeutics for cancer, effective therapeutic agents to combat the disease remain elusive.

Cancer is now primarily treated with one or a combination of three types of therapies, surgery, radiation, and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication or cell metabolism.

Further insult is that current therapeutic agents usually involve significant drawbacks for the patient in the form of toxicity and severe side effects. Therefore, many groups have recently begun to look for new approaches to fighting the war against cancer. These new so-called "innovative therapies" include gene therapy and therapeutic proteins such as monoclonal antibodies.

The first monoclonal used in the clinic for the treatment of cancer was Rituxan (rituximab) which was launched in 1997, and has demonstrated the utility of biospecific monoclonal antibodies as therapeutic agents. Thus, not surprisingly, sixteen other monoclonal antibodies have since been approved for use in the clinic, including six that are prescribed for cancer. The success of these products, as well as the reduced cost and time to develop monoclonal antibodies as compared with small molecules has made monoclonal antibody therapeutics the second largest category of drug candidates behind small molecules. Further, the exquisite specificity of antibodies as compared to small molecule therapeutics has proven to be a major advantage both in terms of efficacy and toxicity. For cancer alone there are currently more than 270 industry antibody R&D projects with more than 50 companies involved in developing new cancer antibody therapeutics. Consequently, monoclonal antibodies are poised to become a major player in the treatment of cancer and they are estimated to capture an increasing share of the cancer therapeutic market.

The identification of extracellular mediators that promote tumor growth and survival is a critical step in discovering therapeutic interventions that will reduce the morbidity and mortality of cancer. As described below, sphingosine-1-phosphate (S1P), a key component of sphingolipid signaling cascade, is considered to be a pleiotropic, tumorigenic growth factor. S1P promotes tumor growth by stimulating cell proliferation, cell survival, and metastasis. S1P also promotes tumor angiogenesis by supporting the migration and survival of endothelial cells as they form new vessels within tumors. Taken together, S1P initiates a proliferative, pro-angiogenic, and anti-apoptotic sequence of events contributing to cancer progression. Thus, therapies that modulate, and, in particular, reduce S1P levels in vivo will be effective in the treatment of cancer.

Research has demonstrated that sphingosine kinase (SPHK) is a recently validated oncogene that produces an extracellular sphingolipid signaling molecule, sphingosine-1-phosphate (S1P) that promotes tumor growth. Tumor growth is promoted both directly and indirectly by S1P's growth factor actions related to tumor cell proliferation and metastasis, as well as S1P's pro-angiogenic effects. The applicant has produced a biospecific monoclonal anti-S1P antibody (anti-S1P mAb) that could be used as a therapeutic molecular sponge to selectively absorb S1P, thus lowering extracellular concentrations of this tumor growth factor with the anticipated reduction in tumor volume and metastatic potential as well as simultaneously blocking new blood vessel formation that would, otherwise, feed the growing tumor. The anticipated success of the molecular absorption concept will represent an innovative approach to the treatment of cancer. As the paragraphs below will demonstrate, the applicant has developed a mAb against an important tumor growth factor, sphingosine-1-phosphate (S1P). The applicant believes that this antibody can be effective in reduced the proliferation, metastatic potential and angiogenesis associated with many cancer types, and therefore, cancer in general as well as the tumor angiogenesis that accompanies the disease.

The neutral form of sphingomyelinase (nSMase) is a key early component of the sphingolipid signaling pathway (Chatterjee, Adv. Lipid Res. 26: 25-46, 1993; Liu, Obein, and Hannun, Semin. Cell Dev. Biol. 8: 311-322, 1997) nSMase is only one of at least five classes of SMase that have been identified, including the alkaline, the acidic, the acidic zinc-dependent, the neutral magnesium-dependent, and the neutral magnesium-independent (Liu, Obein, and Hannun, Semin. Cell Dev. Biol. 8: 311-322, 1997). The nSMase class is commonly associated with surface membranes (Das, Cook, and Spence, Biochim Biophys Acta 777: 339-342, 1984; Dobrowsky, Cell Signal 12: 81-90., 2000) and can be activated by a variety of stimuli to cause apoptosis, such as the pro-inflammatory cytokine, tumor necrosis factor alpha (TNFα) (Ségui, et al., J. Clin. Invest. 108: 143-151, 2001), T cell receptor (Tonnetti, et al., J. Exp. Med. 189: 1581-1589, 1999), ionizing radiation (Haimovitz-Friedman, et al., J. Exp. Med. 180: 525-535, 1994) and the anthracycline anti-neoplastic agents (Andrieu-Abadie, et al., FASEB J. 13: 1501-1510, 1999). Tumor necrosis factor alpha (TNFα) is a well-known activator of nSMase (Adam, et al., J. Bio Chem 271: 14617-14622, 1996; Dressler, Mathias, and Kolesnick, Science 255: 1715-1718, 1992; Kim, et al., J. Biol. Chem. 266:1: 484-489, 1991; Kronke, Chem Phys Lipids 102: 157-66., 1999; Yanaga and Watson, FEBS Letters 314: 297-300, 1992), CER production (Kronke, Chem Phys Lipids 102: 157-66., 1999) and apoptosis (Rath and Aggarwal, J. Clin. Immuno. 19: 350-364, 1999; Robaye, et al., Am J Pathol 138: 447-453, 1991; Takeda et al., Int. Immunol. 5: 691-694, 1993) in many cell types, including cancer cell lines (Andrieu-Abadie, et al., FASEB J. 13: 1501-1510, 1999; Hannun and Obein, Trends in Biol. Sci. 20: 72-76, 1995; Kolesnick, trends Biochem Sci 24: 224-5, 1999; Obeid, et al., Science 259: 1769-1771, 1993), and the activation of nSMase has been shown to be critical for TNFα induced apoptosis (Luberto, et al., J. Biol. Chem. 277: 41128-41139, 2002; Ségui, et al., J. Clin. Invest. 108: 143-151, 2001). As a consequence, nSMase has also been proposed as a target for drug discovery (Wascholowski and Giannis, Drug News Perspect. 14: 581-90, 2001).

The sphingolipid signaling molecule, S1P, is produced from SPH through the action of sphingosine kinase (SPHK). Two isoforms of the kinase have been identified, SPHK1 and SPHK2 (Liu, J Biol Chem 275: 19513-20, 2000; Nava, et al., Exp Cell Res 281: 115-127, 2002). While CER and SPH are commonly associated with apoptosis, conversely S1P is a mediator of cell proliferation and activation of survival pathways (An, Ann N Y Acad Sci 905: 25-33, 2000; Maceyka, et al., BBA 1585: 193-201, 2002; Zhang, et al., J. Cell Biol. 114: 155-167, 1991). It has recently been appreciated as an extracellular mediator that can activate a set of G Protein Coupled Receptors (GPCRs) belonging to the S1P/LPA receptor family, formerly known as Edg receptors (An, Ann N Y Acad Sci 905: 25-33, 2000; An, Goetzl, and Lee, J. cell biochem 30/31: 147-157, 1998; Lee, et al., Science 279: 1552-1555, 1998; Okamoto, et al., Biochem. Biophys. Res. Commun. 260: 203-208, 1999); however, intracellular actions of S1P have also been suggested (Van Brocklyn, et al., J. Cell Biol. 142: 229-240, 1998). Moreover, it has been suggested that the balance between CER/SPH levels versus S1P provides a rheostat mechanism that decides whether a cell is sent into the death pathway or is protected from apoptosis (Kwon, et al., J Biol Chem 276: 10627-10633, 2001; Maceyka, et al., BBA 1585: 193-201, 2002; Pyne, Biochem J. 349: 385-402, 2000). The key regulatory enzyme of the rheostat mechanism is SPHK whose role is to convert the death-promoting sphingolipids (CER/SPH) in to the growth-promoting S1P.

A landmark study first proposing SPHK as an oncogene was published by a group from Adelaide demonstrating that NIH-3T3 fibroblasts stably transfected with the kinase exhibited enhanced cell proliferation accompanied by increased S1P production (Vadas and Gamble, Circ. Res. 79: 1216-1217, 1996; Xia et al., Curr Biol 10: 1527-1530, 2000). In addition, the SPHK over-expressers escaped contact inhibition, a property commonly exhibited by transformed cells. This observation is consistent with a recent report showing that S1P enhances metastatic potential of selected human cancer cell lines (Igarashi, Ann. N.Y. Acad. Sci. 845: 19-31, 1998; Takuwa, Biochim Biophys Acta. 1582: 112-120, 2002). Moreover, the transfectants produced tumors when injected subcutaneous into NOD/SCID mice. These results were recently confirmed in a study showing that a small molecule inhibitor of SPHK given i.p. could reduce tumor volume in SCID mice receiving subcutaneous injections of JC mammary adenocarcinoma cells (French, et al., Cancer Res 63: 5962-5969, 2003). Significantly, the concept that SPHK could be a novel oncogene was cemented by the finding that SPHK was over-expressed in many solid tumors, such as those of the breast, colon, lung, ovary, stomach, uterus, kidney, and rectum (French et al. (2003), above). In addition, it has been demonstrated that several human tumor-derived cell lines could be driven into apoptosis when treated with the SPHK small molecule inhibitors, and that their effectiveness could be accounted for by their abilities to reduce S1P levels. Taken together, these findings demonstrate an important concept that S1P is a growth factor likely produced by tumor cells themselves and that lowering the concentration of S1P may cause the apoptosis seen upon growth factor withdrawal.

S1P and Tumor Angiogenesis

Angiogenesis is the process by which new blood vessels are formed from existing vasculature. Angiogenesis plays a critical role in several physiological processes and is implicated in the pathogenesis of a variety of disorders, including tumor growth, invasion and metastasis. The angiogenesis process associated with solid and circulating tumors (tumor angiogenesis) is considered to be a crucial component of tumorigenesis and disease progression, with the new blood vessels providing a growth advantage to tumor cells compared to non-cancerous cells. Therefore, clinical control of angiogenesis is a critical component for the treatment of cancer and other angiogenesis-dependent diseases. Anti-angiogenic therapeutics is particularly attractive because vascular endothelial cells (ECs) do not mutate as easily as do cancer cells; consequently, ECs are less likely than cancer cells to gain resistance to prolonged therapy, making them good potential targets for therapeutics.

Several growth factors have been implicated in cancerous angiogenesis. The biolipid sphingosine-1-phosphate (S1P) was found to be a mediator of many cellular processes important for cancer. S1P exerts most of its effects as a specific ligand for a family of G-protein-coupled receptors, designated $S1P_{1-5}$. These receptors regulate angiogenesis and vascular maturation, cell movement, and lymphocyte trafficking.

In contrast to S1P, the precursors to S1P, sphingosine and ceramide, have been associated with growth arrest and apoptosis. Finally, there is a complex cross-talk between S1P and other pro-angiogenic growth factors such as VEGF, EGF, PDGF, bFGF and IL-8. S1P, by binding to receptor $S1P_1$, transactivates growth factor receptor tyrosine kinase, such as that found on VEGFR, EGFR, and PDGFR. The importance of S1P in the angiogenesis-dependent tumors makes S1P an exceptional target for cancer treatment. Based on these observations, an antibody approach to neutralize the extracellular S1P could result in a marked decrease in cancer progression in humans as a result of inhibition of blood vessel formation with concomitant loss of the nutrients and oxygen needed to support tumor growth. Furthermore, recent research suggests that many angiogenesis inhibitors may also act as anti-invasive and anti-metastatic compounds which could also aid in the mitigation of the spread of cancer to sites distant from the initial tumor.

A growing body of recent evidence implicating S1P as one of the most potent pro-angiogenic agents comes from studies directly comparing S1P with agents such as VEGF and bFGF. S1P stimulates DNA synthesis and chemotactic motility of human venous endothelial cells (HUVECs), while inducing differentiation of multicellular structures, all of which is suggestive of S1P's role in early blood-vessel formation (Argraves, et al., 2004; Lee et al., 1999; Liu, et al., 2000). Also, S1P promotes the migration of bone marrow-derived EC precursors to neovascularization sites (Annabi, et al., 2003). Cells that over-express S1P, are resistant to the anti-angiogenic agents thalidomide and Neovastat (Annabi et al., 2003). In addition, it has been demonstrated that substantial cross-talk exists between S1P and other pro-angiogenic growth factors such as VEGF, EGF, PDGF, bFGF and IL-8. For example, S1P transactivates EGF (Shida, et al., 2004) and VEGF2 receptors (Spiegel & Milstien, 2003), and VEGF up-regulates S1P, receptor expression (Igarashi, et al., 2003). Also, S1P, acting via S1P and the "VEGF axis," is required for hind-limb angiogenesis and neovascularization (Chae, et al., 2004).

The anti-angiogenic approach to cancer has been greatly advanced by the recent FDA approval of the anti-angiogenic drug, bevacizumab (Avastin®, Genentech) to treat colon cancer as an adjunct to cytotoxic chemotherapy.

An anti-S1P murine MAb, LT1002 was developed recently with high binding affinity and specificity to S1P. LT1002 was shown to significantly slow tumor progression and associated angiogenesis in several animal models of human cancer. In addition, LT1002 attenuated choroidal neovascularization (CNV) lesion formation in the well-established model of angiogenesis for age-related macular degeneration (AMD). CNV occurs in diseases in which there are abnormalities of Bruch's membrane and the retinal pigmented epithelium. The most common disease of this type is AMD, the most prevalent cause of severe loss of vision in elderly patients. These results suggested that LT1002 has several mechanisms of action, including: (1) direct effects on tumor cell growth, (2) an indirect anti-angiogenic effect on vascular endothelia cells, and (3) an indirect anti-angiogenic effect of preventing the release and action of other pro-angiogenic growth factors.

The most direct in vivo evidence that S1P contributes to tumor angiogenesis comes from our recent publication that focused on a murine monoclonal antibody (mAb) designed to neutralize extracellular S1P by molecular absorption (Visentin, et al., 2006). In various in vitro assays using HUVECs, the anti-S1P mAb neutralized tube formation, migration of vascular endothelial cells and protection from cell death, each of which is S1P-induced. S1P increased new capillary growth into Matrigel plugs implanted in mice, an effect that was neutralized by the systemic administration of the anti-S1P mAb. The mAb substantially neutralized bFGF- and VEGF-induced angiogenesis in a murine Matrigel plug assay, and the antibody mitigated S1P stimulated the release of pro-angiogenic cytokines (VEGF, IL-8, IL-6) from tumor cells in vitro and in vivo. Importantly, mice xenografted with orthotopically-placed human cancer cells exhibited substantial retardation of tumor progression with anti-S1P mAb treatment. This was demonstrated in murine models of human breast, ovarian and lung cancer and in one allograft model of murine melanoma (Visentin, et al., 2006).

The use of monoclonal antibodies (mAbs) as a therapeutic treatment for a variety of diseases and disorders is rapidly increasing because they have been shown to be safe and efficacious therapeutic agents. Approved therapeutic mAbs include Avastin®, Erbitux®, and Rituxan®. Additional mAbs are in various phases of clinical development for a variety of diseases with the majority targeting various forms of cancer. In general, monoclonal antibodies are generated in non-human mammals. The therapeutic utility of murine monoclonal antibodies is limited, however, principally due to the fact that human patients mount their own antibody response to murine antibodies. This response, the so-called HAMA (human anti-mouse antibody) response, results in the eventual neutralization and rapid elimination of murine mAbs. This limitation has been overcome with the development of a process called "humanization" of murine antibodies. Humanization greatly lessens the development of an immune response against the administered therapeutic MAb and thereby avoids the reduction of half-life and therapeutic efficacy consequent on HAMA. For the most part, the humanization process consists of grafting the murine complementary determining regions (CDRs) into the framework region (FR) of a human immunoglobulin. This strategy is referred to as "CDR grafting". "Backmutation" to murine amino acid residues of selected residues in the human FR is often required to regain affinity that is lost in the initial grafted construct.

The manufacture of mAbs is a complex process that stems from the variability of the protein itself. The variability of mAbs can be localized to the protein backbone and/or to the carbohydrate moiety. The heterogeneity can be attributed to the formation of alternative disulfide pairings, deamidation and the formation of isoaspartyl residues, methionine and cysteine oxidation, cyclization of N-terminal glutamine residues to pyroglutamate and partial enzymatic cleavage of C-terminal lysines by mammalian carboxypeptidases. Engineering is commonly applied to antibody molecules to improve their properties, such as enhanced stability, resistance to proteases, aggregation behavior and enhance the expression level in heterologous systems.

Here, the humanization of the murine MAb against S1P is described. The overall strategy consisted of grafting the six CDRs from LT1002 into a human framework. Further modifications were engineered to further refine and optimize the antibody performance. The humanized MAb presented the same characteristics as the LT1002 and is thus suitable for testing in clinical trials.

S1P and Fibrosis

Fibroblasts, particularly myofibroblasts, are key cellular elements in scar formation in response to cellular injury and inflammation [Tomasek, et al. (2002), Nat Rev Mol Cell Biol, vol 3: 349-63, and Virag and Murry (2003), Am J Pathol, vol 163: 2433-40]. Collagen gene expression by myofibroblasts is a hallmark of remodeling and necessary for scar formation [Sun and Weber (2000), Cardiovasc Res, vol 46: 250-6, and Sun and Weber (1996), J Mol Cell Cardiol, vol 28: 851-8]. S1P promotes wound healing by activating fibroblast migration and proliferation while increasing collagen production [Sun, et al. (1994), J Biol Chem, vol 269: 16512-7]. S1P produced locally by damaged cells could be responsible for the maladaptive wound healing associated with remodeling and scar formation. Thus it is believed that S1P inhibitors are useful in diseases or conditions characterized, at least in part, by aberrant fibrogenesis or fibrosis. Herein, "fibrogenesis" is defined as excessive activity or number of fibroblasts, and "fibrosis" is defined as excessive activity or number of fibroblasts that leads to excessive or inappropriate collagen production and scarring, destruction of the physiological tissue structure and/or inappropriate contraction of the matrix leading to such pathologies as retinal detachment or other processes leading to impairment of organ function.

S1P and fibroblast collagen expression: S1P promotes the differentiation of quiescent fibroblasts to active myofibroblasts which exhibit enhanced collagen expression during scar formation [Urata, et al. (2005), Kobe J Med Sci, vol 51: 17-27]. Concurrent with the proliferation and migration of fibroblasts into the scarring zone, myofibroblasts deposit a temporary granular network consisting primarily of osteopontin and fibronectin [Sun and Weber (2000), Cardiovasc Res, vol 46: 250-6]. As remodeling proceeds, the temporary matrix is absorbed and a collagen network established [Sun and Weber (2000), Cardiovasc Res, vol 46: 250-6]. We have demonstrated that S1P promotes collagen production by myofibroblasts. TGFβ, a well-known fibrotic mediator, has been shown to up-regulate several pro-fibrotic proteins, convert fibroblasts to myofibroblasts and stimulate inflammatory protein expression possibly through the action of S1P [Squires, et al. (2005), J Mol Cell Cardiol, vol 39: 699-707 and Butt, Laurent and Bishop (1995), Eur J Cell Biol, vol 68: 330-5]. Up-regulation of TIMP1, a signaling molecule implicated in TGFβ-stimulated differentiation of fibroblasts to myofibroblasts, is blocked by siRNA against SPHK1 [Yamanaka, et al., J Biol. Chem. 2004 Dec. 24; 279(52):53994-4001], suggesting that a humanized version of the anti-S1P antibody could mitigate the profibrotic effects of TGFβ as well as mitigating the fibrogenic effects of S1P itself.

Minimizing maladaptive scarring is believed to be useful in treatment of fibrotic diseases and conditions, including but not limited to ocular and cardiovascular diseases, wound healing, and scleroderma.

Anti-S1P Antibodies for the Treatment of Scleroderma

The compositions and methods of the invention will be useful in treating disorders and diseases characterized, at least in part, by aberrant neovascularization, angiogenesis, fibrogenesis, fibrosis, scarring, inflammation, and immune response. One such disease is scleroderma, which is also referred to as systemic sclerosis.

Scleroderma is an autoimmune disease that causes scarring or thickening of the skin, and sometimes involves other areas of the body, including the lungs, heart, and/or kidneys. Scleroderma is characterized by the formation of scar tissue (fibrosis) in the skin and organs of the body, which can lead to thickening and firmness of involved areas, with consequent reduction in function. Today, about 300,000 Americans have scleroderma, according to the Scleroderma Foundation. One-third or less of those affected have widespread disease, while the remaining two-thirds primarily have skin symptoms. When the disease affects the lungs and causing scarring, breathing can become restricted because the lungs can no longer expand as they should. To measure breathing capability, doctors use a device that assesses forced vital capacity (FVC). In people with an FVC of less than 50 percent of the expected reading, the 10-year mortality rate from scleroderma-related lung disease is about 42 percent. One reason the mortality rate is so high is that no effective treatment is currently available.

As described in the examples of this application, existing evidence indicates that S1P is a pro-fibrotic growth factor that can contribute to fibroblast activation, proliferation, and the resulting increased fibroblast activity associated with maladaptive scarring and remodeling. Moreover, potential roles for S1P in activity of skin and other types of fibroblasts have been demonstrated. For example, it has been shown that bioactive lipids stimulate the migration of murine skin fibroblasts (Hama, et al., J Biol Chem. 2004 Apr. 23; 279(17): 17634-9), and human skin fibroblasts express several S1P receptor subtypes (Zhang, et al., Blood. 1999 May 1; 93(9): 2984-90). In addition to the many direct effects of S1P on fibroblast activity, S1P also may have many potential indirect effects on fibroblast activity. For example, S1P may facilitate the action of other well-known pro-fibrotic factors, such as TGF-β and platelet derived growth factor (PDGF). TGF-β is one of the most widely studied and recognized contributors to fibrosis (Desmouliere, et al., J Cell Biol 122: 103-111, 1993). TGF-β upregulates SphK1 expression and activity leading to increased expression of tissue inhibitors of metalloproteinases 1 (TIMP-1), a protein that inhibits ECM degradation (Yamanaka, et al., J Biol Chem 279: 53994-54001, 2004). Increased expression of TIMP-1 is linked to interstitial fibrosis and diastolic dysfunction in heart failure patients (Heymans, et al., Am J Pathol 166: 15-25, 2005). Conversely, S1P stimulates expression and release of TGF-β (Norata, et al., Circulation 111: 2805-2811, 2005). There is also distinct evidence of crosstalk between S1P and PDGF. S1P directly stimulates expression of PDGF (Usui, et al., J Biol Chem 279: 12300-12311, 2004). In addition, the $S1P_1$ receptor and the PDGF receptor bind one another and their association is necessary for PDGF activation of downstream signaling which contributes to proliferation and migration of various cell types (Long, et al., Prostaglandins Other Lipid Mediat 80: 74-80, 2006; Baudhuin et al., Faseb J 18: 341-343, 2004). As such, the effects of TGF-β and PDGF on fibrosis may be due in part to crosstalk with the S1P signaling pathway. As such, the compositions and methods of the invention can be used to treat scleroderma, particularly by decreasing the effective in vivo concentration of a particular target lipid, for example, S1P.

Systemic scleroderma is thought to be exacerbated by stimulatory autoantibodies against PDGF receptors (Baroni, et al., N Engl J Med. 2006 v354(25):2667-76), and PDGF receptors are up-regulated in scleroderma fibroblasts in response to TGF-β (Yamakage, et al., J Exp Med. 1992 May 1; 175(5):1227-34). Because of the substantial cross-talk among the S1P, PDGF and TGF-β signaling systems, blocking S1P bioactivity with and anti-S1P agent (e.g., an anti-S1P mAb) could indirectly mitigate the pro-sclerotic effects of PDGF and TGF-β. Moreover, treatment with such an anti-S1P agent could benefit scleroderma patients by mitigating the direct effects of S1P on skin and other forms of fibroblasts that contribute to disease progression.

S1P and Ocular Diseases and Conditions

Pathologic or aberrant angiogenesis/neovascularization, aberrant remodeling, fibrosis and scarring and inflammation occur in association with retinal and ocular diseases such as age-related macular degeneration (AMD), diabetic retinopathy (DR), and in retinopathy of prematurity (ROP) and other developmental disorders [Eichler, et al. (2006), Curr Pharm Des, vol 12: 2645-60], as well as being a result of infections and mechanical injury to the eye [Ciulla, et al. (2001), Curr Opin Opthalmol, vol 12: 442-9 and Dart et al (2003), Eye, vol 17: 886-92]. It is believed that antibodies against S1P will be useful in treating ocular diseases for which pathologic or aberrant angiogenesis/neovascularization, aberrant remodeling, fibrosis, and scarring or inflammation are a component.

Angiogenesis/Neovascularization of the Eye:

Pathologic ocular angiogenesis is a leading cause of blindness in a variety of clinical conditions. Choroidal neovascularization (CNV) occurs in a number of ocular diseases, the most prevalent of which is the exudative or "wet" form of AMD. As a result of an increasingly aged population, AMD is a modern day epidemic and the leading cause of blindness in the western world in patients over age 60. Despite the epidemic of vision loss caused by AMD, only a few therapies, mostly anti-VEGF based, can slow the progression of AMD and even fewer can reverse vision loss [Bylsma and Guymer (2005), Clin Exp Optom., vol 88: 322-34, Gryziewicz (2005), Adv Drug Deliv Rev, vol 57: 2092-8, and Liu and Regillo (2004), Curr Opin Opthalmol, vol 15: 221-6.]. Therefore, discovering new treatments for pathologic neovascularization is extremely important.

AMD is used here solely for illustrative purposes in describing ocular conditions relating to aberrant angiogenesis/neovascularization, aberrant remodeling, fibrosis and scarring, and inflammation, which conditions are found in other ocular diseases and disorders as disclosed and claimed herein. AMD involves age-related pathologic changes [Tezel, Bora, and Kaplan (2004), Trends Mol Med, vol 10: 417-20 and Zarbin (2004), Arch Opthalmol, 122: 598-614]. Multiple theories exist but, the exact etiology and pathogenesis of AMD are still not well understood. Aging is associated with cumulative oxidative injury, thickening of Bruch's membrane and drusen formation. Oxidative stress results in injury to retinal pigment epithelial (RPE) cells and, in some cases, the choriocapillaris [Zarbin (2004), Arch Opthalmol, vol 122: 598-614, and Gorin, et al. (1999), Mol Vis., vol 5: 29]. Injury to RPE likely elicits a chronic inflammatory response within Bruchs membrane and the choroid [Johnson et al. (2000), Exp Eye Res., vol 70: 441-9]. This injury and inflammation fosters and potentates retinal damage by stimulating CNV and atrophy [Zarbin (2004), Arch Opthalmol, vol 122: 598-614, and Witmer, et al. (2003), Prog Retin Eye Res, vol 22: 1-29]. CNV results in defective and leaky blood vessels (BV) that are likely to be recognized as a wound [Kent and Sheridan (2003), Mol Vis, vol 9: 747-55]. Wound healing arises from the choroid and invades the subretinal space through Bruchs membrane and the RPE. Wound healing responses are characterized by a typical early inflammation response, a prominent angiogenic response and tissue formation followed by end-stage maturation of all involved elements. Wound remodeling may irreversibly compromise photoreceptors and RPEs thereby, justifying the need to treat CNV with more than anti-angiogenic therapies [La Cour, Kiilgaard, and Nissen (2002), Drugs Aging, vol 19: 101-33.12].

Alterations in the normal retinal and sub-retinal architecture as a result of CNV related fibrosis, edema and inflammation individually or cumulatively, leads to AMD related visual loss [Tezel and Kaplan (2004), Trends Mol Med, vol 10: 417-20, and Ambati, et al. (2003), Surv Opthalmol, vol 48: 257-93]. The multiple cellular and cytokine interactions which are associated with exudative AMD greatly complicate the search for effective treatments. While CNV and edema are manageable in part by anti-VEGF therapeutics, potential treatments to mitigate scar formation and inflammation have not been adequately addressed [Bylsma and Guymer (2005), Clin Exp Optom, vol 88: 322-34, and Pauleikhoff (2005), Retina, vol 25: 1065-84]. As long as the neovascular complex remains intact, as appears to be the case in patients treated with anti-VEGF agents, the potential for subretinal fibrosis and future vision loss persists.

Anti-VEGF-A therapies represent a recent, significant advance in the treatment of exudative AMD. However, the phase III VISION Trial with PEGAPTANIB, a high affinity aptamer which selectively inhibits the 165 isoform of VEGF-A, demonstrated that the average patient continues to lose vision and only a small percent gained vision [Gragoudas, et al. (2004), N Engl J Med, vol 351: 2805-16]. Inhibition of all isoforms of VEGF-A (pan-VEGF inhibition) with the antibody fragment RANIBIZUMAB yielded much more impressive results [Brown, et al., N Eng Med (2006), vol. 355:1432-44, Rosenfeld, et al. N Eng J Med (2006), vol. 355:1419-31]. The 2 year MARINA trial and the 1 year ANCHOR trial demonstrated that approximately 40% of patients achieve some visual gain. Although these results represent a major advance in our ability to treat exudative AMD, they also demonstrate that 60% of patients do not have visual improvement. Furthermore, these patients had to meet strictly defined inclusion and exclusion criteria. The results in a larger patient population may be less robust.

There is still a well-defined need to develop further therapeutic agents that target other steps in the development of CNV and the processes that ultimately lead to photoreceptor destruction. First, the growth of choroidal BVs involves an orchestrated interaction among many mediators, not just VEGF, offering an opportunity to modulate or inhibit the entire process [Gragoudas, et al. (2004), N Engl J Med, vol 351: 2805-16]. Second, exudative AMD is comprised of vascular and extravascular components. The vascular component involves vascular endothelial cells (EC), EC precursors and pericytes. The extravascular component, which volumetrically appears to be the largest component, is composed of inflammatory, glial, and retinal pigment epithelium (RPE) cells and fibroblasts. Tissue damage can result from either component. These other aspects of the pathologic process are not addressed by current anti-VEGF treatments. Targeting additional elements of the angiogenic cascade associated with AMD could provide a more effective and synergistic approach to therapy [Spaide, R F (2006), Am J Opthalmol, vol 141: 149-156].

Inflammation in Ocular Disease:

There is increasing evidence that inflammation, specifically macrophages and the complement system [Klein, et al. (2005), Science, vol 308: 385-9; and Hageman, et al. (2005), Proc Natl Acad Sci USA, vol 102: 7227-32], plays an important role in the pathogenesis of exudative AMD. Histopathology of surgically excised choroidal neovascular membranes demonstrates that macrophages are almost universally present [Grossniklaus, et al. (1994), Ophthalmology, vol 101: 1099-111, and Grossniklaus, et al. (2002), Mol Vis, vol 8: 119-26]. There is mounting evidence that macrophages may play an active role in mediating CNV formation and propagation [Grossniklaus, et al. (2003), Mol Vis, vol 8: 119-26; Espinosa-Heidmann, et al. (2003), Invest Opthalmol Vis Sci, vol 44: 3586-92; Oh, et al. (1999), Invest Opthalmol Vis Sci, vol 40: 1891-8; Cousins, et al. (2004), Arch Opthalmol, vol 122: 1013-8; Forrester (2003), Nat Med, vol 9: 1350-1, and Tsutsumi, et al. (2003), J Leukoc Biol, vol 74: 25-32] by multiple effects which include secretion of enzymes that can damage cells and degrade Bruchs membrane as well as release pro-angiogenic cytokines [Otani, et al. (1999), Opthalmol Vis Sci, vol 40: 1912-20, and Amin, Puklin, and Frank (1994), Invest Opthalmol Vis Sci, vol 35: 3178-88]. At the site of injury, macrophages exhibit micro-morphological signs of activation, such as degranulation [Oh, et al. (1999), Invest Opthalmol Vis Sci, vol 40: 1891-8, and Trautmann et al. (2000), J Pathol, vol 190: 100-6]. Thus it is believed that a molecule which limited macrophage infiltration into to the choroidal neovascular complex may help limit CNV formation.

Choroidal Neovascularization and Blood Vessel Maturation in Ocular Disease:

Angiogenesis is an essential component of normal wound healing as it delivers oxygen and nutrients to inflammatory cells and assists in debris removal [Lingen (2001), Arch Pathol Lab Med, vol 125: 67-71]. Progressive angiogenesis is composed of two distinct processes: Stage I: Migration of vascular ECs, in response to nearby stimuli, to the tips of the capillaries where they proliferate and form luminal structures; and Stage II: Pruning of the vessel network and optimization of the vasculature [Guo, et al. (2003), Am J Pathol, vol 162: 1083-93].

Stage I: Neovascularization. Angiogenesis most often aids wound healing. However, new vessels, when uncontrolled, are commonly defective and promote leakage, hemorrhaging, and inflammation. Diminishing dysfunctional and leaky BVs, by targeting pro-angiogenic GFs, has demonstrated some ability to slow the progression of AMD [Pauleikhoff (2005), Retina, vol 25: 1065-84.14, and van Wijngaarden, Coster, and Williams (2005), JAMA, vol 293: 1509-13].

Stage II: Blood vessel maturation and drug desensitization. Pan-VEGF inhibition appears to exert its beneficial effect mostly via an anti-permeability action resulting in resolution of intra- and sub-retinal edema, as the actual CNV lesion does not markedly involute. The lack of marked CNV involution may in part be a result of maturation of the newly formed vessels due to pericyte coverage. Pericytes play a critical role in the development and maintenance of vascular tissue. The presence of pericytes seems to confer a resistance to anti-VEGF agents and compromise their ability to inhibit angiogenesis [Bergers and Song (2005), Neuro-oncol, vol 7: 452-64; Yamagishi and Imaizumi (2005), Int J Tissue React, vol 27: 125-35; Armulik, Abramsson and Betsholtz (2005), Circ Res, vol 97: 512-23; Ishibashi et al. (1995), Arch Opthalmol, vol 113: 227-31]. An agent that has an inhibitory effect on pericyte recruitment would likely disrupt vascular channel assembly and the maturation of the choroidal neovascular channels thereby perpetuating their sensitivity to anti-angiogenic agents.

Remodeling of the vascular network involves adjustments in blood vessel (BV) density to meet nutritional needs [Gariano and Gardner (2005), Nature, 438: 960-6]. Periods of BV immaturity corresponds to a period in which new vessels are functioning but have not yet acquired a pericyte coating [Benjamin, Hemo, and Keshet (1998), Development, 125: 1591-8, and Gerhardt and Betsholtz (2003), Cell Tissue Res, 2003. 314: 15-23]. This delay is essential in providing a window of plasticity for the fine tuning of the developing vasculature according to the nutritional needs of the retina or choroid.

The bioactive lipid sphingosine-1-phosphate (S1P), VEGF, PDGF, angiopoietins (Ang) and other growth factors (GF) augment blood vessel growth and recruit smooth muscle cells (SMC) and pericytes to naive vessels which promote the remodeling of emerging vessels [Allende and Proia (2002), Biochim Biophys Acta, vol 582: 222-7; Gariano and Gardner (2005), Nature, vol 438: 960-6; Grosskreutz, et al. (1999), Microvasc Res, vol 58: 128-36; Nishishita, and Lin (2004), J Cell Biochem, vol 91: 584-93, and Erber, et al. (2004), FASEB J, vol 18: 338-40.32]. Pericytes, most likely generated by in situ differentiation of mesenchymal precursors at the time of EC sprouting or from the migration and de-differentiation of arterial smooth muscle cells, intimately associate and ensheath ECs resulting in overall vascular maturity and survival [Benjamin, Hemo, and Keshet (1998), Development, vol 125: 1591-8]. Recent studies have demonstrated that S1P, and the S1P1 receptor, are involved in cell-surface trafficking and activation of the cell-cell adhesion molecule N-cadherin [Paik, et al. (2004), Genes Dev, vol 18: 2392-403]. N-cadherin is essential for interactions between EC, pericytes and mural cells which promote the development of a stable vascular bed [Gerhardt and Betsholtz (2003), Cell Tissue Res, vol 314: 15-23]. Global deletion of the S1P1 gene results in aberrant mural cell ensheathment of nascent BVs required for BV stabilization during embryonic development [Allende and Proia (2002), Biochim Biophys Acta, vol 1582: 222-7]. Local injection of siRNA to S1P1 suppresses vascular stabilization in tumor xenograft models [Chae, et al. (2004), J Clin Invest, vol 114: 1082-9]. Transgenic mouse studies have demonstrated that VEGF and PDGF-B promote the maturation and stabilization of new BVs [Guo, et al. (2003), Am J Pathol, 162: 1083-93, and Gariano and Gardner (2005), Nature, vol 438: 960-6.50]. VEGF up-regulates Ang-1 (mRNA and protein) [Asahara, et al. (1998), Circ Res, vol 83: 233-40]. Ang-1 plays a major role in recruiting and sustaining peri-endothelial support by pericytes [Asahara, et al. (1998), Circ Res, vol 83: 233-40]. Intraocular injection of VEGF accelerated pericyte coverage of the EC plexus [Benjamin, Hemo, and Keshet (1998), Development, vol 125: 1591-8]. PDGF-B deficient mouse embryos lack micro-vascular pericytes, which leads to edema, micro-aneurisms and lethal hemorrhages [Lindahl, et al. (1997), Science, vol 277: 242-5]. Murine pre-natal studies have demonstrated that additional signals are required for complete VEGF- and PDGF-stimulation of vascular bed maturation. Based upon the trans-activation of S1P noted above, this factor could be S1P [Erber et al. (2004), FASEB J, vol 18: 338-40]. Vessel stabilization and maturation is associated with a loss of plasticity and the absence of regression to VEGF and other GF withdrawal and resistance to anti-angiogenic therapies [Erber, et al. (2004), FASEB J, vol 18: 338-40, and Hughes and Chan-Ling (2004), Invest Opthalmol Vis Sci, vol 45: 2795-806]. Resistance of BVs to angiogenic inhibitors is conferred by pericytes that initially stabilize matured vessels and those that are recruited to immature vessels upon therapy [Erber, et al. (2004), FASEB J, vol 18: 338-40]. After ensheathment of the immature ECs, the pericytes express compensatory survival factors (Ang-1 and PDGF-B) that protect ECs from pro-apoptotic agents.

Edema and Vascular Permeability in Ocular Disease:

CNV membranes are composed of fenestrated vascular ECs that tend to leak their intravascular contents into the surrounding space resulting in subretinal hemorrhage, exudates and fluid accumulation [Gerhardt and Betsholtz (2003), Cell Tissue Res, vol 14: 15-23]. For many years the CNV tissue itself, and more recently intra-retinal neovascularization, have been implicated as being responsible for the decrease in visual acuity associated with AMD. It is now thought however, that macular edema caused by an increase in vascular permeability (VP) and subsequent breakdown of the blood retinal barrier (BRB), plays a major role in vision loss associated with AMD and other ocular diseases, including blindness associated with diabetes. [Hughes and Chan-Ling (2004), Invest Opthalmol V is Sci, vol 45: 2795-806; Felinski and Antonetti (2005), Curr Eye Res, vol 30: 949-57; Joussen, et al. (2003), FASEB J, vol 17: 76-8, and Strom, et al. (2005), Invest Opthalmol Vis Sci, vol 46: 3855-8]. In particular, diabetic retinopathy (DR) and diabetic macular edema (DME) are common microvascular complications in patients with diabetes and are the most common causes of diabetes-associated blindness. DME results from increased microvascular permeability. Joussen, et al. (2003), FASEB J, vol 17: 76-8. Together these are the most common cause of new blindness in the working-age population. It is believed that compounds, such as antibodies that target S1P, will be therapeutically useful for these conditions.

Examples of several classes of ocular diseases that may be treated in accordance with the invention are described below. It will be appreciated that many disease and conditions are characterized, at least in part, by multiple pathological processes (for example, both pathological neovascularization and scarring) and that the classifications provided herein are for descriptive convenience and do not limit the invention.

a. Ischemic Retinopathies Associated with Pathologic Neovascularization and Diseases Characterized by Epiretinal and or Subretinal Membrane Formation.

Ischemic retinopathies (IR) are a diverse group of disorders characterized by a compromised retinal blood flow. Examples of IR include diabetic retinopathy (DR), retinopathy of prematurity (ROP), sickle cell retinopathy and retinal venous occlusive disease. All of these disorders can be associated with a VEGF driven proliferation of pathological retinal neovascularization which can ultimately lead to intraocular hemorrhaging, epi-retinal membrane formation and tractional retinal detachment. Idiopathic epi-retinal membranes (ERMs), also called macular pucker or cellophane retinopathy, can cause a reduction in vision secondary to distortion of the retinal architecture. These membranes sometimes recur despite surgical removal and are sometimes associated with retinal ischemia. VEGF and its receptors are localized to ERMs. The presence of VEGF in membranes associated with proliferative diabetic retinopathy, proliferative vitreoretinopathy, and macular pucker further suggests that this cytokine plays an important role in angiogenesis in ischemic retinal disease and in membrane growth in proliferative vitreoretinal disorders. In addition, VEGF receptors VEGFR1 and VEGFR2 are also identified on cells in ERMs. These data show that VEGF may be an autocrine and/or paracrine stimulator that may contribute to the progression of vascular and avascular ERMs. PDGF and its receptors [Robbins, et al. (1994), Invest Opthalmol Vis Sci; vol 35: 3649-3663] has been described in eyes with proliferative retinal diseases [Cassidy, et al. (1998), Br J Ophthamol; vol 82: 181-85, and Freyberger, et al. (2000), Exp Clin Endocrinol Diabetes, vol 108: 106-109]. These findings suggest that PDGF ligands and receptors are widespread in proliferative retinal membranes of different origin and suggest that autocrine and paracrine stimulation with PDGF may be involved in ERM pathogenesis. Transforming growth factor-β (TGF-β) is involved in the formation of ERMs [Pournaras, et al. (1998), Klin Monatsbl Augenheilkd, vol 212: 356-358] as demonstrated by TGF staining and immunoreactivity. In addition, TGF-β receptor II is expressed in myofibroblasts of ERM of diabetic and PVR membranes. These results suggest that TGF-β, produced in multiple cell types in retina and ERMs, is an attractive target for the treatment of PVR, diabetic and secondary ERMs. Interleukin-6 (IL-6) has been reported to be increased in human vitreous in proliferative diabetic retinopathy (PDR) [La Heij, et al. (2002), Am J Ophthal, 134: 367-375] and in one study 100% of the diabetic ERMs studied expressed IL-6 protein [Yamamoto, et al. (2001) Am J Ophthal, vol 132: 369-377].

Exogenous administration of basic fibroblastic growth factor (bFGF) has been shown to induce endothelial proliferation and VEGF expression [Stavri, et al. (1995), Circulation, vol 92: 11-14]. Consistent with these observations, bFGF concentration is increased in vitreous samples from patients with PDR [Sivalingam, et al. (1990), Arch Opthalmol, vol 108: 869-872, and Boulton, et al. (1997), Br J Opthalmol, vol 81: 228-233]. bFGF is also involved in the formation of ERMs [Hueber, et al. (1996), Int. Opthalmol, vol 20: 345-350] demonstrated bFGF in 8 out of 10 PDR membranes studied. Moreover, these workers found positive staining for the corresponding receptor, FGFR1. Immunoreactivity for bFGF has also been demonstrated in nonvascular idiopathic ERMs. These results implicate bFGF in the formation of both vascular and avascular ERMs. Harada, et al. (2006), Prog in Retinal and Eye Res, vol 25; 149-164. Elevated bFGF has also been detected in the serum of patients with ROP (Becerril, et al. (2005), Opthalmology, vol 112, 2238].

Given the known pleotropic effects of S1P and its interactions with VEGF, bFGF, PDGF, TGF-β and IL-6, it is believed that an agent that binds, antagonizes, inhibits the effects or the production of S1P will be effective at suppressing pathologic retinal neovascularization in ischemic retinopathies and posterior segment diseases characterized by vascular or avascular ERM formation. Other ocular conditions characterized, at least in part, by aberrant neovascularization or angiogenesis include age-related macular degeneration, corneal graft rejection, neovascular glaucoma, contact lens overwear, infections of the cornea, including herpes simplex, herpes zoster and protozoan infection, pterygium, infectious uveitis, chronic retinal detachment, laser injury, sickle cell retinopathy, venous occlusive disease, choroidal neovascularization, retinal angiomatous proliferation, and idiopathic polypoidal choroidal vasculopathy.

b. Proliferative Vitreoretinopathy (PVR).

PVR is observed after spontaneous rhegmatogenous retinal detachment and after traumatic retinal detachment. It is a major cause of failed retinal detachment surgery. It is characterized by the growth and contraction of cellular membranes on both sides of the retina, on the posterior vitreous surface and the vitreous base. This excessive scar tissue development in the eye may lead to the development of tractional retinal detachment, and therefore treatments directed at the prevention or inhibition of proliferative vitreoretinopathy (PVR) are a logical principle of management of retinal detachment. Histopathologically PVR is characterized by excessive collagen production, contraction and cellular proliferation [Michels, Retinal Detachment 2nd Edition. Wilkinsin C P, Rice T A Eds, Complicated types of retinal detachment, pp 641-771, Mosby St Louis 1997]. Cellular types identified in PVR membranes include mainly retinal pigmented epithelial cells, fibroblasts, macrophages and vascular endothelial cells [Jerdan, et al. (1989), Opthalmology, vol 96: 801-10, and Vidinova, et al. (2005), Klin Monatsbl Augenheilkd; vol 222:568-571]. The pathophysiology of this excessive scarring reaction appears to be mediated by a number of cytokines including platelet derived growth factor (PDGF), transforming growth factor (TGF) beta, basic fibroblastic growth factor (bFGF), interleukin-6 (IL)-6, and interleukin-8 (IL)-8 [Nagineni, et al. (2005), J Cell Physiol, vol 203: 35-43; La Heij, et al (2002), Am J Opthalmol, 134: 367-75; Planck, et al. (1992), Curr Eye Res; vol 11: 1031-9; Canataroglu et al. (2005) Ocul Immunol Inflamm; vol 13: 375-81, and Andrews, et al. (1999), Opthalmol Vis Sci; vol 40: 2683-9]. Inhibition of these cytokines may help prevent the development of PVR if given in a timely fashion or limit its severity [Akiyama, et al (2006), J Cell Physiol, vol 207: 407-12, and Zheng, et al (2003), Jpn J Opthalmolm, vol 47:158-65].

Sphingosine-1-Phosphate (S1P) is a bioactive lysolipid with pleotrophic effects. It is pro-angiogenic, pro inflammatory (stimulates the recruitment of macrophages and mast cells) and pro-fibrotic (stimulates scar formation). S1P generally stimulates cells to proliferate and migrate and is anti-apoptotic. S1P achieves these biologically diverse functions through its interactions with numerous cytokines and growth factors. Inhibition of S1P via a monoclonal antibody (SPHINGOMAB) has been demonstrated to block the functions of vascular endothelial growth factor (VEGF), bFGF, IL-6, and IL-8 [Visentin, B et al. (2006), Cancer Cell, vol 9: 1-14]. Binding of S1P to the $S1P_1$ receptor can also increase PDGF production; therefore an agent that binds S1P would also be expected to diminish PDGF production [Milstien and Spiegel (2006), Cancer Cell, vol 9:148-150]. As shown in the Examples below, it has now been demonstrated that in vitro S1P transforms human RPE cells into a myofibroblast-like phenotype similar to the type seen in PVR. Given the pathophysiology that ultimately results in the excessive scarring seen in PVR and the known effects of S1P on these same key mediators, it is believed that an agent that binds, antagonizes, or inhibits the effects or the production of S1P will be effective at eliminating or minimizing the development of PVR and its severely damaging effects on the eye.

c. Uveitis.

Uveitis is an inflammatory disorder of the uveal tract of the eye. It can affect the front (anterior) or back (posterior) of the eye or both. It can be idiopathic or infectious in etiology and can be vision-threatening. Idiopathic uveitis has been associated with increased CD4+ expression in the anterior chamber [Calder, et al. (1999), Invest Opthalmol Vis Sci, vol 40: 2019-24]. Data also suggests a pathologic role of the T lymphocyte and its chemoattractant IP-10 in the pathogenesis of uveitis [Abu El-Asrar (2004), Am J Opthalmol, vol 138: 401-11]. Other chemokines in acute anterior uveitis include macrophage inflammatory proteins, monocyte chemoattractant protein-1 and IL-8. These cytokines probably play a critical role in leukocyte recruitment in acute anterior uveitis. Verma, et al. (1997), Curr Eye Res; vol 16; 1202-8. Given the profound and pleiotropic effects of the S1P signaling cascade, it is believed that SPHINGOMAB and other immune moieties that reduce the effective concentration of bioactive lipid would serve as an effective method of reducing or modulating the intraocular inflammation associated with uveitis.

d. Refractive Surgery.

The corneal wound healing response is of particular relevance for refractive surgical procedures since it is a major determinant of safety and efficacy. These procedures are performed for the treatment of myopia, hyperopia and astigmatism. Laser in situ keratomileusis (LASIK) and photorefractive keratectomy (PRK) are the most common refractive procedures however others have been developed in an attempt to overcome complications. These complications include overcorrection, undercorrection, regression and stromal opacification among others. A number of common complications are related to the healing response and have their roots in the biologic response to surgery. One of the greatest challenges in corneal biology is to promote tissue repair via regeneration rather than fibrosis. It is believed that the choice between regeneration and fibrosis lies in the control of fibroblast activation [Stramer, et al (2003), Invest Opthalmol Vis Sci; vol 44: 4237-4246, and Fini (1999) Prog Retin Eye Res, vol 18: 529-551]. Cells called myofibroblasts may appear in the subepithelial stroma 1-2 weeks after surgery or injury. Myofibroblasts are presumably derived from keratocytes under the influence of TGF-β [Jester, et al. (2003), Exp Eye Res, vol 77: 581-592]. Corneal haze and stromal scarring are characterized by reduced corneal transparency and may be associated with fibroblast and myofibroblast generation. In situ and in vitro studies have suggested that TGF-β and PDGF are important in stimulating myofibroblast differentiation [Folger, et al. (2001), Invest Opthalmol Vis Sci; 42: 2534-2541]. Haze can be noted in the central interface after LASIK under certain circumstances. These include diffuse lamellar keratitis, donut-shaped flaps, and retention of epithelial debris at the interface. It is likely that each of these is associated with increased access of TGF-β from epithelial cells to the activated keratocytes [Netto, et al. (2005), Cornea, vol 24: 509-522]. Regression is most likely due to heightened epithelial-stromal wound healing interactions such as increased production of epithelium modulating growth factors by corneal fibroblasts and or myofibroblasts [Netto, et al. (2005), above]. Inhibition of TGF-β binding to receptors with topical anti-TGF-β antibody has been shown to reduce haze induced by PRK [Jester, et al. (1997), Cornea, vol 16: 177-187]. Given the known effects of anti-bioactive lipid antibody on the fibrotic process and TGF-β, we believe that it may aid in treating some of the complications of refractive surgery such as haze, stromal scarring and regression.

e. Modulation of Glaucoma Filtration Surgery.

Glaucoma is classically thought of a disease whereby elevated intraocular pressure causes damage to the optic nerve and ultimately compromises the visual field and or the visual acuity. Other forms of glaucoma exist where optic nerve damage can occur in the setting of normal pressure or so called "normal tension glaucoma". For many patients medications are able to control their disease, but for others glaucoma filtration surgery is needed whereby a fistula is surgically created in the eye to allow fluid to drain. This can be accomplished via trabeculectomy, the implantation of a medical device or other methods of surgical intervention. Glaucoma filtration surgery fails due to a wound healing process characterized by the proliferation of fibroblasts and ultimately scarring. Anti-metabolites such as 5-fluorouracil and mitomycin C can reduce subsequent scarring; however, even with the use of these drugs long term follow up shows that surgical failure is still a serious clinical problem [Mutsch and Grehn (2000), Graefes Arch Clin Exp Opthalmol; vol 238: 884-91, and Fontana, et al. (2006), Opthalmology, vol 113: 930-936]. Studies of human Tenon's capsule fibroblasts demonstrate that they have the capacity to synthesize bFGF and PDGF and TGF-β and that these growth factors are implicated in the tissue repair process after glaucoma filtration surgery that contributes to the failure of the procedure. Trpathi, et al. (1996), Exp Eye Res, vol 63: 339-46. Additional studies have also implicated these growth factors in the post filtration wound response [Denk, et al. (2003), Curr Eye Res; vol 27: 35-44] concluded that different isoforms of PDGF are major stimulators of proliferation of Tenon's capsule fibroblasts after glaucoma filtration surgery while TGF-β is essential for the transformation of Tenon's capsule fibroblasts into myofibroblasts. We have demonstrated that S1P is present in human Tenon's capsule/conjunctival fibroblasts and that S1P is strongly expressed in the wound healing response. S1P also stimulates the profibrotic function of multiple fibroblast cell types and the transformation into the myofibroblast phenotype and collagen production. Given the specific pleotropic effects of S1P and its known interactions with bFGF, PDGF, and TGF-beta, it is believed that an agent that binds, antagonizes, inhibits the effects or the production of S1P will be effective at modulating the wound healing and/or fibrotic response that leads to failure of glaucoma surgery and will be an effective therapeutic method of enhancing successful surgical outcomes. It is envisioned that the agent could be administered, e.g., via intravitreal or subconjunctival injection or topically.

f. Corneal Transplantation.

Corneal transplantation (penetrating keratoplasty (PK)) is the most successful tissue transplantation procedure in humans. Yet of the 47,000 corneal transplants performed annually in the United States, corneal allograft rejection is still the leading cause of corneal graft failure [1 ng, et al. (1998), Opthalmology, vol 105: 1855-1865]. Currently, there is insufficient ability to avert allograft rejection although immunosuppression and immunomodulation may be a promising approach. Recently it has been discovered that CD4(+) T cells function as directly as effector cells and not helper cells in the rejection of corneal allografts. Hegde, et al. (2005), Transplantation, vol 79: 23-31. Murine studies have shown increased numbers of neutrophils, macrophage and mast cells in the stroma of corneas undergoing rejection. Macrophages were the main infiltrating cell type followed by T-cells, mast cells and neutrophils. The early chemokine expression in high risk corneal transplantation was the mouse homologue of IL-8 (macrophage inflammatory protein-2) and monocyte chemotactic protein-1 (MCP-1) [Yamagami, et al. (2005), Mol Vis, vol 11, 632-40].

FTY720 (FTY) is a novel immunosuppressive drug that acts by altering lymphocyte trafficking; resulting in peripheral blood lymphopenia and increased lymphocyte counts in lymph nodes. FTY mediates its immune-modulating effects by binding to some of the S1P receptors expressed on lymphocytes [Bohler, et al. (2005), Transplantation, vol 79: 492-5]. The drug is administered orally and a single oral dose reduced peripheral lymphocyte counts by 30-70%. FTY reduced T-cell subset, CD4(+) cells more than CD8(+) cells. Bohler, et al. (2004), Nephrol Dial Transplant, vol 19: 702-13. FTY treated mice showed a significant prolongation of orthotopic corneal-graft survival when administered orally. Zhang, et al. (2003), Transplantation, vol 76: 1511-3. FTY oral treatment also significantly delayed rejection and decreased its severity in a rat-to-mouse model of corneal xenotransplantation [Sedlakova, et al. (2005), Transplantation, vol 79, 297-303]. Given the known pathogenesis of allograft rejection combined with the data suggesting that modulating the effects of the S1P signaling can improve corneal graft survival, it is believed that immune moieties that decrease the effective concentration of bioactive lipids, e.g., SPHINGOMAB, will also be useful in treatment of immunologic conditions such as allograft rejection, for example by attenuating the immune response, and thus will likely improve corneal graft survival after PK. The drug may also has the added advantage that in addition to systemic administration, local administration, e.g., via topical periocular or intraocular delivery, is possible.

Other ocular diseases with an inflammatory or immune component include chronic vitritis, infections, including herpes simplex, herpes zoster, and protozoan infections, and ocular histoplasmosis.

g. Anterior Segment Diseases Characterized by Scarring.

Treatment with an antibody targeted to bioactive lipid also is believed to benefit several conditions characterized by scarring of the anterior portion of the eye. These include the following:

i. Trauma

The cornea, as the most anterior structure of the eye, is exposed to various hazards ranging from airborne debris to blunt trauma that can result in mechanical trauma. The cornea and anterior surface of the eye can also be exposed to other forms of trauma from surgery, and chemical, such as acid and alkali, injuries. The results of these types of injuries can be devastating often leading to corneal and conjunctival scarring symblephera formation. In addition, corneal neovascularization may ensue. Neutrophils accumulate, their release of leukotrienes, and the presence of interleukin-1 and interleukin-6, serves to recruit successive waves of inflammatory cells [Sotozono, et al. (1997), Curr Eye Res, vol 19: 670-676] that infiltrate the cornea and release proteolytic enzymes, which leads to further damage and break down of corneal tissue and a corneal melt. In addition, corneal and conjunctival fibroblasts become activated and invade and leading to collagen deposition and fibrosis. The undesirable effects of excessive inflammation and scarring are promoted by TGF-β. Saika, et al. (2006), Am J Pathol vol 168, 1848-60. This process leads to loss of corneal transparency and impaired vision. Reduced inflammation, including decreased neutrophil infiltrates and reduced fibrosis resulted in faster and more complete healing in a murine model of alkali burned corneas [Ueno, et al. (2005), Opthalmol Vis Sci, vol 46: 4097-106].

ii. Ocular Cicatricial Pemphigoid (OCP)

OCP is a chronic cicatrizing (scar-forming) autoinimune disease that primarily affects the conjunctiva. The disease is invariably progressive and the prognosis is quite poor. In its final stages conjunctival scarring and the associated keratopathy lead to bilateral blindness. Histologically the conjunctiva shows submucosal scarring and chronic inflammation in which mast cell participation is surprisingly great [Yao, et al. (2003), Ocul Immunol Inflamm, vol 11: 211-222]. Autoantigens lead to the formation of autoantibodies. The binding of the autoantibody to the autoantigen sets in motion a complex series of events with infiltration of T lymphocytes where CD4 (helper) cells far outnumber CD8 (suppressor) cells. Macrophage and mast cell infiltration also ensue as well as the release of proinflammatory and profibrotic cytokines. Cytokine-induced conjunctival fibroblast proliferation and activation results, with resultant subepithelial fibrosis (see examples hereinbelow). Studies have shown a role of TGF-β and IL-1 in conjunctival fibrosis in patients with OCP [Razzaque, et al. (2004), Invest Opthalmol Vis Sci, vol 45: 1174-81].

iii. Stevens Johnson Syndrome (SJS) and Toxic Epidermal Necrolysis (TEN)

SJS and TEN are life-threatening adverse reactions to medications. The ocular sequelae of these two related conditions can be severe and involve pathologic changes of the bulbar and palpebral conjunctiva, eyelids, and cornea. Drugs and infections are the most common precipitating factors. Chronic eye findings include scarring, symblepharon formation, and cicatrisation of the conjunctiva as a result of the initial inflammatory process. This leads to entropion formation, trichiasis, and instability of the tear film. Breakdown of the ocular surface leads to corneal scarring, neovascularization, and in severe cases keratinization. As in OCP subepithelial fibrosis of the conjunctiva occurs. A vigorous autoimmune lymphocyte response to a drug or infection is believed to play a role in development of SJS/TEN. Harilaos, et al. (2005), Erythema Multiforme, Stevens Johnson Syndrome, and Toxic Epidermal Necrolysis, in Cornea $2^{nd}$ edition. Krachmer, Mannis, Holland eds. Elesevier Mosby Philadelphia. The infiltrating cell population in SJS includes macrophages, CD4 positive T cells, and CD8 positive T cells. This cell population is similar to those seen in chemical injury. Kawasaki, et al. (2000), J Opthalmol, vol 84: 1191-3.

iv. Pterygium

Clinically a pterygium appears as a fleshy, vascular mass that occurs in the interpalpebral fissure. The body of the pterygium is a fleshy fibrovascular mass. Active pterygium is characterized by marked vascular engorgement and progressive growth. They are firmly adherent to the globe. In advanced cases the pterygium encroaches onto the cornea and may cause visual loss secondary to loss of corneal transparency within the visual axis or irregular astigmatism. Symptomatically, patients may experience foreign body sensation, tearing and blurred vision. Histopathology demonstrates hyalinization of the subepithelial connective tissue of the substantia propria, increased number of fibroblasts and increased mast cells. Butrus, et al. (1995), Am J Opthalmol, vol 119: 236-237. Management of pterygium remains problematic. Surgical excision is often performed however recurrence rates are high [Krag, et al. (1992), Acta Opthalmol, vol 70: 530]. In order to help lower the recurrence rate of pterygium, various pharmacologic adjuvants have been employed such as Mitomycin-C and daunorubicin. Although these may be helpful, long term data are limited and they can be associated with scleral thinning and corneal melt. Dougherty, et al. [(1996), Cornea, vol 15: 537-540, and Lee, et al. (2001), Cornea, vol 20: 238-42] were the first to demonstrate that VEGF may play an important role in the development of pterygium and to identify VEGF and nitric oxide in the epithelium of pterygium. These workers hypothesized that these as well as other cytokines are responsible for the fibrovascular ingrowth characteristic of pterygium. The presence of basic FGF and TGF-beta 1 in both primary and recurrent pterygium has been demonstrated [Kira, et al. (1998), Graefes Arch Clin Exp Opthalmol, vol 236: 702-8] and published morphometric and immunohistochemical evidence further supports the notion that angiogenesis may play a role in the formation of pterygium [Marcovich, et al (2002), Curr Eye Res, vol 25:17-22]. Other studies have implicated IL-6 and IL-8 as well as VEGF as mediators that may be relevant to pterygium development [Di Girolamo, et al. (2006), Invest Opthalmol Vis Sci, vol 47: 2430-7]. An effective agent against pterygium formation and growth may diminish the need for surgical intervention or reduce recurrence rates.

Other ocular diseases and conditions with a fibrogenesis, fibrosis or scarring component include AMD, diabetic retinopathy, retinopathy of prematurity, sickle cell retinopathy, ischemic retinopathy, retinal venous occlusive disease, and contact lens overwear.

In summary, excessive scarring is an underlying component of the pathophysiology of many ocular and non-ocular diseases and conditions. Bioactive lipids like S1P play a role in this process and an antibody-related treatment to diminish the concentrations of these agents will likely lead to therapeutic benefit to patients receiving the treatment. In one embodiment, inhibitors of bioactive lipids, particularly monoclonal antibodies directed against S1P and/or it variants, are believed to be useful in modulating surgical and traumatic wound healing responses.

Fibrosis, Fibrogenesis and Scar Formation:

The formation of subretinal fibrosis leads to irreversible damage to the photoreceptors and permanent vision loss. As long as the neovascular complex remains intact, as appears to be the case in patients treated with anti-VEGF agents, the potential for subretinal fibrosis and future vision loss persists. In an update of the PRONTO study of RANIBIZUMAB (Lucentis®), it was discovered that those patients who lost vision did so as a result of either subretinal fibrosis or a RPE tear. An agent that could diminish the degree of fibroblast infiltration and collagen deposition would be of value.

Fibroblasts, particularly myofibroblasts, are key cellular elements in scar formation in response to cellular injury and inflammation [Tomasek, et al. (2002), Nat Rev Mol Cell Biol, vol 3: 349-63, and Virag and Murry (2003), Am J Pathol, vol 163: 2433-40]. Collagen gene expression by myofibroblasts is a hallmark of remodeling and necessary for scar formation [Sun and Weber (2000), Cardiovasc Res, vol 46: 250-6, and Sun and Weber (1996), J Mol Cell Cardiol, vol 28: 851-8]. S1P promotes wound healing by activating fibroblast migration and proliferation while increasing collagen production [Sun, et al. (1994), J Biol Chem, vol 269: 16512-7]. S1P produced locally by damaged cells could be responsible for the maladaptive wound healing associated with remodeling and scar formation. Thus, it is believed that S1P inhibitors are useful in diseases or conditions characterized, at least in part, by aberrant fibrogenesis or fibrosis.

The formation of subretinal fibrosis leads to irreversible damage to the photoreceptors and permanent vision loss. As long as the neovascular complex remains intact, as appears to be the case in patients treated with anti-VEGF agents, the potential for subretinal fibrosis and future vision loss persists.

Minimizing maladaptive scar formation by neutralization of S1P could be beneficial and prevent irreversible losses in visual acuity by limiting the extent of sub-retinal fibrosis and subsequent photoreceptor damage. Growing evidence suggests that S1P could contribute to both the early and late stages of maladaptive retinal remodeling associated with exudative AMD. S1P has a pronounced non-VEGF dependent pro-angiogenic effect. S1P also stimulates migration, proliferation and survival of multiple cell types, including fibroblasts, EC, pericytes and inflammatory cells—the same cells that participate in the multiple maladaptive processes of exudative AMD and other ocular disorders. S1P is linked to the production and activation of VEGF, bFGF, PDGF, and other growth factors (GFs) implicated in the pathogenesis of exudative AMD. Finally, S1P may modulate the maturation of naïve vasculature, a process leading to a loss of sensitivity to anti-angiogenic agents. Inhibiting the action of S1P could be an effective therapeutic treatment for exudative AMD that may offer significant advantages over exclusively anti-VEGF approaches or may act synergistically with them to address the complex processes and multiple steps that ultimately lead to AMD associated visual loss.

Currently favored therapeutic modalities for AMD include Lucentis® and off-label use of Avastin® (Genentech, Inc.), both of which target a single growth factor (VEGF-A) and appear to exert most of their beneficial effect via an anti-permeability action resulting in resolution of sub-retinal and intra-retinal edema, as the actual choroidal neovascular (CNV) lesion does not markedly involute. However, exudative AMD-related vision loss is not solely due to CNV-induced sub-retinal and intra-retinal edema. Pathologic disruption and remodeling of the retinal and subretinal architecture caused collectively by CNV, sub-retinal fibrosis, edema and inflammation together result in the loss of visual acuity associated with AMD. These multiple causes are not addressed by available treatments, including Lucentis™. Thus a therapeutic agent that could treat the multiple mechanisms that cause vision loss would be of great value, either as monotherapy or in combination with another agent, such as an anti-VEGF agent (e.g., Lucentis® or Avastin®).

Thus, without wishing to be bound by any particular theory, it is believed that the level of undesirable sphingolipids such as S1P, and/or one or more of their metabolites, cause or contribute to the development of various ocular diseases and disorders where inappropriate inflammation, fibrosis and/or angiogenesis are involved in the pathogenesis of the disease. Diseases and conditions of the eye in which anti-S1P antibodies are likely to be clinically useful include diabetic retinopathy, retinopathy of prematurity, diabetic macular edema, PVR, anterior segment diseases and age-related macular edema, both wet and dry, and after procedures such as trabeculectomy or valve implantation in glaucoma.

Anti-S1P Antibodies for the Treatment of Scleroderma

The compositions and methods of the invention will be useful in treating disorders and diseases characterized, at least in part, by aberrant neovascularization, angiogenesis, fibrogenesis, fibrosis, scarring, inflammation, and immune response. One such disease is scleroderma, which is also referred to as systemic sclerosis.

Scleroderma is an autoimmune disease that causes scarring or thickening of the skin, and sometimes involves other areas of the body, including the lungs, heart, and/or kidneys. Scleroderma is characterized by the formation of scar tissue (fibrosis) in the skin and organs of the body, which can lead to thickening and firmness of involved areas, with consequent reduction in function. Today, about 300,000 Americans have scleroderma, according to the Scleroderma Foundation. One-third or less of those affected have widespread disease, while the remaining two-thirds primarily have skin symptoms. When the disease affects the lungs and causing scarring, breathing can become restricted because the lungs can no longer expand as they should. To measure breathing capability, doctors use a device that assesses forced vital capacity (FVC). In people with an FVC of less than 50 percent of the expected reading, the 10-year mortality rate from scleroderma-related lung disease is about 42 percent. One reason the mortality rate is so high is that no effective treatment is currently available.

Without wishing to be bound by any particular theory, it is believed that inappropriate concentrations of lipids such as S1P and/or its metabolites, cause or contribute to the development of scleroderma. As such, the compositions and methods of the invention can be used to treat scleroderma, particularly by decreasing the effective in vivo concentration of a particular target lipid, for example, S1P.

As described elsewhere in this application, existing evidence indicates that S1P is a pro-fibrotic growth factor that can contribute to fibroblast activation, proliferation, and the resulting increased fibroblast activity associated with maladaptive scarring and remodeling. It is believed that S1P bioactivity with and anti-S1P agent (e.g., an anti-S1P mAb) could indirectly mitigate the pro-sclerotic effects of PDGF and TGF-β. Moreover, treatment with such an anti-S1P agent could benefit scleroderma patients by mitigating the direct effects of S1P on skin and other forms of fibroblasts that contribute to disease progression.

Cardiovascular and Cerebrovascular Disorders

Without wishing to be bound by any particular theory, the level of undesirable sphingolipids such as CER, SPH, or S1P, and/or one or more of their metabolites, may be directly responsible for cardiac dysfunction, during or after cardiac ischemia such as during reperfusion injury and the resulting cardiac remodeling and heart failure.

Because sphingolipids such as S1P are involved in fibrogenesis and wound healing of liver tissue (Davaille, et al., J. Biol. Chem. 275:34268-34633, 2000; Ikeda, et al., Am J. Physiol. Gastrointest. Liver Physiol 279:G304-G310, 2000), healing of wounded vasculatures (Lee, et al., Am. J. Physiol. Cell Physiol. 278:C612-C618, 2000), and other disease states, or events associated with such diseases, such as cancer, angiogenesis and inflammation (Pyne, et al., Biochem. J. 349:385-402, 2000), the compositions and methods of the disclosure may be applied to treat not only these diseases but cardiac diseases as well.

This suggests that sphingolipids derived from cardiac or other non-cerebral sources could contribute to stroke. Consequently, interfering with sphingolipid production and/or action may be beneficial in mitigating stroke, particularly in stroke caused by peripheral vascular disease, atherosclerosis, and cardiac disorders. Recent evidence suggests that exogenously administered S1P crosses the blood-brain barrier and promotes cerebral vasoconstriction (Tosaka, et al., Stroke 32: 2913-2919.2001).

It has been suggested that an early event in the course of cardiac ischemia (i.e., lack of blood supply to the heart) is an excess production by the heart muscle of the naturally occurring compound sphingosine, and that other metabolites, particularly S1P are also produced either by the heart tissue itself or by components of blood as a consequence of cardiac sphingolipid production and subsequent conversion in the blood. The present invention provides methods for neutralizing S1P with specific humanized monoclonal antibodies. The present invention thus provides humanized anti-sphingolipid antibodies and related compositions and methods to reduce blood and tissue levels of the key sphingolipid, S1P. Such antibodies are useful, for example, for binding and thus lowering the effective concentration of, undesirable sphingolipids in whole blood.

The therapeutic methods and compositions of the invention are said to be "sphingolipid-based" in order to indicate that these therapies can change the relative, absolute or available concentration(s) of certain undesirable, toxic or cardiotoxic sphingolipids. A "toxic sphingolipid" refers to any sphingolipid that can cause or enhance the necrosis and/or apoptosis of cells or otherwise impair function of an organ or tissue (e.g., through excessive fibrosis), including, in some instances, particular cell types that are found in specific tissues or organs. "Cardiotoxic sphingolipids" are toxic sphingolipids that directly or indirectly promote heart failure through maladaptive scarring (fibrogenesis) and cause a negative inotropic state or cause or enhance the necrosis and/or apoptosis of cells found in or associated with the heart, including but not limited to cardiomyocytes, cardiac neurons and the like, and/or can cause loss of cardiac function due to the negative inotropic, arrhythmic coronary vasoconstriction/spasm effects of the sphingolipids and/or their metabolites. "Undesirable sphingolipids" include toxic and cardiotoxic sphingolipids, as well as metabolites, particularly metabolic precursors, of toxic and cardiotoxic sphingolipids. Undesirable, cardiotoxic, and/or toxic sphingolipids of particular interest include, but are not limited to, ceramide (CER), ceraminde-1-phosphate (CIP), sphingosine-1-phosphate (S-1-P), dihydro-S1P (DHS1P), sphingosylphosphoryl choline (SPC), sphingosine (SPH; D(+)-erythro-2-amino-4-trans-octadecene-1,3-diol, or sphinganine) and various metabolites.

It is known that one of the earliest responses of cardiac myocytes to hypoxia and reoxygenation is the activation of neutral sphingomyelinase and the accumulation of ceramide. Hernandez, et al. (2000), Circ. Res. 86:198-204, 2000. SPH has been allegedly implicated as mediating an early signaling event in apoptotic cell death in a variety of cell types (Ohta, et al., FEBS Letters 355:267-270, 1994; Ohta, et al., Cancer Res. 55:691-697, 1995; Cuvlilier, et al., Nature 381:800-803, 1996). It is postulated that the cardiotoxic effects of hypoxia may result in part from sphingolipid production and/or from the inappropriate production of other metabolites (e.g., protons, calcium, and certain free radicals) or signaling molecules (e.g., MAP kinases, caspases) that adversely affect cardiac function.

S1P is stored in platelets and is a normal constituent of human plasma and serum (Yatomi, et al., J. Biochem. 121: 969-973, 1997). S1P is a coronary vasoconstrictor and has other biological effects on canine hearts. Sugiyama, et al. (2000), Cardiovascular Res. 46:119-125. A role for S1P in atherosclerosis has been postulated (Siess, et al., IUBMB Life 49:161-171, 2000). This has been supported by other data, including evidence that the protective effect of HDL is due to blocking S1P production (Xia, et al., PNAS 95:14196-14201, 1988; Xia, et al., J Biol Chem 274:33143-33147, 1999).

Sphingomyelin, the metabolic precursor of ceramide, has been reported to be increased in experimental animals subjected to hypoxia (Sergeev, et al., Kosm. Biol. Aviakosm. Med. (Russian) 15:71-74, 1981). Other studies have reported that internal membranes of muscle cells contain high amounts of SPH and sphingomyelin (Sumnicht, et al., Arch. Biochem. Biophys. 215:628-637, 1982; Sabbadini, et al., Biochem. Biophys. Res. Comm. 193752-758, 1993). Treatment of experimental animals with fumonisinB fungal toxins result in increase serum levels of SPH and DHSPH (S1P was not measured) with coincident negative inotropic effects on the heart (Smithe, et al., Toxicological Sciences 56:240-249, 2000).

Other Diseases or Conditions

Because of the involvement of bioactive lipid signaling in many processes, including neovascularization, angiogenesis, aberrant fibrogenesis, fibrosis and scarring, and inflammation and immune responses, it is believed that inhibitors of these bioactive lipids will be helpful in a variety of diseases and conditions associated with one or more of these processes. Such diseases and conditions may be systemic (e.g., systemic scleroderma) or localized to one or more specific body systems, parts or organs (e.g., skin, lung, cardiovascular system or eye).

One way to control the amount of undesirable sphingolipids in a patient is by providing a composition that comprises one or more humanized anti-sphingolipid antibodies to bind one or more sphingolipids, thereby acting as therapeutic "sponges" that reduce the level of free undesirable sphingolipids. When a compound is referred to as "free", the compound is not in any way restricted from reaching the site or sites where it exerts its undesirable effects. Typically, a free compound is present in blood and tissue, which either is or contains the site(s) of action of the free compound, or from which a compound can freely migrate to its site(s) of action. A free compound may also be available to be acted upon by any enzyme that converts the compound into an undesirable compound.

Without wishing to be bound by any particular theory, it is believed that the level of undesirable sphingolipids such as SPH or S1P, and/or one or more of their metabolites, cause or contribute to the development of cardiac and myocardial diseases and disorders.

Because sphingolipids are also involved in fibrogenesis and wound healing of liver tissue (Davaille, et al., J. Biol. Chem. 275:34268-34633, 2000; Ikeda, et al., Am J. Physiol. Gastrointest. Liver Physiol 279:G304-G310, 2000), healing of wounded vasculatures (Lee, et al., Am. J. Physiol. Cell Physiol. 278:C612-C618, 2000), and other disease states or disorders, or events associated with such diseases or disorders, such as cancer, angiogenesis, various ocular diseases associate with excessive fibrosis and inflammation (Pyne et al., Biochem. J. 349:385-402, 2000), the compositions and methods of the present disclosure may be applied to treat these diseases and disorders as well as cardiac and myocardial diseases and disorders.

One form of sphingolipid-based therapy involves manipulating the metabolic pathways of sphingolipids in order to decrease the actual, relative and/or available in vivo concentrations of undesirable, toxic sphingolipids. The invention provides compositions and methods for treating or preventing diseases, disorders or physical trauma, in which humanized anti-sphingolipid antibodies are administered to a patient to bind undesirable, toxic sphingolipids, or metabolites thereof.

Such humanized anti-sphingolipid antibodies may be formulated in a pharmaceutical composition that are useful for a variety of purposes, including the treatment of diseases, disorders or physical trauma. Pharmaceutical compositions comprising one or more humanized anti-sphingolipid antibodies of the invention may be incorporated into kits and medical devices for such treatment. Medical devices may be used to administer the pharmaceutical compositions of the invention to a patient in need thereof, and according to one embodiment of the invention, kits are provided that include such devices. Such devices and kits may be designed for routine administration, including self-administration, of the pharmaceutical compositions of the invention. Such devices and kits may also be designed for emergency use, for example, in ambulances or emergency rooms, or during surgery, or in activities where injury is possible but where full medical attention may not be immediately forthcoming (for example, hiking and camping, or combat situations).

Methods of Administration.

The treatment for diseases and conditions discussed herein can be achieved by administering agents and compositions of the invention by various routes employing different formulations and devices. Suitable pharmaceutically acceptable diluents, carriers, and excipients are well known in the art. One skilled in the art will appreciate that the amounts to be administered for any particular treatment protocol can readily be determined. Suitable amounts might be expected to fall within the range of 10 µg/dose to 10 g/dose, preferably within 10 mg/dose to 1 g/dose.

Drug substances may be administered by techniques known in the art, including but not limited to systemic, subcutaneous, intradermal, mucosal, including by inhalation, and topical administration. The mucosa refers to the epithelial tissue that lines the internal cavities of the body. For example, the mucosa comprises the alimentary canal, including the mouth, esophagus, stomach, intestines, and anus; the respiratory tract, including the nasal passages, trachea, bronchi, and lungs; and the genitalia. For the purpose of this specification, the mucosa also includes the external surface of the eye, i.e., the cornea and conjunctiva. Local administration (as opposed to systemic administration) may be advantageous because this approach can limit potential systemic side effects, but still allow therapeutic effect.

Pharmaceutical compositions used in the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations used in the present invention may be prepared according to conventional techniques well known in the pharmaceutical industry. Such techniques include the step of bringing into association the active ingredients with the pharmaceutical carrier(s) or excipient(s). Preferred carriers include those that are pharmaceutically acceptable, particularly when the composition is intended for therapeutic use in humans. For non-human therapeutic applications (e.g., in the treatment of companion animals, livestock, fish, or poultry), veterinarily acceptable carriers may be employed. In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment the pharmaceutical compositions may be formulated and used as foams. Pharmaceutical foams include formulations such as, but not limited to, emulsions, microemulsions, creams, jellies, and liposomes.

While basically similar in nature these formulations vary in the components and the consistency of the final product. The know-how on the preparation of such compositions and formulations is generally known to those skilled in the pharmaceutical and formulation arts and may be applied to the formulation of the compositions of the present invention.

In one embodiment, an immune-derived moiety can be delivered to the eye via, for example, topical drops or ointment, periocular injection, intracamerally into the anterior chamber or vitreous, via an implanted depot, or systemically by injection or oral administration. The quantity of antibody used can be readily determined by one skilled in the art.

The traditional approaches to delivering therapeutics to the eye include topical application, redistribution into the eye following systemic administration or direct intraocular/periocular injections [Sultana, et al. (2006), Current Drug Delivery, vol 3: 207-217; Ghate and Edelhauser (2006), Expert Opinion, vol 3: 275-287; and Kaur and Kanwar (2002), Drug Develop Industrial Pharmacy, vol 28: 473-493]. Anti-S1P or other anti-bioactive lipid antibody therapeutics would likely be used with any of these approaches although all have certain perceived advantages and disadvantages. Topical drops are convenient, but wash away primarily because of nasolacrimal drainage often delivering less than 5% of the applied drug into the anterior section of the eye and an even smaller fraction of that dose to the posterior segment of the globe. Besides drops, sprays afford another mode for topical administration. A third mode is ophthalmic ointments or emulsions can be used to prolong the contact time of the formulation with the ocular surface although blurring of vision and matting of the eyelids can be troublesome. Such topical approaches are still preferable, since systemic administration of therapeutics to treat ocular disorders exposes the whole body to the potential toxicity of the drug.

Treatment of the posterior segment of the eye is medically important because age-related macular degeneration, diabetic retinopathy, posterior uveitis, and glaucoma are the leading causes of vision loss in the United States and other developed countries. Myles, et al. (2005), Adv Drug Deliv Rev; 57: 2063-79. The most efficient mode of drug delivery to the posterior segment is intravitreal injection through the pars plana. However, direct injections require a skilled medical practitioner to effect the delivery and can cause treatment-limiting anxiety in many patients. Periocular injections, an approach that includes subconjunctival, retrobulbar, peribulbar and posterior subtenon injections, are somewhat less invasive than intravitreal injections. Repeated and long-term intravitreal injections may cause complications, such as vitreous hemorrhage, retinal detachment, or endophthalmitis.

The anti-bioactive lipid antibody treatment might also be administered using one of the newer ocular delivery systems [Sultana, et al. (2006), Current Drug Delivery, vol 3: 207-217; and Ghate and Edelhauser (2006), Expert Opinion, vol 3: 275-287], including sustained or controlled release systems, such as (a) ocular inserts (soluble, erodible, non-erodible or hydrogel-based), corneal shields, eg, collagen-based bandage and contact lenses that provide controlled delivery of drug to the eye, (b) in situ gelling systems that provide ease of administration as drops that get converted to gel form in the eye, thereby providing some sustained effect of drug in the eye, (c) vesicular systems such as liposomes, niosomes/discomes, etc., that offers advantages of targeted delivery, bio-compatibility and freedom from blurring of vision, (d) mucoadhesive systems that provide better retention in the eye, (e) prodrugs (f) penetration enhancers, (g) lyophilized carrier systems, (h) particulates, (i) submicron emulsions, (j) iontophoresis, (k) dendrimers, (l) microspheres including bioadhesive microspheres, (m) nanospheres and other nanoparticles, (n) collasomes, and (o) drug delivery systems that combine one or more of the above stated systems to provide an additive, or even synergistic, beneficial effect. Most of these approaches target the anterior segment of the eye and may be beneficial for treating anterior segment disease. However, one or more of these approaches still may be useful affecting bioactive lipid concentrations in the posterior region of the eye because the relatively low molecular weights of the lipids will likely permit considerable movement of the lipid within the eye. In addition, the antibody introduced in the anterior region of the eye may be able to migrate throughout the eye especially if it is manufactured in a lower weight antibody variant such as a Fab fragment. Sustained drug delivery systems for the posterior segment such as those approved or under development (see references, supra) could also be employed.

As previously mentioned, the treatment of disease of the posterior retina, choroids, and macula is medically very important. In this regard, transscleral iontophoresis [Eljarrat-Binstock and Domb (2006), Control Release, 110: 479-89] is an important advance and may offer an effective way to deliver antibodies to the posterior segment of the eye.

Various excipients might also be added to the formulated antibody to improve performance of the therapy, make the therapy more convenient or to clearly ensure that the formulated antibody is used only for its intended, approved purpose. Examples of excipients include chemicals to control pH, antimicrobial agents, preservatives to prevent loss of antibody potency, dyes to identify the formulation for ocular use only, solubilizing agents to increase the concentration of antibody in the formulation, penetration enhancers and the use of agents to adjust isotonicity and/or viscosity. Inhibitors of, e.g., proteases, could be added to prolong the half life of the antibody. In one embodiment, the antibody is delivered to the eye by intravitreal injection in a solution comprising phosphate-buffered saline at a suitable pH for the eye.

The anti-S1P agent (e.g., a humanized antibody) can also be chemically modified to yield a pro-drug that is administered in one of the formulations or devices previously described above. The active form of the antibody is then released by action of an endogenous enzyme. Possible ocular enzymes to be considered in this application are the various cytochrome p450s, aldehyde reductases, ketone reductases, esterases or N-acetyl-$\beta$-glucosamidases. Other chemical modifications to the antibody could increase its molecular weight, and as a result, increase the residence time of the antibody in the eye. An example of such a chemical modification is pegylation [Harris and Chess (2003), Nat Rev Drug Discov; 2: 214-21], a process that can be general or specific for a functional group such as disulfide [Shaunak, et al. (2006), Nat Chem Biol; 2:312-3] or a thiol [Doherty, et al. (2005), Bioconjug Chem; 16: 1291-8].

The examples herein below describe the production of humanized and variant anti-sphingolipid antibodies with desirable properties from a therapeutic perspective, including strong binding affinity for sphingolipids. In particular, the invention is drawn to S1P and its variants which may include S1P itself defined as sphingosine-1-phosphate [sphingene-1-phosphate; D-erythro-sphingosine-1-phosphate; sphing-4-enine-1-phosphate; (E,2S,3R)-2-amino-3-hydroxy-octadec-4-enoxy]phosphonic acid (AS 26993-30-6), DHS1P is defined as dihydrosphingosine-1-phosphate [sphinganine-1-phosphate; [(2S,3R)-2-amino-3-hydroxy-octadecoxy]phosphonic acid; D-Erythro-dihydro-D-sphingosine-1-phosphate (CAS 19794-97-9]; SPC is sphingosylphosphoryl choline, lysosphingomyelin, sphingosylphosphocholine, sphingosine phosphorylcholine, ethanaminium; 2-((((2-amino-3-hydroxy-4-octadecenyl)oxy)hydroxyphosphinyl)oxy)-N,N,N-trimethyl-, chloride, (R—(R*,S*-(E))), 2-[[(E,2R,3S)-2-amino-3-hydroxy-octadec-4-enoxy]-hydroxy-phosphoryl] oxyethyl-trimethyl-azanium chloride (CAS 10216-23-6).

Antibody Generation and Characterization

Antibody affinities may be determined as described in the examples herein below. Preferred humanized or variant antibodies are those which bind a sphingolipid with a $K_d$ value of no more than about $1\times10^{-7}$ M, preferably no more than about $1\times10^{-8}$ M, and most preferably no more than about $5\times10^{-9}$ M.

Aside from antibodies with strong binding affinity for sphingolipids, it is also desirable to select humanized or variant antibodies that have other beneficial properties from a therapeutic perspective. For example, the antibody may be one that reduce angiogenesis and alter tumor progression. Preferably, the antibody has an effective concentration 50 (EC50) value of no more than about 10 ug/ml, preferably no more than about 1 ug/ml, and most preferably no more than about 0.1 ug/ml, as measured in a direct binding ELISA assay. Preferably, the antibody has an effective concentration value of no more than about 10 ug/ml, preferably no more than about 1 ug/ml, and most preferably no more than about 0.1 ug/ml, as measured in cell assays in presence of 1 uM of S1P, for example, at these concentrations the antibody is able to inhibit sphingolipid-induced IL-8 release in vitro by at least 10%. Preferably, the antibody has an effective concentration value of no more than about 10 ug/ml, preferably no more than about 1 ug/ml, and most preferably no more than about 0.1 ug/ml, as measured in the CNV animal model after laser burn, for example, at these concentrations the antibody is able to inhibit sphingolipid-induced neovascularization in vivo by at least 50%.

Assays for determining the activity of the anti-sphingolipid antibodies of the invention include ELISA assays as shown in the examples hereinbelow.

Preferably the humanized or variant antibody fails to elicit an immunogenic response upon administration of a therapeutically effective amount of the antibody to a human patient. If an immunogenic response is elicited, preferably the response will be such that the antibody still provides a therapeutic benefit to the patient treated therewith.

According to one embodiment of the invention, humanized anti-sphingolipid antibodies bind the "epitope" as herein defined. To screen for antibodies that bind to the epitope on a sphingolipid bound by an antibody of interest (e.g., those that block binding of the antibody to sphingolipid), a routine cross-blocking assay such as that described in Antibodies, A Laboratory Manual, Cold Spring Harbor Laboratory, Ed Harlow and David Lane (1988), can be performed. Alternatively, epitope mapping, e.g., as described in Champe, et al. [J. Biol. Chem. 270:1388-1394 (1995)], can be performed to determine whether the antibody binds an epitope of interest.

The antibodies of the invention have a heavy chain variable domain comprising an amino acid sequence represented by the formula: FR1-CDRHI-FR2-CDRH2-FR3-CDRH3-FR4, wherein "FR1-4" represents the four framework regions and "CDRHI-3" represents the three hypervariable regions of an anti-sphingolipid antibody variable heavy domain. FR1-4 may be derived from a "consensus sequence" (for example the most common amino acids of a class, subclass or subgroup of heavy or light chains of human immunoglobulins) as in the examples below or may be derived from an individual human antibody framework region or from a combination of different framework region sequences. Many human antibody framework region sequences are compiled in Kabat, et al., supra, for example. In one embodiment, the variable heavy FR is provided by a consensus sequence of a human immunoglobulin subgroup as compiled by Kabat, et al., above. Preferably, the human immunoglobulin subgroup is human heavy chain subgroup III (e.g., as in SEQ ID NO: 16).

The human variable heavy FR sequence preferably has one or more substitutions therein, e.g., wherein the human FR residue is replaced by a corresponding nonhuman residue (by "corresponding nonhuman residue" is meant the nonhuman residue with the same Kabat positional numbering as the human residue of interest when the human and nonhuman sequences are aligned), but replacement with the nonhuman residue is not necessary. For example, a replacement FR residue other than the corresponding nonhuman residue can be selected by phage display. Exemplary variable heavy FR residues which may be substituted include any one or more of FR residue numbers: 37H, 49H, 67H, 69H, 71H, 73H, 75H, 76H, 78H, and 94H (Kabat residue numbering employed here). Preferably at least two, or at least three, or at least four of these residues are substituted. A particularly preferred combination of FR substitutions is: 49H, 69H, 71H, 73H, 76H, 78H, and 94H. With respect to the heavy chain hypervariable regions, these preferably have amino acid sequences listed in Table 2, below.

The antibodies of the preferred embodiment herein have a light chain variable domain comprising an amino acid sequence represented by the formula: FR1-CDRL1-FR2-CDRL2-FR3-CDRL3-FR4, wherein "FR1-4" represents the four framework regions and "CDRL1-3" represents the three hypervariable regions of an anti-sphingolipid antibody variable heavy domain. FR1-4 may be derived from a "consensus sequence" (for example, the most common amino acids of a class, subclass or subgroup of heavy or light chains of human immunoglobulins) as in the examples below or may be derived from an individual human antibody framework region or from a combination of different framework region sequences. In one preferred embodiment, the variable light FR is provided by a consensus sequence of a human immunoglobulin subgroup as compiled by Kabat, et al., above. Preferably, the human immunoglobulin subgroup is human kappa light chains subgroup I (e.g., as in SEQ ID NO: 17).

The human variable light FR sequence preferably has substitutions therein, e.g., wherein a human FR residue is replaced by a corresponding mouse residue, but replacement with the nonhuman residue is not necessary. For example, a replacement residue other than the corresponding nonhuman residue may be selected by phage display. Exemplary variable light FR residues that may be substituted include any one or more of FR residue numbers, including, but not limited to, F4, Y36, Y49, G64, S67.

With respect to the CDRs, these preferably have amino acid sequences listed in Table 2, below.

Methods for generating humanized anti-sphingolipid antibodies of interest herein are elaborated in more detail below.

A. Antibody Preparation

Methods for humanizing nonhuman anti-sphingolipid antibodies and generating variants of anti-sphingolipid antibodies are described in the Examples below. In order to humanize an anti-sphingolipid antibody, the nonhuman antibody starting material is prepared. Where a variant is to be generated, the parent antibody is prepared. Exemplary techniques for generating such nonhuman antibody starting material and parent antibodies will be described in the following sections.

(i) Antigen Preparation.

The sphingolipid antigen to be used for production of antibodies may be, e.g., intact sphingolipid or a portion of a sphingolipid (e.g., a sphingolipid fragment comprising an "epitope"). Other forms of antigens useful for generating antibodies will be apparent to those skilled in the art. The sphingolipid antigen used to generate the antibody, is described in the examples below. In one embodiment, the antigen is a derivatized form of the sphingolipid, and may be associated with a carrier protein.

(ii) Polyclonal Antibodies.

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 ug or 5 ug of the protein or conjugate (for rabbits or mice, respectively) with three volumes of Freund's complete adjuvant and injecting the solution intradermally at multiple sites. One month later the animals are boosted with 0.1 to 0.2 times the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum may be suitably used to enhance the immune response.

(iii) Monoclonal Antibodies.

Monoclonal antibodies may be made using the hybridoma method first described by Kohler, et al., Nature, 256:495 (1975), or by other suitable methods, including by recombinant DNA methods (see, e.g., U.S. Pat. No. 4,816,567). In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur, et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbant assay (ELISA).

The binding affinity of a monoclonal antibody can, for example, be determined by the Scatchard analysis of Munson, et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

(iv) Humanization and Amino Acid Sequence Variants.

Example 12, below, describes procedures for humanization of an anti-sphingolipid antibody. General methods for humanization are described in, for example, U.S. Pat. No. 5,861,155, US19960652558, U.S. Pat. No. 6,479,284, US20000660169, U.S. Pat. No. 6,407,213, US19930146206, U.S. Pat. No. 6,639,055, US20000705686, U.S. Pat. No. 6,500,931, US19950435516, U.S. Pat. No. 5,530,101, U.S. Pat. No. 5,585,089, US19950477728, U.S. Pat. No. 5,693,761, US19950474040, U.S. Pat. No. 5,693,762, US19950487200, U.S. Pat. No. 6,180,370, US19950484537, US2003229208, US20030389155, U.S. Pat. No. 5,714,350, US19950372262, U.S. Pat. No. 6,350,861, US19970862871, U.S. Pat. No. 5,777,085, US19950458516, U.S. Pat. No. 5,834,597, US19960656586, U.S. Pat. No. 5,882,644, US19960621751, U.S. Pat. No. 5,932,448, US19910801798, U.S. Pat. No. 6,013,256, US19970934841, U.S. Pat. No. 6,129,914, US19950397411, U.S. Pat. No. 6,210,671, U.S. Pat. No. 6,329,511, US19990450520, US2003166871, US20020078757, U.S. Pat. No. 5,225,539, US19910782717, U.S. Pat. No. 6,548,640, US19950452462, U.S. Pat. No. 5,624,821, and US19950479752. In certain embodiments, it may be desirable to generate amino acid sequence variants of these humanized antibodies, particularly where these improve the binding affinity or other biological properties of the humanized antibody. Example 12 describes methodologies for generating amino acid sequence variants of an anti-sphingolipid antibody with enhanced affinity relative to the parent antibody.

Amino acid sequence variants of the anti-sphingolipid antibody are prepared by introducing appropriate nucleotide changes into the anti-sphingolipid antibody DNA, or by peptide synthesis. Such variants include, for example, deletions from, and/or insertions into and/or substitutions of, residues within the amino acid sequences of the anti-sphingolipid antibodies of the examples herein. Any combination of deletion, insertion, and substitution is made to arrive at the final construct, provided that the final construct possesses the desired characteristics. The amino acid changes also may alter post-translational processes of the humanized or variant anti-sphingolipid antibody, such as changing the number or position of glycosylation sites.

A useful method for identification of certain residues or regions of the anti-sphingolipid antibody that are preferred locations for mutagenesis is called "alanine scanning mutagenesis," as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with sphingolipid antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-sphingolipid antibody variants are screened for the desired activity. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-sphingolipid antibody with an N-terminal methionyl residue or the antibody fused to an epitope tag. Other insertional variants of the anti-sphingolipid antibody molecule include the fusion to the N- or C-terminus of the anti-sphingolipid antibody of an enzyme or a polypeptide which increases the serum half-life of the antibody.

Another type of variant is an amino acid substitution variant. These variants have at least one amino acid residue in the anti-sphingolipid antibody molecule removed and a different residue inserted in its place. The sites of greatest interest for substitutional mutagenesis include the hypervariable regions, but FR alterations are also contemplated. Conservative substitutions are preferred substitutions. If such substitutions result in a change in biological activity, then more substantial changes, denominated "exemplary" substitutions listed below, or as further described below in reference to amino acid classes, may be introduced and the products screened.

TABLE 1

Exemplary Amino Acid Residue Substitutions

| Amino acid residue (symbol) | Exemplary substitutions |
| --- | --- |
| Ala (A) | val; leu; ile val |
| Arg (R) | lys; gln; asn lys |
| Asn (N) | gln; his; asp, lys; gln arg |
| Asp (D) | glu; asn glu |
| Cys (C) | ser; ala ser |
| Gln (Q) | asn; glu asn |
| Glu (E) | asp; gln asp |
| Gly (G) | ala ala |
| His (H) | asn; gln; lys; arg arg |
| Ile (I) | leu; val; met; ala; leu phe; norleucine |
| Leu (L) | norleucine; ile; val; ile met; ala; phe |
| Lys (K) | arg; gln; asn arg |
| Met (M) | leu; phe; ile leu |
| Phe (F) | leu; val; ile; ala; tyr tyr |
| Pro (P) | ala ala |
| Ser (S) | thr thr |
| Thr (T) | ser ser |
| Trp (W) | tyr; phe tyr |
| Tyr (Y) | trp; phe; thr; ser phe |
| Val (V) | ile; leu; met; phe; leu ala; norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the humanized or variant anti-sphingolipid antibody also may be substituted, to improve the oxidative stability of the molecule and prevent aberrant crosslinking. Conversely, cysteine bond(s) may be added to the antibody to improve its stability (particularly where the antibody is an antibody fragment such as an Fv fragment).

One type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and sphingolipid. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked and/or or O-linked. N-linked refers to the attachment of the carbohydrate moiety to the side chain of an asparagine residue. The tripeptide sequences asparagine-X-serine and asparagine-X-threonine, where X is any amino acid except proline, are the most common recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-sphingolipid antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-sphingolipid antibody.

(v) Human Antibodies.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits, et al., Proc. Natl. Acad. Sci. USA, 90:2551 (1993); Jakobovits, et al., Nature, 362:255-258 (1993); Bruggermann, et al., Year in Immuno., 7:33 (1993); and U.S. Pat. Nos. 5,591,669, 5,589,369 and 5,545,807. Human antibodies can also be derived from phage-display libraries (Hoogenboom, et al., J. Mol. Biol., 227:381 (1991); Marks, et al., J. Mol. Biol., 222:581-597 (1991); and U.S. Pat. Nos. 5,565,332 and 5,573,905). As discussed above, human antibodies may also be generated by in vitro activated B cells (see, e.g., U.S. Pat. Nos. 5,567,610 and 5,229,275) or by other suitable methods.

(vi) Antibody Fragments.

In certain embodiments, the humanized or variant anti-sphingolipid antibody is an antibody fragment. Various techniques have been developed for the production of antibody fragments. Traditionally, these fragments were derived via proteolytic digestion of intact antibodies (see, e.g., Morimoto, et al., Journal of Biochemical and Biophysical Methods 24:107-117 (1992); and Brennan, et al., Science 229:81 (1985)). However, these fragments can now be produced directly by recombinant host cells. For example, Fab'-SH fragments can be directly recovered from *E. coli* and chemically coupled to form $F(ab')_2$ fragments (Carter, et al., Bio/Technology 10:163-167 (1992)). In another embodiment, the $F(ab')_2$ is formed using the leucine zipper GCN4 to promote assembly of the $F(ab')_2$ molecule. According to another approach, Fv, Fab or $F(ab')_2$ fragments can be isolated directly from recombinant host cell culture. Other techniques for the production of antibody fragments will be apparent to the skilled practitioner.

(vii) Multispecific Antibodies.

In some embodiments, it may be desirable to generate multispecific (e.g., bispecific) humanized or variant anti-sphingolipid antibodies having binding specificities for at least two different epitopes. Exemplary bispecific antibodies may bind to two different epitopes of the sphingolipid. Alternatively, an anti-sphingolipid arm may be combined with an arm which binds to a different molecule. Bispecific antibodies can be prepared as full length antibodies or antibody fragments (e.g., $F(ab')_2$ bispecific antibodies).

According to another approach for making bispecific antibodies, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See, e.g., U.S. Pat. No. 5,731,168.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in, for example, U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan, et al., Science 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. In yet a further embodiment, Fab'-SH fragments directly recovered from *E. coli* can be chemically coupled in vitro to form bispecific antibodies. Shalaby, et al., J. Exp. Med. 175:217-225 (1992).

Various techniques for making and isolating bispecific antibody fragments directly from recombinant cell culture have also been described. For example, bispecific antibodies have been produced using leucine zippers. Kostelny, et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger, et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, e.g., Gruber, et al., J. Immunol. 152:5368 (1994). Alternatively, the bispecific antibody may be a "linear antibody" produced as described in, fror example, Zapata, et al. Protein Eng. 8(10): 1057-1062 (1995).

Antibodies with more than two valencies are also contemplated. For example, trispecific antibodies can be prepared. Tutt et al., J. Immunol. 147:60 (1991).

An antibody (or polymer or polypeptide) of the invention comprising one or more binding sites per arm or fragment thereof will be referred to herein as "multivalent" antibody. For example a "bivalent" antibody of the invention comprises two binding sites per Fab or fragment thereof whereas a "trivalent" polypeptide of the invention comprises three binding sites per Fab or fragment thereof. In a multivalent polymer of the invention, the two or more binding sites per Fab may be binding to the same or different antigens. For example, the two or more binding sites in a multivalent polypeptide of the invention may be directed against the same antigen, for example against the same parts or epitopes of said antigen or against two or more same or different parts or epitopes of said antigen; and/or may be directed against different antigens; or a combination thereof. Thus, a bivalent polypeptide of the invention for example may comprise two identical binding sites, may comprise a first binding sites directed against a first part or epitope of an antigen and a second binding site directed against the same part or epitope of said antigen or against another part or epitope of said antigen; or may comprise a first binding sites directed against a first part or epitope of an antigen and a second binding site directed against the a different antigen. However, as will be clear from the description hereinabove, the invention is not limited thereto, in the sense that a multivalent polypeptide of the invention may comprise any number of binding sites directed against the same or different antigens.

An antibody (or polymer or polypeptide) of the invention that contains at least two binding sites per Fab or fragment thereof, in which at least one binding site is directed against a first antigen and a second binding site directed against a second antigen different from the first antigen, will also be referred to as "multispecific". Thus, a "bispecific" polymer comprises at least one site directed against a first antigen and at least one a second site directed against a second antigen, whereas a "trispecific" is a polymer that comprises at least one binding site directed against a first antigen, at least one further binding site directed against a second antigen, and at least one further binding site directed against a third antigen, etc. Accordingly, in their simplest form, a bispecific polypeptide of the invention is a bivalent polypeptide (per Fab) of the invention. However, as will be clear from the description hereinabove, the invention is not limited thereto, in the sense that a multispecific polypeptide of the invention may comprise any number of binding sites directed against two or more different antigens.

(viii) Other Modifications.

Other modifications of the humanized or variant anti-sphingolipid antibody are contemplated. For example, the invention also pertains to immunoconjugates comprising the antibody described herein conjugated to a cytotoxic agent such as a toxin (e.g., an enzymatically active toxin of bacterial, fungal, plant or animal origin, or fragments thereof), or a radioactive isotope (for example, a radioconjugate). Conjugates are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

The anti-sphingolipid antibodies disclosed herein may also be formulated as immunoliposomes. Liposomes containing the antibody are prepared by methods known in the art, such as described in Epstein et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. For example, liposomes can be generated by the reverse phase evaporation method with a lipid composition comprising phosphatidyl choline, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin, et al., J. Biol. Chem. 257: 286-288 (1982) via a disulfide interchange reaction. Another active ingredient is optionally contained within the liposome.

Enzymes or other polypeptides can be covalently bound to the anti-sphingolipid antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger, et al., Nature 312:604-608 (1984)).

In certain embodiments of the invention, it may be desirable to use an antibody fragment, rather than an intact antibody, to increase penetration of target tissues and cells, for example. In this case, it may be desirable to modify the antibody fragment in order to increase its serum half life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis). See, e.g., U.S. Pat. No. 6,096,871.

Covalent modifications of the humanized or variant anti-sphingolipid antibody are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. Exemplary covalent modifications of polypeptides are described in U.S. Pat. No. 5,534,615, specifically incorporated herein by reference. A preferred type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

B. Vectors, Host Cells and Recombinant Methods

The invention also provides isolated nucleic acid encoding the humanized or variant anti-sphingolipid antibody, vectors and host cells comprising the nucleic acid, and recombinant techniques for the production of the antibody.

For recombinant production of the antibody, the nucleic acid encoding it may be isolated and inserted into a replicable vector for further cloning (amplification of the DNA) or for expression. In another embodiment, the antibody may be produced by homologous recombination, e.g., as described in U.S. Pat. No. 5,204,244. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, as described, for example, in U.S. Pat. No. 5,534,615.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-sphingolipid antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244, 234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated anti-sphingolipid antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham, et al., J. Gen Virol. 36:59 (1977)); baby hamster kidney cells (BHK, ATCC CCL 10); Chinese hamster ovary cells/−DHFR (CHO, Urlaub, et al., Proc. Natl. Acad. Sci. USA 77:4216 (1980)); mouse Sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather, et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-sphingolipid antibody production and cultured in conventional nutrient media modified as appropriate for inducing promoters, selecting transformants, or amplifying the genes encoding the desired sequences.

The host cells used to produce the anti-sphingolipid antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham, et al., Meth. Enz. 58:44 (1979), Barnes, et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter, et al., Bio/Technology 10:163-167 (1992) describe a procedure for isolating antibodies that are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human heavy chains (Lindmark, et al., J. Immunol. Meth. 62:1-13 (1983)). Protein G is recommended for all mouse isotypes and for human γ3 (Guss, et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification, such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

C. Pharmaceutical Formulations

Therapeutic formulations of an antibody or immune-derived moiety of the invention are prepared for storage by mixing the antibody having the desired degree of purity with optional physiologically acceptable carriers, excipients, or stabilizers (see, e.g., Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

The formulations to be used for in vivo administration must be sterile. This is readily accomplished for instance by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

D. Non-Therapeutic Uses for the Antibodies

The antibodies of the invention may be used as affinity purification agents. In this process, the antibodies are immobilized on a solid phase such a Sephadex resin or filter paper, using methods well known in the art. The immobilized antibody is contacted with a sample containing the sphingolipid to be purified, and thereafter the support is washed with a suitable solvent that will remove substantially all the material in the sample except the sphingolipid, which is bound to the immobilized antibody. Finally, the support is washed with another suitable solvent, such as glycine buffer, for instance between pH 3 to pH 5.0, that will release the sphingolipid from the antibody.

Anti-sphingolipid antibodies may also be useful in diagnostic assays for sphingolipid, e.g., detecting its expression in specific cells, tissues (such as biopsy samples), or bodily fluids. Such diagnostic methods may be useful in diagnosis of a cardiovascular or cerebrovascular disease or disorder.

For diagnostic applications, the antibody typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in Current Protocols in Immunology, Volumes 1 and 2, Coligen et al., Ed. Wiley-Interscience, New York, N.Y., Pubs. (1991), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available. For example, U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclicoxidases (such as uricase and xanthine oxidase), lactoperoxidase, microperoxidase, and the like. Techniques for conjugating enzymes to antibodies are described in O'Sullivan, et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-sphingolipid antibody need not be labeled, and the presence thereof can be detected using a labeled antibody which binds to the anti-sphingolipid antibody.

The antibodies of the present invention may be employed in any known assay method, such as competitive binding assays, direct and indirect sandwich assays, and immunoprecipitation assays. See, e.g., Zola, Monoclonal Antibodies: A Manual of Techniques, pp. 147-158 (CRC Press, Inc. 1987).

Competitive binding assays rely on the ability of a labeled standard to compete with the test sample analyte for binding with a limited amount of antibody. The amount of sphingolipid in the test sample is inversely proportional to the amount of standard that becomes bound to the antibodies. To facilitate determining the amount of standard that becomes bound, the antibodies generally are insoluble before or after the competition, so that the standard and analyte that are bound to the antibodies may conveniently be separated from the standard and analyte that remain unbound.

Sandwich assays involve the use of two antibodies, each capable of binding to a different immunogenic portion, or epitope, of the protein to be detected. In a sandwich assay, the test sample analyte is bound by a first antibody that is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the blood or tissue sample may be fresh or frozen or may be embedded in paraffin and fixed with a preservative such as formalin, for example.

The antibodies may also be used for in vivo diagnostic assays. Generally, the antibody is labeled with a radionuclide (such as $^{111}In$, $^{99}Tc$, $^{14}C$, $^{131}I$, $^{125}I$, $^{3}H$, $^{32}P$, or $^{35}S$) so that the bound target molecule can be localized using immunoscintillography.

E. Diagnostic Kits

As a matter of convenience, the antibody of the present invention can be provided in a kit, for example, a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

F. Therapeutic Uses for the Antibody

For therapeutic applications, the anti-sphingolipid antibodies of the invention are administered to a mammal, preferably a human, in a pharmaceutically acceptable dosage form such as those discussed above, including those that may be administered to a human intravenously as a bolus or by continuous infusion over a period of time, by intramuscular, intraperitoneal, intra-cerebrospinal, subcutaneous, intra-articular, intrasynovial, intrathecal, oral, topical, or inhalation routes.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 ug/kg to about 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 μg/kg to about 20 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic imaging.

According to another embodiment of the invention, the effectiveness of the antibody in preventing or treating disease may be improved by administering the antibody serially or in combination with another agent that is effective for those purposes, such as chemotherapeutic anti-cancer drugs, for example. Such other agents may be present in the composition being administered or may be administered separately. The antibody is suitably administered serially or in combination with the other agent.

G. Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-sphingolipid antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention will be better understood by reference to the following Examples, which are intended to merely illustrate the best mode now known for practicing the invention. The scope of the invention is not to be considered limited thereto.

EXAMPLES

Example 1

Murine Monoclonal Antibody to S1P
(Sphinsomab™; LT1002)

One type of therapeutic antibody specifically binds undesirable sphingolipids to achieve beneficial effects such as, e.g., (1) lowering the effective concentration of undesirable, toxic sphingolipids (and/or the concentration of their metabolic precursors) that would promote an undesirable effect such as a cardiotoxic, tumorigenic, or angiogenic effect; (2) to inhibit the binding of an undesirable, toxic, tumorigenic, or angiogenic sphingolipids to a cellular receptor therefore, and/or to lower the concentration of a sphingolipid that is available for binding to such a receptor. Examples of such therapeutic effects include, but are not limited to, the use of anti-S1P antibodies to lower the effective in vivo serum concentration of available S1P, thereby blocking or at least limiting S1P's tumorigenic and angiogenic effects and its role in post-MI heart failure, cancer, or fibrongenic diseases.

Thiolated S1P was synthesized to contain a reactive group capable of cross-linking the essential structural features of S1P to a carrier molecule such as KLH. Prior to immunization, the thio-S1P analog was conjugated via IOA or SMCC cross-linking to protein carriers (e.g., KLH) using standard protocols. SMCC is a heterobifunctional crosslinker that reacts with primary amines and sulfhydryl groups, and represents a preferred crosslinker.

Swiss Webster or BALB-C mice were immunized four times over a two month period with 50 μg of immunogen (SMCC facilitated conjugate of thiolated-S1P and KLH) per injection. Serum samples were collected two weeks after the second, third, and fourth immunizations and screened by direct ELISA for the presence of anti-S1P antibodies. Spleens from animals that displayed high titers of the antibody were subsequently used to generate hybridomas per standard fusion procedures. The resulting hybridomas were grown to confluency, after which the cell supernatant was collected for ELISA analysis. Of the 55 mice that were immunized, 8 were good responders, showing significant serum titers of antibodies reactive to S1P. Fusions were subsequently carried out using the spleens of these mice and myeloma cells according to established procedures. The resulting 1,500 hybridomas were then screened by direct ELISA, yielding 287 positive hybridomas. Of these 287 hybridomas screened by direct ELISA, 159 showed significant titers. Each of the 159 hybridomas was then expanded into 24-well plates. The cell-conditioned media of the expanded hybridomas were then re-screened to identify stable hybridomas capable of secreting antibodies of interest. Competitive ELISAs were performed on the 60 highest titer stable hybridomas.

Of the 55 mice and almost 1,500 hybridomas screened, one hybridoma was discovered that displayed performance characteristics that justified limited dilution cloning, as is required to ultimately generate a true monoclonal antibody. This process yielded 47 clones, the majority of which were deemed positive for producing S1P antibodies. Of these 47 clones, 6 were expanded into 24-well plates and subsequently screened by competitive ELISA. From the 4 clones that remained positive, one was chosen to initiate large-scale production of the S1P monoclonal antibody. SCID mice were injected with these cells and the resulting ascites was protein A-purified (50% yield) and analyzed for endotoxin levels (<3 EU/mg). For one round of ascites production, 50 mice were injected, producing a total of 125 mL of ascites. The antibodies were isotyped as IgG1 kappa, and were deemed >95% pure by HPLC. The antibody was prepared in 20 mM sodium phosphate with 150 mM sodium chloride (pH 7.2) and stored at −70° C. This antibody is designated LT1002 or Sphingomab™.

The positive hybridoma clone (designated as clone 306D326.26) was deposited with the ATCC (safety deposit storage number SD-5362), and represents the first murine mAb directed against S1P. The clone also contains the variable regions of the antibody heavy and light chains that could be used for the generation of a "humanized" antibody variant, as well as the sequence information needed to construct a chimeric antibody.

Screening of serum and cell supernatant for S1P-specific antibodies was by direct ELISA using a thiolated S1P analog as the antigen. A standard ELISA was performed, as described below, except that 50 ul of sample (serum or cell supernatant) was diluted with an equal volume of PBS/0.1% Tween-20 (PBST) during the primary incubation. ELISAs were performed in 96-well high binding ELISA plates (Costar) coated with 0.1 µg of chemically-synthesized thiolated-S1P conjugated to BSA in binding buffer (33.6 mM $Na_2CO_3$, 100 mM $NaHCO_3$; pH 9.5). The thiolated-S1P-BSA was incubated at 37° C. for 1 hr. at 4° C. overnight in the ELISA plate wells. The plates were then washed four times with PBS (137 mM NaCl, 2.68 mM KCl, 10.14 mM $Na_2HPO_4$, 1.76 mM $KH_2PO_4$; pH 7.4) and blocked with PBST for 1 hr. at room temperature. For the primary incubation step, 75 uL of the sample (containing the S1P to be measured), was incubated with 25 uL of 0.1 ug/mL anti-S1P mAb diluted in PBST and added to a well of the ELISA plate. Each sample was performed in triplicate wells. Following a 1 hr. incubation at room temperature, the ELISA plates were washed four times with PBS and incubated with 100 ul per well of 0.1 ug/mL HRP goat anti-mouse secondary (Jackson Immunoresearch) for 1 hr. at room temperature. Plates were then washed four times with PBS and exposed to tetramethylbenzidine (Sigma) for 1-10 minutes. The detection reaction was stopped by the addition of an equal volume of 1M $H_2SO_4$. Optical density of the samples was determined by measurement at 450 nm using an EL-X-800 ELISA plate reader (Bio-Tech).

For cross reactivity, a competitive ELISA was performed as described above, except for the following alterations. The primary incubation consisted of the competitor (S1P, SPH, LPA, etc.) and a biotin-conjugated anti-S1P mAb. Biotinylation of the purified monoclonal antibody was performed using the EZ-Link Sulfo-NHS-Biotinylation kit (Pierce). Biotin incorporation was determined as per kit protocol and ranged from 7 to 11 biotin molecules per antibody. The competitor was prepared as follows: lipid stocks were sonicated and dried under argon before reconstitution in DPBS/BSA [1 mg/ml fatty acid free BSA (Calbiochem) in DPBS (Invitrogen 14040-133)]. Purified anti-S1P mAb was diluted as necessary in PBS/0.5% Triton X-100. Competitor and antibody solutions were mixed together so to generate 3 parts competitor to 1 part antibody. A HRP-conjugated streptavidin secondary antibody (Jackson Immunoresearch) was used to generate signal.

Figure 1B:
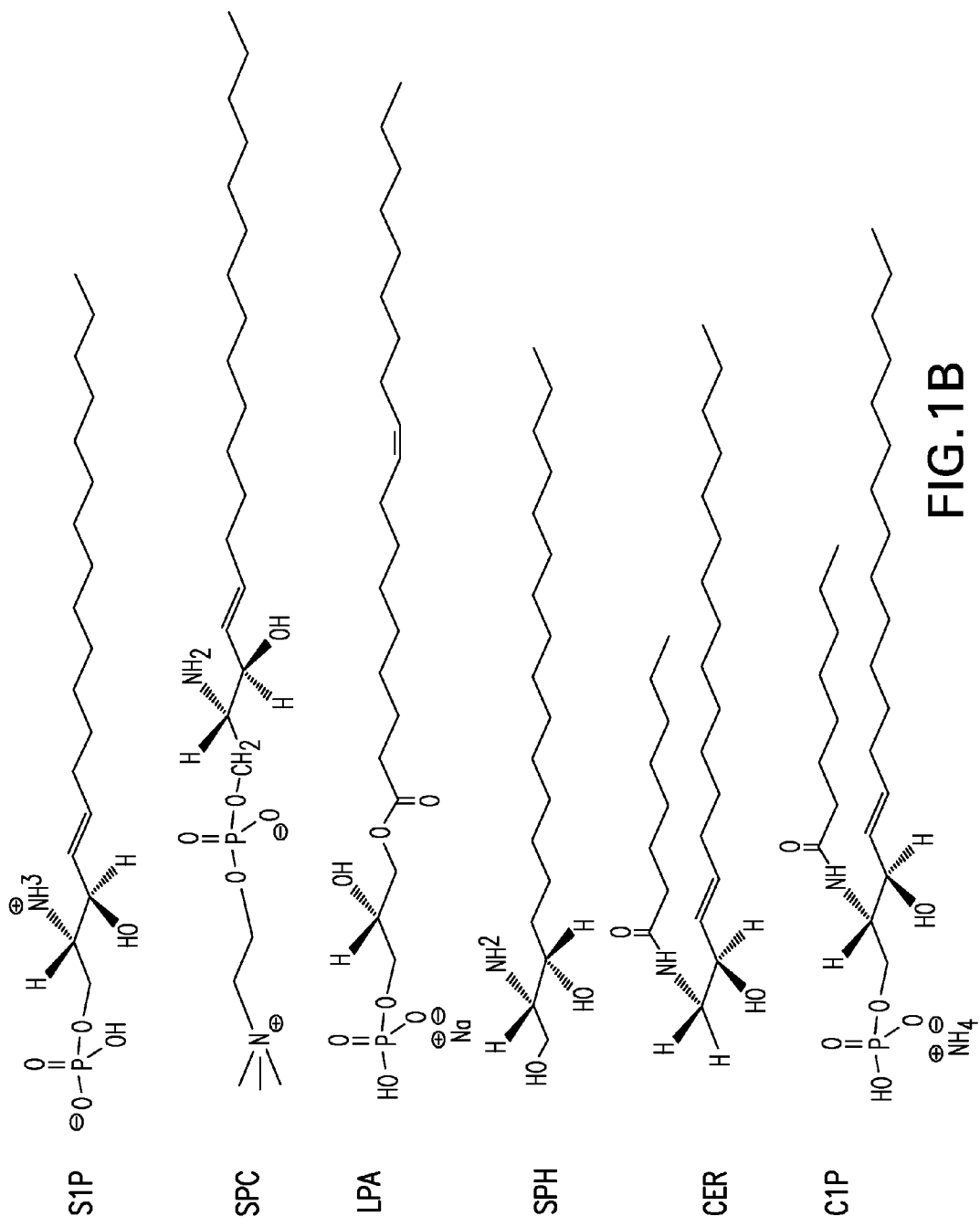

Another aspect of the competitive ELISA data (shown in FIG. 1, panel A) is that it shows that the anti-S1P mAb was unable to distinguish the thiolated-S1P analog from the natural S1P that was added in the competition experiment. It also demonstrates that the antibody does not recognize any oxidation products since the analog was constructed without any double bonds. The anti-S1P mAb was also tested against natural product containing the double bond that was allowed to sit at room temperature for 48 hours. Reverse phase HPLC of the natural S1P was performed according to methods reported previously (Deutschman, et al. (July 2003), *Am Heart J.*, vol. 146(1):62-8), and the results showed no difference in retention time. Further, a comparison of the binding characteristics of the monoclonal antibody to the various lipids shown in FIG. 1, panel A, indicates that the epitope recognized by the antibody do not involve the hydrocarbon chain in the region of the double bond of natural S1P. On the other hand, the epitope recognized by the monoclonal antibody is the region containing the amino alcohol on the sphingosine base backbone plus the free phosphate. If the free phosphate is linked with a choline (as is the case with SPC), then the binding was somewhat reduced. If the amino group is esterfied to a fatty acid (as is the case with C1P), no antibody binding was observed. If the sphingosine amino alcohol backbone was replaced by a glycerol backbone (as is the case with LPA), there the S1P-specific monoclonal exhibited no binding. These epitope mapping data indicate that there is only one epitope on S1P recognized by the monoclonal antibody, and that this epitope is defined by the unique polar headgroup of S1P.

In a similar experiment using ELISA measurements, suitable control materials were evaluated to ensure that this anti-S1P monoclonal antibody did not recognize either the protein carrier or the crosslinking agent. For example, the normal crosslinker SMCC was exchanged for IOA in conjugating the thiolated-S1P to BSA as the laydown material in the ELISA. When IOA was used, the antibody's binding characteristics were nearly identical to when BSA-SMCC-thiolated-S1P was used. Similarly, KLH was exchanged for BSA as the protein that was complexed with thiolated-S1P as the laydown material. In this experiment, there was also no significant difference in the binding characteristics of the antibody.

Figure 2:
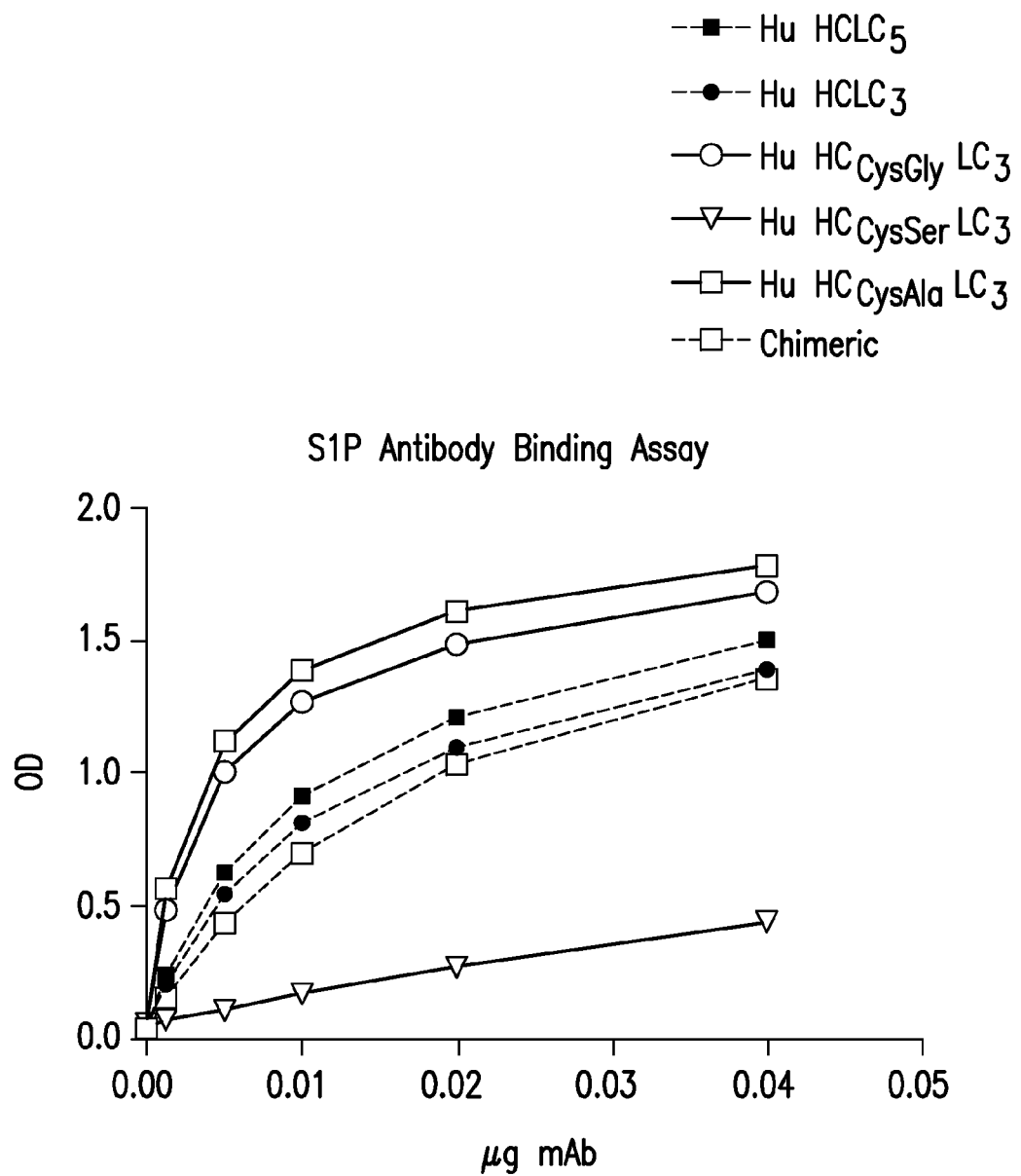
FIG. 2. This figure shows the binding properties of several chimeric and recombinant humanized anti-S1P antibody variants. The binding to S1P for a chimeric antibody (pATH10+pATH50) was compared in an ELISA binding assay to two versions of the humanized anti-S1P monoclonal antibody (pATH201+pATH308) and (pATH201+pATH309). pATH308 is the humanized light chain with five murine backmutations and pATH309 is the humanized light chain with three backmutations in the framework region. The humanized heavy chain (pATH201) contains only one murine backmutation in the framework region.

Binding kinetics: The binding kinetics of S1P to its receptor or other moieties has, traditionally, been problematic because of the nature of lipids. Many problems have been associated with the insolubility of lipids. For BIAcore measurements, these problems were overcome by directly immobilizing S1P to a BIAcore chip. Antibody was then flowed over the surface of the chip and alterations in optical density were measured to determine the binding characteristics of the antibody to S1P. To circumvent the bivalent binding nature of antibodies, S1P was coated on the chip at low densities. Additionally, the chip was coated with various densities of S1P (7, 20, and 1000 RU) and antibody binding data was globally fit to a 1:1 interaction model. The results shown in FIG. 2 demonstrate the changes in optical density due to the binding of the monoclonal antibody to S1P at three different densities of S1P. Overall, the affinity of the monoclonal antibody to S1P was determined to be very high, in the range of approximately 88 picomolar (pM) to 99 nM, depending on whether a monovalent or bivalent binding model was used to analyze the binding data.

Example 2

ELISA Assays

1. Quantitative ELISAs

Microtiter ELISA plates (Costar, Cat No. 3361) were coated with rabbit anti-mouse IgG, F(ab')$_2$ fragment specific antibody (Jackson, 315-005-047) diluted in 1M Carbonate Buffer (pH 9.5) at 37° C. for 1 h. Plates were washed with PBS and blocked with PBS/BSA/Tween-20 for 1 hr at 37° C. For the primary incubation, dilutions of non-specific mouse IgG or human IgG, whole molecule (used for calibration curve) and samples to be measured were added to the wells. Plates were washed and incubated with 100 ul per well of HRP conjugated goat anti-mouse (H+L) diluted 1:40,000 (Jackson, cat No 115-035-146) for 1 hr at 37° C. After washing, the enzymatic reaction was detected with tetramethylbenzidine (Sigma, cat No T0440) and stopped by adding 1 M $H_2SO_4$. The optical density (OD) was measured at 450 nm using a Thermo Multiskan EX. Raw data were transferred to GraphPad software for analysis.

2. Direct ELISAs

Microtiter ELISA plates (Costar, Cat No. 3361) were coated with LPA-BSA diluted in 1M Carbonate Buffer (pH 9.5) at 37° C. for 1 h. Plates were washed with PBS (137 mM NaCl, 2.68 mM KCl, 10.1 mM $Na_2HPO_4$, 1.76 mM $KH_2PO_4$; pH 7.4) and blocked with PBS/BSA/Tween-20 for 1 h at room temperature or overnight at 4° C. The samples to be tested were diluted at 0.4 ug/mL, 0.2 ug/mL, 0.1 ug/mL, 0.05 ug/mL, 0.0125 ug/mL, and 0 ug/mL and 100 ul added to each well. Plates were washed and incubated with 100 ul per well of HRP conjugated goat anti-mouse (1:20,000 dilution) (Jackson, cat. no. 115-035-003) for 1 h at room temperature. After washing, the enzymatic reaction was detected with tetramethylbenzidine (Sigma, cat. no. T0440) and stopped by adding 1 M $H_2SO_4$. The optical density (OD) was measured at 450 nm using a Thermo Multiskan EX. Raw data were transferred to GraphPad software for analysis.

3. Competition Assays

The specificity of mAbs was tested in ELISA assays. Microtiter plates ELISA plates (Costar, Cat No. 3361) were coated with 18:0 LPA-BSA diluted in 1M Carbonate Buffer (pH 9.5) at 37° C. for 1 h. Plates were washed with PBS (137 mM NaCl, 2.68 mM KCl, 10.1 mM $Na_2HPO_4$, 1.76 mM $KH_2PO_4$; pH 7.4) and blocked with PBS/BSA/Tween-20 at 37° C. for 1 h or overnight at room temperature. For the primary incubation 0.4 ug/mL anti-LPA mAb and designated amounts of (14:0, 16:0, 18:0, 18:1, 18:2 and 20:4) LPA, DSPA, 18:1 LPC (lysophosphatidylcholine), S1P, ceramide and ceramide-1-phosphate were added to wells of the ELISA plates and incubated at 37° C. for 1 h. Plates were washed and incubated with 100 ul per well of HRP conjugated goat anti-mouse (1:20,000 dilution) (Jackson, cat No 115-035-003) or HRP conjugated goat anti-human (H+L) diluted 1:50,000 (Jackson, cat No 109-035-003) at 37° C. for 1 h. After washing, the enzymatic reaction was detected with tetramethylbenzidine and stopped by adding 1 M $H_2SO_4$. The optical density (OD) was measured at 450 nm using a Thermo Multiskan EX. Raw data were transferred to GraphPad software for analysis.

Example 3

SPHINGOMAB Murine mAb is Highly Specific for S1P

Figure 3:
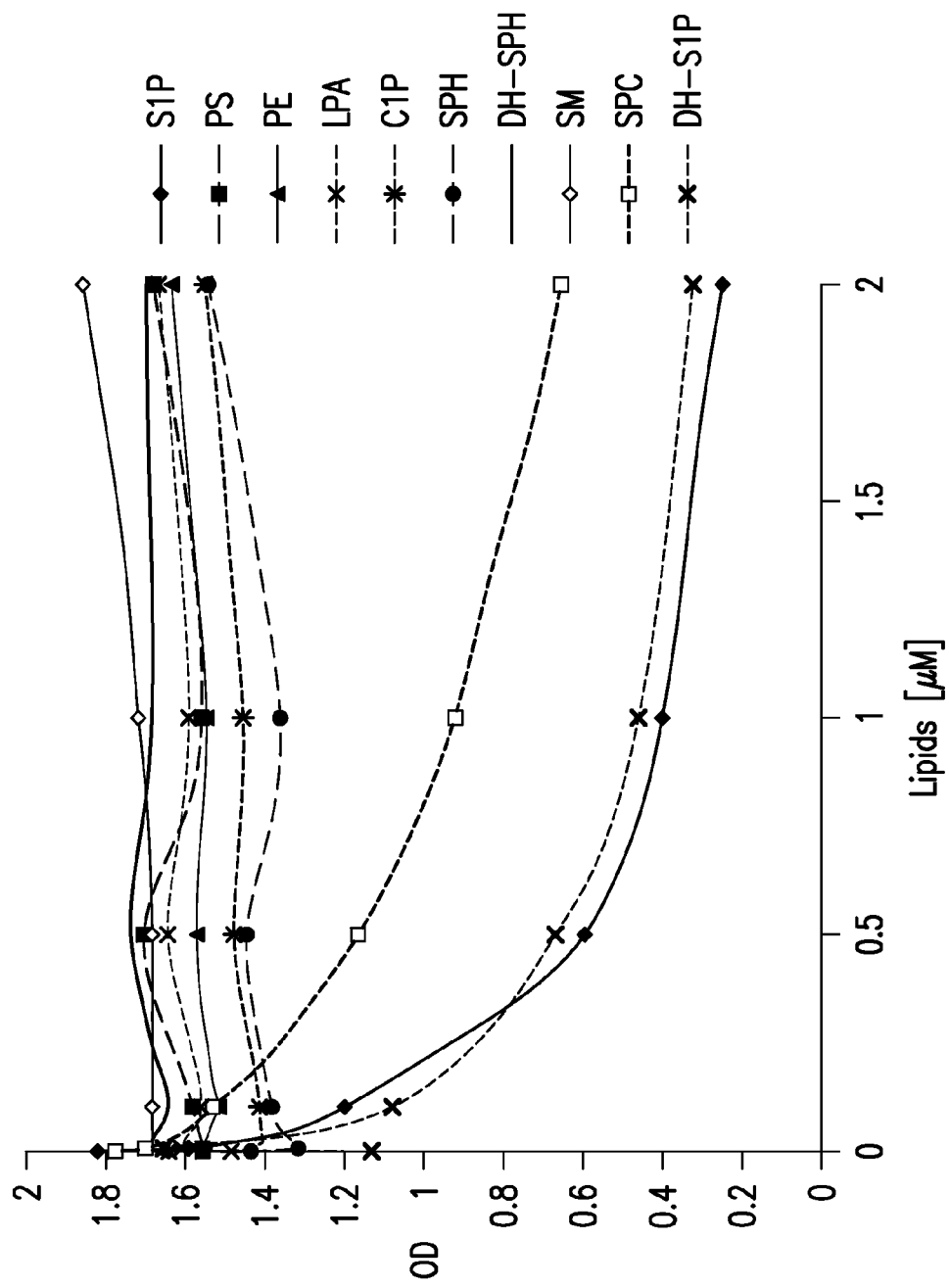
FIG. 3 is a graph showing that SPHINGOMAB is highly specific for S1P. The graph, the data for which were generated using a competitive ELISA, demonstrates SPHINGOMAB's specificity for S1P as compared to other bioactive lipids. SPHINGOMAB demonstrated no cross-reactivity to sphingosine (SPH), the immediate metabolic precursor of S1P or lysophosphatidic acid (LPA), an important extracellular signaling molecule that is structurally and functionally similar to S1P. SPHINGOMAB did not recognize other structurally similar lipids and metabolites, including ceramide-1-phosphate (C1P), dihydrosphingosine (DH-SPH), phosphatidyl serine (PS), phosphatidyl ethanolamine (PE), or sphingomyelin (SM). SPHINGOMAB did cross react with dihydrosphingosine-1-phosphate (DH-S1P) and, to a lesser extent, sphingosylphoryl choline (SPC). The affinity (Kd) of SPHINGOMAB for S1P is less than 100 μM, much higher than most therapeutic antibodies, particularly other molecular sponges.

A competitive ELISA demonstrates SPHINGOMAB's specificity for S1P compared to other bioactive lipids. SPHINGOMAB demonstrated no cross-reactivity to sphingosine (SPH), the immediate metabolic precursor of S1P or lysophosphatidic acid (LPA), an important extracellular signaling molecule that is structurally and functionally similar to S1P. SPHINGOMAB did not recognize other structurally similar lipids and metabolites, including ceramide-1-phosphate (C1P), dihydrosphingosine (DH-SPH), phosphatidyl serine (PS), phosphatidyl ethanolamine (PE), or sphingomyelin (SM). SPHINGOMAB did cross react with dihydrosphingosine-1-phosphate (DH-S1P) and, to a lesser extent, sphingosylphorylcholine (SPC) (FIG. 3).

Example 4

SPHINGOMAB Significantly Reduces CNV and Scar Formation in a Murine Model of CNV Female C57BL6/J mice were subjected to laser-induced rupture of Bruch's membrane and administered either 0.5 µg of Sphingomab or an isotype-matched non-specific (NS) antibody diluted in 2 µl of physiological saline. Mice were sacrificed 14 and 28 days after laser rupture.

To induce CNV lesions, the pupils were dilated with ophthalmic tropicamide (0.5%) and phenylephrine (2.5%). A coverslip was placed on the eye. An Oculight GL 532 nm (Iridex Corporation, Mountain View, Calif.) coupled to a slit lamp set to deliver a 100 msec pulse at 150 mW with a 50 µm spot size was used to rupture Bruch's membrane in three quadrants of the right eye located approximately 50 µm from the optic disc at relative 9, 12 and 3 o'clock positions. The left eye served as an uninjured control in all cases. Any lesion not associated with a vapor bubble or lesions that became confluent were excluded from analysis.

To measure CNV lesion size, choroidal flatmounts of the sclera-choroid-RPE complex were prepared and stained for vasculature (R. communis agglutinin I; red) and pericytes (CD140b; green). Digital images were captured using an epifluorescence Zeiss Axioplan 2 with RGB Spot high-resolution digital camera and laser scanning confocal microscope (BioRad MRC 1024, BioRad Corporation, Temecula, Calif.). For volumetric analysis, a z-series capture was used and the sum of lesion area throughout the z-series was multiplied by the z thickness (4 µm) to obtain the lesion volume.

To assess collagen deposition, the sclera-choroid-RPE complex was stained with Masson's Trichrome. The sclera-choroid-RPE complex was embedded in paraffin and then serially sectioned at a thickness of 6 microns. Approximately 30 sections per lesion were evaluated. Quantitation of the volume of collagen deposition was calculated in the same manner as described for CNV lesion volume.

Figure 4A:
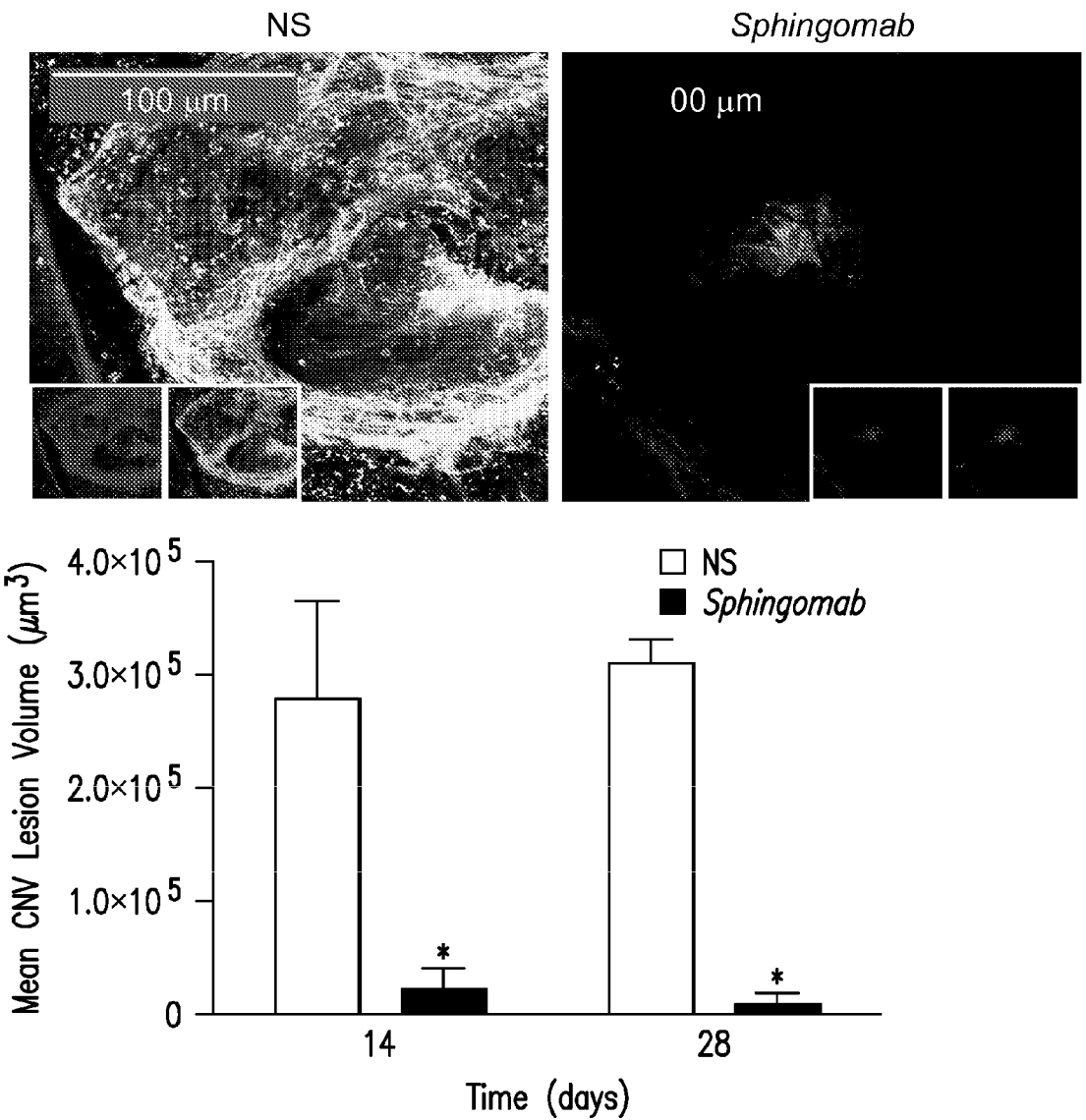
FIG. 4A shows that in a murine CNV lesion formation model SPHINGOMAB dramatically attenuates choroidal neovascularization 14 and 28 days after laser-induced rupture of Bruch's membranes.
Figure 4B:
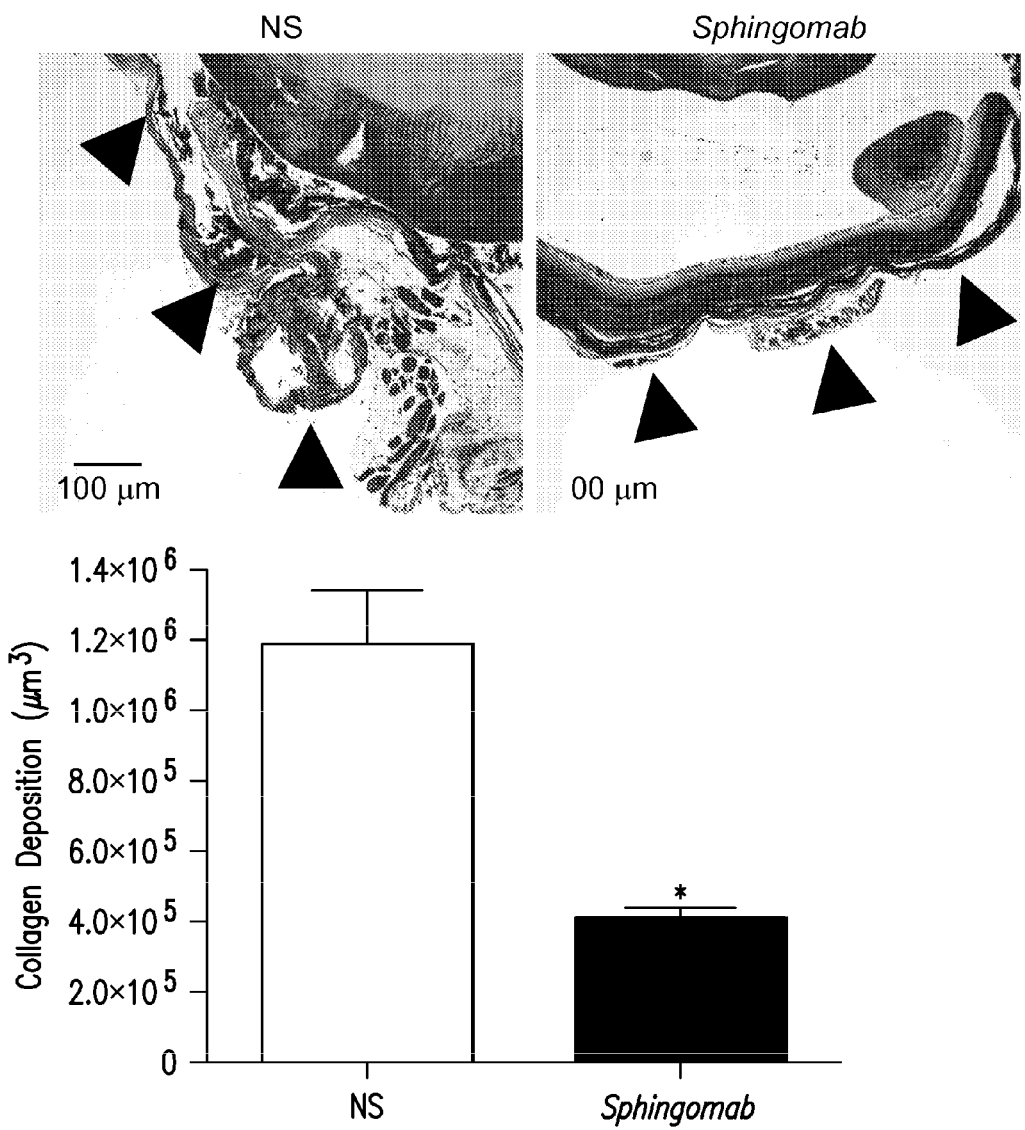
FIG. 4B shows that SPHINGOMAB significantly reduces fibrosis associated with CNV lesion formation 28 days after laser-induced rupture of Bruchs's membrane.

Captured digital images were evaluated morphometrically using ImageJ software (Research Services Branch, National Institutes of Health, Bethesda, Md.). FIG. 4A shows that SPHINGOMAB dramatically attenuates choroidal neovascularization 14 and 28 days after laser-induced rupture of Bruch's membrane. FIG. 4B shows that SPHINGOMAB significantly reduces fibrosis associated with CNV lesion formation 28 days after laser-induced rupture of Bruch's membrane.

Example 5

Figure 5A:
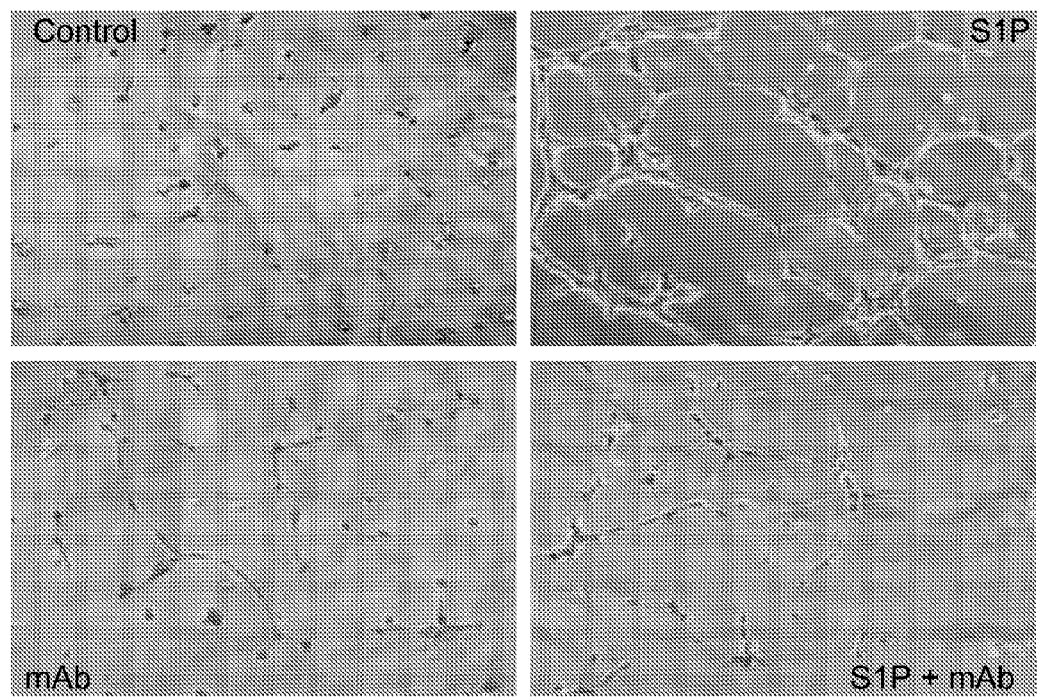
FIG. 5.
Figure 5B:
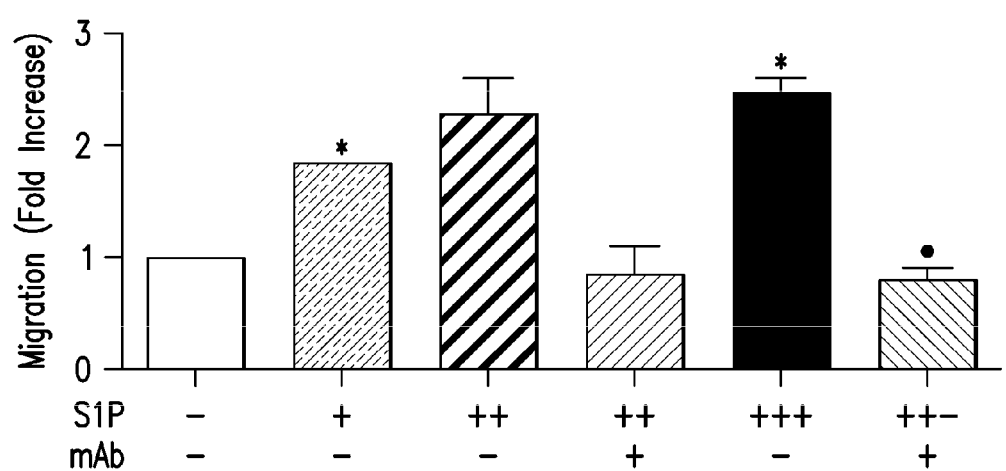

SPHINGOMAB Inhibits Neovascularization Through Multiple Mechanisms Including Inhibition of Endothelial Cell Migration and Tube Formation S1P promotes the migration of human umbilical vein endothelial cells (HUVECs) and, in Matrigel and other assays, the formation of de novo BV formation in vitro; SPHINGOMAB can neutralize these effects of S1P. Experiments were performed as described by Visentin et al. (Cancer Cell 2006 Mar.; 9(3):225-38). Data in FIG. 5A suggest that HUVECs seeded onto GF-reduced Matrigel formed multiple capillary-like structures in the presence of S1P and failed to form capillary-like structures in the absence of S1P or when co-incubated with SPHINGOMAB and S1P. Data in FIG. 5B demonstrate the potent ability of 0.1-1 µM S1P to stimulate HUVEC migration 2-2.5 fold over non-treated HUVECs, or HUVECs co-incubated with SPHINGOMAB in a Matrigel chemoinvasion assay. Combined, these studies demonstrate that SPHINGOMAB can efficiently mitigate the pro-angiogenic effects of S1P on ECs.

Example 6

Figure 6A:
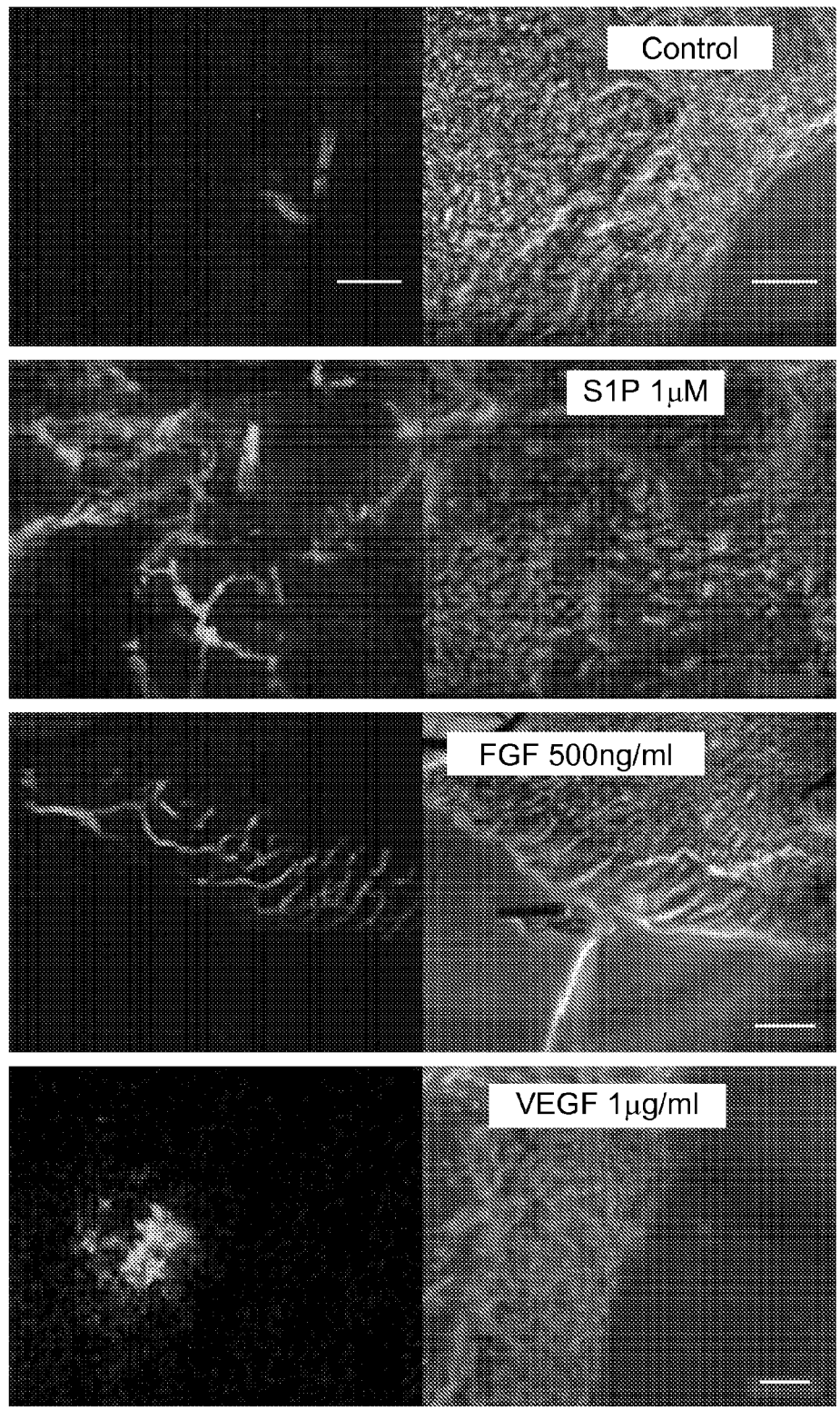
FIG. 6A shows photos of several representative FITC-stained blood vessels from sections of Matrigel plugs±the indicated growth factors.

SPHINGOMAB Inhibits Neovascularization Through Multiple Mechanisms Including Mitigation of the Effects of S1P, VEGF and bFGF In Vivo Based on in vivo studies showing that S1P increased endothelial capillary growth into subcutaneously implanted Matrigel plugs, we speculated that SPHINGOMAB could reduce de novo BV formation in vivo. To investigate this, we employed the in vivo Matrigel Plug assay for neovascularization. In one set of experiments, Matrigel was supplemented with either IlM S1P, 0.5 µg/mL bFGF or 1 µg/mL VEGF and then injected I.P. into mice (n=4). After 10 days, the mice were heparinized and injected with the fluorescent lectin, Isolectin B4-FITC, which binds to adhesion molecules expressed by vascular EC that form the growing BVs. The plugs were then excised, frozen in OCT, sectioned and viewed for FITC-stained BVs. Data in FIG. 6A suggest that S1P is a more potent stimulator of neovascularization in vivo than bFGF or VEGF [Lee, et al., (1999), Biochem Biophys Res Commun., vol 264: 743-50], as evidenced by the vast amount of FITC-stained BVs in the plugs containing S1P compared to the plugs containing bFGF or VEGF.

Figure 6B:
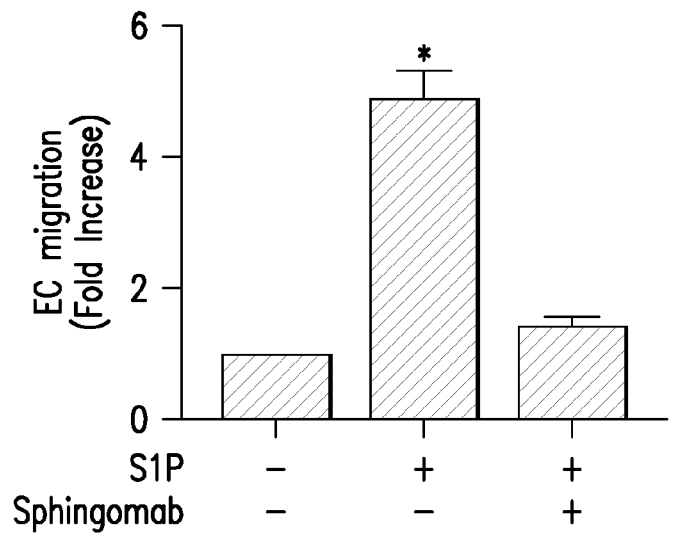
FIG. 6B shows that S1P stimulates endothelial cell (EC) infiltration.

Sections of the plugs were then stained with hemotoxyln & eosin for evaluation of EC infiltration (FIG. 6B). The infiltration of ECs is a critical step in neo-vascularization. Plugs containing S1P had a 3-fold increase of EC infiltration in comparison to the Matrigel only plugs. Cell infiltration is presumed to be ECs although we recognize that other cell types such as immune cells may also be stained. Mice systemically administered SPHINGOMAB every 48 hrs (initiated 1 day prior to plug implantation), demonstrated a reduced amount of EC infiltration even when S1P was added to the Matrigel plugs. These results demonstrate the ability of SPHINGOMAB to inhibit EC infiltration in vivo.

Figure 6C:
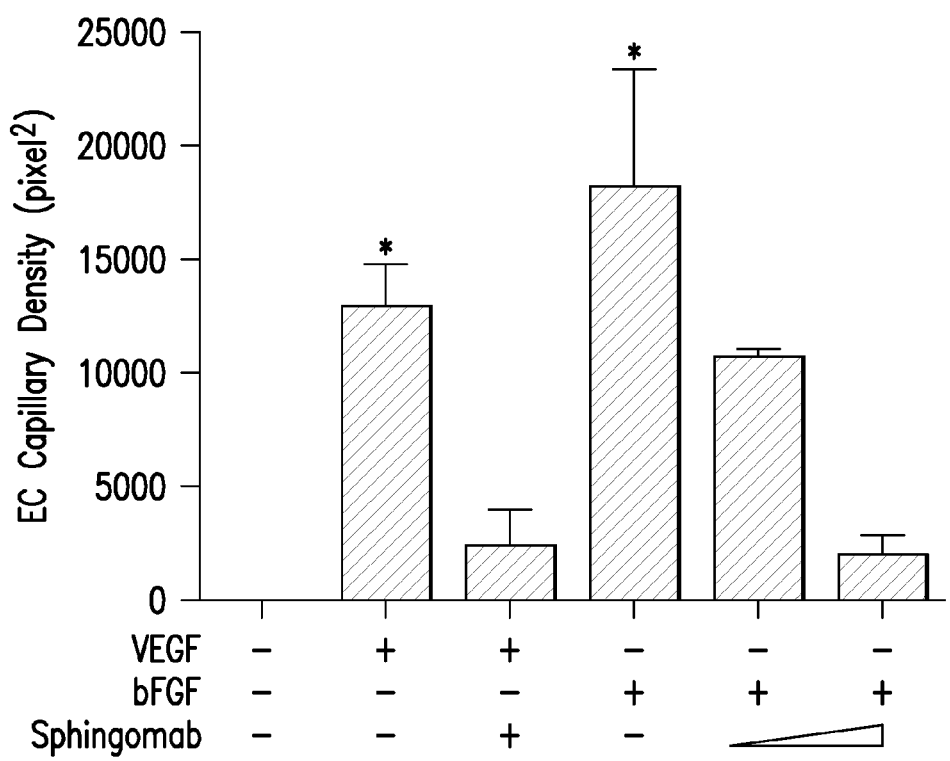
FIG. 6C represents the quantification of relative fluorescence from Matrigel plugs stimulated with VEGF or bFGF as an indicator of neovascularization. The effects of S1P, VEGF, and bFGF were inhibited when mice were systemically treated with 1 or 25 mg/kg of SPHINGOMAB.

Endogenous S1P from the blood and surrounding tissue could supply a wound with pro-angiogenic stimuli. The ability of SPHINGOMAB to reduce endogenous S1P in a wound was investigated. Optimally stimulated plugs (Matrigel supplemented with 0.5 µg/mL bFGF or 10 mg/mL VEGF) were implanted into mice. Mice received i.p. injections of 25 mg/kg SPHINGOMAB or saline every 48 hrs starting 1 day prior to Matrigel implantation. Each treatment group (Matrigel, Matrigel plus GF or Matrigel plus GF and administered SPHINGOMAB) consisted of a minimum of 6 mice. After 10 days, the mice were treated with heparin, injected with Isolectin B4-FITC, the plugs excised, embedded in OCT freezing medium and sectioned. Micro-vascular density was qualitatively accessed by lectin-FITC stained vessels as shown in FIG. 6C. BV staining was sporadic in control (untreated) plugs, whereas the plugs containing bFGF or VEGF demonstrated significant evidence of vascularization. The plugs from mice treated with the SPHINGOMAB demonstrated a significant reduction in BV formation compared to the bFGF or VEGF plugs from saline-treated mice. Quantification of stained vessels revealed a 5 to 8.5-fold decrease in neovascularization of VEGF- or bFGF-containing plugs, respectively, from animals treated with SPHINGOMAB in comparison to saline-treated animals (FIG. 6C). This evaluation further demonstrates the ability of endogenous serum and tissue S1P to enhance micro-vascularization as well as the ability of SPHINGOMAB to neutralize endogenous S1P's pro-angiogenic effects.

Example 7

SPHINGOMAB Inhibits Scar Formation In Vivo

Figure 7A:
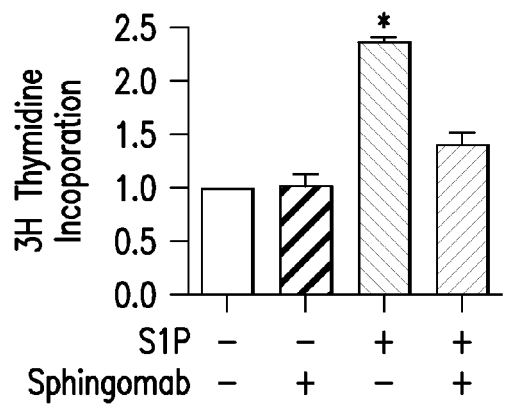
FIG. 7.
Figure 7B:
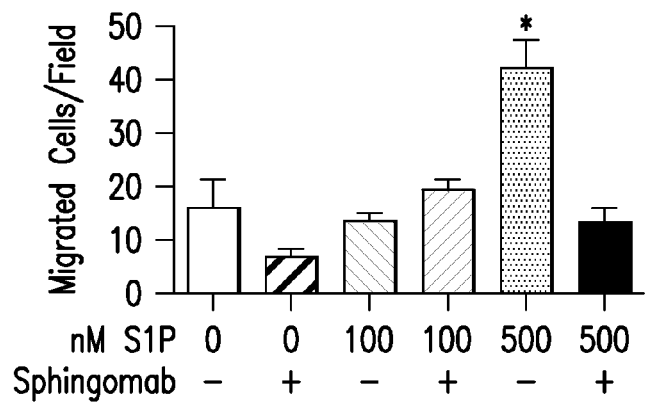
Figure 7C:
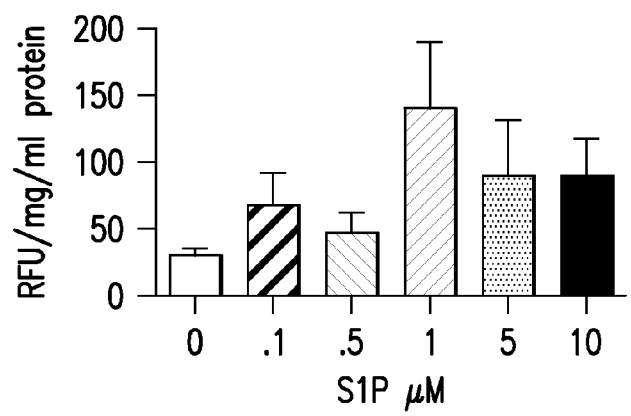
Figure 7D:
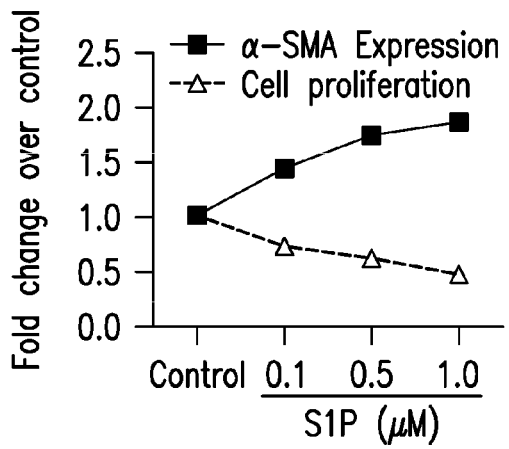

S1P makes profound contributions to wound healing by activating fibroblast migration, proliferation and collagen production; SPHINGOMAB neutralizes these effects. Several studies using multiple types of fibroblasts confirm S1P's ability to promote wound healing: 1) S1P increased Swiss-3T3 fibroblast proliferation as measured by $^3$H-thymidine incorporation using standard methods (FIG. 7A); 2) S1P promoted the migration of cardiac fibroblasts in a standard scratch wound healing assay. (FIG. 7B); 3) S1P promoted collagen expression by cardiac fibroblasts isolated from transgenic mice possessing the collagen 1a GFP reporter, as indicated by immunofluorescence microscopy (FIG. 7C); and 4) S1P induced the differentiation of WI-38 lung fibroblasts into myofibroblasts, cells that are active in scar remodeling, as indicated by increased expression of myofibroblast marker protein, smooth muscle actin, using immunoblot analysis (FIG. 7D). In each of these assays, SPHINGOMAB neutralized S1P's. It is anticipated that ocular fibroblasts would respond similarly to S1P and SPHINGOMAB. Similarities between cardiovascular disease and neovascular lesions of AMD, including scar remodeling and subsequent, maladaptive fibrous tissue formation, have been noted (Vine, et al. (2005), Opthalmology., vol 112: 2076-80 and Seddon and Chen (2004), Int Opthalmol Clin., vol 44: 17-39); thus, it is believed that SPHINGOMAB would have effects on ocular neovascularization and scarring similar to those it has demonstrated in cardiovascular systems.

Figure 7E:
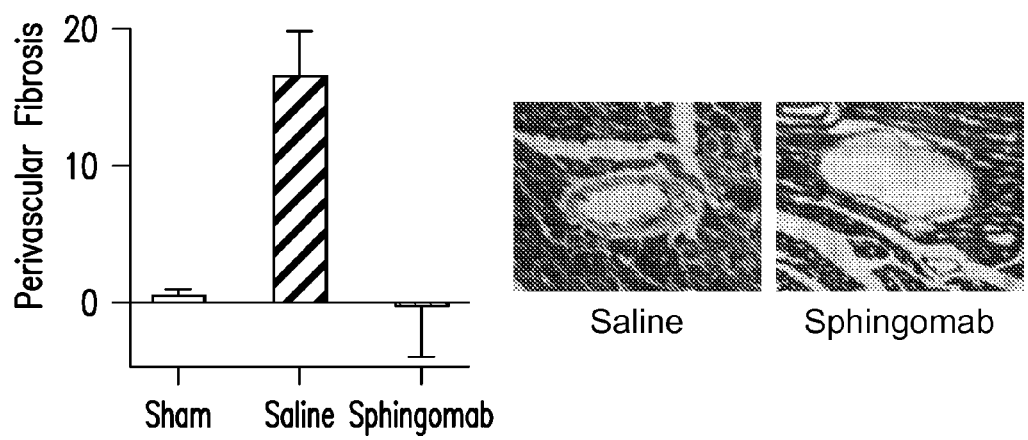

Studies evaluated the efficacy of SPHINGOMAB to reduce cardiac scar formation after permanent myocardial infarction (MI) via ligation of the left descending coronary artery in mice. Systemic administration of 25 mg/kg SPHINGOMAB or saline was initiated 48 hrs after surgery. Antibody administration at 48 hr. was chosen to allow normal, reparative scar formation to occur during the early remodeling phase and permit beneficial, S1P-stimulated angiogenesis immediately after the MI. Two weeks after the infarct, mice were sacrificed and fibrosis was accessed by Masson's trichrome staining of the cardiac tissue. Animals receiving SPHINGOMAB treatments exhibited almost complete abrogation of perivascular fibrosis (FIG. 7, photos). As a control for any non-specific wound-healing responses, sham animals underwent thoracotomy without coronary artery ligation (FIG. 7E).

Example 8

S1P Promotes Transformation of Ocular Epithelial Cells and Fibroblasts into Contractile, Scar Tissue-Producing Myofibroblasts Pathological tissue fibrosis (scar formation) is a primary, contributing factor in a number of ocular disorders, including: age-related macular degeneration, diabetic retinopathy, retinopathy of prematurity, proliferative vitreoretinopathy and consequences of glaucoma surgery.

Figure 8A:
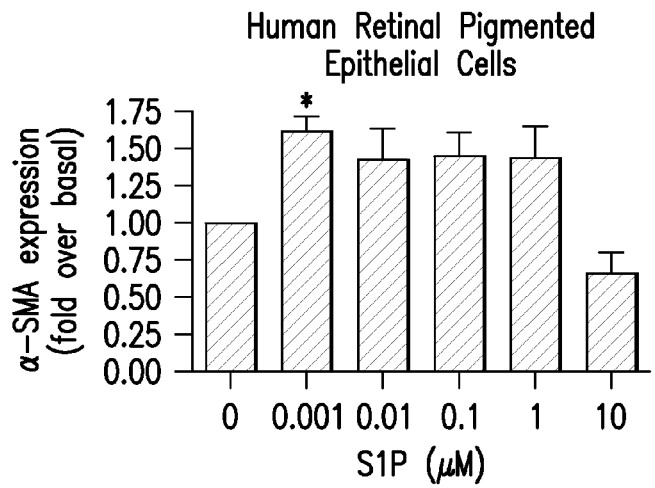
FIG. 8.
As shown in FIG. 8C, S1P stimulates the PAI-1 expression in a dose-dependent manner.
Figure 8B:
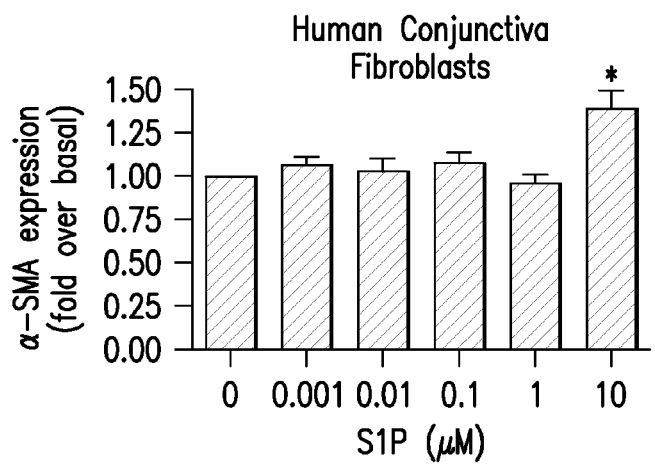

In many of these disorders, circulating growth factors and chemokines promote the transformation of normal ocular cells into fibrocontractile, scar tissue-producing cells that have been termed "myofibroblasts". Normally, myofibroblasts are responsible for tissue repair as part of the wound healing response following injury. However altered number and function of myofibroblasts are implicated in diseases characterized by pathological scar tissue formation in the liver, skin, lung, kidney, heart and eyes. In the eye, transformation of retinal pigmented epithelial (RPE) cells to a myofibroblast phenotype is linked to formation of fibro-contractile membranes which cause retinal detachment and subsequent vision impairment. In addition, myofibroblast transformation of ocular fibroblasts can result in abnormal scar tissue production after eye injury leading to subsequent vision loss. Although many of the circulating protein factors in the eye that promote myofibroblast formation have been identified, nothing is known regarding the role of lysolipids such as S1P in this process. Therefore, we examined the effects of S1P on myofibroblast transformation of several human ocular cell lines. As shown in FIG. 8, S1P stimulates production of α-Smooth muscle actin (α-SMA; a myofibroblast marker) in human retinal pigmented epithelial cells (FIG. 8A) and human conjunctiva fibroblasts (FIG. 8B). These data demonstrate for the first time, that S1P is among the milieu of circulating chemical factors that promote transformation of ocular epithelial cells and fibroblasts into contractile, scar tissue-producing myofibroblasts which may contribute to retinal detachment, ocular fibrosis and subsequent vision impairment.

In these experiments, the ability of S1P to promote α-SMA expression differed in a concentration dependent manner between the retinal pigmented epithelial cells and conjunctiva fibroblasts. As shown, a significant increase in α-SMA expression was observed at the 0.001 µM concentration in the epithelial cells which then decreased to basal levels at the 10 µM concentration. In contrast, a significant increase in α-SMA expression was observed only at the 10 µM concentration in the conjunctiva fibroblasts. This difference is believed to result from increased S1P receptor expression in the epithelial cells compared to the fibroblasts. Due to increased S1P receptor expression levels, retinal pigmented epithelial cells are likely more sensitive to S1P at low concentrations. In contrast, at high S1P levels the receptors become sensitized or possibly even internalized leading to decreased stimulation by S1P.

Figure 8C:
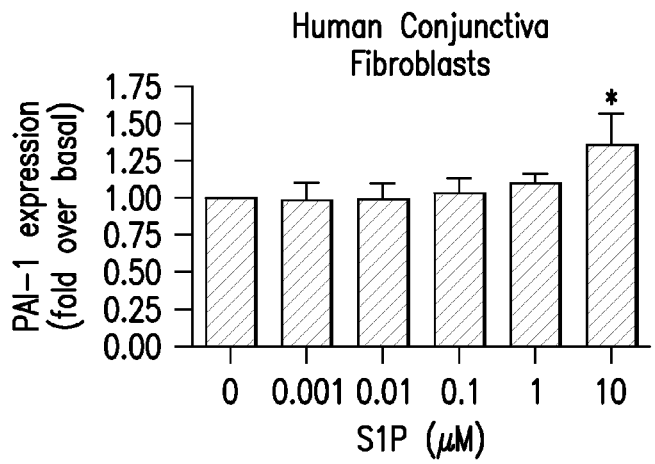

Collagen is one of the primary structural proteins that supports all tissues in the body and is one of the main components of scar tissue. In the non-pathological setting, total collagen content within tissue is maintained via a balance between collagen production by fibroblasts and degradation by certain enzymes. A number of disorders that involve increased levels of scar tissue result, in part, from physiological and molecular processes that inhibit degradation of collagen that is need for scar formation. It was hypothesized that the ability of S1P to promote scar tissue formation may result from its ability to inhibit collagen degradation, thereby leading to net increases in scar tissue within organs. Therefore, the effects of S1P on expression of plasminogen activator inhibitor (PAI-1) in human conjunctiva fibroblasts were examined. Increased PAI-1 expression correlates with a decrease in the proteolytic degradation of connective tissue and is upregulated in association with several fibrotic diseases that involve increased scarring. As shown in FIG. 8C, S1P stimulates the PAI-1 expression in a dose-dependent manner. These data suggest that, may also promote scar tissue formation by stimulating the expression of proteins that inhibit its degradation, suggesting that S1P functions through multiple mechanistic pathways to promote and maintain pathological scarring associated with ocular diseases.

Example 9

SPHINGOMAB Inhibits Inflammatory and Immune Cell Infiltration

Inflammation is the first response in the remodeling process. It is triggered both by ischemia and by cellular damage and results in up-regulation of cytokine expression which stimulates the migration of macrophages and neutrophils to the injured area for phagocytosis of dead cells and to further up-regulate the inflammatory response [Jordan, et al. (1999), Cardiovasc Res., vol 43: 860-78]. Mast cells are also important cellular mediators of the inflammatory response. S1P released from mast cells is responsible for many of the adverse responses seen in experimental animal models of inflammation [Jolly, et al (2004), J Exp Med., vol 199: 959-70 and Jolly et al (2005), Blood., vol 105: 4736-42].

Figure 9A:
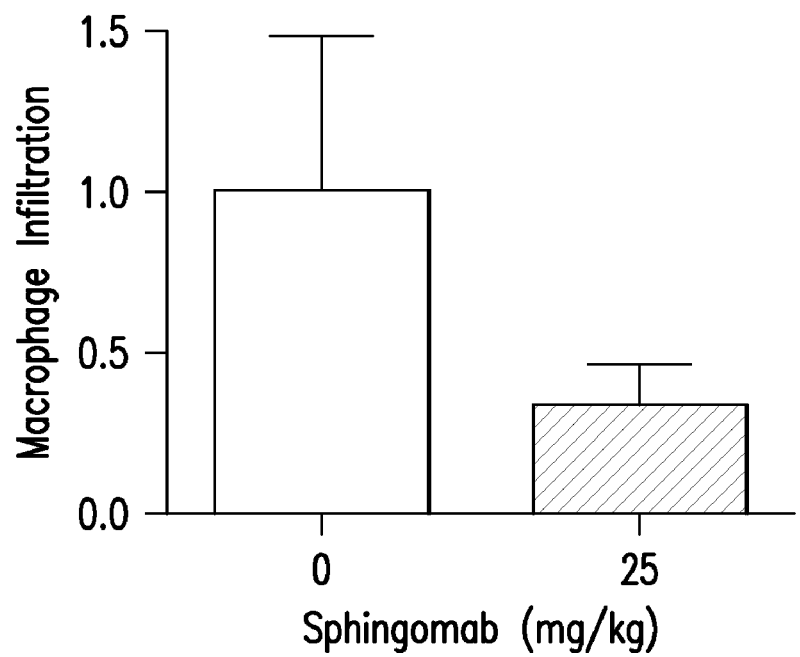
FIG. 9.
Figure 9B:
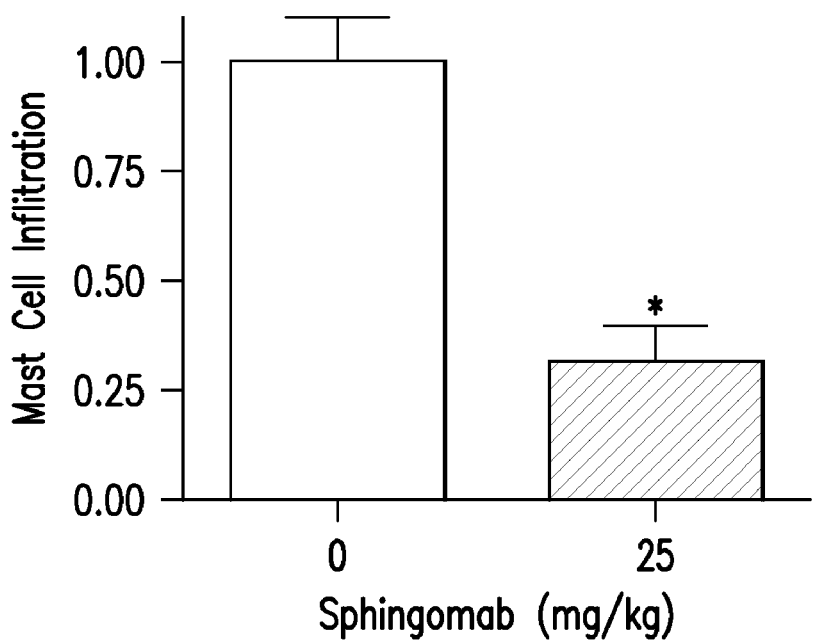

Based upon the similarities of immune and inflammatory responses in CNV and CVD, the efficacy of SPHINGOMAB to mitigate immune cell infiltration into a wound was evaluated in a murine infarct model as an indication of SPHINGOMAB's potential effects in mitigating these damages during AMD [Vine, et al. (2005), Opthalmology., vol 112: 2076-80; and Seddon and Chen (2004), Int Opthalmol Clin., vol 44: 17-39]. Four days post-MI, macrophage and mast cell infiltration was evaluated using MAC-1 and MCG35 antibodies, respectively, within the area at risk. SPHINGOMAB dramatically attenuated the density of inflammatory macrophages (FIG. 9A) and mast cells (FIG. 9B) suggesting that SPHINGOMAB may neutralize immune and inflammatory damages during AMD.

Example 10

Cloning and Characterization of the Variable Domains of an S1P Murine Monoclonal Antibody (LT1002; Sphingomab)

This example reports the cloning of the murine mAb against S1P. The overall strategy consisted of cloning the murine variable domains of both the light chain (VL) and the heavy chain (VH). The consensus sequence of 306D VH shows that the constant region fragment is consistent with a gamma 2b isotype. The murine variable domains were cloned together with the constant domain of the light chain (CL) and with the constant domain of the heavy chain (CH1, CH2, and CH3), resulting in a chimeric antibody construct.

1. Cloning of the Murine mAb

A clone from the anti-S1P hybridoma cell line 306D326.1 (ATCC#SD-5362) was grown in DMEM (Dulbecco's Dulbecco's Modified Eagle Medium with GlutaMAX™ 1,4500 mg/L D-Glucose, Sodium Puruvate; Gibco/Invitrogen, Carlsbad, Calif., 111-035-003), 10% FBS (Sterile Fetal Clone I, Perbio Science), and 1× glutamine/Penicillin/Streptomycin (Gibco/Invitrogen). Total RNA was isolated from $10^7$ hybridoma cells using a procedure based on the RNeasy Mini kit (Qiagen, Hilden Germany). The RNA was used to generate first strand cDNA following the manufacturer's protocol ($1^{st}$ strand synthesis kit, Amersham Biosciences).

Figure 10A:
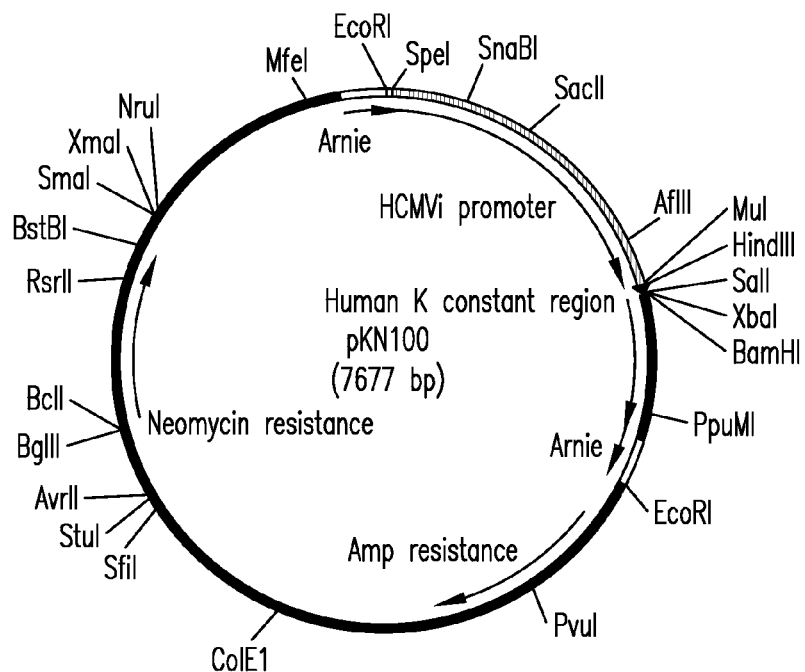
FIG. 10A is a map of a pKN100 vector for the cloning of the $V_L$ domain.
Figure 10B:
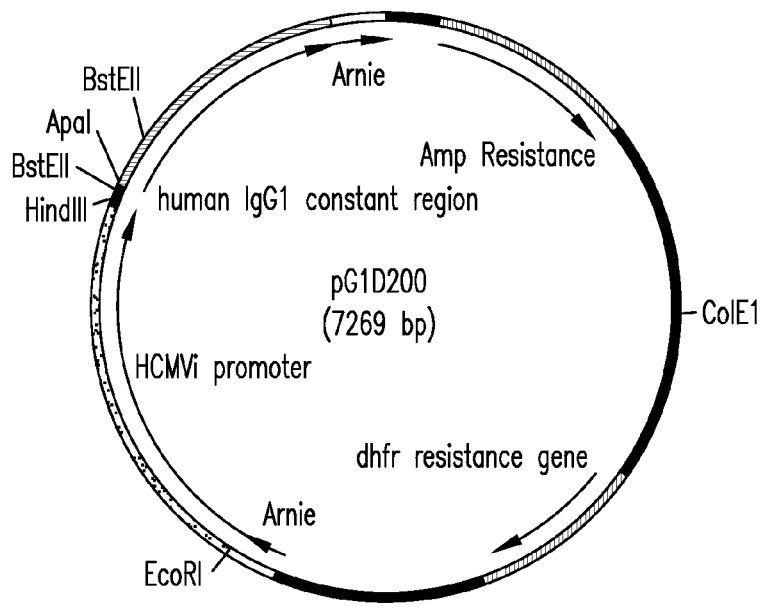
FIG. 10.

The immunoglobulin heavy chain variable region (VH) cDNA was amplified by PCR using an MHV7 primer (MHV7: 5'-ATGGRATGGAGCKGGRTCTTTMTCTT-3' [SEQ ID NO: 1]) in combination with a IgG2b constant region primer MHCG1/2a/2b/3 mixture (MHCG1: 5'-CAGTGGATAGACAGATGGGGG-3' [SEQ ID NO: 2]; MHCG2a: 5'-CAGTGGATAGACCGATGGGGC-3 [SEQ ID NO: 3]; MHCG2b: 5'-CAGTGGATAGACTGATGGGGG-3' [SEQ ID NO: 4]; MHCG3: 5'-CAAGGGATAGACA-GATGGGGC-3' [SEQ ID NO: 5]). The product of the reaction was ligated into the pCR2.1®-TOPO® vector (Invitrogen) using the TOPO-TA Cloning® kit and sequence. The variable domain of the heavy chain was then amplified by PCR from this vector and inserted as a Hind III and Apa I fragment and ligated into the expression vector pG1D200 (see U.S. Pat. No. 7,060,808) or pG4D200 (id.) containing the HCMVi promoter, a leader sequence, and the gamma-1 constant region to generate the plasmid pG1D200306DVH (FIG. 10). The consensus sequence of 306D $V_H$ (shown below) showed that the constant region fragment was consistent with a gamma 2b isotype.

Similarly, the immunoglobulin kappa chain variable region (VK) was amplified using the MKV 20 primer (5'-GTCTCT-GATTCTAGGGCA-3' [SEQ ID NO: 6]) in combination with the kappa constant region primer MKC (5'-ACTGGATG-GTGGGAAGATGG-3' [SEQ ID NO: 7]). The product of this reaction was ligated into the pCR2.1®-TOPO® vector using the TOPO-TA Cloning® kit and sequence. The variable domain of the light chain was then amplified by PCR and then inserted as a Bam HI and Hind III fragment into the expression vector pKN100 (see U.S. Pat. No. 7,060,808) containing the HCMV promoter, a leader sequence, and the human kappa constant domain, generating plasmid pKN100306DVK.

The heavy and light chain plasmids pG1D200306DVH plus pKN100306DVK were transformed into DH4a bacteria and stocked in glycerol. Large-scale plasmid DNA was prepared as described by the manufacturer (Qiagen, endotoxin-free MAXIPREP™ kit). DNA samples, purified using Qiagen's QIAprep Spin Miniprep Kit or EndoFree Plasmid Mega/Maxi Kit, were sequenced using an ABI 3730xl automated sequencer, which also translates the fluorescent signals into their corresponding nucleobase sequence. Primers were designed at the 5' and 3' ends so that the sequence obtained would overlap. The length of the primers was 18-24 bases, and preferably they contained 50% GC content and no predicted dimers or secondary structure. The amino acid sequences for the mouse $V_H$ and $V_L$ domains from Sphingomab™ are SEQ ID NOS: 8 and 9, respectively (Table 2). The CDR residues (see Kabat, E A (1982), Pharmacol Rev, vol. 34: 23-38) are underlined in Table 2, and are shown separately below in Table 3.

TABLE 2

| $V_H$ and $V_L$ domains from the murine mAb, Sphingomab™ | |
|---|---|
| mouse $V_H$ domains | QAHLQQSDAELVKPGASVKISCKVSGFIFI DHTIHWMKQRPEQGLEWIGCISPRHDITKY NEMFRGKATLTADKSSTTAYIQVNSLTFED SAVYFCARGGFYGSTIWfDFWGQGTTLTVS  SEQ ID NO: 8 |
| mouse $V_L$ domains | ETTVTQSPASLSMAIGEKVTIRCITTTDID DDMNWFQQKPGEPPNLLISEGNILRPGVPS RFSSSGYGTDFLFTIENMLSEDVADYYCLQ SDNLPFTFGSGTKLEIK  SEQ ID NO: 9 |

TABLE 3

| Mouse Sphingomab™ CDR sequences of the mouse $V_H$ and $V_L$ domains | | |
|---|---|---|
| | | CDR |
| $V_L$ CDR | | |
| ITTTDIDDDMN | (SEQ ID NO: 10) | CDR1 |
| EGNILRP | (SEQ ID NO: 11) | CDR2 |
| LQSDNLPFT | (SEQ ID NO: 12) | CDR3 |
| $V_H$ CDR | | |
| DHTIH | (SEQ ID NO: 13) | CDR1 |
| CISPRHDITKYNEMFRG | (SEQ ID NO: 14) | CDR2 |
| GGFYGSTIWFDF | (SEQ ID NO: 15) | CDR3 |

The amino acid sequences of several chimeric antibody variable ($V_H$ and $V_L$) domains are compared in Table 4. These variants were cloned in the Lonza expression vectors. Sequences of the murine $V_H$ and $V_L$ domains were used to construct a molecular model to determine which framework residues should be incorporated into the humanized antibody.

TABLE 4

Amino acid sequences of the humanized $V_H$ and $V_L$ domains from the humanized anti-S1P antibody variants $V_H$ Variants pATH200  mgstailalllavlqgvcsevqlvqsgaevkkpgeslkiscqsifgyifidhtihwvrqmpgqglewmgcisprhditkyn
SEQ ID NO: 16 pATH201  .............................................m...............
SEQ ID NO: 39 pATH202  .......................................f........m.........i...........
SEQ ID NO: 40 pATH203  ..................................................................i...........
SEQ ID NO: 41 pATH204  .........................................f....................
SEQ ID NO: 42 pATH205  .......................................f........m.........i...........
SEQ ID NO: 43

TABLE 4-continued

Amino acid sequences of the humanized V$_H$ and V$_L$ domains from the humanized anti-S1P antibody variants

```
pATH206            .............a.....................f......m..........i..............
SEQ ID NO: 44 pATH207            ...................................................m...........a.....
SEQ ID NO: 45 pATH200            emfrgqvtisadkssstaylqwsslkasdtamyfcarggfygstiwfdfwgqgtmvtvssastkgps pATH201            ...................................................................

pATH202            ...................................................................

pATH203            ...................................................................

pATH204            ...................................................................

pATH205            ......a.l...........................................................

pATH206            ......a.l...........................................................

pATH207            ...................................................................
```

V$_L$ Variants

```
pATH300            mdmrvpaqllglllwlpgarcettltqspsflsasvgdrvtitcittttdidddmnwyqqepgkapklliyegnilrpgv
SEQ ID NO: 17 pATH301            ..............................................................................s.........
SEQ ID NO: 46 pATH302            ...................................................................f.....................
SEQ ID NO: 47 pATH303            .........................v.........................................f.....s.............
SEQ ID NO: 48 pATH304            ....................................................................f.....s.............
SEQ ID NO: 49 pATH305            .........................v.........................................f.....s.............
SEQ ID NO: 50 pATH306            .........................v.........................................f.....s.............
SEQ ID NO: 51 pATH308            .........................v.........................................f.....s.............
SEQ ID NO: 52 pATH309            ..............................................................................s.........
SEQ ID NO: 53 pATH300            psrfsgsgsgtdftltisklqpedfatyyclqsdnlpftfgqgtkleikrewip pATH301            ......................................................

pATH302            ......................................................

pATH303            ....................................................- pATH304            ......................................................

pATH305            ...................................................-- pATH306            .....s.............................................-- pATH308            .....s..y.............................................

pATH309            .....s..y.............................................
```

Corresponding nucleotide sequences are shown in Table 5:

TABLE 5 pATH and CDR sequences

| Name | Sequence | SEQ ID NO: |
|---|---|---|
| CDR1 $V_L$: | ataaccaccactgatattgatgatga tatgaac | 18 |
| CDR2 $V_L$: | gaaggcaatattcttcgtcct | 19 |
| CDR3 $V_L$: | ttgcagagtgataacttaccattcac g | 20 |
| CDR1 $V_H$ | gaccatacttcac | 21 |
| CDR2 $V_H$: | tgtatttctcccagacatgatattac taaatacaatgagatgttcaggggc | 22 |
| CDR3 $V_H$: | ggggggttctacggtagtactatctg gtttgacttt | 23 |
| CDR2 $V_H$ (pATH 207) | gctatttctcccagacatgatattac taaatacaatgagatgttcaggggc | 24 |
| pATH200 nucleotide sequence: | cgccaagcttgccgccacc<u>atggggt caaccgccatcctcgccctcctcctg gctgttctccaaggagtctgttccga</u> ggtgcagctggtgcagtctggagcag aggtgaaaaagcccggggagtctctg aagatcctgtcagagttttggata catctttatcgaccatacttcactgg gtgcgccagatgcccgggcaaggcct ggagtggatgtgtatttctcccagac atgatattactaaatacaatgagatg ttcaggggccaggtcaccatctcagc cgacaagtccagcagcaccgcctact tgcagtggagcagcctgaaggcctcg gacaccgccatgtatttctgtgcgag aggggggttctacggtagtactatct ggtttgacttttggggccaagggaca atggtcaccgtctcttcagcctccac caagggcccatcg | 25 |
| pATH207 nucleotide sequence | cgccaagcttgccgccacc<u>atggggt caaccgccatcctcgccctcctcctg : gctgttctccaaggagtctgttccga</u> gcagctggtgcagtctggagcagagg tggtgaaaaagcccggggagtctctg aagatcctgtcagagttttggata catcgaccatacttcactggatgcgc cagatgcccgggcaaggcctggagtg gatggggctatttctcccagacatg atattactaaatacaatgagatgttc aggggccaggtcaccatctcagccga caagtccagcagcaccgcctacttgc agtggagcagcctgaaggcctcggac accgccatgtatttctgtgcgagagg ggggttctacggtagtactatctggt ttgacttttggggccaagggacaatg gtcaccgtctcttcagcctccaccaa gggcccatcg | 26 |
| pATH207 amino acid sequence | mgstailalllavlqgvcsevqlvqs gaevkkpgeslkiscqsfgyifidht ihwmrqmpgqglewmgaisprhditk ynemfrgqvtisadkssstaylqwss lkasdtamyfcarggfygstiwfdfw gqgtmvtvssastkgps | 27 |
| pATH300 nucleotide sequence: | cgccaagcttgccgccacc<u>atggaca tgagggtccccgctcagctcctgggg ctcctgctgctctggctcccaggtgc cagatgt</u>gaaacgacactcacgcagt ctccatccttcctgtctgcatctgta ggagacagagtcaccatcacataacc accactgatattgatgatgatatgaa ctggtatcagcaggaaccagggaaag cccctaagctcctgatctatgaaggc | 28 |
| pATH308 nucleotide sequence | cgccaagcttgccgccaccatggaca tgagggtccccgctcagctcctgggg ctcctgctgctctggctcccaggtgc cagatgtgaaacgacagtgacgcagt ctccatccttcctgtctgcatctgta ggagacagagtcaccatcacttgcat aaccaccactgatattgatgatgata tgaactggttccagcaggaaccaggg aaagcccctaagctcctgatctccga aggcaatattcttcgtcctggggtcc catcaagattcagcagcagtggatat ggcacagatttcactctcaccatcag caaattgcagcctgaagattttgcaa cttattactgtttgcagagtgataac ttaccattcactttcccaaaccaact aatcaaac | 29 |
| | aatattcttcgtcctggggtcccatc aaggttcagcggcagtggatctggca cagatttcactctcaccatcagcaaa ttgcagcctgaagattttgcaactta ttactgtttgcagagtgataacttac cattcacgttcggccaagggaccaag ctggagatcaaacgtgagtggatccc gcg | |
| pATH308 amino acid sequence | mrvpaqllgllllwlpgarcettvtq spsflsasvgdrvtitcitttdiddd mnwfqepgkapkllisegnilrpgvp srfsssgygtdftltisklqpedfat yyclqsdnlpfifgqgtkleik | 30 |

2. Expression and Binding Properties of the Chimeric Antibody

The heavy and light chain plasmids of both pG1D200306DVH plus pKN100306DVK were transformed into DH4a bacteria and stocked in glycerol. Large scale plasmid DNA was prepared as described by the manufacturer (Qiagen, endotoxin-free MAXIPREP™ kit Cat. No. 12362).

For antibody expression in a non-human mammalian system, plasmids were transfected into the African green monkey kidney fibroblast cell line COS 7 by electroporation (0.7 ml at $10^7$ cells/ml) using 10 ug of each plasmid. Transfected cells were plated in 8 ml of growth medium for 4 days. The chimeric 306DH1×306DVK-2 antibody was expressed at 1.5 μg/ml in transiently co-transfected COS cell conditioned medium. The binding of this antibody to S1P was measured using the S1P ELISA.

Figure 11:
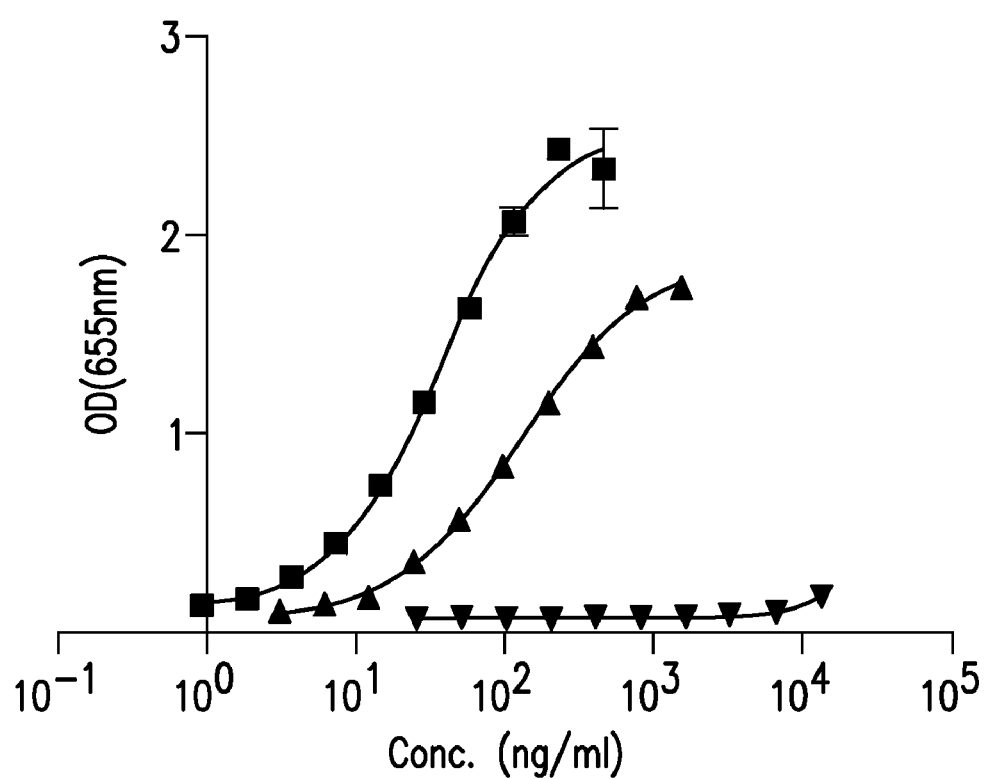
FIG. 11.

The expression level of the chimeric antibody was determined in a quantitative ELISA as follows. Microtiter plates (Nunc MaxiSorp immunoplate, Invitrogen) were coated with 100 μl aliquots of 0.4 μg/ml goat anti-human IgG antibody (Sigma, St. Louis, Mo.) diluted in PBS and incubate overnight at 4° C. The plates were then washed three times with 200 μl/well of washing buffer (1×PBS, 0.1% TWEEN). Aliquots of 200 μL of each diluted serum sample or fusion supernatant were transferred to the toxin-coated plates and incubated for 37° C. for 1 hr. Following 6 washes with washing buffer, the goat anti-human kappa light chain peroxidase conjugate (Jackson Immuno Research) was added to each well at a 1:5000 dilution. The reaction was carried out for 1 hr at room temperature, plates were washed 6 times with the washing buffer, and 150 μL of the K-BLUE substrate (Sigma) was added to each well, incubated in the dark at room temperature for 10 min. The reaction was stopped by adding 50 μl of RED STOP solution (SkyBio Ltd.) and the absorption was determined at 655 nm using a Microplater Reader 3550 (Bio-Rad Laboratories Ltd.). Results from the antibody binding assays are shown in FIG. 11.

3. 293F Expression

The heavy and light chain plasmids were transformed into Top 10 *E. coli* (One Shot Top 10 chemically competent *E. coli* cells (Invitrogen, C4040-10)) and stocked in glycerol. Large scale plasmid DNA was prepared as described by the manufacturer (Qiagen, endotoxin-free MAXIPREP™ kit CatNo 12362).

For antibody expression in a human system, plasmids were transfected into the human embryonic kidney cell line 293F (Invitrogen) using 293fectin (Invitrogen) and using 293F-FreeStyle Media (Invitrogen) for culture. Light and heavy chain plasmids were both transfected at 0.5 g/mL. Transfections were performed at a cell density of $10^6$ cells/mL. Supernatants were collected by centrifugation at 1100 rpm for 5 minutes at 25° C. 3 days after transfection. Expression levels were quantified by quantitative ELISA (see previous examples) and varied from ~0.25-0.5 g/mL for the chimeric antibody.

4. Antibody Purification

Monoclonal antibodies were purified from culture supernatants by passing culture supernatants over protein A/G columns (Pierce, Cat. No 53133) at 0.5 mL/min. Mobile phases consisted of 1× Pierce IgG binding Buffer (Cat. No 21001) and 0.1 M glycine pH 2.7 (Pierce, Elution Buffer, Cat. No 21004). Antibody collections in 0.1 M glycine were diluted 10% (v/v) with 1 M Phosphate Buffer, pH 8.0, to neutralize the pH. IgG, collections were pooled and dialyzed exhaustively against 1×PBS (Pierce Slide-A-Lyzer Cassette, 3,500 MWCO, Cat. No 66382). Eluates were concentrated using Centricon YM-3 (10,000 MWCO Amicon Cat. No 4203) by centrifugation for 1 h at 2,500 rcf. The antibody concentration was determined by quantitative ELISA as described above using a commercial myeloma IgG, stock solution as a standard. Heavy chain types of mAbs were determined by ELISA using Monoclonal Antibody Isotyping Kit (Sigma, ISO-2).

5. Comparative Binding of Antibody Variants to S1P

Table 6, below, shows a comparative analysis of mutants with the chimeric antibody. To generate these results, bound antibody was detected by a second antibody, specific for the mouse or human IgG, conjugated with HRP. The chromogenic reaction was measured and reported as optical density (OD). The concentration of the panel of antibodies was 0.1 ug/ml. No interaction of the second antibody with S1P-coated matrix alone was detected.

TABLE 6

Comparative binding to S1P on variants of the chimeric anti-S1P antibody.

| Variable Domain | Mutation | Plasmids | Binding |
|---|---|---|---|
|  | Chimeric | pATH50 + pATH10 | 1.5 |
| HC | CysAla | pATH50 + pATH11 | 2 |
|  | CysSer | pATH50 + pATH12 | 0.6 |
|  | CysArg | pATH50 + pATH14 | 0.4 |
|  | CysPhe | pATH50 + pATH16 | 2 |
| LC | MetLeu | pATH53 + pATH10 | 1.6 |

6. Determination of Binding Kinetics by Surface Plasmon Resonance (SPR)

All binding data were collected on a Biacore 2000 optical biosensor (Biacore AB, Uppsala Sweden). S1P was coupled to a maleimide CM5 sensor chip. First the CM5 chip was activated with an equal mixture of NHS/EDC for seven minutes followed by a 7 minute blocking step with ethyldiamine. Next sulfo-MBS (Pierce Co.) was passed over the surfaces at a concentration of 0.5 mM in HBS running buffer (10 mM HEPES, 150 mM NaCl, 0.005% p20, pH 7.4). S1P was diluted into the HBS running buffer to a concentration of 0.1 mM and injected for different lengths of time producing 2 different density S1P surfaces (305 and 470 RU). Next, binding data for the mAb was collected using a 3-fold dilution series starting with 16.7 nM, 50.0 nM, 50.0 nM, 16.7 nM, and 16.7 nM for the mouse, 201308, 201309, and 207308 antibodies respectively.

Each concentration was tested in duplicate. Surfaces were regenerated with 50 mM NaOH. All data were collected at 25° C. Responses data were processed using a reference surface as well as blank injections. The data sets (responses from two surfaces and each variant tested twice were fit to interaction models to obtain binding parameters. Data from the different mAb concentrations were globally fitted using a 1:1 (mouse) or 1:2 (variants) interaction model to determine apparent binding rate constants. The number in parentheses indicates the error in the last digit.

Example 11

Chimeric mAb to S1P

As used herein, the term "chimeric" antibody (or "immunoglobulin") refers to a molecule comprising a heavy and/or light chain which is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly, et al., supra; Morrison et al., Proc. Natl. Acad. Sci. U.S.A. 81:6851 (1984)).

A chimeric antibody to S1P was generated using the variable regions (Fv) containing the active S1P binding regions of the murine antibody from a particular hybridoma (ATCC safety deposit storage number SD-5362) with the Fc region of a human IgG1 immunoglobulin. The Fc regions contained the CL, ChL, and Ch3 domains of the human antibody. Without being limited to a particular method, chimeric antibodies could also have been generated from Fc regions of human IgG1, IgG2, IgG3, IgG4, IgA, or IgM. As those in the art will appreciate, "humanized" antibodies can been generated by grafting the complementarity determining regions (CDRs, e.g. CDR1-4) of the murine anti-S1P mAb with a human antibody framework regions (e.g., Fr1, Fr4, etc.) such as the framework regions of an IgG1. FIG. 11 shows the binding of the chimeric and full murine mAbs in a direct ELISA measurement using thiolated-S1P as lay down material.

For the direct ELISA experiments shown in FIG. 11, the chimeric antibody to S1P had similar binding characteristics to the fully murine monoclonal antibody. ELISAs were performed in 96-well high-binding ELISA plates (Costar) coated with 0.1 ug of chemically-synthesized, thiolated S1P conjugated to BSA in binding buffer (33.6 mM $Na_2CO_3$, 100 mM $NaHCO_3$; pH 9.5). The thiolated S1P-BSA was incubated at 37° C. for 1 hr. or at 4° C. overnight in the ELISA plate. Plates were then washed four times with PBS (137 mM NaCl, 2.68 mM KCl, 10.14 mM $Na_2HPO_4$, 1.76 mM $KH_2PO_4$; pH 7.4) and blocked with PBST for 1 hr. at room temperature. For the primary incubation step, 75 uL of the sample (containing the S1P to be measured), was incubated with 25 μL of 0.1 μg/mL anti-S1P monoclonal antibody diluted in PBST and added to a well of the ELISA plate. Each sample was performed in triplicate wells. Following a 1 hr. incubation at room temperature, the ELISA plates were washed four times with PBS and incubated with 100 ul per well of 0.1 ug/mL HRP goat anti-mouse secondary (Jackson Immunoresearch) for 1 hr. at room temperature. Plates were then washed four times with PBS and exposed to tetramethylbenzidine (Sigma) for 1-10 minutes. The detection reaction was stopped by the addition of an equal volume of 1 M $H_2SO_4$. Optical density of the samples was determined by measurement at 450 nm using an EL-X-800 ELISA plate reader (Bio-Tech).

Again, the preferred method of measuring either antibody titer in the serum of an immunized animal or in cell-conditioned media (for example, supernatant) of an antibody-producing cell such as a hybridoma, involves coating the ELISA plate with a target ligand (e.g., a thiolated analog of S1P, LPA, etc.) that has been covalently linked to a protein carrier such as BSA.

Without being limited to particular method or example, chimeric antibodies could be generated against other lipid targets such as LPA, PAF, ceramides, sulfatides, cerebrosides, cardiolipins, phosphotidylserines, phosphotidylinositols, phosphatidic acids, phosphotidylcholines, phosphatidylethanolamines, eicosinoids, and other leukotrienes, etc. Further, many of these lipids could also be glycosylated and/or acetylated, if desired.

Example 12

Generation and Characterization of Humanized Anti-S1P Monoclonal Antibody LT1009 (Sonepcizumab)

The murine anti-S1P monoclonal antibody 306D (LT1002; Sphingomab™), which specifically binds S1P, has been shown to potently suppress angiogenesis and tumor growth in various animal models. As discussed below, LT1002 was humanized using sequence identity and homology searches for human frameworks into which to graft the murine CDRs and a computer-generated model to guide some framework backmutations. Two variants, HuMAbHCLC$_3$ (LT1004) (with 3 backmutations in the light chain) and HuMAbHCLC$_5$ (LT1006) (with 5 backmutations in the light chain) exhibited binding affinity in the nanomolar range. Further engineering was performed in an effort to improve the biophysical and biological properties of the humanized variants. The humanized variants HuMAbHC$_{CysAla}$LC$_3$ (LT1007) and HuMAbHC$_{CysAla}$LC$_5$ (LT1009) in which a free-cysteine residue in HCDR2 was replaced with alanine exhibited a binding affinity in the picomolar range. All humanized variants inhibited angiogenesis in the choroid neovascularization (CNV) model of age-related macular degeneration (AMD), with HuMAb-HC$_{CysAla}$LC$_5$ (LT1009) exhibiting superior stability and in vivo efficacy compared to the parent murine antibody. The variant huMAbHCcysalaLC$_5$ (LT1009) was designated Sonepcizumab™.

a. Humanization Design for the Anti-S1P Antibody

The variable domains of murine mAb LT1002 (Sphingomab™) were humanized via CDR grafting (Winter U.S. Pat. No. 5,225,539). The CDR residues were identified based on sequence hypervariability as described by Kabat et al. 1991.

In this study, suitable acceptor structures were selected based on a homology search of human antibodies in the IMGT and Kabat databases using a structural alignment program (SR v7.6). The initial step was to query these human heavy variable (VH) and light variable (VL) sequence databases with LT1002 VH and VL protein sequences respectively, to identify human frameworks (FR) with high sequence identity in the FR, at Vernier (Foote, J. & Winter, G. Antibody framework residues affecting the conformation of the hypervariable loops. *J Mol. Biol.* 224, 487-499 (1992)), Canonical (Morea, et al., Antibody modeling: implications for engineering and design, Methods 20, 267-279 (2000)) and VH-VL interface (Chothia, C., Novotny, J., Bruccoleri, R., & Karplus, M. Domain association in immunoglobulin molecules. The packing of variable domains. J. Mol. Biol. 186, 651-663 (1985)) residues and with CDRs of identical canonical class and/or length. The identity of each member of this library to individual aligned residues of the mouse antibody was calculated using the program. Those human sequences with FR sequence most identical to the mouse FR were identified, producing an initial shortlist of human "acceptor" sequences. Those sequences with most identity to the mouse antibody, at Vernier, Canonical and VH-VL Interface (VCI) residues, were also calculated. Differences at these positions between human and mouse were classified into conservative and non-conservative substitutions, so that the best framework choice would have the lowest number of non-conservative VCI differences from LT1002. The CDR loops L3 and H1 of LT1002 could be classified into canonical structures. These L3 and H1 structures were used to select human antibody FRs with identical canonical structures. For unclassified CDRs, an attempt was made to select human frameworks with CDR lengths identical to the mouse antibody. The rationale is that CDR loop structures are dependent not only on the CDR loop sequence itself, but also on the underlying framework residues (canonical residues). Therefore a human framework with matching canonical CDR structures and/or CDR lengths is likely to hold the grafted mouse CDRs in the most appropriate orientation to maintain antigen binding affinity. This was achieved for all CDRs except CDR H3, by the choice of human framework sequences. Additionally, frameworks with unusual cysteine or proline residues were excluded where possible. These calculations were performed separately for the heavy and light chain sequences. Finally, individual sequence differences, throughout the framework region, in the best matching sequences were compared. Of the human antibodies that best fit the above comparative calculations, the antibodies AY050707 and AJ002773 were selected as the most appropriate human framework provider for the light chain and the heavy chain respectively.

The second step was to generate a molecular model of the variable regions of LT1002 and to identify FR residues which might affect antigen binding but were not included in the group of Vernier, Canonical and Interface residues. Many structural features of the graft donor and acceptor variable domains were examined in order to better understand how various FR residues influence the conformation of the CDR loops and vice versa. Non-conserved FR residues in LT1002 that were likely to impact the CDRs were identified from the Vernier and Canonical definitions (see above) and thus several residues of the human FR were restored to the original murine amino acids (backmutated).

b. Mutagenesis

Mutations within the variable domain sequences were created using the QuikChange Site-Directed Mutagenesis Kit (Stratagene, Catalog #200524). Individual reactions were carried out with 50 ng of double-stranded DNA template, 2.5 U of PfuUltre HF DNA polymerase and its corresponding buffer (Stratagene, Catalog #200524), 10 mM dNTP mix and 125 ng of each of the mutagenic oligonucleotides resuspended in 5 mM Tris-HCl (pH 8.0), and 0.1 mM EDTA. The initial denaturation was carried out at 95° C. for 30 s, followed by 16 cycles of amplification: 95° C. for 30 s, 55° C. for 60 s and 68° C. for 8 min. Following temperature cycling, the final reaction was then digested with DpnI digest at 37° C. for 1 h to remove methylated parental DNA. The resultant mutant was transformed into competent XL I-Blue *E. coli* and plated on LB-agar containing 50 μg/ml Ampicillin. The colonies were then checked by sequencing. Each of the mutants were then cultured in 1 liter shake flasks and purified using the EndoFree Plasmid Purification Kit from Qiagen, catalog #12362.

c. Generation of the Humanized Antibody Variants

A mouse-human chimeric antibody (chMAb S1P) was constructed by cloning the variable domains of LT1002 into a vector that contained the human constant regions of the kappa and heavy chains to allow expression of the full length antibody into mammalian cells. The generation of the humanized heavy chain was the result of the graft of the Kabat CDRs 1, 2 and 3 from LT1002 V$_H$ into the acceptor framework of AJ002773. The nearest germ line gene to AJ002773 was VH5-51, whose leader sequence was incorporated, as a leader sequence, into the humanized heavy chain variant. The protein sequence of pATH200, the first humanized version of LT1002 $V_H$, with the VH5-51 leader sequence, is shown in Table 4. In the case of the $V_H$ domain of LT1002, residues at position 2, 27, 37, 48, 67 and 69 were Vernier residues or at the interface of the $V_H$ and $V_L$ domains and likely to influence CDR orientation. Position 37 appeared to be critical for the interface between the $V_H$ and $V_L$ domains. The residues at these positions in the human framework were backmutated with the murine residue found at the corresponding position. The mutations, V37M, M48I and Y27F, were tested individually. One version (pATH205) contained all 3 mutations together with V67A plus I69 L and another version (pATH206) contained all 5 mutations plus V2A.

The generation of the humanized light chain was the result of the graft of the Kabat CDRs 1, 2 and 3 from LT1002 $V_L$ into the acceptor framework of AY050707. The nearest germ line gene to AY050707 was L11, whose leader sequence was incorporated into the humanized light chain construct. The protein and DNA sequences of pATH300 (LT1002 light chain) are SEQ ID NO: 17 and 28, respectively (see Table 4 for amino acid sequence). In the case of $V_L$, four non-conserved Vernier positions 4, 36, 49, 64 were selected for backmutation to murine residues as they are involved in supporting the structure of the CDR loops. Inspection of the molecular model of LT1002 suggested that Tyr 67 is close to the CDR surface and oriented towards the antigen binding plane and could interact with S1P. Therefore the S67Y backmutation was also added to later humanized versions. Two mutations were introduced separately to generate two versions containing either Y49S or Y36F. Several versions were created with the following combinations of mutations: (Y49S, F4V), (Y49S, Y36F), (Y49S, Y36F, F4V), (Y49S, G64S), (Y49S, Y36F, F4V, G64S), (Y49S, Y36F, F4V, G64S, S67Y), (Y49S, G64S, S67Y).

d. Selection of the Humanized Lead Candidates

The variable regions of the basic grafted versions (pATH 200 and pATH 300) and all the variants containing backmutations were cloned into expression vectors containing the human $V_H$ or $V_L$ constant regions. All the humanized variants were produced in mammalian cells under the same conditions as the chimeric (chMAb) antibody and were tested for binding to S1P by ELISA. The yield was approximately 10-20 mg/l for the humanized variants and 0.3-0.5 mg/l for chMAb S1P. SDS-PAGE under reducing conditions revealed two bands at 25 kDa and 50 kDa with high purity (>98%), consistent with the expected masses of the light and heavy chains. A single band was observed under non-reducing conditions with the expected mass of ~150 k. chMAb was used as a standard in the humanized antibody binding assays because it contained the same variable regions as the parent mouse antibody and bore the same constant regions as the humanized antibodies and therefore could be detected using the same ELISA protocol.

The initial humanized antibody, in which the six murine CDRs were grafted into unmutated human frameworks, did not show any detectable binding to S1P (FIG. 11). The kappa light chain containing the 4 backmutations (Y49S, Y36F, F4V and G64S), in association with chimeric heavy chain, exhibited suboptimal binding to S1P as measured by ELISA. The incorporation of an additional mutation at position Y67 significantly improved the binding. Version pATH308 which contained backmutations Y49S, Y36F, F4V, G64S and S67Y and version pATH309 which contained the backmutations Y49S, G64S and S67Y, in association with chimeric heavy chain, both generated antibodies which bound S1P similarly to the chimeric antibody as determined by ELISA. The 2 mutations Y36F and F4V were not considered necessary backmutations from the viewpoint of S1P binding. The engineering of 3 to 5 backmutations in the $V_L$ framework was required to restore activity.

The incorporation of the Vernier backmutation V37M into the human framework of the heavy chain, in association with the chimeric light chain, was sufficient to restore a binding behavior similar to the chimeric antibody (FIG. 11).

In summary, humanization of the LT1002 $V_H$ domain required only one amino acid from the murine framework sequence whereas the murine $V_L$ framework domain, three or five murine residues had to be retained to achieve binding equivalent to the murine parent LT1002.

e. Optimization of a Humanized Lead Candidate

The murine anti-S1P antibody contains a free cysteine residue in CDR2 (Cys50) of the heavy chain that could potentially cause some instability of the antibody molecule. Using site directed mutagenesis, variants of pATH201 were created with substitution of the cysteine residue with alanine (huMAbHCcysalaLC$_3$) (pATH207), glycine (huMAbHCcysalaLC$_3$), serine (huMAbHCcysserLC$_3$), and phenylalanine (huMAbHCcyspheLC$_3$). The cysteine mutant heavy chain was also tested with the humanized light chain (pATH 308) containing 5 backmutations (huMAbHCcysalaLC$_5$=LT1009). The variants were expressed in mammalian cells and then characterized in a panel of in vitro assays. Importantly, the expression rate of the humanized variants was significantly higher than for chMAb S1P.

f. In-Depth Characterization of the Humanized Lead Candidate i. Specificity. The humanized variants were tested for specificity in a competitive ELISA assay (FIG. 1) against S1P and several other biolipids. This assay has the added benefit to allow for epitope mapping. The humanized antibody LT1009 demonstrated no cross-reactivity to sphingosine (SPH), the immediate metabolic precursor of S1P, or LPA (lysophosphatidic acid), an important extracellular signaling molecule that is structurally and functionally similar to S1P. Moreover, rhuMAb S1P did not recognize other structurally similar lipids and metabolites, including ceramide (CER), ceramide-1-phosphate (C1P). However as expected LT1009 did cross react with sphingosyl phosphocholine (SPC), a lipid in which the free phosphate group of S1P is tied up with a choline residue. Importantly, all the humanized variants exhibited a specificity profile comparable to the mouse antibody.

ii. Binding affinity. Biacore measurements of IgG binding to a S1P coated chip showed that the variants LT1004 or LT1006 exhibited binding affinity in the low nanomolar range similar to chMAb S1P as shown in FIG. 11. The humanized variants LT1007 and LT1009 in which the cysteine residue was replaced with alanine exhibited a binding affinity in the picomolar range similar to the murine parent LT1002 (Sphingomab™).

iii. Stability. The humanized variants were tested for stability after challenge at high temperature. The approximate midpoints of the thermal unfolding transitions ($T_M$) were determined for every humanized variant by subjecting the supernatants to temperatures ranging from 60 to 74° C. These temperatures were chosen based on the denaturation profile observed for the murine antibody molecule after thermochallenging between a broad range of temperatures between 50 and 80° C. The binding properties of each variant were determined before and after thermochallenge. The murine antibody exhibited a $T_M$ of 65° C. The variant huMAbHCcysalaLC$_5$ (LT1009) exhibited superior $T_M$ compared to all other variants. Table 7 shows the lead humanized candidates and their characteristics.

TABLE 7

Lead humanized S1P mAb candidates and characteristics

| mAb | Description | Mutations in the Heavy Chain | | Mutations in the Light Chain | | In vitro Activity | |
|---|---|---|---|---|---|---|---|
| | | CDR | Framework | CDR | Framework | Binding Affinity ($K_{D1}$) | Specificity (ELISA) |
| LT1002 | Murine mAb Sphingomab | N/A | N/A | N/A | N/A | 0.026 ± 0.000 nM | High |
| LT1004 | HuHCLC$_3$ pATH201HC pATH309LC | 0 | 1 | 0 | 3 | 1.060 ± 0.010 nM | High |
| LT1006 | HuHCLC$_5$ pATH201HC pATH308LC | 0 | 1 | 0 | 5 | 0.690 ± 0.010 nM | High |
| LT1007 | HuHCcysalaLC$_3$ pATH207HC pATH309LC | 1 | 1 | 0 | 3 | 0.0414 ± 0.0004 nM | |
| LT1009 | HuHCcysalaLC$_5$ pATH207HC pATH308LC | 1 | 1 | 0 | 5 | 0.056 ± 0.001 nM | High |

The number of mutations in the heavy and light chains are indicated. The description column gives the identity of the heavy and light chains.

iv. Sequences

As with naturally occurring antibodies, LT1009 includes three complementarity determining regions (each a "CDR") in each of the two light chain polypeptides and each of the two heavy chain polypeptides that comprise each antibody molecule. The amino acid sequences for each of these six CDRs is provided immediately below ("VL" designates the variable region of the immunoglobulin light chain, whereas "VH" designates the variable region of the immunoglobulin heavy chain):

```
CDR1 VL:  ITTTDIDDDMN       [SEQ ID NO: 10]

CDR2 VL:  EGNILRP           [SEQ ID NO: 11]

CDR3 VL:  LQSDNLPFT         [SEQ ID NO: 12]

CDR1 VH:  DHTIH             [SEQ ID NO: 13]

CDR3 VH:  GGFYGSTIWFDF      [SEQ ID NO: 15]

CDR2 VH:  AISPRHDITKYNEMFRG [SEQ ID NO: 31]
```

The nucleotide and amino acid sequences for the heavy and light chain polypeptides of LT1009 are listed immediately below:

```
LT1009 HC amino acid sequence of the variable domain [SEQ ID NO: 32]:
  1 mewswvflff lsvttgvhse vqlvqsgaev kkpgeslkis cqsfgyifid
 51 htihwmrqmp gqglewmgai sprhditkyn emfrgqvtis adkssstayl
101 qwsslkasdt amyfcarggf ygstiwfdfw gqgtmvtvss LT1009 LC amino acid sequence of the variable domain [SEQ ID NO: 33]:
  1 msvptqvlgl lllwltdarc ettvtqspsf lsasvgdrvt itcitttdid
 51 ddmnwfqqep gkapkllise gnilrpgvps rfsssgygtd ftltisklqp
101 edfatyyclq sdnlpftfgq gtkleik LT1009 HC nucleotide sequence [SEQ ID NO: 34]:
  1 aagcttgccg ccaccatgga atggagctgg gtgttcctgt tctttctgtc
 51 cgtgaccaca ggcgtgcatt ctgaggtgca gctggtgcag tctggagcag
101 aggtgaaaaa gcccggggag tctctgaaga tctcctgtca gagttttgga
151 tacatcttta tcgaccatac tattcactgg atgcgccaga tgcccggcca
201 aggcctggag tggatggggg ctatttctcc cagacatgat attactaaat
251 acaatgagat gttcagggc caggtcacca tctcagccga caagtccagc
301 agcaccgcct acttgcagtg gagcagcctg aaggcctcgg acaccgccat
351 gtatttctgt gcgagagggg ggttctacgg tagtactatc tggtttgact
401 tttggggcca aggacaatg gtcaccgtct cttcagcctc caccaaggc
```

-continued

```
 451 ccatcggtct tcccoctggc accctcctcc aagagcacct ctgggggcac
 501 agcggccctg ggctgcctgg tcaaggacta cttccccgaa ccgtgacgg
 551 tgtcgtggaa ctcaggcgcc ctgaccagcg gcgtgcacac cttcccggct
 601 gtcctacagt cctcaggact ctactccctc agcagcgtgg tgaccgtgcc
 651 ctccagcagc ttgggcaccc agacctacat ctgcaacgtg aatcacaagc
 701 ccagcaacac caaggtggac aagagagttg gtgagaggcc agcacaggga
 751 gggagggtgt ctgctggaag ccaggctcag cgctcctgcc tggacgcatc
 801 ccggctatgc agtcccagtc cagggcagca aggcaggccc cgtctgcctc
 851 ttcacccgga ggcctctgcc cgccccactc atgctcaggg agagggtctt
 901 ctggcttttt ccccaggctc tgggcaggca caggctaggt gcccctaacc
 951 caggccctgc acacaaaggg gcaggtgctg ggctcagacc tgccaagagc
1001 catatccggg aggaccctgc ccctgaccta agcccacccc aaaggccaaa
1051 ctctccactc cctcagctcg dacaccttct ctcctcccag attccagtaa
1101 ctcccaatct tctctctgca gagcccaaat cttgtgacaa aactcacaca
1151 tgcccaccgt gcccaggtaa gccagcccag gcctcgccct ccagctcaag
1201 gcgggacagg tgccctagag tagcctgcat ccagggacag gccccagccg
1251 ggtgctgaca cgtccacctc catctcttcc tcagcacctg aactcctggg
1301 gggaccgtca gtcttcctct tccccccaaa acccaaggac accctcatga
1351 tctcccggac ccctgaggtc acatgcgtgg tggtggacgt gagccacgaa
1401 gaccctgagg tcaagttcaa ctggtacgtg gacggcgtgg aggtgcataa
1451 tgccaagaca aagccgcggg aggagcagta caacagcacg taccgtgtgg
1501 tcagcgtcct caccgtcctg caccaggact ggctgaatgg caaggagtac
1551 aagtgcaagg tctccaacaa agccctccca gcccccatcg agaaaaccat
1601 ctccaaagcc aaaggtggga cccgtggggt gcgagggcca catggacaga
1651 ggccggctcg gcccaccctc tgccctgaga gtgaccgctg taccaacctc
1701 tgtccctaca gggcagcccc gagaaccaca ggtgtacacc ctgcccccat
1751 cccgggagga gatgaccaag aaccaggtca gcctgacctg cctggtcaaa
1801 ggcttctatc ccagcgacat cgccgtggag tgggagagca atgggcagcc
1851 ggagaacaac tacaagacca cgcctcccgt gctggactcc gacggctcct
1901 tcttcctcta tagcaagctc accgtggaca agagcaggtg gcagcagggg
1951 aacgtcttct catgctccgt gatgcatgag gctctgcaca accactacac
2001 gcagaagagc ctctccctgt ctccgggtaa atag
```

LT1009 HC amino acid sequence [SEQ ID NO: 35]:
```
  1 mewswvflff lsvttgvhse vqlvqsgaev kkpgeslkis cqsfgyifid
 51 htihwmrqmp gqglewmgai sprhditkyn emfrgqvtis adkssstayl
101 qwsslkasdt amyfcarggf ygstiwfdfw gqgtmvtvss astkgpsvfp
151 lapssksts9 gtaalgclvk dyfpepvtvs wnsgaltsgv htfpavlqss
201 glyslssvvt vpssslgtqt yicnvnhkps ntkvdkrvap ellggpsvfl
251 fppkpkdtlm isrtpevtcv vvdvshedpe vkfnwyvdgv evhnaktkpr
301 eeqynstyrv vsvltvlhqd wlngkeykck vsnkalpapi ektiskakgq
351 prepqvytlp psreemtknq vsltclvkgf ypsdiavewe sngqpennyk
```

```
-continued
401 ttppvldsdg sfflyskltv dksrwqqgnv fscsvmheal hnhytqksls 451 lspgk LT1009 LC nucleotide sequence [SEQ ID NO: 36]:
  1 aagcttgccg ccaccatgtc tgtgcctacc caggtgctgg gactgctgct 51 gctgtggctg acagacgccc gctgtgaaac gacagtgacg cagtctccat 101 ccttcctgtc tgcatctgta ggagacagag tcaccatcac ttgcataacc 151 accactgata ttgatgatga tatgaactgg ttccagcagg aaccagggaa 201 agcccctaag ctcctgatct ccgaaggcaa tattcttcgt cctggggtcc 251 catcaagatt cagcagcagt ggatatggca cagatttcac tctcaccatc 301 agcaaattgc agcctgaaga ttttgcaact tattactgtt tgcagagtga 351 taacttacca ttcactttcg gccaagggac caagctggag atcaaacgta 401 cggtggctgc accatctgtc ttcatcttcc cgccatctga tgagcagttg 451 aaatctggaa ctgcctctgt tgtgtgcctg ctgaataact tctatcccag 501 agaggccaaa gtacagtgga aggtggataa cgccctccaa tcgggtaact 551 cccaggagag tgtcacagag caggacagca aggacagcac ctacagcctc 601 agcagcaccc tgacgctgag caaagcagac tacgagaaac acaaagtcta 651 cgcctgcgaa gtcacccatc agggcctgag ctcgcccgtc acaaagagct 701 tcaacagggg agagtgttag LT1009 LC amino acid sequence [SEQ ID NO: 37]:
  1 msvptqvlgl lllwltdarc ettvtqspsf lsasvgdrvt itcittidid 51 ddmnwfqqep gkapkllise gnilrpgvps rfsssgygtd ftltisklqp 101 edfatyyclq sdnlpftfgq gtkleikrtv aapsvfifpp sdeqlksgta 151 svvcllnnfy preakvqwkv dnalqsgnsq esvteqdskd styslsstlt 201 lskadyekhk vyacevthqg lsspvtksfn rgec
```

Example 13

Humanized S1P mAb Production and Purification

This example describes the production of a recombinant humanized monoclonal antibody (LT1009; Sonepcizumab™) that binds with high affinity to the bioactive lipid sphingosine-1-phosphate (S1P). LT1009 is a full-length IgG1k isotype antibody composed of two identical light chains and two identical heavy chains with a total molecular weight of 150 kDa. The heavy chain contains an N-linked glycosylation site. The nature of the oligosaccharide structure has not yet been determined but is anticipated to be a complex biantennary structure with a core fucose. The nature of the glycoform that will be predominant is not known at this stage. Some C-terminal heterogeneity is expected because of the presence of lysine residues in the constant domain of the heavy chain. The two heavy chains are covalently coupled to each other through two inter-chain disulfide bonds, which is consistent with the structure of a human IgG1.

LT1009 was originally derived from a murine monoclonal antibody (LT1002; Sphingomab™) that was produced using hybridomas generated from mice immunized with S1P. The humanization of the murine antibody involved the insertion of the six murine CDRs in place of those of a human antibody framework selected for its structure similarity to the murine parent antibody. A series of substitutions were made in the framework to engineer the humanized antibody. These substitutions are called back mutations and replace human with murine residues that are play a significant role in the interaction of the antibody with the antigen. The final humanized version contains one murine back mutation in the human framework of variable domain of the heavy chain and five murine back mutations in the human framework of the variable domain of the light chain. In addition, one residue present in the CDR #2 of the heavy chain was substituted to an alanine residue. This substitution was shown to increase stability and potency of the antibody molecule.

The humanized variable domains were cloned into the Lonza's GS gene expression system to generate the plasmid pATH1009. This expression system consists of an expression vector carrying the constant domains of the antibody genes and the selectable marker glutamine synthetase (GS). GS is the enzyme responsible for the biosynthesis of glutamine from glutamate and ammonia. The vector carrying both the antibody genes and the selectable marker is transfected into proprietary Chinese hamster ovary (CHOK1SV) host cell line adapted for growth in serum-free medium and provides sufficient glutamine for the cell to survive without exogenous glutamine. In addition, the specific GS inhibitor, methionine sulphoximine (MSX), is supplemented in the medium to inhibit endogenous GS activity such that only the cell lines with GS activity provided by the vector can survive. The transfected cells were selected for their ability to grow in glutamine-free medium in the presence of MSX and isolates were selected for high level of secretion of active LT1009.

Material for toxicology studies and clinical development were then produced for tox and clinical development.

ATCC deposits: *E. coli* StB12 containing the pATH1009 plasmid has been deposited with the American Type Culture Collection (deposit number PTA-8421). CHO cell line LH1 275 transfected with DNA plasmid pATH1009 has also been deposited with the American Type Culture Collection (deposit number PTA-8422).

Example 14

Manufacturing of Humanized mAb

Typically, the production process involves three stages: seed train, inoculum train, and the production culture. All stages use serum-free reagents and low protein cell culture growth medium. To initiate a seed train, cells from the working cell bank are used; cells are subcultured every three to four days and after a prescribed period in the seed train culture, the inoculation train is initiated. The non-selective medium (MTX-freee medium) is preferably used to expand the cell for introduction into the production stage. The cells are expanded by serial sub-cultivation into vessels of increasing volume. At a certain number of days in the inoculum train, the production stage is initiated. The production culture is performed in a bioreactor of volume of 200 L, 400 L, 2000 L, or 20000 L. An example of a bioreactor is described below.

Example of bioreactor: Scale-up from the 2 L bioreactors will proceed first to a Applikon 15 L stirred tank, then sequentially to a 50 L bioreactor, a 200 L bioreactor and finally a 2000 L bioreactor (all built to same scale). The characteristics of these tanks are as follows:

Manufacturer: ABEC, Inc.

Fabricated to ASME, Section VIII Pressure Vessel Code; Contact surfaces are 316L SS.

Bottom offset drive, ABEC design

Lowshear impellor 316LSS, polished to 15-20 microinch and passivated. Diameter ~½ of vessel diameter.

Controls: Allen Bradley Control Logic PLC, with Versa view operator interface.

Agitation: Allen Bradley sensor, A-B PLC control of output for VFI for RPM control Temperature: Dual control 100 ohm platinum RTD sensor, A-B PLC control heat, cold and steam valves w/recirculation pump. Automatic sterilization cycle with bioreactor empty.

pH: Ingold sensor, gel filled, pressurizable, A-B PLC control of CO2 to sparge.

Dissolved oxygen: Ingold polarographic electrode sensor, A-B PLC control of O2 sparge.

Air and gas flow: Sensors are Four Brooks Thermal Mass Flowmeters for air, O2, N2 and CO2 sparging, a Brooks thermal mass is also supplied for air overlay, A-B PLC control of gas flows for pH auto, DO auto or manual control of all gas flow through A-B PLC.

Vessel Pressure: Sensor is a Rosemount sanitary diaphragm type transducer, control is A-B PLC control of transducer with back pressure control valve.

Programmable Logic Controller (PLC): Allen Bradley Control Logix System for sequential loop control of processes as indicated. Software: PLC programming utilizes Rockwell Software (Allen Bradley) RS Logix 5000.

Human Machine Interface (HMI): Local operator interface is on an Allen Bradley HMI Verso View Industrial computer with integrated FPD/touch screen entry communicating to the PLC via Ethernet. Software is Rockwell Software RS View 32.

Example of Production Process.

Stirred stainless bioreactor with control of temperature, dissolved oxygen and pH.

Seeding density is determined for optimal yield.

Serum-free medium is typically utilized.

Typically a fed-batch process.

Typically with a temperature shift.

Duration of culture in the bioreactor expected to be 8 to 14 days.

Viability at time of harvest to be defined.

Harvest will be clarified by filtration.

Harvest will be stored at 2-8° C. following clarification and prior to purification.

Example 15

Large-Scale Purification of Humanized mAb

The drug substance purification process typically consists of four steps: protein A chromatography, anion exchange chromatography (Q sepharose), cation exchange chromatography (CM sepharose), and ultrafiltration/diafiltration (UF/DF). The affinity column is the generally the first step after harvest and clarification. This column typically utilizes an immobilized protein A resin. This affinity step purifies the antibody with respect to host cell proteins and DNA. In order to inactivate potential viruses, the eluate is typically subjected to a virus inactivation process followed by an anion exchange chromatographic step to reduce host cell proteins, DNA, protein A, and potential viruses. Next, a cation exchange chromatographic step is typically used to further reduce the residual amounts of host cell proteins and antibody aggregates. Finally, the pool is then diafiltered and further concentrated.

Representative Purification Process:

Harvest may be concentrated and buffer-exchanged prior to Protein A column. The next step in the process is Protein A column affinity chromatography. The bound antibody is eluted with a low pH buffer. The Protein A eluate is held for a time in order to inactivate viruses.

The next step in the process can be an ion-exchange chromatography on a Q(+) column under conditions in which the antibody product flows through and contaminants, such as DNA and host cell proteins bind to the column resin.

The next step in the process can be a second ion-exchange chromatography on an S(−) column under conditions in which contaminants flow through the column. A hydrophobic interaction column step may be used in place of the S(−) column step. The next step in the process is likely to be a nanofiltration virus removal step, using a DV20 or Planova filter. The product flows through the filter. The final steps in the process are diafiltration into the final drug substance formulation buffer and ultrafiltration to achieve the target protein concentration.

Example 16

Biological Activity of Humanized Variants of a Murine Anti-S1P Antibody

In Vitro Cell Assays

Figure 12A:
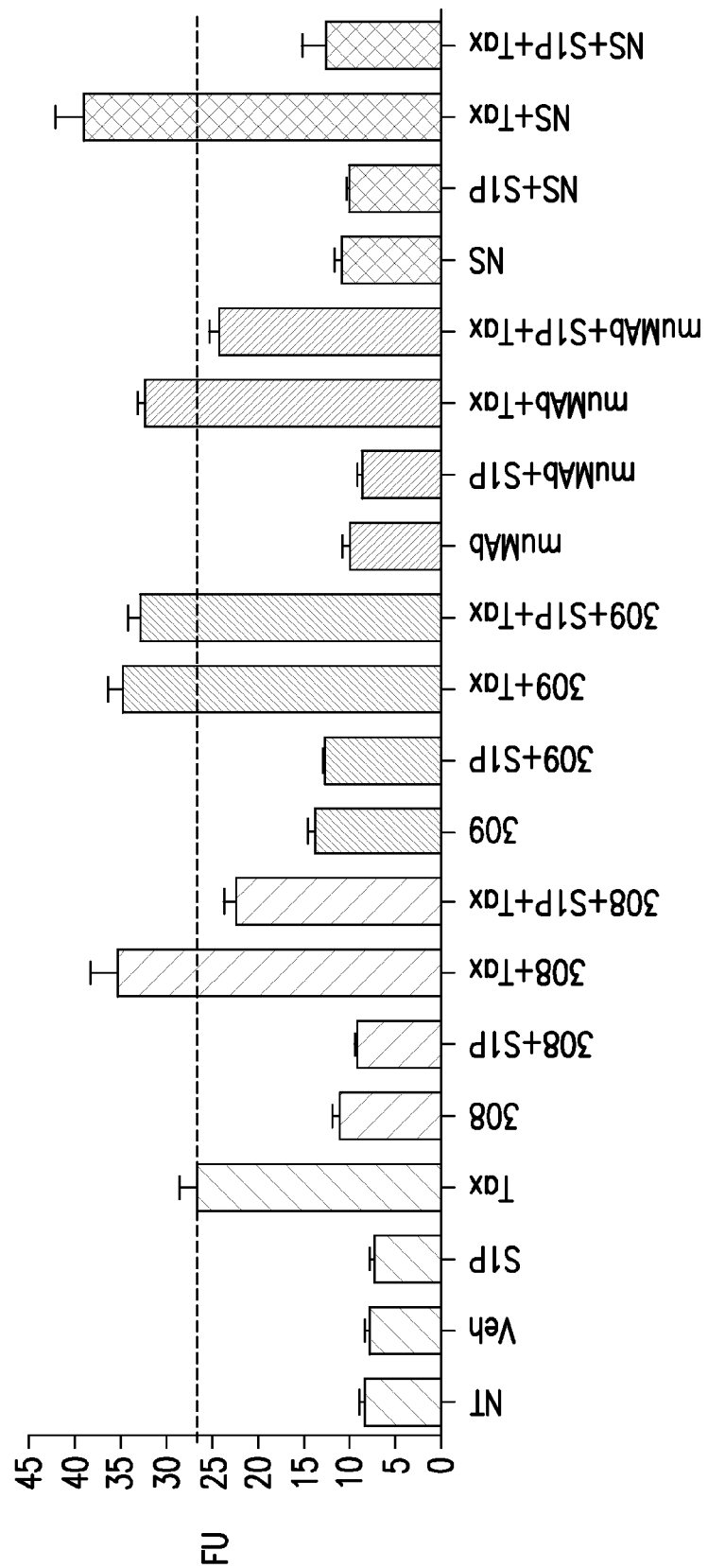
FIG. 12.
Figure 12B:
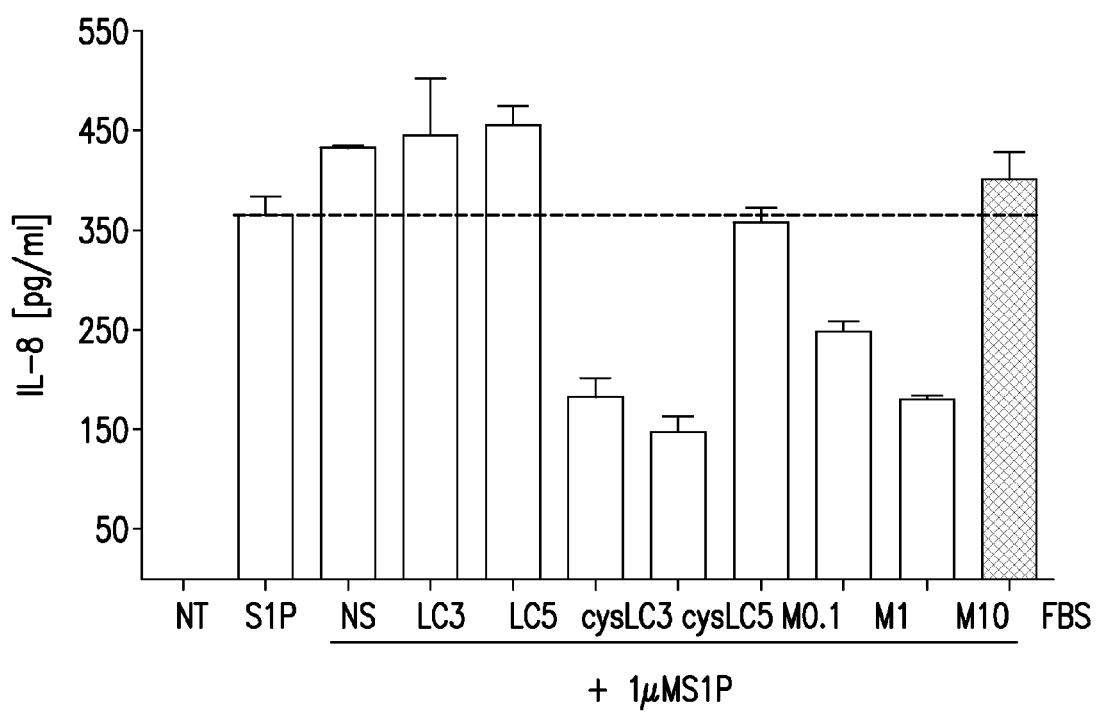

The humanized antibodies were tested for their ability to alter tumor cell survival in presence of chemotherapeutic agents as shown in FIG. 12. SKOV3 tumor cells were exposed to Taxol, a chemotherapeutic agent that induces tumor cell death by activation of the apoptotic executioner, caspase-3. S1P was able to decrease Taxol-induced caspase-3 activation and/or cell death compared to the control non-treated cells. Apoptosis assays were performed as recommended by the manufacturer (Promega, Cat. No G7792). Briefly, A549 cells (2500 cells per well) were seeded into 96-well plates and allowed to grow to 80% confluence prior to treatment. The cells were then treated with and without 0.1-1 µM Paclitaxel (Sigma, Cat. No T 7409), 0.1-1 µM S1P and 1 µg/mL of the anti-S1P mAb, in McCoy's media for 48 hrs. After 48 hrs, the caspase assay buffer was added to the cells. Caspase-3 activity in the supernatant was measured by Apo-One Homogeneous Caspase-3/7 Assay kit (Promega, Cat. No G7792) according to the manufacturer's protocol. Caspase-3/7 activity is expressed as the fold increase in fluorescence signal with respect to vehicle treated cells.

Caspase-3 activation was increased by the addition of anti-S1P mAb in presence of S1P, suggesting that the protective anti-apoptotic effect of S1P was eliminated by selective absorption of S1P by the antibody. Both humanized antibody variants, huMAbHCLC$_3$ (LT1004) and huMAbHCLC$_5$ (LT1006), exhibited superior activity compared to LT1002. In parallel, all the variants were tested for their effects on S1P-induced cytokine release from cancer cells. S1P is known to elicit significant release of IL-8 into the cell-conditioned media from cancer cells. Addition of the mouse control anti-S1P mAb reduced IL-8 release from ovarian cancer cells in a concentration-dependent manner. The two humanized variants huMAbHCcysalaLC$_3$ (LT1007) and huMAbHCcysalaLC$_5$ (LT1009) exhibited greater reduction of IL-8 release compared to HuMAbHCLC$_3$ (LT1004) and huMAbHCLC$_5$ (LT1006).

Example 17

In Vivo Efficacy of Murine mAb (Sphingomab) Vs. Humanized mAb (Sonepcizumab) in an Animal Model of Neovascularization Choroidal neovascularization (CNV) refers to the growth of new blood vessels that originate from the choroid through a break in the Bruch membrane into the sub-retinal pigment epithelium (sub-RPE) or subretinal space in the eye. CNV is a major cause of visual loss in macular degeneration and other ocular conditions. A mouse model of CNV is used in this example for evaluation of mAbs against S1P.

Figure 13:
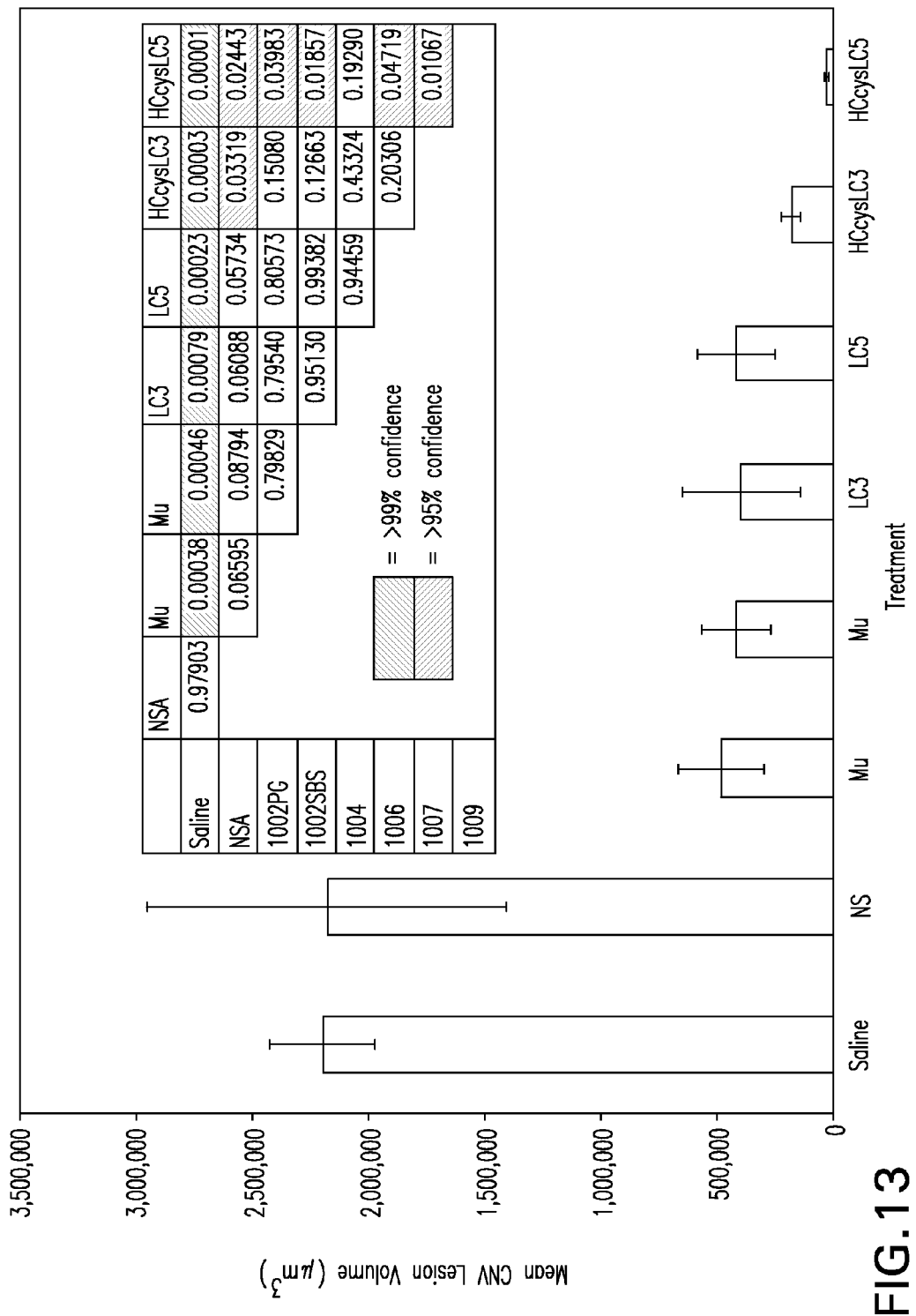
FIG. 13.

The humanized antibody variants and the murine antibody were compared for their ability to inhibit neo-vascularization in the CNV animal model of AMD as shown in FIG. 13. Mice were administered 0.5 ug twice (Day 0 and Day 6) of the murine (Mu; LT1002), the humanized variants [LC3 (LT1004), LC5 (LT1006), HCcysLC3 (LT1007) and HCcysLC5 (LT1009)] or the nonspecific mAb (NS) by intravitreal administration and then subjected to laser rupture of Bruchs membrane. Mice were sacrificed 14 days post laser surgery. Control mice were treated with aqueous buffer (PBS) or an isotype-matched non-specific antibody. Three of the humanized variants inhibited angiogenesis essentially equivalently to the murine antibody as assessed by measurement of CNV area. CNV lesion volumes are represented as means±SEM. The humanized variant containing 5 backmutations in the light chain and with a cysteine mutation in CDR2 of the heavy chain (huMAbHCcysLC$_5$; LT1009) markedly suppressed neovascularization. This difference was highly statistically significant.

For the induction of CNV, mice were anesthetized with a mixture of ketamine (14 mg/kg) and xylazine (30 mg/kg) in sterile saline administered intraperitoneally at a dose of 5 µL per 20 g of body weight. Their pupils were then dilated with one drop each of ophthalmic tropicamide (0.5%) and phenylephrine (2.5%). An argon green ophthalmic laser (Oculight GL 532 nm, Iridex Corporation, Mountain View, Calif.) coupled to a slit lamp set to deliver a 100 msec pulse at 150 mW with a 50 µm spot size will then be used to rupture Bruch's membrane in three quadrants of the right eye located approximately 50 µm from the optic disc at relative 9, 12 and 3'oclock positions. The left eye served as uninjured control in all cases.

The morphometric and volumetric CNV lesions were measured as follows. Two weeks after laser induction of CNV, the animals were euthanized by overdose of ketamine-xylazine mixture, then undergo whole body perfusion via cardiac puncture with 6 ml 4% paraformaldehyde in PBS, pH 7.5, (fixative) as previously described (Sengupta et al., 2003). The eyes will then be enucleated, punctured with a 27 g needle 1 mm posterior to the limbus, and immersed in fixative for 1 hr at room temperature, then washed 2× by immersion in PBS for 30 min. The eyes will then be dissected to isolate the posterior segment consisting of the retinal pigment epithelium, the choriocapillaris and the sclera. This tissue was then permeabilized and reacted with rhodamine-conjugated *R. communis* agglutinin I (Vector Laboratories, Burlingame, Calif.) to detect the CNV lesion as previously described (Sengupta et al., 2003; Sengupta et al., 2005). The posterior cups was then cut with 4-7 radial slices, and mounted flat on microscope slides with a drop of Vectashield anti-fade medium (Vector Laboratories, Burlingame, Vt.) for digital image capture by epifluorescence Zeiss Axioplan 2 with RGB Spot high-resolution digital camera) and laser scanning confocal microscopy (BioRad MRC 1024, BioRad Corporation, Temecula, Calif.).

Captured digital images were evaluated morphometrically using ImageJ software (Research Services Branch, National Institutes of Health, Bethesda, Md.). Images were split into separate RGB channels for analysis of the red and green channels as follows: 1) a calibration for the specific objective and microscope was applied to set the pixel-to-length ratio; 2) a threshold was applied using the Otsu algorithm; 3) images will be made binary; 4) a region-of-interest (ROI) was outlined to include the entire lesion area; 5) a particle analysis was performed to quantify the pixel area above the threshold level within the ROI. For volumetric analysis, the process was similar to that described above, except that a z-series capture was used. The sum of lesion area throughout the z-series was then multiplied by the z thickness (typically 4 µm) to obtain the lesion volume.

Drug products tested in this model were LT1002 (murine mAb to S1P; Sphingomab™); LT1004 (humanized mAb), LT1006 (humanized mAb), LT1007 (humanized mAb) and LT1009 (humanized mAb; Sonepcizumab™). Also included were saline vehicle and non-specific antibody (NSA) controls. As shown in FIG. 13, both the murine mAb LT1002 (Sphingomab™) and the humanized mAb LT1009 (Sonepcizumab™) significantly decreased lesion size in this mouse model of CNV. All mAbs tested showed approximately 80-98% reduction of lesion size, which was significant ($p<0.001$ vs. saline) in all cases. In addition, LT1007 and LT1009 also showed significant inhibition ($p<0.05$) compared to non-specific antibody control. Percent inhibition of lesion size was approximately 80% for LT1002 (murine), 82% for LT1004 (humanized), 81% for LT1006 and 99% for LT1009. Thus, LT1009 was the humanized mAb variant most active in this in vivo model of neovascularization.

Example 18

Determination of the Sonepcizumab Dose Response

Mice (n=10) received a single, bilateral intravitreal injection of escalating doses of sonepcizumab (0.05, 0.5, 1.0 or 3.0 µg/eye) or a high dose nonspecific (NS) antibody (3.0 µg/eye) one day prior to laser-induced rupture of Bruch's membrane. Fourteen days after laser rupture, mice were anesthetized and perfused with fluorescein-labeled dextran and choroidal flatmounts were prepared for analysis of CNV lesion size.

In this study, the effect of sonepcizumab dose amount and dose interval on CNV inhibition were examined using another validated method of quantifying CNV area in which animals were perfused with fluorescein-labeled dextran just before sacrifice. Sonepcizumab induced a dose-dependent reduction in the area of CNV resulting in a maximal inhibition of approximately 50%, at a dose of 3.0 µg/eye. This reduction was significant (p<0.0001 compared to non-specific antibody control using an unpaired t-test). In the dosing frequency study, similar efficacy was observed between groups treated with Sonepcizumab at a single timepoint (day 0) or at multiple timepoints (days 0 and 7) over the 14-day study.

The maximal inhibition of approximately 50% seen with Sonepcizumab treatment (3.0 ug/eye) compares favorably with previously published data in the same model and conducted by the same investigator demonstrating the reduction in CNV area by the VEGF-Trap (4.92 µg/eye). Saishin, et al. *J Cell Physiol*, 2003. 195(2): p. 241-8. "Traps" (Regeneron Pharmaceuticals, Inc.) are fusions between two distinct receptor components and the Fc region of an antibody molecule called the Fc region and the VEGF-Trap is being pursued for ocular disease and cancer by Regeneron. A comparison of these two independent studies reveals that the reduction in CNV lesion size by Sonepcizumab was 20 percentage points greater than that observed with the VEGF-Trap. Thus, these data not only confirm our preliminary findings regarding the ability of an anti-S1P therapy to reduce lesion formation in murine model of CNV, but they also demonstrate the increased efficacy of the humanized antibody, sonepcizumab, to inhibit CNV lesion formation and provide insight into an anti-permeability effect.

Example 19

Efficacy of Sonepcizumab in Reducing the Development of Retinal Neovascularization in a Murine Model of Retinopathy of Prematurity C57BL/6 mice (n=7) were placed in 75% oxygen at day 7 of life and at day 12 of life were returned to room air and given an intraocular injection of 31 g of sonepcizumab in one eye and vehicle in the contralateral eye. At day 17, the mice received an intraocular injection of anti-PECAM antibody labeled with FITC and after 8 hours, mice were euthanized and eyes were removed and fixed in PBS-buffered formalin at room temperature for 5 hours. Retinas were dissected and washed with phosphate-buffered saline containing 0.25% Triton X-100 and whole mounted. Slides were viewed with a Nikon Fluorescence Microscope and the area of retinal NV per retina was measured by image analysis.

Consistent with the reduction in CNV observed in the murine laser rupture model, we also observed a dramatic reduction in CNV in a murine model of retinopathy of prematurity (ROP). Intravitreal administration of Sonepcizumab (3.0 µg/eye) resulted in a nearly 4-fold reduction in retinal neovascularization compared to saline control. These data confirm the efficacy of sonepcizumab to inhibit pathological ocular angiogenesis in both the retinal and choroidal vascular beds whether induced via ischemia or rupture of Bruch's membrane.

Example 20

Effect of Sonepcizumab on VEGF-Induced Angiogenesis in a Matrigel Plus Assay

Neovascularization in vivo was performed using the GFR Matrigel plug assay as described in Staton, et al., *Int J Exp Pathol*, 2004. 85(5): p. 233-48. 4-6 week old nu/nu mice were injected in the left flank with 500 uL of ice-cold GFR Matrigel. The GFR Matrigel was injected either alone (control) or after addition of 10 ug/mL VEGF supplemented with 100 ug/ml heparin. Groups consisted of 3 animals for control and sonepcizumab treatment. Animals were treated with the saline or sonepcizumab (10 mg/kg) 1 day prior to the implantation of GFR Matrigel and doses were administrated i.p. every 72 hrs for the duration of the experiment. After 12 days animals were sacrificed; the plugs were excised and immediately fixed in zinc and formalin-free fixative overnight, embedded in paraffin and sectioned (5 um). Paraffin-embedded sections were then stained for CD31 (Pharmingen). Images (9 images per section, 3 sections per plug) were taken by digital camera at 20× magnification and the CD31 positive staining was then quantified by PhotoShop 6.0 program and expressed as angiogenesis score (pixel$^2$) by ImageJ.

The anti-angiogenic effects of sonepcizumab were evident in this Matrigel plug assay. As expected extensive neovascularization (approx. 5.75× that seen in untreated control lacking VEGF or sonepcizumab) was induced in the Matrigel plugs supplemented with 10 ug/ml VEGF. Importantly, systemic i.p. treatment with sonepcizumab prior to Matrigel injection prevented nearly 80% of this VEGF-stimulated increase in cellularity and microvessel density. This reduction is significant (p<0.05 compared to VEGF alone) and confirms the potent anti-angiogenic activity of sonepcizumab when administered systemically to animals and strongly suggest that sonepcizumab is capable of significantly inhibiting VEGF induced angiogenesis. This finding is consistent with data from Lpath's oncology program whereby that S1P antibody reduced serum levels of several angiogenic factors, including VEGF, in a murine orthotopic breast cancer model.

A primary component of blood vessel growth associated with AMD is the recruitment of pericytes which ensheath and support the growing endothelial tube. Jo, et al., *Am J Pathol*, 2006. 168(6): p. 2036-53. Transgenic mouse studies have shown that VEGF and PDGF-B are the primary factors that stimulate infiltration and differentiation of pericytes leading to blood vessel maturation and stabilization. Guo, et al., *Am J Pathol*, 2003. 162(4): p. 1083-93; Benjamin, L. E., I. Hemo, and E. Keshet, *Development*, 1998. 125(9): p. 1591-8. Importantly, S1P promotes trans-activation of VEGF and PDGF. Therefore, the ability of sonepcizumab to indirectly neutralize these growth factors suggests that sonepcizumab could prevent abnormal blood vessel growth during AMD.

Example 21

Sonepcizumab Significantly Reduces Vascular Leakage Following Laser Rupture of Bruch's Membrane The efficacy of sonepcizumab, administered to inhibit vascular leakage (in addition to inhibiting neovascularization as shown above) was evaluated in a murine model of laser rupture of Bruch's membrane.

C57BL/6 mice (n=10) underwent laser rupture of Bruch's membrane in 3 locations in each eye and were given an intraocular injection of 3 µg of sonepcizumab in one eye and vehicle in the contralateral eye. At one week after laser rupture, the mice were given an intraperitoneal injection of 12 µl/g body weight of 1% fluorescein sodium and were euthanized 5 minutes later. The eyes were removed and fixed in PBS-buffered formalin at room temperature for 5 hours. Then the retinas were dissected, washed, and incubated with primary anti-PECAM-1. The retinas were then washed, incubated with secondary antibody (goat anti-rat IgG conjugated with rhodamine), and then flat mounted.

Quantification of CNV lesion area is measured by PECAM-1 staining. Quantification of vascular leakage is measured by fluorescein sodium staining. The total area of leakage from CNV=CNV+leakage (green)–area of CNV (red). Values represent the mean±SEM for n=10 mice/group. The area of choroidal neovascularization (stained by PECAM-1) was approximately 0.015 mm$^2$ for animals treated with LT1009 and approximately 0.03 mm$^2$ for saline-treated control animals. This is a 50% reduction in neovascularization (p-0.018). The area of leakage from choroidal neovascularization (stained by fluorescein) was approximately 0.125 mm$^2$ for animals treated with LT1009 and approximately 0.2 mm$^2$ for saline-treated control animals. This is approximately a 38% reduction (p-0.017) in blood vessel leakage.

Representative immunohistochemical images of the reduction in choroidal neovascularization and vascular leakage in mice treated with 3.0 µg/eye of Sonepcizumab or PBS control are consistent with these results. Thus, in addition to reducing CNV, sonepcizumab significantly reduced vascular leakage following laser rupture of Bruch's membrane retinal edema, which plays a major role in the loss of visual acuity, is associated with: (i) choroidal neovasculature leakage in AMD and (ii) the breakdown of the blood-retinal barrier in diabetes. Gerhardt, H. and C. Betsholtz, *Cell Tissue Res*, 2003. 314(1): p. 15-23 Sonepcizumab reduces pathological blood vessel formation in the eye as well as vascular leakage that results in retinal edema. These findings are consistent with the data generated from the CNV-area-quantification experiment in which mice were perfused with fluorescein-labeled dextran. CNV quantification via this method surely is affected by vascular permeability. The highly favorable results argue for an anti-permeability effect in the choroidal vascular bed. Given these data, we believe that sonepcizumab has the potential to be a monotherapy. The possibility of a synergistic effect with current pan-VEGF-A blocking agents also exists.

Example 22

Reduction of Macrophage Infiltration in the Retina after Treatment with Antibody to S1P Age-related macular degeneration (AMD) is a disease associated with aging that gradually destroys sharp, central vision. There are two main types of macular degeneration. The dry or atrophic form which accounts for 85-90% of AMD cases, and the wet form of AMD characterized by the growth of abnormal blood vessels. Dry macular degeneration is diagnosed when yellowish spots known as drusen begin to accumulate from deposits or debris from deteriorating tissue primarily in the area of the macula. Gradual central vision loss may occur. There is no effective treatment for the most prevalent atrophic (dry) form of AMD. Atrophic AMD is triggered by abnormalities in the retinal pigment epithelium (RPE) that lies beneath the photoreceptor cells and normally provides critical metabolic support to these light-sensing cells. Secondary to RPE dysfunction, macular rods and cones degenerate leading to the irreversible loss of vision. Oxidative stress, ischemia, formation of drusen, accumulation of lipofuscin, local inflammation and reactive gliosis represent the pathologic processes implicated in pathogenesis of atrophic AMD. Of these processes, inflammation is emerging as a key contributor to tissue damage. Macrophage infiltration into the macula of patients with dry AMD has been demonstrated to be an important component of the damaging inflammatory response. Therefore an agent which could mitigate macrophage infiltration would be a valuable therapeutic, as inhibition of macrophage infiltration would likely diminish macular tissue damage. Such an agent may also decrease the rate at which dry AMD converts to wet AMD.

In a model of ischemic and inflammatory retinopathy, a 55% inhibition of macrophage infiltration has now been demonstrated after treatment with an anti S1P antibody. These data were generated using the well established murine oxygen induced retinopathy model (also known as the retinopathy of prematurity (ROP) model). Specifically, C57BL/6 mice were placed in 75% oxygen on day 7 of life and at day 12 of life were returned to room air and given an intraocular injection of 3 µg of humanized anti S1P antibody (LT1009, Sonepcizumab™) in one eye and vehicle in the fellow eye. At day 17 of life, the mice received an intraocular injection of FITC-labeled antibody to F4/80 (a pan-macrophage marker) and after 8 hours, mice were euthanized. The globes were removed and fixed in PBS-buffered formalin at room temperature for 5 hours. Retinas were dissected and washed with phosphate-buffered saline containing 0.25% Triton X-100 and whole mounted. Slides were viewed with a Nikon Fluorescence Microscope and retinal macrophages were quantified. The results are shown in Table 8 below.

TABLE 8

| Reduction in macrophage infiltration in the retina by treatment with humanized monoclonal antibody to S1P | | | |
|---|---|---|---|
| # of macrophages per retina | | % reduction in macrophage density | |
| Saline control | S1P antibody | Saline control | S1P antibody |
| 2513 ± 115 | 1136 ± 33 | 100 ± 0.5 | 55.4 ± 1.3 |
| P < 0.001 | | P < 0.0001 | |

On the basis of these data and the known role of macrophages in the pathogenesis of dry AMD it is believed that anti-S1P antibodies represent an effective therapeutic agent for the treatment of dry AMD.

Example 23

Response of SC COLO205 Colorectal Tumor Xenograft in Nude NCr Mice to Treatment with 25-75 mg/kg LT1009, Alone and in Combination with Avastin or Paclitaxel The objective of this study was to determine the efficacy of LT1009, alone and in combination with other anti-cancer agents, to retard the progression of human colorectal (COLO0205) carcinoma tumors grafted subcutaneous (sc) and established in female Ncr (nu/nu) mice.

Nude mice were implanted sc near the right flank with one fragment per mouse of COLO 205 tumor from an in vivo passage. All treatments were initiated the day when 60 mice in each experiment established tumors ranging in size from approximately 100 to 200 mm3. The mice (n=10 per group) were then treated with either 25 mg/kg of LT1009, 50 mg/kg LT1009, 40 mg/kg Avastin, 50 mg/kg LT1009 plus 40 mg/kg Avastin, 15 mg/kg Paclitaxel or vehicle (saline). 25 or 50 mg/kg LT1009 and saline were administered ip once q3d in a volume of 0.1 mL/20 g body weight for the duration of the experiment. Avastin was administered iv at a dosage of 40 mg/kg/dose on a q7d schedule, injected in a volume of 0.1 mL/20 g body weight. Paclitaxel (positive control), was administered iv at a dosage of 15 mg/kg/dose on a q1d×5 schedule, injected in a volume of 0.1 mL/10 g body weight. On Day 21, the dose of 25 mg/kg LT1009 was increased to 75 mg/kg LT1009 for the duration for the study.

Animals were observed daily for mortality. Tumor dimensions and body weights were collected twice weekly starting with the first day of treatment and including the day of study termination. When the median tumor in the vehicle-treated control group in each study reached approximately 4,000 mg, the study was terminated. Tumors from each animal were harvested, wet weights were recorded, tumors were processed for determination of microvascular densities (MVD) by CD-31 staining. Tumor weights (mg) were calculated using the equation for an ellipsoid sphere $(l \times w^2)/2 = mm^3$, where l and w refer to the larger and smaller dimensions collected at each measurement and assuming unit density (1 $mm^3$=1 mg).

TABLE 9

Numerical summary of findings -Colo205

| Treatment | Final Tumor Weights (mg) | % Reduction Compared to Vehicle-Treated Mice |
|---|---|---|
| Vehicle | 3047.25 | — |
| 50 mg/kg LT1009 | 2071.17 | 32% |
| 25/75 mg/kg LT1009 | 2465.60 | 20% |
| Avastin | 1967.90 | 35% |
| Avastin + 50 mg/kg LT1009 | 1614.40 | 48% |
| Paclitaxel | 0 | 100% |

50 mg/kg LT1009 substantially inhibited tumor progression (p<0.018), as measured by final tumor weights, by 32% when compared to tumors from saline-treated animals. 25/75 mg/kg LT1009 was also effective in reducing final tumor weights by 20%; however, this reduction was not statistically significant. 50 mg/kg LT1009 was as effective as Avastin in reducing final tumor weights (32% versus 35% reduction, respectively). The combination of LT1009 and Avastin was more effective than either agent alone, demonstrating a 48% reduction in tumor weights when compared to saline-treated animals. Thus the effects of LT1009 and Avastin appear to be additive. The positive control, Paclitaxel, completely eliminated the pre-established tumors.

Example 24

Response of SC HT29 Colorectal Tumor Xenograft in Nude NCr Mice to Treatment with 50 mg/kg LT1009, Alone and in Combination with Avastin and 5-FU The objective of this study is to evaluate the antitumor efficacy of LT1009, alone and in combination with other anti-cancer agents, against human HT29 colon tumor xenografts implanted sc in female athymic NCr-nu/nu mice.

Nude mice were implanted sc near the right flank with one fragment per mouse of HT29 tumor from an in vivo passage. All treatments were initiated the day when 60 mice in each experiment established tumors ranging in size from approximately 100 to 200 $mm^3$. There were ten mice per treatment group. 50 mg/kg LT1009 and saline were administered ip q2d in a volume of 0.1 mL/20 g body weight for the duration of the experiment. 75 mg/kg 5-FU and 20 mg/kg Avastin were administered ip and iv at a dosage of 75 mg/kg/dose and 20 mg/kg/dose, respectively, q4d, injected in a volume of 0.1 mL/10 g body weight. The first dose of LT1009 consisted of 100 mg/kg administered iv.

Animals were observed daily for mortality. Tumor dimensions and body weights were collected twice weekly starting with the first day of treatment and including the day of study termination. When the median tumor in the vehicle-treated control group in each study reached approximately 4,000 mg, the study was terminated. Tumors from each animal were harvested, wet weights were recorded, and tumors were processed for determination of MVD by CD-31 staining. Tumor weights (mg) were calculated using the equation for an ellipsoid sphere $(l \times w^2)/2 = mm^3$, where l and w refer to the larger and smaller dimensions collected at each measurement and assuming unit density (1 $mm^3$=1 mg).

TABLE 10

Final Tumor Weights- HT29

| Treatment | Final Tumor Weights (mg) | Significance (p-value) | % Reduction compared to Vehicle-Treated Mice |
|---|---|---|---|
| Vehicle | 2723.67 | — | — |
| LT1009 | 2390.63 | 1.00 | 13% |
| Avastin | 1927.44 | 0.39 | 30% |
| LT1009 + Avastin | 1624.90 | 0.001 | 41% |
| 5-FU | 1963.71 | 0.099 | 28% |
| LT1009 + 5-FU | 1948.00 | 0.049 | 29% |

50 mg/kg LT1009 reduced tumor progression, as measured by tumor weights, by 13% while Avastin reduced tumor weights by 30% when compared to tumors from saline-treated animals. The combination of LT1009 and Avastin was more effective than either agent alone demonstrating a statistically significant 41% reduction in tumor weights when compared to saline-treated animals. Treatment with 5-FU reduced tumor weights by 28%. 5-FU showed minimal additive effect with LT1009 demonstrating a 29% inhibition of final tumor weights.

Example 25

Response of SC DU145 Prostate Tumor Xenograft in Nude NCr Mice to Treatment with 50 mg/kg LT1009, Alone or in Combination with Avastin or Paclitaxel The objective of this study was to determine the efficacy of LT1009, alone and in combination with other anti-cancer agents, to retard the progression of human prostate (DU145) carcinoma tumors grafted subcutaneous (sc) and established in female Ncr (nu/nu) mice.

Nude mice were implanted sc near the right flank with one fragment per mouse of DU145 tumor from an in vivo passage. All treatments were initiated the day when 60 mice in each experiment established tumors ranging in size from approximately 100 to 200 $mm^3$. The mice (n=10/group) were then treated with either 50 mg/kg of LT1009, 20 mg/kg Avastin, 7.5 mg/kg Paclitaxel, 50 mg/kg LT1009 plus 20 mg/kg Avastin, 50 mg/kg LT1009 plus 7.5 mg/kg Paclitaxel or vehicle (saline). 50 mg/kg LT1009 and saline were administered ip q2d in a volume of 0.1 mL/20 g body weight for the duration of the experiment. Paclitaxel and Avastin were administered iv and ip at a dosage of 7.5 mg/kg/dose and 20 mg/kg/dose, q1dx5 and q4d, respectively, injected in a volume of 0.1 mL/10 g body weight. The first dose of LT1009 consisted of 100 mg/kg administered iv.

During the course of the study tumor growth was monitored by measuring the sc tumors on three axes and calculating the volume. At the end of the study final tumor weights and volumes were determined and then the mice were sacrificed, the tumors harvested. Microvascular densities (MVD) of the tumors were then determined by CD-31 staining.

TABLE 11

Numerical summary of findings- DU145

| Treatment | Final Tumor Weights (mg) | Significance (p-value) | % Reduction compared to Vehicle-Treated Mice |
|---|---|---|---|
| Vehicle | 2703 | — | — |
| LT1009 | 2242 | 0.00 | 28% |
| Avastin | 578 | 0.00 | 79% |
| LT1009 + Avastin | 676 | 0.00 | 75% |
| Paclitaxel | 539 | 0.00 | 80% |
| LT1009 + Paclitaxel | 373 | 0.00 | 84% |

50 mg/kg LT1009 significantly (p<0.00) reduced tumor progression, as measured by final tumor weights, by 28%. Avastin and Paclitaxel also significantly (p<0.00) reduced final tumor weights by 80% when compared to tumors from saline-treated animals. LT1009 did not significantly increase the anti-tumor activity, as measured by final tumor volumes, of Avastin or Paclitaxel.

Example 26

Response of RPMI 8226 Human Myeloma Tumor Xenograft in CB17 SCID Mice to Treatment with 25 ml/kg or 50 mg/kg LT1009, Alone and in Combination with Bortezomib The objective of this study is to evaluate the antitumor efficacy of LT1009, alone and in combination with the anticancer agent Bortezomib, against human RPMI human myeloma tumor xenografts implanted sc in female CB17 SCID mice.

Nude mice (CB17 SCID, aged 4-5 weeks, weight 18-22 gm, female mice obtained from Harlan) were injected sc with RPMI 8226 cells harvested from tissue culture ($\sim 1\times 10^7$ cells/mouse). When tumors grew to approximately 100 mm$^3$ in size, animals were pair-matched by tumor size into treatment and control groups (10 mice per group). Initial dosing began Day 1 following pair-matching. Animals in all groups were dosed by weight (0.01 ml per gram; 10 ml/kg). LT1009 in vehicle was administered by intraperitoneal (IP) injection once every three days until study completion (Q3D to end). Bortezomib was administered by intravenous injection via tail vein once every three days for six treatments (Q3Dx6). To serve as a negative control, LT1009 vehicle (0.9% saline) was administered IP on a Q3D to end schedule.

Individual and group mean tumor volumes SEM are recorded twice weekly until study completion beginning Day 1. Final mean tumor volume SEM for each group are reported at study completion; animals experiencing partial or complete tumor regressions or animals experiencing technical or drug-related deaths are censored from these calculations.

TABLE 12

Final Tumor Volumes- RPMI

| Treatment | Final Tumor Weights (mg) | % Reduction compared to Vehicle-Treated Mice |
|---|---|---|
| Vehicle | 2083 | 0 |
| Bortezomib | 1664 | 20% |
| 25 mg/kg LT1009 | 1860 | 11% |
| 50 mg/kg LT1009 | 1978 | 5% |
| 50 mg/kg LT1009 + Bortezomib | 1832 | 12% |

All of the compositions and methods described and claimed herein can be made and executed without undue experimentation in light of the present disclosure. While the compositions and methods of this invention have been described in terms of preferred embodiments, it will be apparent to those of skill in the art that variations may be applied to the compositions and methods. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An isolated, non-naturally occurring nucleic acid molecule that encodes an immunoglobulin heavy chain or an immunoglobulin light chain of an antibody or antigen binding fragment thereof that binds sphingosine-1-phosphate (S1P), wherein:
   A. when the nucleic acid molecule encodes an immunoglobulin heavy chain, wherein the immunoglobulin heavy chain is selected from the group consisting of:
      (i) an immunoglobulin heavy chain that comprises a first sequence of amino acid residues of sequence DHTIH (SEQ ID NO: 13), a second sequence of amino acid residues AISPRHDITKYNEMFRG (SEQ ID NO: 31), and a third sequence of amino acid residues of sequence GGFYGSTIWFDF (SEQ ID NO: 15);
      (ii) an immunoglobulin heavy chain that comprises a heavy chain variable domain comprising a sequence of amino acid residues having an amino acid sequence:

```
EVQLVQSGAEVKKPGESLKISCQSFGYIFIDHTIHWMRQMPGQGLE

WMGAISPRHDITKYNEMFRGQVTISADKSSSTAYLQWSSLKASDT

AMYFCARGGFYGSTIWFDFWGQGTMVTVSS (SEQ ID NO: 32, residues 20-140, inclusive); and
```

(iii) an immunoglobulin heavy chain that comprises a sequence of amino acid residues having an amino acid sequence:

```
                                       (SEQ ID NO: 38)
EVQLVQSGAEVKKPGESLKISCQSFGYIFIDHTIHWMRQMPGQGLEWMGA

ISPRHDITKYNEMFRGQVTISADKSSSTAYLQWSSLKASDTAMYFCARGG

GFYGSTIWFDFWGQGTMVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK,
residues 20-455, inclusive); and
```
and
   B. when the nucleic acid molecule encodes an immunoglobulin light chain, the immunoglobulin light chain is selected from the group consisting of:
      (i) an immunoglobulin light chain that comprises a first sequence of amino acid residues of sequence ITTT-DIDDDMN (SEQ ID NO: 10), a second sequence of amino acid residues of sequence EGNILRP (SEQ ID NO: 11), a third sequence of amino acid residues of sequence LQSDNLPFT (SEQ ID NO: 12);
      (ii) an immunoglobulin light chain that comprises a light chain variable domain comprising a sequence of amino acid residues having an amino acid sequence:

```
ETTVTQSPSFLSASVGDRVTITCITTTDIDDDMNWFQQEPGKAPKLL

ISEGNILRPGVPSRFSSSGYGTDFTLTISKLQPEDFATYYCLQSDNL

PFTFGQGTKLEIK (SEQ ID NO: 33, residues 21-127, inclusive); and
```

(iii) an immunoglobulin light chain that comprises a sequence of amino acid residues having an amino acid sequence:

```
                                       (SEQ ID NO: 37)
ETTVTQSPSFLSASVGDRVTITCITTTDIDDDMNWFQQEPGKAPKLLISE

GNILRPGVPSRFSSSGYGTDFTLTISKLQPEDFATYYCLQSDNLPFTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC,
residues 21-234, inclusive).
```

2. An expression cassette that comprises a promoter and an isolated, non-naturally occurring nucleic acid molecule according to claim 1.

3. An engineered plasmid comprising an expression cassette according to claim 2.

4. An engineered host cell transfected with an isolated, non-naturally occurring nucleic acid molecule according to claim 1, optionally wherein the host cell is a non-human mammalian cell, optionally a CHO cell.

5. An engineered host cell transfected with a plasmid according to claim 3, optionally wherein the host cell is a non-human mammalian cell, optionally a CHO cell.

6. An engineered plasmid comprising a first expression cassette and a second expression cassette, wherein each of the first and second expression cassettes comprises a promoter and an isolated, non-naturally occurring nucleic acid molecule according to claim 1, wherein the first expression cassette directs the expression of an immunoglobulin heavy chain and the second expression cassette directs the expression of an immunoglobulin light chain.

7. An engineered host cell transfected with a plasmid according to claim 6, optionally wherein the host cell is a non-human mammalian cell, optionally a CHO cell.

8. An engineered host cell transfected with a first plasmid and a second plasmid, wherein each of the first and second plasmids is a plasmid according to claim 2, wherein the first plasmid comprises a first expression cassette that comprises a promoter and an isolated, non-naturally occurring nucleic acid molecule that encodes an immunoglobulin heavy chain and the second plasmid comprises a second expression cassette that comprises a promoter and an isolated, non-naturally occurring nucleic acid molecule that encodes an immunoglobulin light chain.

9. An isolated, non-naturally occurring nucleic acid molecule according to claim 1 that comprises a first nucleic acid molecule that encodes an immunoglobulin heavy chain and a second nucleic acid molecule that encodes an immunoglobulin light chain, wherein:
  A. the immunoglobulin heavy chain encoded by the first nucleic acid molecule is selected from the group consisting of:
   (i) an immunoglobulin heavy chain that comprises a first sequence of amino acid residues of sequence DHTIH (SEQ ID NO: 13), a second sequence of amino acid residues AISPRHDITKYNEMFRG (SEQ ID NO: 31), and a third sequence of amino acid residues of sequence GGFYGSTIWFDF (SEQ ID NO: 15);
   (ii) an immunoglobulin heavy chain that comprises a heavy chain variable domain comprising a sequence of amino acid residues having an amino acid sequence: EVQLVQSGAEVKKPGESLKISCQSFGYIFIDHTIHWMRQMPGQGLE WMGAISPRHDITKYNEMFRGQVTISADKSSSTAYLQWSSLKASDT AMYFCARGGFYGSTIWFDFWGQGTMVTVSS (SEQ ID NO: 32, residues 20-140, inclusive); and
   (iii) an immunoglobulin heavy chain that comprises a sequence of amino acid residues having an amino acid sequence:

(SEQ ID NO: 38)
   EVQLVQSGAEVKKPGESLKISCQSFGYIFIDHTIHWMRQMPGQGLEWMGA

ISPRHDITKYNEMFRGQVTISADKSSSTAYLQWSSLKASDTAMYFCARGG

GFYGSTIWFDFWGQGTMVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK,
   residues 20-455, inclusive); and
  B. the immunoglobulin light chain encoded by the second nucleic acid molecule is selected from the group consisting of:
   (i) an immunoglobulin light chain that comprises a first sequence of amino acid residues of sequence ITTTDIDDDMN (SEQ ID NO: 10), a second sequence of amino acid residues of sequence EGNILRP (SEQ ID NO: 11), a third sequence of amino acid residues of sequence LQSDNLPFT (SEQ ID NO: 12);
   (ii) an immunoglobulin light chain that comprises a light chain variable domain comprising a sequence of amino acid residues having an amino acid sequence:

ETTVTQSPSFLSASVGDRVTITCITTTDIDDDMNWFQQEPGKAPKLL

ISEGNILRPGVPSRFSSSGYGTDFTLTISKLQPEDFATYYCLQSDNL

PFTFGQGTKLEIK (SEQ ID NO: 33, residues 21-127, inclusive); and (iii) an immunoglobulin light chain that comprises a sequence of amino acid residues havina an amino acid sequence:

(SEQ ID NO: 37)
   ETTVTQSPSFLSASVGDRVTITCITTTDIDDDMNWFQQEPGKAPKLLISE

GNILRPGVPSRFSSSGYGTDFTLTISKLQPEDFATYYCLQSDNLPFTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC,
   residues 21-234, inclusive).

10. An isolated, non-naturally occurring nucleic acid molecule according to claim 9 wherein (i) the first nucleic acid molecule is disposed in a first expression cassette that further comprises a promoter to direct expression of the immunoglobulin heavy chain encoded by the first nucleic acid molecule and (ii) the second nucleic acid molecule is disposed in a first expression cassette that further comprises a promoter to direct expression of the immunoglobulin heavy chain encoded by the first nucleic acid molecule.

11. An engineered plasmid comprising an isolated, non-naturally occurring nucleic acid molecule according to claim 10.

12. An engineered host cell transfected with a plasmid according to claim 11, optionally wherein the host cell is a non-human mammalian cell, optionally a CHO cell.

13. An engineered host cell that comprises an isolated, non-naturally occurring nucleic acid molecule according to claim 1, wherein the engineered host cell is selected from the group consisting of an engineered host cell deposited under accession number ATCC PTA-8421 and an engineered host cell deposited under accession number ATCC PTA-8422.

14. An engineered plasmid that encodes an antibody that binds sphingosine-1-phosphate (S1P), wherein the plasmid comprises a first protein coding sequence that encodes an immunoglobulin light chain and a second protein coding sequence that encodes an immunoglobulin heavy chain, each of which immunoglobulin heavy and light chains can be expressed in a recombinant host cell, wherein:
  A. the immunoglobulin heavy chain is selected from the group consisting of:
   (i) an immunoglobulin heavy chain that comprises a first sequence of amino acid residues of sequence DHTIH (SEQ ID NO: 13), a second sequence of amino acid residues AISPRHDITKYNEMFRG (SEQ ID NO: 31), and a third sequence of amino acid residues of sequence GGFYGSTIWFDF (SEQ ID NO: 15);
   (ii) an immunoglobulin heavy chain that comprises a heavy chain variable domain comprising a sequence of amino acid residues having an amino acid sequence:

EVQLVQSGAEVKKPGESLKISCQSFGYIFIDHTIHWMRQMPGQGLE

WMGAISPRHDITKYNEMFRGQVTISADKSSSTAYLQWSSLKASDT

AMYFCARGGFYGSTIWFDFWGQGTMVTVSS (SEQ ID NO: 32, residues 20-140, inclusive); and (iii) an immunoglobulin heavy chain that comprises a sequence of amino acid residues having an amino acid sequence:

(SEQ ID NO: 38)
EVQLVQSGAEVKKPGESLKISCQSFGYIFIDHTIHWMRQMPGQGLEWMGA

ISPRHDITKYNEMFRGQVTISADKSSSTAYLQWSSLKASDTAMYFCARGG

GFYGSTIWFDFWGQGTMVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK,
residues 20-455, inclusive); and

B. the immunoglobulin light chain is selected from the group consisting of:
    (i) an immunoglobulin light chain that comprises a first sequence of amino acid residues of sequence ITTTDIDDDMN (SEQ ID NO: 10), a second sequence of amino acid residues of sequence EGNILRP (SEQ ID NO: 11), a third sequence of amino acid residues of sequence LQSDNLPFT (SEQ ID NO: 12);
    (ii) an immunoglobulin light chain that comprises a light chain variable domain comprising a sequence of amino acid residues having an amino acid sequence:

ETTVTQSPSFLSASVGDRVTITCITTTDIDDDMNWFQQEPGKAPKLL

ISEGNILRPGVPSRFSSSGYGTDFTLTISKLQPEDFATYYCLQSDNL

PFTFGQGTKLEIK (SEQ ID NO: 33, residues 21-127, inclusive); and (iii) an immunoglobulin light chain that comprises a sequence of amino acid residues having an amino acid sequence:

(SEQ ID NO: 37)
ETTVTQSPSFLSASVGDRVTITCITTTDIDDDMNWFQQEPGKAPKLLISE

GNILRPGVPSRFSSSGYGTDFTLTISKLQPEDFATYYCLQSDNLPFTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC,
residues 21-234, inclusive).

15. An engineered plasmid according to claim 14 wherein the first protein coding sequence further comprises a promoter to direct expression of the immunoglobulin light chain from the first protein coding sequence and the second protein coding sequence further comprises a promoter to direct expression of the immunoglobulin heavy chain from the second protein coding sequence.

16. An engineered host cell transfected with a plasmid according to claim 15, optionally wherein the host cell is a non-human mammalian cell, optionally a CHO cell.

17. A recombinant host cell capable of expressing an antibody that binds sphingosine-1-phosphate (S1P), wherein:
    A. the host cell includes a first nucleic acid molecule that encodes an immunoglobulin heavy chain of the antibody that binds S1P, wherein the immunoglobulin heavy chain is selected from the group consisting of:
        (i) an immunoglobulin heavy chain that comprises a first sequence of amino acid residues of sequence DHTIH (SEQ ID NO: 13), a second sequence of amino acid residues AISPRHDITKYNEMFRG (SEQ ID NO: 31), and a third sequence of amino acid residues of sequence GGFYGSTIWFDF (SEQ ID NO: 15);
        (ii) an immunoglobulin heavy chain that comprises a heavy chain variable domain comprising a sequence of amino acid residues having an amino acid sequence:

EVQLVQSGAEVKKPGESLKISCQSFGYIFIDHTIHWMRQMPGQGLE

WMGAISPRHDITKYNEMFRGQVTISADKSSSTAYLQWSSLKASDT

AMYFCARGGFYGSTIWFDFWGQGTMVTVSS (SEQ ID NO: 32, residues 20-140, inclusive); and (iii) an immunoglobulin heavy chain that comprises a sequence of amino acid residues having an amino acid sequence:

(SEQ ID NO: 38)
EVQLVQSGAEVKKPGESLKISCQSFGYIFIDHTIHWMRQMPGQGLEWMGA

ISPRHDITKYNEMFRGQVTISADKSSSTAYLQWSSLKASDTAMYFCARGG

GFYGSTIWFDFWGQGTMVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK,
residues 20-455, inclusive); and

B. the host cell includes a second nucleic acid molecule that encodes an immunoglobulin light chain of the antibody that binds S1P, wherein the immunoglobulin light chain is selected from the group consisting of:
        (i) an immunoglobulin light chain that comprises a first sequence of amino acid residues of sequence ITTTDIDDDMN (SEQ ID NO: 10), a second sequence of amino acid residues of sequence EGNILRP (SEQ ID NO: 11), a third sequence of amino acid residues of sequence LQSDNLPFT (SEQ ID NO: 12);
        (ii) an immunoglobulin light chain that comprises a light chain variable domain comprising a sequence of amino acid residues having an amino acid sequence:

ETTVTQSPSFLSASVGDRVTITCITTTDIDDDMNWFQQEPGKAPKLL
ISEGNILRPGVPSRFSSSGYGTDFTLTISKLQPEDFATYYCLQSDNL
PFTFGQGTKLEIK (SEQ ID NO: 33, residues 21-127,
inclusive); and (iii) an immunoglobulin light chain that comprises a sequence of amino acid residues having an amino acid sequence:

(SEQ ID NO: 37)
ETTVTQSPSFLSASVGDRVTITCITTTDIDDDMNWFQQEPGKAPKLLISE
GNILRPGVPSRFSSSGYGTDFTLTISKLQPEDFATYYCLQSDNLPFTFGQ
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC,
residues 21-234, inclusive).

* * * * *